(12) United States Patent
Kohane et al.

(10) Patent No.: US 11,110,175 B2
(45) Date of Patent: Sep. 7, 2021

(54) COMPOSITIONS WITH PERMEATION ENHANCERS FOR DRUG DELIVERY

(71) Applicants: Children's Medical Center Corporation, Boston, MA (US); Massachusetts Institute of Technology, Cambridge, MA (US)

(72) Inventors: Daniel S. Kohane, Newton, MA (US); Rong Yang, Cambridge, MA (US); Lily Yun Lin, Austin, TX (US)

(73) Assignees: Children's Medical Center Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 20 days.

(21) Appl. No.: 15/749,951

(22) PCT Filed: Aug. 5, 2016

(86) PCT No.: PCT/US2016/045908
§ 371 (c)(1),
(2) Date: Feb. 2, 2018

(87) PCT Pub. No.: WO2017/024282
PCT Pub. Date: Feb. 9, 2017

(65) Prior Publication Data
US 2018/0228903 A1 Aug. 16, 2018

Related U.S. Application Data

(60) Provisional application No. 62/201,199, filed on Aug. 5, 2015.

(51) Int. Cl.
| | |
|---|---|
| *A61K 47/34* | (2017.01) |
| *A61K 9/46* | (2006.01) |
| *A61K 9/06* | (2006.01) |
| *A61K 31/407* | (2006.01) |
| *A61K 31/424* | (2006.01) |
| *A61K 31/431* | (2006.01) |
| *A61K 31/455* | (2006.01) |
| *A61K 31/4709* | (2006.01) |
| *A61K 31/496* | (2006.01) |
| *A61K 31/5383* | (2006.01) |
| *A61K 31/573* | (2006.01) |
| *A61K 45/06* | (2006.01) |
| *A61K 47/06* | (2006.01) |
| *A61K 47/10* | (2017.01) |
| *A61K 47/12* | (2006.01) |
| *A61K 47/20* | (2006.01) |
| *A61K 47/22* | (2006.01) |

(Continued)

(52) U.S. Cl.
CPC ............ *A61K 47/34* (2013.01); *A61K 9/0046* (2013.01); *A61K 9/06* (2013.01); *A61K 31/407* (2013.01); *A61K 31/424* (2013.01); *A61K 31/431* (2013.01); *A61K 31/445* (2013.01); *A61K 31/4709* (2013.01); *A61K 31/496* (2013.01); *A61K 31/5383* (2013.01); *A61K 31/573* (2013.01); *A61K 38/12* (2013.01); *A61K 45/06* (2013.01); *A61K 47/06* (2013.01); *A61K 47/10* (2013.01); *A61K 47/12* (2013.01); *A61K 47/20* (2013.01); *A61K 47/22* (2013.01); *A61K 47/26* (2013.01); *A61P 27/16* (2018.01); *A61P 31/04* (2018.01); *C08G 65/3355* (2013.01); *C08G 79/04* (2013.01)

(58) Field of Classification Search
CPC combination set(s) only.
See application file for complete search history.

(56) References Cited

U.S. PATENT DOCUMENTS

| | | |
|---|---|---|
| 3,798,290 A | 3/1974 | Shim |
| 6,004,578 A | 12/1999 | Lee et al. |

(Continued)

FOREIGN PATENT DOCUMENTS

| | | |
|---|---|---|
| CN | 1829510 A | 9/2006 |
| WO | WO 96/06597 | 3/1996 |

(Continued)

OTHER PUBLICATIONS

Dahiyatetal., "Controlled release from poly(phosphoester) matrices," Journal of Controlled Release 33 (1995) 13-21.*

(Continued)

*Primary Examiner* — Jared Barsky
(74) *Attorney, Agent, or Firm* — Wolf, Greenfield & Sacks, P.C.

(57) ABSTRACT

The present invention provides compositions and methods for delivery of therapeutic agents across an barrier. The compositions include a therapeutic agent (e.g., antimicrobial agent, antibiotic, or anesthetic agent), a permeation enhancer which increases the flux of the therapeutic agent across the barrier, and a matrix forming agent. The matrix forming agent forms a gel at a suitable gelation temperature and rheological properties for use in drug delivery, and in some cases, the gelation temperature and rheological properties are not significantly changed from those of the composition without the permeation enhancer. The invention also provides a matrix forming agent and compositions thereof. Such compositions are particularly useful in the treatment of otitis media. Methods of treatment, methods of delivery, and kits for the compositions described herein are also provided.

26 Claims, 26 Drawing Sheets

(51) Int. Cl.
| | |
|---|---|
| A61P 27/16 | (2006.01) |
| A61P 31/04 | (2006.01) |
| C08G 79/04 | (2006.01) |
| A61K 31/445 | (2006.01) |
| A61K 9/00 | (2006.01) |
| A61K 38/12 | (2006.01) |
| A61K 47/26 | (2006.01) |
| C08G 65/335 | (2006.01) |

(56) References Cited

U.S. PATENT DOCUMENTS

| | | | |
|---|---|---|---|
| 6,201,065 B1 * | 3/2001 | Pathak | A61K 9/0014 424/486 |
| 6,316,011 B1 | 11/2001 | Ron et al. | |
| 6,515,016 B2 | 2/2003 | Hunter | |
| 6,685,697 B1 * | 2/2004 | Arenberg | A61F 11/00 604/11 |
| 8,822,410 B2 * | 9/2014 | Simons | A61K 9/0046 514/2.8 |
| 9,505,737 B2 | 11/2016 | Becker et al. | |
| 2004/0101560 A1 | 5/2004 | Sawchuk et al. | |
| 2004/0141949 A1 | 7/2004 | Rosenthal et al. | |
| 2005/0137189 A1 | 6/2005 | van Duzer et al. | |
| 2007/0098772 A1 | 5/2007 | Westcott et al. | |
| 2007/0269379 A1 | 11/2007 | Mitragotri et al. | |
| 2008/0069857 A1 | 3/2008 | Yeo et al. | |
| 2011/0166060 A1 * | 7/2011 | Simons | A61K 9/0046 514/2.8 |
| 2018/0125781 A1 | 5/2018 | Dellamary et al. | |
| 2020/0138710 A1 | 5/2020 | Kohane et al. | |

FOREIGN PATENT DOCUMENTS

| | | |
|---|---|---|
| WO | WO 2005/009436 A1 | 2/2005 |
| WO | WO 2007/120818 A2 | 10/2007 |
| WO | WO 2009/142719 A2 | 11/2009 |
| WO | WO 2010/074992 A2 | 7/2010 |
| WO | WO 2015/030393 A1 | 3/2015 |
| WO | WO 2017/024282 A1 | 2/2017 |
| WO | WO 2018/053140 A1 | 3/2018 |

OTHER PUBLICATIONS

International Search Report and Written Opinion for PCT/US2016/045908 dated Oct. 26, 2016.
International Preliminary Report on Patentability for PCT/US2016/045908 dated Feb. 15, 2018.
International Search Report and Written Opinion for PCT/US2017/051577 dated Nov. 7, 2017.
[No Author Listed], BASF—Pluronic Block Copolymer. 2004, p. 1, table 1. Retrieved on Oct. 6, 2016 from http://worldaccount.basf.com/wa/NAFTA/Catalog/ChemicalsNAFT/info/BASF/PRD/30085239. 2 pages.
[No Author Listed], Antibiotic / Antimicrobial Resistance, https://web.archive.org/web/20140103173935/http://www.cdc.gov/drugresistance/ Retrieved from the WayBack Machine on Jun. 28, 2018, noting date of Jan. 3, 2014, 2 pages.
Bluestone, C. D. & Klein, J. O. Otitis media in infants and children. 4th edn, (BC Decker, 2007). Chapter 8.
Adzima et al., Rheological and chemical analysis of reverse gelation in a covalently crosslinked Diels-Alder polymer network. Macromolecules. Dec. 9, 2008;41(23):9112-9117.
Babl et al., Experimental acute otitis media due to nontypeable Haemophilus influenzae: comparison of high and low azithromycin doses with placebo. Antimicrob Agents Chemother. Jul. 2002;46(7):2194-9.
Barreiro-Iglesias et al., Pluronic-g-poly(acrylic acid) copolymers as novel excipients for site specific, sustained release tablets. Eur J Pharm Sci. Dec. 2005;26(5):374-85. Epub Sep. 13, 2005.

Bouchet et al., Host-derived sialic acid is incorporated into Haemophilus influenzae lipopolysaccharide and is a major virulence factor in experimental otitis media. Proc Natl Acad Sci U S A. Jul. 22, 2003;100(15):8898-903. Epub Jul. 10, 2003.
Bromberg, Properties of Aqueous Solutions and Gels of Poly(ethylene oxide)-b-poly(propylene oxide)-b-poly(ethylene oxide)-g-poly(acrylic acid). The Journal of Physical Chemistry B 1998, 102 (52), 10736-10744.
Chen et al., Injectable microparticle-gel system for prolonged and localized lidocaine release. I. In vitro characterization. J Biomed Mater Res A. Sep. 1, 2004;70(3):412-9.
Chen et al., Injectable microparticle-gel system for prolonged and localized lidocaine release. II. In vivo anesthetic effects. J Biomed Mater Res A. Sep. 1, 2004;70(3):459-66.
Cole et al., Interaction of Nonionic Block Copolymeric (Poloxamer) Surfactants with Poly (Acrylic Acid), Studied by Photon Correlation Spectroscopy. Journal of Colloid and Interface Science 1996, 180 (2), 421-427.
Colombo et al., Effect of excipient composition on the biocompatibility of bupivacaine-containing microparticles at the sciatic nerve. J Biomed Mater Res A. Mar. 15, 2004;68(4):651-9.
Colombo et al., Prolonged duration local anesthesia with lipid-protein-sugar particles containing bupivacaine and dexamethasone. J Biomed Mater Res A. Nov. 1, 2005;75(2):458-64.
Dumortier et al., A review of poloxamer 407 pharmaceutical and pharmacological characteristics. Pharm Res. Dec. 2006;23(12):2709-28. Epub Nov. 11, 2006.
Figueira et al., Variation of pneumococcal Pilus-1 expression results in vaccine escape during Experimental Otitis Media [EOM]. PLoS One. Jan. 8, 2014;9(1):e83798. doi: 10.1371/journal.pone.0083798. eCollection 2014.
Gabriel et al., A photo-triggered layered surface coating producing reactive oxygen species. Biomaterials. Dec. 2013;34(38):9763-9. doi: 10.1016/j.biomaterials.2013.09.021. Epub Sep. 25, 2013.
Hall-Stoodley et al., Direct detection of bacterial biofilms on the middle-ear mucosa of children with chronic otitis media. JAMA. Jul. 12, 2006;296(2):202-11.
Hecht et al., Interaction of ABA block copolymers with ionic surfactants: influence on micellization and gelation. The Journal of Physical Chemistry 1995, 99 (13), 4866-4874.
Hoa et al., Demonstration of nasopharyngeal and middle ear mucosal biofilms in an animal model of acute otitis media. Ann Otol Rhinol Laryngol. Apr. 2009;118(4):292-8.
Hoa et al., Identification of adenoid biofilms with middle ear pathogens in otitis-prone children utilizing SEM and FISH. Int J Pediatr Otorhinolaryngol. Sep. 2009;73(9):1242-8. doi: 10.1016/j.ijporl.2009.05.016. Epub Jun. 13, 2009.
Hoa et al., Biofilms and chronic otitis media: an initial exploration into the role of biofilms in the pathogenesis of chronic otitis media. Am J Otolaryngol. Jul.-Aug. 2010;31(4):241-5. doi: 10.1016/j.amjoto.2009.02.015. Epub Jun. 3, 2009.
Hoare et al., Hydrogels in drug delivery: progress and challenges. Polymer 2008, 49, 1993-2007.
Hoare et al., Rheological blends for drug delivery. I. Characterization in vitro. J Biomed Mater Res A. Feb. 2008;92(2):575-85. doi: 10.1002/jbm.a.32392.
Hoare et al., Rheological blends for drug delivery. II. Prolongation of nerve blockade, biocompatibility, and in vitro-in vivo correlations. J Biomed Mater Res A. Feb. 2008;92(2):586-95. doi: 10.1002/jbm.a.32420.
Hoare et al., Prevention of peritoneal adhesions using polymeric rheological blends. Acta Biomater. Mar. 2014;10(3):1187-93. doi: 10.1016/j.actbio.2013.12.029. Epub Dec. 21, 2013.
Hudson et al., Injectable in situ cross-linking hydrogels for local antifungal therapy. Biomaterials. Feb. 2010;31(6):1444-52. doi: 10.1016/j.biomaterials.2009.11.016. Epub Nov. 26, 2009.
Hunter et al., Enhancement of antibiotic susceptibility and suppression of *Mycobacterium avium* complex growth by poloxamer 331. Antimicrob Agents Chemother. Feb. 1995;39(2):435-9.
Ito et al., The prevention of peritoneal adhesions by in situ cross-linking hydrogels of hyaluronic acid and cellulose derivatives. Biomaterials. Feb. 2007;28(6):975-83. Epub Nov. 15, 2006.

(56) References Cited

OTHER PUBLICATIONS

Ito et al., Anti-inflammatory function of an in situ cross-linkable conjugate hydrogel of hyaluronic acid and dexamethasone. Biomaterials. Apr. 2007;28(10):1778-86. Epub Jan. 3, 2007.
Ito et al., Dextran-based in situ cross-linked injectable hydrogels to prevent peritoneal adhesions. Biomaterials. Aug. 2007;28(23):3418-26. Epub Apr. 18, 2007.
Iwasaki et al., Novel Thermoresponsive Polymers Having Biodegradable Phosphoester Backbones. Macromolecules 2007, 40 (23), 8136-8138.
Jia et al., Prolongation of sciatic nerve blockade by in situ cross-linked hyaluronic acid. Biomaterials. Aug. 2004;25(19):4797-804.
Jones et al., Rheological, mechanical and mucoadhesive properties of thermoresponsive, bioadhesive binary mixtures composed of poloxamer 407 and carbopol 974P designed as platforms for implantable drug delivery systems for use in the oral cavity. Int J Pharm. May 8, 2009;372(1-2):49-58. doi: 10.1016/j.ijpharm.2009.01.006. Epub Jan. 18, 2009.
Karande et al., Design principles of chemical penetration enhancers for transdermal drug delivery. Proc Natl Acad Sci U S A. Mar. 29, 2005;102(13):4688-93. Epub Mar. 17, 2005.
Karasic et al., Modification of otitis media in chinchillas rechallenged with nontypable Haemophilus influenzae and serological response to outer membrane antigens. J Infect Dis. Feb. 1985;151(2):273-9.
Khoo et al., Formulations for trans-tympanic antibiotic delivery. Biomaterials. Jan. 2013;34(4):1281-8. doi: 10.1016/j.biomaterials.2012.10.025. Epub Nov. 9, 2012.
Kohane et al., Vanilloid receptor agonists potentiate the in vivo local anesthetic activity of percutaneously injected site 1 sodium channel blockers. Anesthesiology. Feb. 1999;90(2):524-34.
Kohane et al., A re-examination of tetrodotoxin for prolonged duration local anesthesia. Anesthesiology. Jul. 1998;89(1):119-31.
Kohane et al., Sciatic nerve blockade in infant, adolescent, and adult rats: a comparison of ropivacaine with bupivacaine. Anesthesiology. Nov. 1998;89(5):1199-208; discussion 10A.
Kohane et al., The local anesthetic properties and toxicity of saxitonin homologues for rat sciatic nerve block in vivo. Reg Anesth Pain Med. Jan.-Feb. 2000;25(1):52-9.
Kohane et al., Effects of adrenergic agonists and antagonists on tetrodotoxin-induced nerve block. Reg Anesth Pain Med. May-Jun. 2001;26(3):239-45.
Kohane et al., High concentrations of adrenergic antagonists prolong sciatic nerve blockade by tetrodotoxin. Acta Anaesthesiol Scand. Aug. 2001;45(7):899-905.
Kohane et al., Biocompatibility of lipid-protein-sugar particles containing bupivacaine in the epineurium. J Biomed Mater Res. Mar. 5, 2002;59(3):450-9.
Kohane et al., Sciatic nerve blockade with lipid-protein-sugar particles containing bupivacaine. Pharm Res. Oct. 2000;17(10):1243-9.
Kohane et al., Lipid-sugar particles for intracranial drug delivery: safety and biocompatibility. Brain Res. Aug. 16, 2002;946(2):206-13.
Kohane et al., Prolonged duration local anesthesia from tetrodotoxin-enhanced local anesthetic microspheres. Pain. Jul. 2001;104(1-2):415-21.
Kuroiwa et al., Heat-set gel-like networks of lipophilic Co(II) triazole complexes in organic media and their thermochromic structural transitions. J Am Chem Soc. Feb. 25, 2004;126(7):2016-21.
Lee et al., Biofilm presence in humans with chronic suppurative otitis media. Otolaryngol Head Neck Surg. Nov. 2009;141(5):567-71. doi: 10.1016/j.otohns.2009.08.010.
Li et al., Biodegradable and photocrosslinkable polyphosphoester hydrogel. Biomaterials. Mar. 2006;27(7):1027-34. Epub Aug. 24, 2005.
Liu et al., Biofilms in pediatric respiratory and related infections. Curr Allergy Asthma Rep. Nov. 2009;9(6):449-55.

McCormick et al., Raft-synthesized diblock and triblock copolymers: thermally-induced supramolecular assembly in aqueous media. Soft Matter 2008, 4 (9), 1760-1773.
Nistico et al., Adenoid reservoir for pathogenic biofilm bacteria. J Clin Microbial. Apr. 2011;49(4):1411-20. doi: 10.1128/JCM.00756-10. Epub Feb. 9, 2011.
Padera et al., Local myotoxicity from sustained release of bupivacaine from microparticles. Anesthesiology. May 2008;108(5):921-8. doi: 10.1097/ALN.0b013e31816c8a48.
Paradise, Short-course antimicrobial treatment for acute otitis media: not best for infants and young children. JAMA. Nov. 26, 1997;278(20):1640-2.
Pelton et al., Efficacy of linezolid in experimental otitis media. Antimicrob Agents Chemother. Mar. 2000;44(3):654-7.
Post et al., The role of biofilms in otolaryngologic infections: update 2007. Curr Opin Otolaryngol Head Neck Surg. Oct. 2007;15(5):347-51.
Ribot et al., Aqueous gelation of ionic liquids: reverse thermoresponsive ion gels. Chem Commun (Camb). Oct. 7, 2010;46(37):6971-3. doi: 10.1039/c0cc01671c. Epub Aug. 23, 2010.
Sabharwal et al., Virulence of Streptococcus pneumoniae serotype 6C in experimental otitis media. Microbes Infect. Aug. 2012;14(9):712-8. doi: 10.1016/j.micinf.2012.02.008. Epub Mar. 3, 2012.
Sabharwal et al., Capsular switching as a strategy to increase pneumococcal virulence in experimental otitis media model. Microbes Infect. Apr. 2014;16(4):292-9. doi:10.1016/j.micinf.2013.12.002. Epub Dec. 20, 2013.
Sagie et al., Prolonged sensory-selective nerve blockade. Proc Natl Acad Sci U S A. Feb. 23, 2010;107(8):3740-5. doi: 10.1073/pnas.0911542107. Epub Feb. 4, 2010.
Sahoo et al., Reverse thermal gelation of aromatic solvents by a series of easily accessible organic salt based gelators. Soft Matter, 2012,8, 2595-2598.
Simons et al., Chemical penetration enhancers and in situ-forming reservoirs for trans-tympanic drug delivery: progress toward improved treatment of Otitis media. (Massachusetts Institute of Technology) (2008)).
Simons et al., Effect of chemical permeation enhancers on nerve blockade. Mol Pharm. Jan.-Feb. 2009;6(1):265-73. doi: 10.1021/mp800167a.
Suzuki et al., Antimicrobial ear drop medication therapy. Acta Otolaryngol Suppl. 1996;525:68-72.
Tapiainen et al., Biofilm formation by *Streptococcus pneumoniae* isolates from paediatric patients. APMIS. Apr. 2010;118(4):255-60. doi: 10.1111/J.1600-0463.2010.02587.x.
Teele et al., Epidemiology of otitis media during the first seven years of life in children in greater Boston: a prospective, cohort study. J Infect Dis. Jul. 1989;160(1):83-94.
Tsifansky et al., Microparticles for inhalational delivery of antipseudomonal antibiotics. AAPS J. Jun. 2008;10(2):254-60. doi: 10.1208/s12248-008-9033-8. Epub May 3, 2008.
Walker et al., The role of percutaneous penetration enhancers. Adv Drug Deliv Rev 1996, 18, 295-301.
Wall et al., Ciprofloxacin 0.3%/dexamethasone 0.1% sterile otic suspension for the topical treatment of ear infections: a review of the literature. Pediatr Infect Dis J. Feb. 2009;28(2):141-4. doi: 10.1097/INF.0b013e31818b0c9c.
Wan et al., Poly(phosphoester) ionomers as tissue-engineering scaffolds. J Biomed Mater Res B Appl Biomater. Jul. 15, 2004;70(1):91-102.
Wen et al., Biodegradable polyphosphoester micelles for gene delivery. J Pharm Sci. Aug. 2004;93(8):2142-57.
Wetton et al., The dynamic mechanical properties of some polyethers. Polymer 1966, 7 (7), 331-365.
Yang et al., Treatment of otitis media by transtympanic delivery of antibiotics. Sci Transl Med. Sep. 14, 2016;8(356):356ra120. doi: 10.1126/scitranslmed.aaf4363.
Yeo et al., Complex coacervates for thermally sensitive controlled release of flavor compounds. J Agric Food Chem. Sep. 21, 2005;53(19):7518-25.
Yeo et al., In situ cross-linkable hyaluronic acid hydrogels prevent post-operative abdominal adhesions in a rabbit model. Biomaterials. Sep. 2006;27(27):4698-705. Epub Jun. 5, 2006.

(56) References Cited

OTHER PUBLICATIONS

Yeo et al., Peritoneal application of chitosan and UV-cross-linkable chitosan. J Biomed Mater Res A. Sep. 15, 2006;78(4):668-75.

Yeo et al., In situ cross-linkable hyaluronan hydrogels containing polymeric nanoparticles for preventing postsurgical adhesions. Ann Surg. May 2007;245(5):819-24.

Yeo et al., Prevention of peritoneal adhesions with an in situ cross-linkable hyaluronan hydrogel delivering budesonide. J Control Release. Jul. 31, 2007;120(3):178-85. Epub May 3, 2007.

Yeo et al., Peritoneal adhesion prevention with an in situ cross-linkable hyaluronan gel containing tissue-type plasminogen activator in a rabbit repeated-injury model. Biomaterials. Sep. 2007;28(28):3704-13. Epub May 3, 2007.

Yeo et al., Polymers in the prevention of peritoneal adhesions. Eur J Pharm Biopharm. Jan. 2008;68(1):57-66. Epub Jul. 20, 2007.

Zhang et al., Poly(ethylene oxide)-block-polyphosphester-based Paclitaxel Conjugates as a Platform for Ultra-high Paclitaxel-loaded Multifunctional Nanoparticles. Chem Sci. 2013;4(5):2122-2126.

Zhao et al., Polyphosphoesters in drug and gene delivery. Adv Drug Deliv Rev. Apr. 25, 2003;55(4):483-99.

Zumbuehl et al., Antifungal hydrogels. Proc Natl Acad Sci U S A. Aug. 7, 2007;104(32):12994-8. Epub Jul. 30, 2007.

Supplemental European Search Report dated Mar. 18, 2019 for Application No. 16833979.

International Preliminary Report on Patentability dated Mar. 28, 2019 for Application No. PCT/U52017/051577.

Wang et al., Synthesis and Thermoresponsive Behaviors of Biodegradable Pluronic Analogs. Journal of Polymer Science. Jul. 22, 2009; 47:6168-6179.

EP 16833979.4, Jul. 23, 2019, Extended European Search Report. Extended European Search Report for Application No. EP 16833979.4 dated Jul. 23, 2019.

Shin et al., Effects of non-ionic surfactants as permeation enhancers towards piroxicam from the poloxamer gel through rat skins. Int J Pharm. Jul. 17, 2001;222(2):199-203.

Shin et al., Permeation of piroxicam from the poloxamer gels. Drug Dev Ind Pharm. Mar. 1999;25(3):273-8.

Xuan et al., Rheological characterization and in vivo evaluation of thermosensitive poloxamer-based hydrogel for intramuscular injection of piroxicam. Int J Pharm. Aug. 16, 2010;395(1-2):317-23.

PCT/US/1949084, Nov. 15, 2019, International Search Report and Written Opinion.

Tikhonov et al., Mechanism of sodium channel block by local anesthetics, antiarrhythmics, and anticonvulsants. J Gen Physiol. Apr. 3, 2017;149(4):465-481. doi: 10.1085/jgp.201611668. Epub Mar. 3, 2017.

U.S. Appl. No. 12/993,358, filed Mar. 21, 2011, Simons et al.

U.S. Appl. No. 11/734,537, filed Apr. 12, 2007, Yeo et al.

PCT/US2016/045908, Oct. 26, 2016, International Search Report and Written Opinion.

PCT/US2016/045908, Feb. 15, 2018, International Preliminary Report on Patentability.

PCT/US2017/051577, Nov. 7, 2017, International Search Report and Written Opinion.

CN 201680057343.9, Nov. 4, 2020, Chinese Office Action.

JP 2018-506186, Jun. 30, 2020, Japanese Office Action.

JP 2018-506186, Nov. 9, 2020, Japanese Office Action.

CN 201780069720.5, Nov. 2, 2020, Chinese Office Action.

EP 17851534.2, Apr. 1, 2020, Extended European Search Report.

Anderson, The process of structure-based drug design. Chem Biol. Sep. 2003;10(9):787-97.

U.S. Appl. No. 16/333,368, filed Mar. 14, 2019, Kohane et al.

EP 16833979.4, Mar. 18, 2019, Supplementary European Search Report.

PCT/US2017/051577, Mar. 28, 2019, International Preliminary Report on Patentability.

* cited by examiner

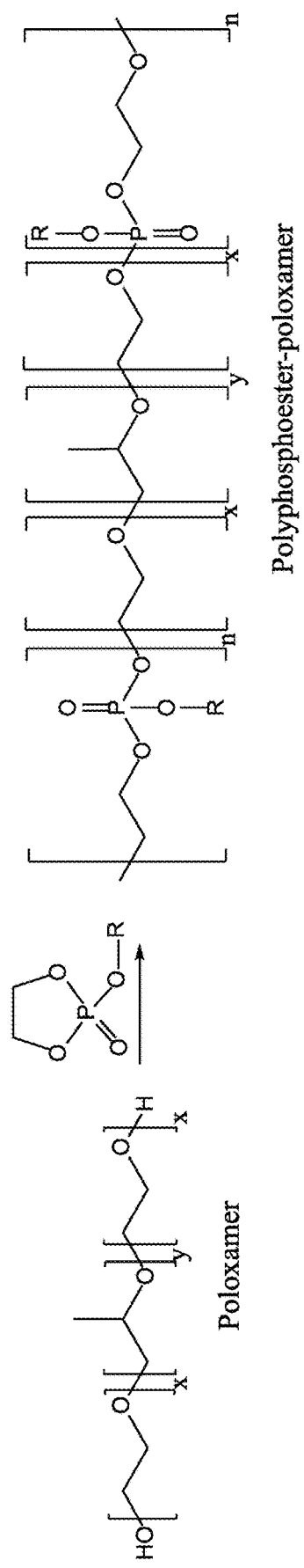
Figure 7A
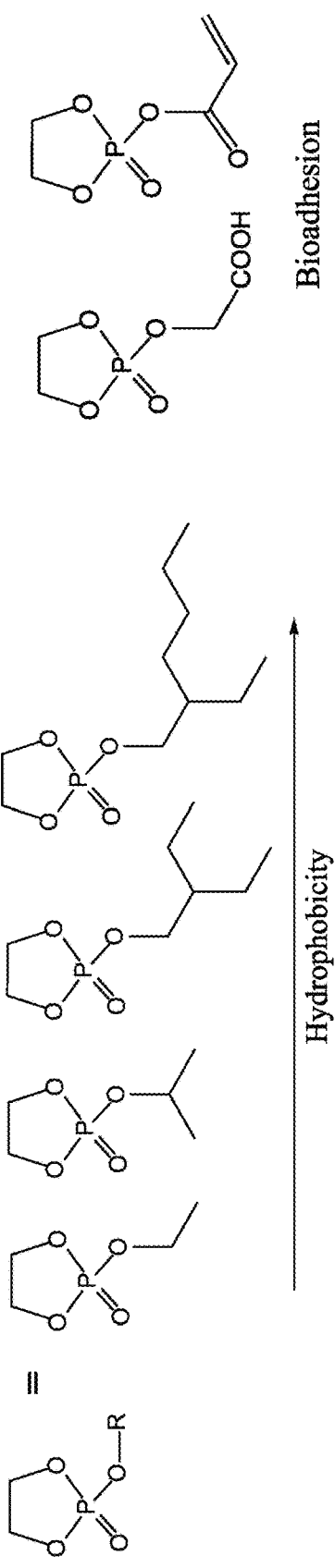
Figure 7B
Figure 7C

COMPOSITIONS WITH PERMEATION ENHANCERS FOR DRUG DELIVERY

RELATED APPLICATIONS

This application is a national stage filing under 35 U.S.C. 371 of International Patent Application Serial No. PCT/US2016/045908, filed Aug. 5, 2016, entitled "COMPOSITIONS WITH PERMEATION ENHANCERS FOR DRUG DELIVERY", which claims priority under 35 U.S.C. § 119(e) of U.S. Provisional Application Ser. No. 62/201,199, filed Aug. 5, 2015, the entire contents of which are incorporated herein by reference.
International Application PCT/US2016/045908 was published under PCT Article 21(2) in English.

FEDERALLY SPONSORED RESEARCH

This invention was made with government support under Grant Nos. GM073626 and DC009986 awarded by the National Institutes of Health. The government has certain rights in the invention.

BACKGROUND

Twelve to 16 million physician visits per year in the United States are attributed to otitis media (OM), making it the most common specifically treated childhood disease. [1] Acute OM (AOM) has a prevalence of 90% within the first 5 years of life, [2] and 90-95% of all U.S. children have at least one documented middle ear effusion by age 2. [3] 25% percent of all prescriptions written for children are for treatment of acute otitis media. Recurrence of the disease is also striking, with one third of all children in the U.S. having 6 or more episodes of AOM by age 7. [4] Moreover, epidemiological studies suggest that the prevalence of recurrent OM among children, particularly infants, is on the rise. [5] The incidence of OM in children of other industrialized nations is similar to that in the U.S. In the developing world, OM remains a significant cause of childhood mortality due to the development of chronic suppurative otitis media which frequently results in permanent hearing sequelae, and due to intracranial complications estimated to result in more than 25,000 deaths worldwide. [6]

Acute OM is the most common reason for antimicrobial prescribing in U.S. children and due to the high prevalence of disease and frequent recurrences is believed to be partially responsible for the ongoing increase in antibiotic resistance among pathogenic bacteria. Despite the success in reducing antimicrobial use in children by approximately 25% over the past decade, the increase in antimicrobial resistance has continued.

Present treatment of ear infections consists of systemic oral antibiotics, a treatment which requires multiple doses over 5-10 days and systemic exposure to antibiotics. The rise in antibiotic resistance, coupled with the many multifactorial etiology of OM pose difficulties in diagnosis and treatment of OM. Furthermore, current treatment presents a number of drawbacks including patient compliance issues due to gastrointestinal side effects, lack of an effective concentration of drug at the site of infection, and the potential for opportunistic infections. Even after acute signs of infection subside, generally within 72 hours, the root cause of the infection may persist for the remainder of the treatment, and beyond, even up to 2 months. Thus, making compliance with a physician's prescription important to prevent reoccurrence of infection.

Local, sustained delivery of active therapeutics directly to the middle ear for the treatment of OM could allow for much higher concentrations of the drug in the middle ear than from systemic administration, while minimizing systemic exposure and its adverse effects. However, the tympanic membrane (TM), while only 10 cell-layers thick, presents a barrier that is largely impermeable to all but the smallest, moderately hydrophobic molecules. Despite being the thinnest layer of skin, it is still a barrier to trans-tympanic membrane diffusion. Therefore, the direct treatment of middle ear infections is problematic. The shortcomings of the current treatment of ear diseases, such as middle ear infections, suggest the need for a new treatment which is noninvasive and direct acting.

SUMMARY

Provided herein are compositions and methods aimed at non-invasive trans-tympanic otitis media (OM) treatment with sustained drug flux across the tympanic membrane (TM) (See, e.g., FIG. 1). Chemical permeation enhancers (CPEs), commonly employed for trans-dermal delivery, can enable such a trans-tympanic flux. In certain embodiments, a single application of an optimized formulation could provide high concentrations of antibiotics localized to the middle ear, resulting in eradication of bacterial otitis media without the drawbacks of oral therapy. Such formulations may also useful in the treatment of other diseases of the ear requiring drug delivery across the tympanic membrane.

Typical OM treatments consists of a 10-day course of broad spectrum oral antibiotics. The widespread use of systemic antibiotics against a disease of such high prevalence and recurrence is believed to be partially responsible for the ongoing increase in antibiotic resistance seen in pathogenic bacteria in the nasopharynx. In most cases, antibiotic-resistant infections like pneumonia, skin, soft tissue, and gastrointestinal infections require prolonged and/or costlier treatments, extend hospital stays, necessitate additional doctor visits and healthcare use, and result in greater disability and death compared with infections that are easily treatable with antibiotics. Compliance with multi-dose regimens can also be difficult in some parts of the world. Compliance and antibiotic resistance may also be more problematic in the long-term prophylaxis of recurrent OM. An effective sustained local therapy could address the issue of compliance, affect the development of drug-resistant and chronic suppurative otitis media, and reduce the need for tympanostomy tube placement (devices implanted in the TM to enhance middle ear drainage in recurrent OM). [8]

The TM is a tri-layer membrane whose outer layer is a stratified squamous keratinizing epithelium continuous with the skin of the external auditory canal. The inner-most layer is a simple cuboidal mucosal epithelium. Between these epithelia is a layer of fibro-elastic connective tissue and associated blood vessels and nerves. The human TM is only about 100 µm thick, but the 6-10 cell layer outer epithelium forms an impenetrable barrier against all but the smallest lipophilic molecules due to its keratin- and lipid-rich stratum corneum. [11]

Localized, sustained drug delivery directly to target tissues has several advantages over systemic application, including fewer adverse systemic effects, smaller quantities of drug used, potentially better therapeutic outcomes, and reduced costs. The impermeability of the TM is a central challenge for the development of local therapies.

Chemical permeation enhancers (CPEs) are used to safely increase small molecule flux in transdermal drug delivery.

Several are FDA approved for use in humans. These agents are often surfactants, comprising a heterogeneous group of amphiphilic organic molecules with hydrophilic heads and hydrophobic tails. Several classes of surfactants have been studied. Surfactants reversibly modify lipids by adsorption at interfaces and removal of water-soluble agents that act as plasticizers. Cationic surfactants are known to produce greater increases in permeant flux than anionic surfactants, which in turn increase permeability more than nonionic surfactants. A broad range of non-surfactant chemical enhancers (e.g., terpenes) has also been used with mechanisms of action including denaturation of proteins within and between keratinocytes, and/or modification or disruption of lipids that results in increased lipid bilayer fluidity.

In a composition provided herein, the therapeutic agents and permeation enhancers are combined with matrix forming agents, to form compositions which form a hydrogels under suitable conditions. Such conditions may include exposure to body heat during administration (e.g., in the ear canal), or following mixing of two components of the composition or matrix-forming agent. The matrix forming agent is a compound or mixture of compounds that forms a gel after administration. The compositions are generally liquid at ambient conditions, however, once administered to a subject, the matrix forming agent or combination of matrix forming agents causes a phase transition to a hydrogel. Hydrogels have a highly porous structure that allows for the loading of drugs and other small molecules, and subsequent drug elution out of the gel creates a high local concentration in the surrounded tissues over an extended period. In certain embodiments, the drugs are loaded in the liquid composition. Hydrogels can conform and adhere to the shape of the surface to which they are applied and tend to be biocompatible.

For the compositions provided herein, the combination of the permeation enhancer with the matrix forming agent and therapeutic agent provides a composition with improved flux of the therapeutic agent, and also improved, or not significantly impaired, properties of the resulting hydrogel relative to the hydrogel formed by the composition in the absence of the permeation enhancer. For example, the phase transition temperature of the composition with the permeation enhancer may be lower than the composition without the permeation enhancer, or even if higher, may still fall into a useful range for formation of a hydrogel upon exposure to a biological surface (e.g., a phase transition temperature between about 0° C. and about 37° C. As another example, the storage modulus and/or loss modulus of the composition with the permeation enhancer may be about the same (e.g., within about 20%) as for the composition without the permeation enhancer, or the storage modulus of the composition with the permeation enhancer may be higher than the composition without the permeation enhancer. As another example, the storage modulus and/or loss modulus of the composition with the permeation enhancer may be about the same (e.g., within about 20% or 3 kPa, whichever is greater) as for the composition without the permeation enhancer, or the storage modulus of the composition with the permeation enhancer may be higher than the composition without the permeation enhancer. For the compositions provided herein, the combination of the permeation enhancer with the matrix forming agent and therapeutic agent provides a composition with improved flux of the therapeutic agent, and additional improved properties including, but not limited to extended drug release, adherence of the composition to the tympanic membrane over time, degradation, or combinations thereof, and also improved, or not significantly impaired, properties of the resulting hydrogel relative to the hydrogel formed by the composition in the absence of the permeation enhancer.

In one aspect, provided herein are compositions comprising:
(a) a therapeutic agent or a combination of therapeutic agents;
(b) a permeation enhancer or a combination of permeation enhancers, wherein the permeation enhancer or combination of permeation enhancers increases the flux of the therapeutic agent or combination of therapeutic agents across a barrier; and
(c) a matrix forming agent or a combination of matrix forming agents, wherein the matrix forming agent or combination of matrix forming agents comprises a polymer;
wherein:
the composition forms a gel at temperatures above a phase transition temperature; and
the phase transition temperature is less than about 37° C.;
and at least one of conditions (i), (ii), and (iii) are met:
(i) the phase transition temperature of the composition is less than the phase transition temperature of a reference composition plus about 5° C.;
(ii) the storage modulus of the composition is greater than about 15% of the storage modulus of the reference composition at a temperature of about 37° C.; and
(iii) the loss modulus of the composition is between about 80% and about 120% of the loss modulus of the reference composition at a temperature of about 37° C.;
wherein the reference composition is the composition in the absence of (b) the permeation enhancer or combination of permeation enhancers.

In one aspect, provided herein are compositions comprising:
(a) a therapeutic agent or a combination of therapeutic agents;
(b) a permeation enhancer or a combination of permeation enhancers, wherein the permeation enhancer or combination of permeation enhancers increases the flux of the therapeutic agent or combination of therapeutic agents across a barrier; and
(c) a matrix forming agent or a combination of matrix forming agents, wherein the matrix forming agent or combination of matrix forming agents comprises a polymer;
wherein:
the composition forms a gel at temperatures above a phase transition temperature; and
the phase transition temperature is less than about 37° C.;
and at least one of conditions (i), (ii), and (iii) are met:
(i) the phase transition temperature of the composition is less than the phase transition temperature of a reference composition plus about 5° C.;
(ii) the storage modulus of the composition is greater than about 15% of the storage modulus of the reference composition or greater than about 500 Pa, whichever is smaller, at a temperature of about 37° C.; and
(iii) the loss modulus of the composition is between about 15% and about 150% of the loss modulus of the reference composition at a temperature of about 37° C.;
wherein the reference composition is the composition in the absence of (b) the permeation enhancer or combination of permeation enhancers.

In certain embodiments, condition (i), the phase transition temperature of the composition is less than the phase transition temperature of the reference composition plus about 5° C., is met. In certain embodiments, condition (ii), the storage modulus of the composition is greater than about 15% of the storage modulus of the reference composition, is met. In certain embodiments, condition (ii), the storage modulus of the composition is greater than about 15% of the storage modulus of the reference composition, or greater than about 500 Pa, whichever is smaller, is met. In certain embodiments, condition (ii), the storage modulus of the composition is greater than about 15% of the storage modulus of the reference composition, or greater than about 1000 Pa, whichever is smaller, is met. In certain embodiments, condition (iii), the loss modulus of the composition is between about 80% and about 120% of the loss modulus of the reference composition, is met. In certain embodiments, condition (iii), the loss modulus of the composition is between about 15% and about 150% of the loss modulus of the reference composition, is met. In certain embodiments, both conditions (i) and (ii) are met. In certain embodiments, both conditions (ii) and (iii) are met. In certain embodiments, both conditions (i) and (iii) are met. In certain embodiments, each of conditions (i), (ii), and (iii) are met.

In certain embodiments, the polymer is biodegradable. In certain embodiments, the polymer is a copolymer. In certain embodiments, the copolymer is biodegradable or comprises biodegradable monomers. In certain embodiments, the copolymer is a block copolymer. In certain embodiments the copolymer comprises at least one block of hydrophobic monomers. In certain embodiments, the copolymer comprises at least one block of hydrophobic monomers, and at least one block of non-hydrophobic monomers.

In certain embodiments, the copolymer comprises a vinylic polymer (e.g. PE, PVC, PVDC, PS), a polyacrylate (e.g., polyacrylic acid polymethacrylic acid), a polyether (e.g., PEO, PPO, POM), a fluoropolymer (e.g., PTFE), a polysiloxane (e.g., PDMS), a polysaccharide (e.g., cellulose, dextran, hyaluronic acid, chitosan), a polyester (e.g, PET, a polyhydroxyalkanoate (e.g., PHB)), a polyamide (e.g., poly(lactic acid), poly(glycolic acid)), a polyphosphoester, a polyurethane, or a polycarbonate, or copolymers of combinations thereof. In certain embodiments, the copolymer comprises polyethylene oxide, polypropylene oxide, a poloxamer, poloxamer 407, poloxamer 188, a poloxamine, methylcellulose, hydroxypropyl methylcellulose, ethyl(hydroxyethyl) cellulose, xyloglucan, cellulose, acetate phthalate, latex, poly(acrylic acid), N-isopropylacrylamide-based systems, hyaluronic acid, chitosan, dextran, or gellan gum, or a derivative thereof, or a copolymer of a combination thereof. In certain embodiments, the copolymer comprises a poloxamer. In some embodiments, the copolymer comprises poloxamer 407. In certain embodiments, the copolymer comprises phosphoester monomers. In certain embodiments, the copolymer comprises a poloxamer and phosphoester monomers.

In certain embodiments, the composition has a high degree of hydrophobicity. In certain embodiments, the composition is optically transparent.

In certain embodiments, the phase transition temperature of the composition is at or below the body temperature of a subject. In certain embodiments, the phase transition temperature of the composition is between about 10° C. and about 40° C. In certain embodiments, the phase transition temperature of the composition is between about 20° C. and about 40° C. In certain embodiments, the phase transition temperature of the composition is less than the phase transition temperature of the same composition without the permeation enhancer plus about 5° C.

In certain embodiments, the composition is useful in treating a disease. In some embodiments, the composition is useful in treating an infectious disease. In some embodiments, the composition is useful in treating an ear disease (e.g., the barrier is the tympanic membrane). In some embodiments, the composition is useful in treating otitis media.

In another aspect, provided herein are compositions for treating an infectious disease or ear disease comprising:
 (a) a therapeutic agent or a combination of therapeutic agents;
 (b) a permeation enhancer or a combination of permeation enhancers, wherein the permeation enhancer or combination of permeation enhancers increases the flux of the therapeutic agent or combination of therapeutic agents across a barrier; and
 (c) a matrix forming agent or a combination of matrix forming agents, wherein the matrix forming agent or combination of matrix forming agents comprises a copolymer comprising phosphoester monomers.

The therapeutic agent may be an antibiotic agent, anesthetic agent, anti-inflammatory agent, analgesic agent, antifibrotic agent, anti-sclerotic agent, or anticoagulant agent. In certain embodiments, the therapeutic agent is an antibiotic selected form the group consisting of ciprofloxacin, cefuroxime, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, enoxacin, gatifloxacin, levofloxacin, lomefloxacin, moxifloxacin, norfloxacin, ofloxacin, trovafloxacin, bacitracin, colistin, polymyxin B, azithromycin, clarithromycin, dirithromycin, erythromycin, roxithromycin, troleandomycin, telithromycin, spectinomycin, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin, mafenide, sulfacetamide, sulfamethizole, sulfasalazine, sulfisoxazole, trimethoprim, and trimethoprim-sulfamethoxazole. In some embodiments, the antibiotic is ciprofloxacin. In some embodiments, the antibiotic is amoxicillin, azithromycin, cefuroxime, ceftriaxone, or trimethoprim. In some embodiments, the antibiotic is levofloxacin.

The permeation enhancer may be a surfactant, terpene, amino amide, amino ester, azide-containing compound, alcohol, or anesthetic agent. The permeation enhancer may be a surfactant, terpene, amino amide, amino ester, azide-containing compound, alcohol, pyrrolidone, sulfoxide, fatty acid, or anesthetic agent. In some embodiments, the permeation enhancer is a surfactant (e.g., cationic surfactant, anionic surfactant, nonionic surfactant). In some embodiments, the permeation enhancer is a terpene. In some embodiments, the composition comprises a surfactant permeation enhancer and a terpene permeation enhancer.

In certain embodiments, the permeation enhancer is sodium dodecyl sulfate, ammonium lauryl sulfate, sodium lauryl sulfate, cetyl trimethylammonium bromide, cetylpyridinium chloride, benzethonium chloride, cocamidopropyl betaine, cetyl alcohol, oleyl alcohol, octyl glucoside, decyl maltoside, sodium octyl sulfate, sodium decyl sulfate, sodium tetradecyl sulfate, sodium heptadecyl sulfate, sodium eicosyl sulfate, nicotine sulfate, sodium taurocholic sulfate, dimethyl sulfoxide, sodium tridecyl phosphate; decyldimethyl ammonio propane sulfonate, chembetaine oleyl, myristyldimethyl ammonio propane sulfonate; benzyl pyridinium chloride, dodecyl pyridinium chloride, cetyl pyridinium chloride, benzyldimethyl dodecyl ammonium chloride, benzyldimethyl dodecyl ammonium chloride, benzyldimethyl myristyl ammonium chloride, benzyldimethyl stearyl ammonium chloride, octyltrimethylammonium bromide, dodecyltrimethylammonium bromide, Polysorbate 20, Polysorbate 40, Polysorbate 60, or Polysorbate 80. In certain embodiments, the permeation enhancer is sodium octyl sulfate, sodium dodecyl sulfate, octyl trimethylammonium bromide, dodecyl trimethylammonium bromide, Polysorbate 20, or Polysorbate 80. In some embodiments, the permeation enhancer is sodium dodecyl sulfate.

In certain embodiments, the permeation enhancer is sodium lauroyl sarcosinate, sorbitan monooleate, octoxynol-9, diethyl sebacate, sodium polyacrylate (2500000 molecular weight (MW)), or octyldodecanol.

In certain embodiments, the permeation enhancer is an azone-like compound. In certain embodiments, the permeation enhancer is a compound similar to azone (e.g., laurocapram) of the formula:

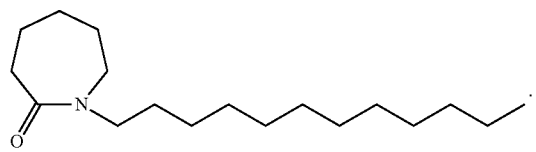 [SMILES: CCCCCCCCCCCCN1CCCCCC1=O]

In certain embodiments, the permeation enhancer is a compound containing piperazine. In certain embodiments, the permeation enhancer is 1-benzyl-4-(2-((1,1-biphenyl)-4-yloxy)ethyl)piperazine.

In certain embodiments, the permeation enhancer is a terpene (e.g., limonene). In certain embodiments, the permeation enhancer is limonene, cymene, pinene, camphor, menthol, comphone, phellandrine, sabinene, terpinene, borneol, cineole, geraniol, linalol, pipertone, terpineol, eugenol, eugenol acetate, safrole, benzyl benzoate, humulene, beta-caryophylene, eucakytol, hexanoic acid, octanoic acid, decanoic acid, undecanoic acid, dodecanoic acid, tridecanoic acid, myristic acid, palmitic acid, stearic acid, oleic acid, linoleic acid, linolenic acid, cholic acid; ethyl undecanoate, methyl laurate, methyl myristate, isopropyl myristate, isopropyl palmitate, palmityl palmitate, diethyl sebaccate, glyceryl monolaurate, glyceryl monooleate, or ethylpiperazine carboxylate. In some embodiments, the permeation enhancer is limonene.

In certain embodiments, the permeation enhancer is bupivacaine, tetracaine, procaine, proparacaine, propoxycaine, dimethocaine, cyclomethycaine, chloroprocaine, benzocaine, lidocaine, prilocaine, levobupivicaine, ropivacaine, dibucaine, articaine, carticaine, etidocaine, mepivacaine, piperocaine, or trimecaine. In some embodiments, the permeation enhancer is bupivacaine.

In some embodiments, the permeation enhancer is a combination of a surfactant and a terpene. In some embodiments, the permeation enhancer is a combination of a surfactant, a terpene, and an anesthetic. In some embodiments, the permeation enhancer is a combination of a surfactant selected from: sodium octyl sulfate, sodium dodecyl sulfate, octyl trimethylammonium bromide, dodecyl trimethylammonium bromide, Polysorbate 20, and Polysorbate 80; and a terpene. In some embodiments, the permeation enhancer is a combination of a surfactant selected from: sodium octyl sulfate, sodium dodecyl sulfate, octyl trimethylammonium bromide, dodecyl trimethylammonium bromide, Polysorbate 20, and Polysorbate 80; and limonene. In some embodiments, the permeation enhancer is sodium dodecyl sulfate, limonene, or bupivacaine, or a combination thereof. In some embodiments, the permeation enhancer is a combination of sodium dodecyl sulfate and limonene. In some embodiments, the permeation enhancer is a combination of sodium dodecyl sulfate, limonene, and bupivacaine.

The compositions may also include additional therapeutic agents, including anti-inflammatory agents (e.g., dexamethasone), anesthetics (e.g., bupivacaine), or β-lactamase inhibitors. In some embodiments, a therapeutic agent or additional therapeutic agent also acts as a permeation enhancer. In some embodiments, an amino amide (e.g., bupivacaine) or amino ester (e.g., tetracaine) local anesthetic acts as both a permeation enhancer and a therapeutic agent. In some embodiments, the composition comprises an amino amide (e.g., bupivacaine) or amino ester (e.g., tetracaine) local anesthetic acting as both a permeation enhancer and a therapeutic agent, and does not comprise an additional therapeutic agent. In some embodiments, the composition comprises bupivacaine acting as both a permeation enhancer and a therapeutic agent, and does not comprise an additional therapeutic agent.

In certain embodiments, the therapeutic agents comprises between about 0.01 percent to about 10 percent of the composition. In certain embodiments, the percent weight of permeation enhancer in the composition is between about 0.1% to about 1%, between about 1% to about 3%, or between about 3% to about 10%. In certain embodiments, the percent weight of matrix forming agent in the composition is between about 1% to about 10%, between about 10% to about 20%, between about 20% to about 30%, between about 30% to about 40%, or between about 40% to about 50%. Unless otherwise state, percent compositions herein refer to weight of the component per volume of the composition.

In certain embodiments, the matrix forming agent comprises monomers of Formula (M):

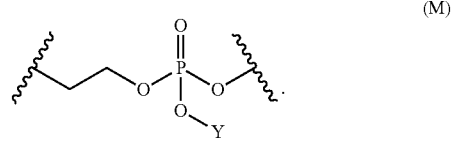

In certain embodiments, the matrix forming agent is a block copolymer of Formula (I):

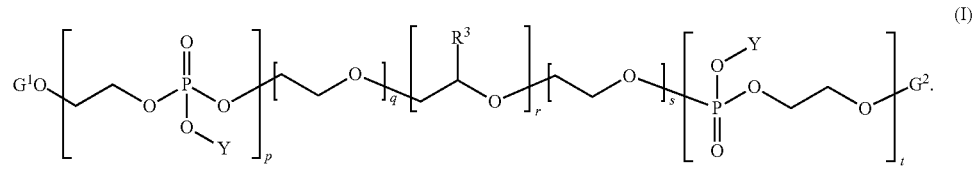

For Formulae (M) and (I):

each occurrence of Y is independently —$R^1$ or -$L^2R^2$;

each occurrence of $R^1$ is independently hydrogen, optionally substituted alkyl, optionally substituted alkenyl, optionally substituted alkynyl, optionally substituted aryl, or optionally substituted heteroaryl;

each occurrence of $L^2$ is independently a bond, optionally substituted alkylene, optionally substituted alkenylene, optionally substituted alkynylene, optionally substituted heteroalkylene, optionally substituted heteroalkenylene, or optionally substituted heteroalkynylene;

each occurrence of $R^2$ is independently optionally substituted acyl, optionally substituted carbocyclyl, optionally substituted heterocyclyl, optionally substituted aryl, optionally substituted heteroaryl, —$OR^b$, —$N(R^b)_2$, or an oxygen protecting group;

each occurrence of $R^3$ is independently optionally substituted alkyl, optionally substituted alkenyl, optionally substituted alkynyl, optionally substituted aryl, optionally substituted heteryaryl, optionally substituted acyl, —$OR^b$, or —$N(R^b)_2$;

each occurrence of $R^b$ is independently optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, an oxygen protecting group, or a nitrogen protecting group, or two $R^b$ taken together with the nitrogen to which they are attached form an optionally substituted heterocyclic or optionally substituted heteroaryl ring;

each of $G^1$ and $G^2$ is independently hydrogen, optionally substituted alkyl, optionally substituted aryl, or optionally substituted heteroaryl, optionally substituted acyl, optionally substituted phosphate, or an oxygen protecting group; and each of p, q, r, s, and t is independently an integer between 0 and 200, inclusive, wherein the sum of p and t is at least 1, and the sum of q, r, and s is at least 1.

In certain embodiments, the matrix forming agent comprises a block copolymer comprising poloxamer 407 (P407), or a similar analog, linked by its terminal hydroxyl groups to polyphosphoester (PPE) blocks (See FIG. 7). Hydrophobic PPE side chains may increase the hydrogel modulus, decrease erosion of the hydrogel in situ, enhance micelle packing during gelation, decrease the gelation temperature, or a combination thereof. The thermo-responsiveness and bioadhesion characteristics of the composition may be tuned by selection of side chains (e.g., alkyl side chains, acryl side chains).

In another aspect, provided herein are a matrix forming agent or a combination of matrix forming agents of Formula (I'):

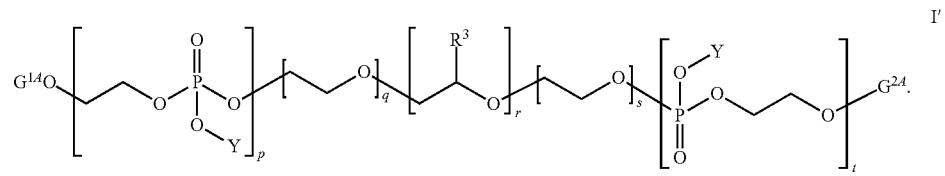

wherein each occurrence of Y is independently —$R^1$ or -$L^2R^2$;
- each occurrence of $R^1$ is independently hydrogen, optionally substituted alkyl, optionally substituted alkenyl, optionally substituted alkynyl, optionally substituted aryl, or optionally substituted heteroaryl;
- each occurrence of $L^2$ is independently a bond, optionally substituted alkylene, optionally substituted alkenylene, optionally substituted alkynylene, optionally substituted heteroalkylene, optionally substituted heteroalkenylene, or optionally substituted heteroalkynylene;
- each occurrence of $R^2$ is independently optionally substituted acyl, optionally substituted carbocyclyl, optionally substituted heterocyclyl, optionally substituted aryl, optionally substituted heteroaryl, —$OR^b$, —$N(R^b)_2$, or an oxygen protecting group;
- each occurrence of $R^{3A}$ is independently hydrogen, optionally substituted alkyl, optionally substituted alkenyl, optionally substituted alkynyl, optionally substituted aryl, optionally substituted heteryaryl, optionally substituted acyl, —$OR^b$, or —$N(R^b)_2$;
- each occurrence of $R^b$ is independently optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, an oxygen protecting group, or a nitrogen protecting group, or two $R^b$ taken together with the nitrogen to which they are attached form an optionally substituted heterocyclic or optionally substituted heteroaryl ring;
- each of $G^{1A}$ and $G^{2A}$ is independently hydrogen, halogen, optionally substituted amine, optionally substituted alkyl, optionally substituted aryl, or optionally substituted heteroaryl, optionally substituted acyl, optionally substituted phosphate, or an oxygen protecting group; and
- each of p, q, r, s, and t is independently an integer between 0 and 200, inclusive, wherein the sum of p and t is at least 1, and the sum of q, r, and s is at least 1.

In another aspect, provided herein are compositions comprising a a matrix forming agent or a combination of matrix forming agents of Formula (I'),

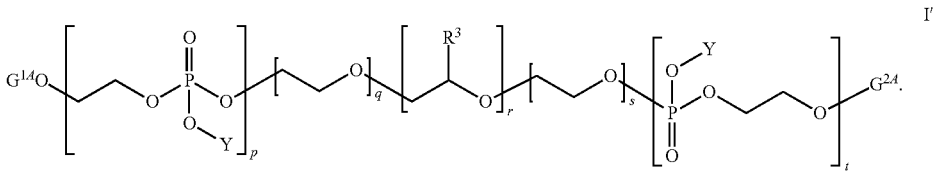

In another aspect, provided herein are methods for treating an infectious disease comprising administering a composition comprising a therapeutic agent, permeation enhancer, and a matrix forming agent, as described herein, to a subject in need thereof.

In another aspect, provided herein are methods for treating an ear disease comprising administering a composition comprising a therapeutic agent, permeation enhancer, and a matrix forming agent, as described herein, to a subject in need thereof. In certain embodiments, the composition is administered into the ear canal or to the tympanic membrane. In certain embodiments, the disease is otitis media. In certain embodiments, the disease is an ear infection. In certain embodiments, the disease is a bacterial infection (e.g., a *H. influenzae*, *S. pneumoniae*, or *M. catarhallis* infection).

In another aspect, provided herein are methods for eradicating a biofilm comprising administering to a subject in need thereof, or contacting a biofilm with, a composition described herein.

In another aspect, provided herein are methods for inhibiting the formation of a biofilm comprising administering to a subject in need thereof, or contacting a surface with, a composition described herein.

In an additional aspect, provided herein are methods for delivering a composition described herein, the method comprising administering into an ear canal of a subject the composition, wherein the composition contacts the surface of a tympanic membrane. The composition may be administered with an eye dropper, syringe, double barrel syringe, or catheter (e.g., angiocatheter).

In an additional aspect, the provided herein are kits comprising a container, a composition described herein, and instructions for administering the composition to a subject in need thereof. The kit may further comprise a device for administration of the composition to a subject, such as a dropper, syringe, catheter, double barrel syringe, or combination thereof.

The compositions, composition components (e.g., matrix forming agents, therapeutic agents, and permeation enhancers), methods, kits, and uses of the present disclosure may also incorporate any feature described in: Khoo et al., *Biomaterials.* (2013) 34, 1281-8; U.S. Pat. No. 8,822,410; U.S. patent application Ser. No. 12/993,358, filed May 19, 2009; U.S. patent application Ser. No. 11/734,537; filed Apr. 12, 2007; WIPO Patent Application No. PCT/US2009/003084, filed May 19, 2009, and WIPO Patent Application No. PCT/US2007/009121, filed Apr. 12 2007, each of which is incorporated herein by reference.

The details of certain embodiments of the invention are set forth in the Detailed Description of Certain Embodiments, as described below. Other features, objects, and advantages of the invention will be apparent from the Definitions, Examples, Figures, and Claims.

BRIEF DESCRIPTION OF THE DRAWINGS

The accompanying drawings, which constitute a part of this specification, illustrate several embodiments of the invention and together with the description, serve to explain the principles of the invention.

FIGS. 7A-7C. (7A) Syntheses of poloxamer-polyphosphoester block copolymers. (7B) Exemplary phosphoester pendant groups for modulating hydrophobicity. (7C) Exemplary phosphoester groups for enhancing bioadhesiveness.

FIG. 11. P407-PBP with n-butyl groups and DP of 5.

FIG. 13 (A), Gelation of aqueous solutions of 18%[P407] without CPE; FIG. 13 (B), 3CPE-18%[P407]; FIG. 13(C) 18%[P407-PBP], and FIG. 13 (D), 3CPE-18%[P407-PBP], as a function of temperature. Note: 3CPE=2% limonene, 1% SDS, and 0.5% bupivacaine. Data are means±SD, n=4.

FIG. 14(A) Effect of individual CPEs on gelation temperature. FIG. 15(B) Effect of individual CPEs on the storage and loss shear moduli of Cip-18%[P407-PBP] solutions at 37° C. FIG. 15(C) Effect of P407-PBP concentration on gelation temperature. All formulations contain 3CPE. FIG. 15 (D) Effect of P407-PBP concentration on storage and loss shear moduli at 37° C. (from the dotted line in FIG. 15(B). Data are means±SD, n=4.

FIG. 17 (A) Hematoxylin and eosin (H&E)-stained sections of TM cross-sections in healthy TMs and of TMs after 7 days of OM, without or after treatment with Cip-3CPE-12% [P407-PBP]. Scale bar represents 12 μm. FIG. 17 (B) H&E-stained cross-sections of the umbo-malleus region after 7 days of OM, without or after treatment with Cip-3CPE-12%[P407-PBP]. Scale bar represents 20 μm.

FIG. 18. In vivo efficacy, pharmacokinetics, impact on hearing sensitivity, and effect on tissue for Cip-3CPE-12% [P407-PBP]. FIG. 18(A) Percentage of animals with OM (defined as non-zero cfu values in their middle ear fluid aspirates) before (Day 0) and after receiving Cip-3CPE-12% [P407-PBP] (n=10), Cip-3CPE-18%[P407] (n=5), 1% ciprofloxacin ear drop (n=8), or no treatment (n=10). Day 0 reflects status immediately prior to administration of therapeutics. *p=0.0065 by Fisher's exact test. FIG. 18(B) The time course of bacterial colony forming units (cfu) from middle ear fluid from animals with OM from NTHi treated with Cip (n=4), Cip-3CPE-18%[P407] (n=5), Cip-3CPE-12%[P407-PBP] (n=10), or no treatment (n=10). Data are means±SD. (Log 10 cfu is set to zero instead of minus infinity for the purpose of this illustration.). FIG. 18(C) Concentration of ciprofloxacin over time in the middle ear fluid of the same animals as in (A). The black dotted line indicates the MIC for NTHi. Inset is magnified drug concentration range of 0-10 µg/mL. Data are means±SD. (D) Shifts in ABR thresholds in response to acoustic clicks and brief (8 ms) tone bursts of varied frequencies. All data here had the threshold median prior to the treatment subtracted from them. The red lines indicate the interquartile range of values prior to treatment (n=8). Measurements following application of 200 µL of Cip-3CPE-12%[P407-PBP] formulation are in black (n=8): Black boxes and the lines within indicate the interquartile ranges and medians respectively. Small black squares indicate the means, and crosses indicate the range.

FIG. 21(A). Permeation enhancement effect of individual CPEs. All curves show the cumulative amount of ciprofloxacin permeated across the TM over time. All solutions are made with 12% P407-PBP, 1% Ciprofloxacin, and 1% CPE except the group 'no CPE' which does not contain CPEs.

FIG. 22(A). Dose-response curves of SDS, LIM and BUP. The cumulative amount of ciprofloxacin that permeated across the TM after 48 hours increases with the concentration of the CPE in the formulation. All formulations were prepared with: 12% P407-PBP, 4% Ciprofloxacin, and corresponding concentrations (x-axis) of the individual CPEs. The colored dots demonstrate the permeation when two CPEs are added. For example, the red dot in the SDS plot represents the permeation when 1% BUP+1% SDS are added to the formulation, instead of 2% SDS. FIG. 22 (C). Permeation of ciprofloxacin (left) and dexamethasone (right) across the TM over time. 4% Cip-0.1% Dex=4% ciprofloxacin and 0.1% dexamethasone aqueous solution; 4% Cip-0.1% Dex-3CPE=4% ciprofloxacin, 0.1% dexamethasone, 1% SDS, 2% LIM, 0.5% BUP; 4% Cip-0.1% Dex-3CPE-18%[P407]=4% ciprofloxacin, 0.1% dexamethasone, 1% SDS, 2% LIM, 0.5% BUP, 18% P407.

FIG. 23(A). *Streptococcus pneumoniae* (SP) cure rate, showing change in percentage of infected ears over time, for 4% Ciproflaxin formulation with either Ciproflaxin-3CPE or Ciproflaxin-3CPE-12%[P407-PBP]. FIG. 23(B). Middle ear fluid (MEF) Ciproflaxin concentration over time for various concentrations of Ciproflaxin-3CPE-12%[P407-PBP] and 1% Ciproflaxin-3CPE.

DETAILED DESCRIPTION OF CERTAIN EMBODIMENTS

Figure 1:
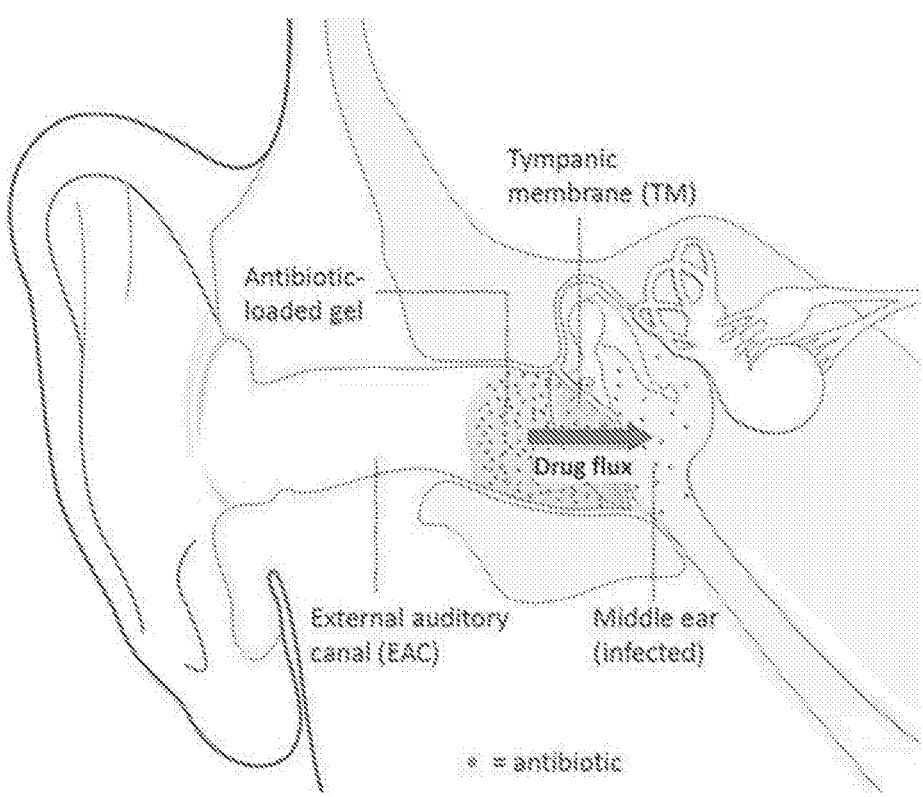
FIG. 1. Scheme for trans-tympanic antibiotic delivery.

Provided herein are compositions and methods for administering a therapeutic agent to a subject through a barrier. In some embodiments, the composition is for administering a therapeutic agent to the ear of a subject, and the barrier is a tympanic membrane. The compositions and methods provide for the efficient delivery of the agent to the middle and/or inner ear of the subject. In one aspect, the composition comprises a combination of a permeation enhancer, a therapeutic agent, and a matrix forming agent. The permeation enhancer increases the flux of the therapeutic agent across the barrier (e.g., tympanic membrane), compared to the flux for a composition lacking the permeation enhancer. In various aspects, the composition is a single application composition for localized, sustained delivery of a therapeutic agent across the tympanic membrane. In various aspects, the composition is a multiple application composition for localized, sustained delivery of a therapeutic agent across the tympanic membrane. The inventive compositions and methods are particularly useful in treating otitis media by providing sustained release and delivery of an antibiotic to the middle ear.

In one aspect, provided herein are compositions comprising:
  (a) a therapeutic agent or a combination of therapeutic agents;
  (b) a permeation enhancer or a combination of permeation enhancers, wherein the permeation enhancer or combination of permeation enhancers increases the flux of flux of the therapeutic agent or combination of therapeutic agents across a barrier; and
  (c) a matrix forming agent or a combination of matrix forming agents, wherein the matrix forming agent or combination of matrix forming agents comprises a polymer;
wherein:
  the composition forms a gel at temperatures above a phase transition temperature;
  the phase transition temperature is less than about 37° C.; and and at least one of conditions (i), (ii), and (iii) are met:
 (i) the phase transition temperature of the composition is less than the phase transition temperature of a reference composition plus about 5° C.;
 (ii) the storage modulus of the composition is greater than about 15% of the storage modulus of the reference composition at a temperature of about 37° C.; and
 (iii) the loss modulus of the composition is between about 80% and about 120% of the loss modulus of the reference composition at a temperature of about 37° C.;
wherein the reference composition is the composition in the absence of (b) the permeation enhancer or combination of permeation enhancers.

In another aspect, provided herein are compositions comprising:
 (a) a therapeutic agent or a combination of therapeutic agents;
 (b) a permeation enhancer or a combination of permeation enhancers, wherein the permeation enhancer or combination of permeation enhancers increases the flux of flux of the therapeutic agent or combination of therapeutic agents across a barrier; and
 (c) a matrix forming agent or a combination of matrix forming agents, wherein the matrix forming agent or combination of matrix forming agents comprises a polymer;
wherein:
 the composition forms a gel at temperatures above a phase transition temperature;
 the phase transition temperature is less than about 37° C.; and
 and at least one of conditions (i), (ii), and (iii) are met:
  (i) the phase transition temperature of the composition is less than the phase transition temperature of a reference composition plus about 5° C.;
  (ii) the storage modulus of the composition is greater than about 15% of the storage modulus of the reference composition or greater than about 500 Pa, whichever is smaller, at a temperature of about 37° C.; and
  (iii) the loss modulus of the composition is between about 15% and about 150% of the loss modulus of the reference composition at a temperature of about 37° C.;
wherein the reference composition is the composition in the absence of (b) the permeation enhancer or combination of permeation enhancers.

In certain embodiments, condition (i), the phase transition temperature of the composition is less than the phase transition temperature of the reference composition plus about 5° C., is met. In certain embodiments, condition (ii), the storage modulus of the composition is greater than about 15% of the storage modulus of the reference composition, is met. In certain embodiments, condition (ii), the storage modulus of the composition is greater than about 15% of the storage modulus of the reference composition, or 500 Pa, whichever is smaller, is met. In certain embodiments, condition (ii), the storage modulus of the composition is greater than about 15% of the storage modulus of the reference composition, or greater than about 1000 Pa, whichever is smaller, is met. In certain embodiments, condition (iii), the loss modulus of the composition is between about 80% and about 120% of the loss modulus of the reference composition, is met. In certain embodiments, condition (iii), the loss modulus of the composition is between about 15% and about 150% of the loss modulus of the reference composition, is met. In certain embodiments, both conditions (i) and (ii) are met. In certain embodiments, both conditions (ii) and (iii) are met. In certain embodiments, both conditions (i) and (iii) are met. In certain embodiments, each of conditions (i), (ii), and (iii) are met.

In certain embodiments, the therapeutic agent is a single therapeutic agent. In certain embodiments, the therapeutic agent is combination of two or more therapeutic agents (e.g., two, three, four). In certain embodiments, the permeation enhancer is a single therapeutic agent. In certain embodiments, the therapeutic agent is combination of two or more therapeutic agents (e.g., two, three, four). In certain embodiments, the matrix forming agent is a single matrix forming agent. In certain embodiments, the matrix forming agent is a combination of two or more matrix forming agents (e.g., two, three, four). In certain embodiments, a therapeutic agent or permeation enhancer may act as both a therapeutic agent and a permeation enhancer. In certain embodiments, a therapeutic agent may act as both a therapeutic agent and a permeation enhancer. In certain embodiments, a permeation enhancer may act as both a therapeutic agent and a permeation enhancer. In certain embodiments, a local anesthetic may act as both a therapeutic agent and a permeation enhancer. In certain embodiments, an amino amide or amino ester local anesthetic may act as both a therapeutic agent and a permeation enhancer. In certain embodiments, an amino amide or amino ester local anesthetic may act as both a therapeutic agent and a permeation enhancer. In certain embodiments, an amino ester local anesthetic may act as both a therapeutic agent and a permeation enhancer. In certain embodiments, bupivacaine may act as both a therapeutic agent and a permeation enhancer. In certain embodiments, tetracaine may act as both a therapeutic agent and a permeation enhancer.

In certain embodiments, the permeation enhancer or combination of permeation enhancers is present in an amount effective to increase the flux of the therapeutic agent across a barrier compared to the reference composition (e.g., the composition without the permeation enhancer). In certain embodiments, the permeation enhancer or combination of permeation enhancers is present in an amount effective to increase the flux of the therapeutic agent across a barrier compared to the reference composition (e.g., the composition without the permeation enhancer) by at least about 1.05 fold, at least about 1.10 fold, at least about 1.2 fold, at least about, at least about 1.3 fold, at least about 1.4 fold, at least about 1.5 fold, at least about 1.6 fold, at least about 1.7 fold, at least about 1.8 fold, or at least about 1.9 fold. In certain embodiments, the permeation enhancer or combination of permeation enhancers is present in an amount effective to increase the flux of the therapeutic agent across a barrier compared to a reference composition by at least about 2 fold, at least about 2.5 fold, at least about 3 fold, at least about 4 fold, at least about 5 fold, at least about 10 fold, at least about 25 fold, at least about 50 fold, at least about 100 fold, at least about 250 fold, at least about 500 fold, or at least about 1000 fold. In certain embodiments, the permeation enhancer or combination of permeation enhancers is present in an amount effective to increase the flux of the therapeutic agent across a barrier compared to a reference composition by between about 1.5 fold and about 100 fold.

In certain embodiments, the polymer is a copolymer. In some embodiments, the polymer is biodegradable. In certain embodiments, the copolymer is a block copolymer. In certain embodiments the copolymer comprises at least one block of hydrophobic monomers. In certain embodiments, the copolymer is biodegradable, or contains at least one biodegradable block.

As used herein "hydrophobic" refers to a polymer which tends to not dissolve in water and is fat soluble. As used herein "a high degree of hydrophobicity" refers to a polymer which has a low water water solubility and that has a high degree of fat solubility. In some embodiments, a hydrophobic polymer comprises hydrophobic side-chains. In some embodiments, a polymer with a high degree of hydrophobicity comprises hydrophobic side-chains. Hydrophobic side-chains include but are not limited to, side-chains comprising hydrocarbon radicals, such as alkyl (e.g., methyl), alkenyl, alkynyl, carbocyclyl and aryl. Hydrophobic moieties may also include groups selected from heteroalkyl, heteroalkenyl, heteroalkynyl, heterocyclyl, and heteroaryl, wherein the heteroatom containing group is substantially similar to a hydrocarbon group (e.g., only 1 or 2 carbons is replaced with a heteroatom). Hydrophobic side-chains may contain groups that are the same as or are derivatives of the side chains of hydrophobic amino acids, including but not limited to, glycine, alanine, valine, leucine, isoleucine, methionine, phenylalanine, amino isobutyric acid, alloisoleucine, tyrosine, and tryptophan. A non-hydrophobic or hydrophilic polymer is a polymer that tends to dissolve in water.

In certain embodiments, the polymer or copolymer comprises a vinylic polymer (e.g., PE, PVC, PVDC, PS), a polyacrylate (e.g., polyacrylic acid polymethacrylic acid), a polyether (e.g., PEO, PPO, POM), a fluoropolymer (e.g., PTFE), a polysiloxane (e.g., PDMS), a polysaccharide (e.g., cellulose, dextran, hyaluronic acid, chitosan), a polyester (e.g, PET, a polyhydroxyalkanoate (e.g., PHB)), a polyamide (e.g., poly(lactic acid), poly(glycolic acid)), a polyphosphoester, a polyurethane, or a polycarbonate, or copolymers of combinations thereof. In certain embodiments, the copolymer comprises a natural polymer. In some embodiments, the copolymer comprises a polysaccharide, proteoglycan, glycosaminoglycan, collagen, fibrin, gelatin, or a derivative thereof, or copolymers of combinations thereof.

Exemplary polymer types suitable for the polymer or copolymer include, but are not limited to: polyethers (e.g., polyethylene oxide, polypropylene oxide, polyethylene oxide-polypropylene oxide co-polymers), poloxamers, poloxamines, celluloses and hemicelluloses (e.g., methylcellulose, hydroxypropyl methylcellulose, ethyl(hydroxyethyl) cellulose, xlyoglucan), acetates, phthalates, latexes, polyacrylates (e.g., polyacrylica acid), N-alkylacrylamides (e.g., poly(N-isoproylacrylamide), hyaluronic acids, chitosan, dextran and gellan gum, and derivatives thereof. In some embodiments, the polymer or copolymer comprises polyethylene oxide or polypropylene oxide. In some embodiments, the copolymer comprises a polyethylene/polypropylene copolymer or polyethylene/polypropylene block copolymer. In some embodiments, the copolymer comprises a poloxamer. In some embodiments, the copolymer comprises poloxamer 407, poloxamer 188, poloxalene, poloxamer 124, poloxamer 237, or poloxamer 338. In some embodiments, the copolymer comprises poloxamer 407. In certain embodiments, the polymer or copolymer comprises phosphoester monomers. In certain embodiments, the copolymer comprises a poloxamer and phosphoester monomers.

Additional exemplary polymers suitable for the polymer or copolymer include aliphatic polyesters such as poly(lactic acid), poly(glycolic acid) and poly(lactic acid-co-glycolic acid); poly(trimethylene carbonate); polydioxanone and copolymers; poly(butylenes succinate) (such as polybutylene succinate/adipate copolymers, sold as BIONOLLE®, Showa Highpolymer Co. Ltd.) and poly(butylene adipate); polyanhydrides, such as poly(adipic anhydride) and poly (sebacic acid-co-1,3-bis(p-carboxyphenoxy) carboxyphenoxy) propane; poly(ortho ester)s; poly(ester amide)s, such as polymers based on 1,4-butanediol, adipic acid, and 1,6-aminohexanoic acid (BAK1095, Bayer AG, Leverkusen); poly(ester urethane)s; poly(ester anhydride)s; poly(ester carbonate)s, such as tyrosine-poly (alkylene oxide)-derived poly(ether carbonate)s; polyphosphazenes, polyarylates, such as tyrosine-derived polyacrylates; poly(ether ester)s, such as poly(butylene terephthalate)-poly(ethylene glycol) copolymers (PolyActiveo®), poly(c-caprolactone)-poly (ethylene glycol)) block copolymers and poly(ethylene oxide)-poly(hydroxy butyrate) block copolymers; polypropylfumerates; polyacetals; polyethers; biodegradable polycyanoacrylates; biodegradable polyurethanes; polyphosphoesters; poly(amide-enamines); polyamides; poly (amino acids); polycaprolactones; and polyhydroxyalkanoates.

In certain embodiments, the polymer or copolymer comprises poly (lactic acid) (PLA), poly (glycolic acid) (PGA), a copolymers of PLA and PGA, (e.g., poly (lactide-co-glycolide) (PLG)), poly (caprolactone) (PCL), poly (lactide-co-caprolactone) (PLC), or poly (glycolide-co-caprolactone) (PGC).

In certain embodiments, the copolymer is a block copolymer of formula A-B-A, wherein B is a hydrophobic block and each A is a non-hydrophobic blocks. In certain embodiments, the copolymer is a block copolymer of formula C-A-B-A-C, wherein each B or C is a hydrophobic blocks, and A are non-hydrophobic blocks. Polymers A-B-A and C-A-B-A-C may also comprise terminal groups attached to end block A or C. In certain embodiments, B and C are different polymers, In certain embodiments, B and C are the same polymer. In certain embodiments, each block A is a polymer of between 1 and 400 monomers. In certain embodiments, block A is a polymer of between 20 and 200 monomers. In certain embodiments each block B, is a polymer of between 1 and 400 monomers. In certain embodiments, block B is a polymer of between 20 and 200 monomers. In certain embodiments each block C, is a polymer of between 1 and 400 monomers. In certain embodiments, block C is a polymer of between 20 and 200 monomers. In certain embodiments, each block A comprises a single type of monomer. In certain embodiments, each block A comprises more than one type of monomer. In certain embodiments, each block B comprises a single type of monomer. In certain embodiments, each block B comprises more than one type of monomer. In certain embodiments, each block C comprises a single type of monomer. In certain embodiments, each block C comprises more than one type of monomer.

In certain embodiments, polymer A is a hydrophilic polyether (e.g., polyethylene oxide). In certain embodiments, polymer A is a hydrophilic polyester (e.g., polyglycolic acid). In certain embodiments, polymer B is a hydrophobic polyether (e.g., polypropylene oxide). In certain embodiments, polymer B is a hydrophobic polyester (e.g., polylactic acid). In certain embodiments, polymer B is a hydrophobic polyether (e.g., polypropylene oxide). In certain embodiments, polymer B is a hydrophobic polyester (e.g., polylactic acid). In certain embodiments, polymer C is a polyphosphoester.

The composition may be a liquid prior to warming above the phase transition temperature. In some embodiments, the phase transition temperature is at or below the body temperature of a subject (e.g., about 37° C.). Thus, the composition may form a gel when administered to a subject, e.g., when the composition contacts a biological surface. In some embodiments, the phase transition temperature is between about 0° C. and about 37° C., between about 10° C. and about 37° C., between about 15° C. and about 37° C., between about 20° C. and about 37° C., between about 25° C. between about 30° C. and about 37° C., between about 30° C. and about 35° C., or between about 35° C. and about 40° C. In some embodiments, the phase transition temperature is between about 20° C. and about 37° C. In some embodiments, the phase transition temperature is between about 0° C. and about 60° C., between about 10° C. and about 50° C., between about 20° C. and about 40° C., or between about 25° C. and about 35° C. In some embodiments, the phase transition temperature is between about 20° C. and 25° C., between about 25° C. and about 30° C., between about 30° C. and about 35° C., or between about 35° C. and about 40° C. In some embodiments, the phase transition temperature is between about 10° C. and about 50° C. In some embodiments, the phase transition temperature is between about 20° C. and about 40° C. In some embodiments, the phase transition temperature is between about 15° C. and about 40° C.

For any composition comprising a matrix forming agent, the phase transition temperature of the composition may change if an additive is added to the composition. The phase transition temperature of a composition with an additive versus a reference composition without the additive may be higher, lower, or the same depending on characteristics of the composition and the additive. The term reference composition as used herein, refers to a composition which contains the same components as the composition to which it is being compared, with the exception of a specified component (e.g., the permeation enhancer). Unless otherwise stated, the difference in % weight/volume from including or excluding the permeation enhancer is made up by a change in % weight/volume of the solvent (e.g., water). In certain embodiments, the reference composition comprises the therapeutic agent and the matrix forming agent, but not the permeation enhancer. In certain embodiments, the reference composition comprises the matrix forming agent, but not the therapeutic agent or the permeation enhancer. In certain embodiments, the reference composition comprises the permeation enhancer and the matrix forming agent, but not the therapeutic agent.

In certain embodiments, the phase transition temperature of the composition is greater than the phase transition temperature of the reference composition (e.g., the composition without the permeation enhancer). In certain embodiments, the phase transition temperature of the composition is less than the phase transition temperature of the reference composition (e.g., the composition without the permeation enhancer) plus about 5° C., 4° C., about 3° C., about 2° C., or about 1° C. In certain embodiments, the phase transition temperature of the composition is less than the phase transition temperature of the reference composition (e.g., the composition without the permeation enhancer) plus about 5° C. In certain embodiments, the phase transition temperature of the composition is less than the phase transition temperature of the reference composition (e.g., the composition without the permeation enhancer) plus about 37° C. In certain embodiments, the phase transition temperature of the composition is less than the phase transition temperature of the reference composition (e.g., the composition without the permeation enhancer) plus about 30° C., about 20° C., or about 10° C. In certain embodiments, the phase transition temperature of the composition is less than the phase transition temperature of the reference composition (e.g., the composition without the permeation enhancer).

In certain embodiments, the phase transition temperature of the composition is less than the phase transition temperature of the reference composition (e.g., the composition without the permeation enhancer) plus about 5° C., plus about 2° C., or plus about 1° C., and is higher than about 0° C., about 10° C., about 15° C., about 20° C., about 25° C., or about 30° C. In certain embodiments, the phase transition temperature of the composition is less than the phase transition temperature of the reference composition (e.g., the composition without the permeation enhancer) plus about 5° C., and is higher than about 20° C.

As a non-limiting example consider the following compositions. The phase transition temperature of a composition "A" comprising: (i) 1% ciprofloxacin and (ii) 18% poloxamer 407/polybutylphosphoester copolymer is about 33° C. For the corresponding composition "B" comprising the component of "A" and (iii) 1% sodium dodecyl sulfate, the phase transition temperature decreases to about 31° C. For the corresponding composition "C" comprising the components of "A" and (iii) 0.5% bupivacaine, the phase transition temperature remains about 33° C. Compositions "B" and "C" would both meet the criteria for the phase transition temperature of the composition with the permeation enhancer being less than, or slightly higher (e.g., <5° C.) than, the phase transition temperature of the composition without the permeation enhancer.

In certain embodiments, the composition is a gel at temperatures above the phase transition temperature and below about 60° C., below about 50° C., or below about 40° C. In certain embodiments, the composition is a gel at temperatures above the phase transition temperature and below about 50° C. In certain embodiments, the composition is a gel at temperatures between about 0° C. and about 60° C., between about 10° C. and about 50° C., between about 20° C. and about 40° C., or between about 25° C. and about 35° C. In some embodiments, the composition is a gel is at temperatures between about 20° C. and 25° C., between about 25° C. and about 30° C., between about 30° C. and about 35° C., or between about 35° C. and about 40° C. In some embodiments, the composition is a gel at temperatures between about 10° C. and about 50° C. In some embodiments, the composition is a gel at temperatures between about 20° C. and about 40° C. In some embodiments, the composition is a gel at temperatures between about 15° C. and about 40° C.

For any composition comprising a matrix forming agent, the storage modulus and loss modulus of the composition may change if an additive is added to the composition. The storage modulus of a composition with an additive versus the same composition without the additive may be higher, lower, or the same depending on characteristics of the composition and the additive. The loss modulus of a composition with an additive versus a reference composition without the additive may be higher, lower, or the same depending on characteristics of the composition and the additive. In certain embodiments, the reference composition comprises the therapeutic agent and the matrix forming agent, but not the permeation enhancer. In certain embodiments, the reference composition comprises the matrix forming agent, but not the therapeutic agent or the permeation enhancer. In certain embodiments, the reference composition comprises the permeation enhancer and the matrix forming agent, but not the therapeutic agent.

In certain embodiments, condition (ii), the storage modulus of the composition is greater than about 15% of the storage modulus of the reference composition, or greater than about 500 Pa, whichever is smaller, is met. In certain embodiments, condition (ii), the storage modulus of the composition is greater than about 15% of the storage modulus of the reference composition, or greater than about 1000 Pa, whichever is smaller, is met. In certain embodiments, the storage modulus of the composition is greater than about 15%, greater than about 30%, greater than about 50%, greater than about 60%, greater than about 70%, greater than about 80%, greater than about 90%, or greater than about 100% of the storage modulus of the reference composition (e.g., the composition without the permeation enhancer) at a given temperature. In certain embodiments, the storage modulus of the composition is greater than about 15% of the storage modulus of the reference composition (e.g., the composition without the permeation enhancer) at a given temperature. In certain embodiments, the storage modulus of the composition is greater than about 30% of the storage modulus of the reference composition (e.g., the composition without the permeation enhancer) at a given temperature. In certain embodiments, the storage modulus of the composition is greater than about 50% of the storage modulus of the reference composition (e.g., the composition without the permeation enhancer) at a given temperature. In certain embodiments, the storage modulus of the composition is greater than about 70% of the storage modulus of the reference composition (e.g., the composition without the permeation enhancer) at a given temperature. In certain embodiments, the storage modulus of the composition is greater than about 80% or about 90% of the storage modulus of the reference composition (e.g., the composition without the permeation enhancer) at a given temperature. In certain embodiments, the storage modulus of the composition is greater than about 100% of the storage modulus of the reference composition (e.g., the composition without the permeation enhancer) at a given temperature. In certain embodiments, the storage modulus of the composition is greater than about 110%, greater than about 120%, greater than about 130%, greater than about 140%, greater than about 150%, greater than about 175%, or greater than about 200% of the storage modulus of the reference composition (e.g., the composition without the permeation enhancer) at a given temperature. In certain embodiments, the storage modulus of the composition is less than about 200%, less than about 500%, or less than about 1000% of the storage modulus of the reference composition (e.g., the composition without the permeation enhancer) at a given temperature. In certain embodiments, the given temperature is about 37° C. In certain embodiments, the given temperature is a temperature between the phase transition temperature and about 37° C.

In certain embodiments, the loss modulus of the composition is less than about 200%, less than about 150%, less than about 125%, less than about 110%, or less than about 100% of the storage modulus of the reference composition (e.g., the composition without the permeation enhancer) at a given temperature. In certain embodiments, the loss modulus of the composition is greater than about 50%, less than about 75%, or greater than about 90% of the loss modulus of the reference composition (e.g., the composition without the permeation enhancer) at a given temperature. In certain embodiments, the loss modulus of the composition is between about 50%, and about 150%, between about 70%, and about 130%, between about 80%, and about 120%, or between about 90%, and about 110% of the loss modulus of the reference composition (e.g., the composition without the permeation enhancer) at a given temperature. In certain embodiments, the loss modulus of the composition is between about 80%, and about 120% of the loss modulus of the reference composition (e.g., the composition without the permeation enhancer) at a given temperature. In certain embodiments, condition (iii), the loss modulus of the composition is between about 15% and about 150% of the loss modulus of the reference composition at a temperature of about 37° C. In certain embodiments, the given temperature is about 37° C. In certain embodiments, the given temperature is a temperature between the phase transition temperature and about 37° C.

In certain embodiments, the composition comprises at least about 0.1% permeation enhancer. In certain embodiments, the composition comprises at least about 0.5% permeation enhancer. In certain embodiments, the composition comprises at least about 1% permeation enhancer. In certain embodiments, the composition comprises at least about 2% permeation enhancer. In certain embodiments, the composition comprises at least about 3% permeation enhancer. In certain embodiments, the composition comprises at least about 4% permeation enhancer. In certain embodiments, the composition comprises at least about 5% permeation enhancer. In certain embodiments, the composition comprises at least about 6%, at least about 7%, at least about 8%, at least about 9%, or at least about 10% permeation enhancer. In certain embodiments, the composition comprises at least about 0.5% weight per volume composition (wt/vol) permeation enhancer. In certain embodiments, the composition comprises at least about 1% wt/vol permeation enhancer. In certain embodiments, the composition comprises at least about 2% wt/vol permeation enhancer. In certain embodiments, the composition comprises at least about 3% wt/vol permeation enhancer. In certain embodiments, the composition comprises at least about 4% wt/vol permeation enhancer. In certain embodiments, the composition comprises at least about 5% permeation enhancer. In certain embodiments, the composition comprises at least about 6% wt/vol permeation enhancer. In certain embodiments, the composition comprises at least about 7% wt/vol permeation enhancer. In certain embodiments, the composition comprises at least about 8% wt/vol permeation enhancer, In certain embodiments, the composition comprises at between about 0.1% and about 1% permeation enhancer. In certain embodiments, the composition comprises at between about 0.5% and about 3% permeation enhancer. In certain embodiments, the composition comprises at between about 0.5% and about 10% permeation enhancer. In certain embodiments, the composition comprises at between about 2% and about 10% permeation enhancer.

In certain embodiments, the composition is applied to a surface of temperature equal to or above the phase transition temperature. In some embodiments, the surface is a biological surface. In certain embodiments, the surface is skin. In certain embodiments, the surface is a surface in the ear canal of a subject. In certain embodiments, the subject is a tympanic membrane. In certain embodiments, the surface is a surface in the respiratory tract of a subject (e.g., in the nasal cavity or buccal cavity). In certain embodiments, the surface is a surface in the mouth (e.g., surface of teeth or gums) of a subject. The composition may be administered to an interior body surface, for example, by intradermal or interdermal delivery or during a surgical procedure. In certain embodiments, the surface is an intradermal surface. In certain embodiments, the surface is the surface of an organ (e.g., heart, lung, spleen, pancreas, kidney, liver, stomach, intestine, bladder). In certain embodiments, the surface is connective tissue. In certain embodiments, the surface is muscle tissue (e.g., smooth muscle, skeletal muscle, cardiac muscle). In certain embodiments, the surface is nervous tissue (e.g., brain, spinal cord). In certain embodiments, the surface is epithelial tissue. In certain embodiments, the surface is a surface of the alimentary canal (e.g., colon, rectum). In certain embodiments, the surface is epithelial tissue. In certain embodiments, the surface is a surface of the reproductive tract (e.g., vagina, cervix). In certain embodiments, the surface is bone. In certain embodiments, the surface is vascular tissue. In certain embodiments, the surface is a wound bed. In certain embodiments, the surface is a biofilm. In certain embodiments, the surface is hair or fur. In certain embodiments, the surface is the surface of a medical implant.

Generally, for addition of a permeation enhancer a small change or no change in the phase transition temperature, storage modulus, or loss modulus is preferred. A small change is considered a phase transition temperature change of less than 5° C., or a modulus change of less than 10%. For changes in the phase transition temperature, a lower phase transition temperature for the composition with the permeation enhancer is preferred. A shift to a lower phase transition temperature may referred to as a 'left-shift' or 'L-shift' as opposed to a 'right-shift' or 'R-shift'. For changes in the storage modulus, a higher storage modulus for the composition with the permeation enhancer is preferred. For changes in the loss modulus, a lower loss modulus for the composition with the permeation enhancer is preferred.

In certain embodiments, the phase transition temperature of the composition is within about 5° C., within about 3° C., or within about 1° C. of the phase transition temperature of a reference composition, wherein the composition comprises permeation enhancer P1 and the reference composition does not comprise permeation enhancer P1. In certain embodiments, the storage modulus of the composition is within about 10%, within about 5%, or within about 2% ° C. of the storage modulus of a reference composition, wherein the composition comprises permeation enhancer P1 and the reference composition does not comprise permeation enhancer P1. In certain embodiments, the loss modulus of the composition is within about 10%, within about 5%, or within about 2% ° C. of the loss modulus of a reference composition, wherein the composition comprises permeation enhancer P1 and the reference composition does not comprise permeation enhancer P1. In certain embodiments, the phase transition temperature of the composition is within about 5° C., within about 3° C., or within about 1° C. of the phase transition temperature of a reference composition, and the storage modulus of the composition is within about 10%, within about 5%, or within about 2% ° C. of the storage modulus of the reference composition, wherein the composition comprises permeation enhancer P1 and the reference composition does not comprise permeation enhancer P1.

In certain embodiments, permeation enhancer P1 is a surfactant (anionic, cationic, nonionic, zwitterionic), terpene, anesthetic, amino amide, amino ester, azide-containing compound, or alcohol. In certain embodiments, permeation enhancer P1 is a surfactant (anionic, cationic, nonionic, zwitterionic), terpene, anesthetic, amino amide, amino ester, azide-containing compound, pyrrolidone, sulfoxide, fatty acid, or alcohol. In certain embodiments, permeation enhancer P1 is a surfactant (e.g., sodium dodecyl sulfate, ammonium lauryl sulfate, sodium lauryl sulfate, cetyl trimethylammonium bromide, cetylpyridinium chloride, benzethonium chloride, cocamidopropyl betaine, cetyl alcohol, oleyl alcohol, octyl glucoside, decyl maltoside, sodium octyl sulfate, sodium decyl sulfate, sodium tetradecyl sulfate, sodium heptadecyl sulfate, sodium eicosyl sulfate, nicotine sulfate, sodium taurocholic sulfate, dimethyl sulfoxide, sodium tridecyl phosphate; decyldimethyl ammonio propane sulfonate, chembetaine oleyl, myristyldimethyl ammonio propane sulfonate; benzyl pyridinium chloride, dodecyl pyridinium chloride, cetyl pyridinium chloride, benzyldimethyl dodecyl ammonium chloride, benzyldimethyl dodecyl ammonium chloride, benzyldimethyl myristyl ammonium chloride, benzyldimethyl stearyl ammonium chloride, octyltrimethylammonium bromide, dodecyltrimethylammonium bromide, Polysorbate 20, Polysorbate 40, Polysorbate 60, Polysorbate 80). In certain embodiments, permeation enhancer P1 is a terpene (e.g., limonene, cymene, pinene, camphor, menthol, comphone, phellandrine, sabinene, terpinene, borneol, cineole, geraniol, linalol, pipertone, terpineol, eugenol, eugenol acetate, safrole, benzyl benzoate, humulene, beta-caryophylene, eucakytol, hexanoic acid, octanoic acid, decanoic acid, undecanoic acid, dodecanoic acid, tridecanoic acid, myristic acid, palmitic acid, stearic acid, oleic acid, linoleic acid, linolenic acid, cholic acid; ethyl undecanoate, methyl laurate, methyl myristate, isopropyl myristate, isopropyl palmitate, palmityl palmitate, diethyl sebaccate, glyceryl monolaurate, glyceryl monooleate, ethylpiperazine carboxylate). In certain embodiments, permeation enhancer P1 is a terpene. In certain embodiments, the composition comprises between 0.5-6.0% terpene by weight. In certain embodiments, the composition comprises between 1.5-3.0% terpene by weight. In certain embodiments, the composition comprises between 1.5-2.0% terpene by weight. In certain embodiments, the composition comprises 2.0% terpene by weight. In certain embodiments, the composition comprises between 1.5-3.0% limonene by weight. In certain embodiments, the composition comprises between 1.5-2.0% limonene by weight. In certain embodiments, the composition comprises 2.0% limonene by weight. In certain embodiments, permeation enhancer P1 is an anesthetic (e.g., bupivacaine, tetracaine, procaine, proparacaine, propoxycaine, dimethocaine, cyclomethycaine, chloroprocaine, benzocaine, lidocaine, prilocaine, levobupivicaine, ropivacaine, dibucaine, articaine, carticaine, etidocaine, mepivacaine, piperocaine, trimecaine). In some embodiments, permeation enhancer P1 is bupivacaine. In some embodiments, permeation enhancer P1 is sodium dodecyl sulfate. In some embodiments, permeation enhancer P1 is limonene. In some embodiments, permeation enhancer P1 is a combination of at least two of a surfactant, terpene, and anesthetic. In some embodiments, permeation enhancer P1 is a combination of bupivacaine, sodium dodecyl sulfate, and limonene. In certain embodiments, permeation enhancer P1 is sodium lauroyl sarcosinate, sorbitan monooleate, octoxynol-9, diethyl sebacate, sodium polyacrylate (2500000 MW), or octyldodecanol.

In certain embodiments, the phase transition temperature of the composition is less than the phase transition temperature of a reference composition, wherein the composition comprises permeation enhancer P2 and the reference composition does not comprise permeation enhancer P2. In certain embodiments, the storage modulus of the composition is within about 10%, within about 5%, or within about 2% ° C. of the storage modulus of a reference composition, wherein the composition comprises permeation enhancer P2 and the reference composition does not comprise permeation enhancer P2. In certain embodiments, the storage modulus of the composition is within about 100%, within about 10%, within about 5%, or within about 2% ° C. of the storage modulus of a reference composition, wherein the composition comprises permeation enhancer P2 and the reference composition does not comprise permeation enhancer P2. In certain embodiments, the loss modulus of the composition is within about 10%, within about 5%, or within about 2% ° C. of the loss modulus of a reference composition, wherein the composition comprises permeation enhancer P2 and the reference composition does not comprise permeation enhancer P2. In certain embodiments, the phase transition temperature of the composition is less than the phase transition temperature of a reference composition, and the storage modulus of the composition is within about 10%, within about 5%, or within about 2% ° C. of the storage modulus of a reference composition, wherein the composition comprises permeation enhancer P2 and the reference composition does not comprise permeation enhancer P2.

In certain embodiments, permeation enhancer P2 is a surfactant (anionic, cationic, nonionic, zwitterionic), terpene, anesthetic, amino amide, amino ester, azide-containing compound, or alcohol. In certain embodiments, permeation enhancer P2 is a surfactant (anionic, cationic, nonionic, zwitterionic), terpene, anesthetic, amino amide, amino ester, azide-containing compound, pyrrolidone, sulfoxide, fatty acid, or alcohol. In certain embodiments, permeation enhancer P2 is a surfactant (e.g., sodium dodecyl sulfate, ammonium lauryl sulfate, sodium lauryl sulfate, cetyl trimethylammonium bromide, cetylpyridinium chloride, benzethonium chloride, cocamidopropyl betaine, cetyl alcohol, oleyl alcohol, octyl glucoside, decyl maltoside, sodium octyl sulfate, sodium decyl sulfate, sodium tetradecyl sulfate, sodium heptadecyl sulfate, sodium eicosyl sulfate, nicotine sulfate, sodium taurocholic sulfate, dimethyl sulfoxide, sodium tridecyl phosphate; decyldimethyl ammonio propane sulfonate, chembetaine oleyl, myristyldimethyl ammonio propane sulfonate; benzyl pyridinium chloride, dodecyl pyridinium chloride, cetyl pyridinium chloride, benzyldimethyl dodecyl ammonium chloride, benzyldimethyl dodecyl ammonium chloride, benzyldimethyl myristyl ammonium chloride, benzyldimethyl stearyl ammonium chloride, octyltrimethylammonium bromide, dodecyltrimethylammonium bromide, Polysorbate 20, Polysorbate 40, Polysorbate 60, Polysorbate 80). In certain embodiments, permeation enhancer P2 is a terpene (e.g., limonene, cymene, pinene, camphor, menthol, comphone, phellandrine, sabinene, terpinene, borneol, cineole, geraniol, linalol, pipertone, terpineol, eugenol, eugenol acetate, safrole, benzyl benzoate, humulene, beta-caryophylene, eucakytol, hexanoic acid, octanoic acid, decanoic acid, undecanoic acid, dodecanoic acid, tridecanoic acid, myristic acid, palmitic acid, stearic acid, oleic acid, linoleic acid, linolenic acid, cholic acid; ethyl undecanoate, methyl laurate, methyl myristate, isopropyl myristate, isopropyl palmitate, palmityl palmitate, diethyl sebaccate, glyceryl monolaurate, glyceryl monooleate, ethylpiperazine carboxylate). In certain embodiments, permeation enhancer P2 is a terpene. In certain embodiments, the composition comprises between 0.5-6.0% terpene by weight. In certain embodiments, the composition comprises between 1.5-3.0% terpene by weight. In certain embodiments, the composition comprises between 1.5-2.0% terpene by weight. In certain embodiments, the composition comprises 2.0% terpene by weight. In certain embodiments, the composition comprises between 1.5-3.0% limonene by weight. In certain embodiments, the composition comprises between 1.5-2.0% limonene by weight. In certain embodiments, the composition comprises 2.0% limonene by weight. In certain embodiments, permeation enhancer P2 is an anesthetic (e.g., bupivacaine, tetracaine, procaine, proparacaine, propoxycaine, dimethocaine, cyclomethycaine, chloroprocaine, benzocaine, lidocaine, prilocaine, levobupivicaine, ropivacaine, dibucaine, articaine, carticaine, etidocaine, mepivacaine, piperocaine, trimecaine). In some embodiments, permeation enhancer P2 is bupivacaine. In some embodiments, permeation enhancer P2 is sodium dodecyl sulfate. In some embodiments, permeation enhancer P2 is limonene. In some embodiments, permeation enhancer P2 is a combination of at least two of a surfactant, terpene, and anesthetic. In some embodiments, permeation enhancer P2 is a combination of bupivacaine, sodium dodecyl sulfate, and limonene. In certain embodiments, permeation enhancer P2 is sodium lauroyl sarcosinate, sorbitan monooleate, octoxynol-9, diethyl sebacate, sodium polyacrylate (2500000 MW), or octyldodecanol.

In certain embodiments, the phase transition temperature of the composition is less than the phase transition temperature of a reference composition, wherein the composition comprises permeation enhancer P3 and the reference composition does not comprise permeation enhancer P3. In certain embodiments, the storage modulus of the composition is greater than the storage modulus of a reference composition, wherein the composition comprises permeation enhancer P3 and the reference composition does not comprise permeation enhancer P3. In certain embodiments, the loss modulus of the composition is greater than the loss modulus of a reference composition, wherein the composition comprises permeation enhancer P3 and the reference composition does not comprise permeation enhancer P3. In certain embodiments, the phase transition temperature of the composition is less than the phase transition temperature of a reference composition, and the storage modulus of the composition is greater than the storage modulus of a reference composition, wherein the composition comprises permeation enhancer P3 and the reference composition does not comprise permeation enhancer P3.

In certain embodiments, permeation enhancer P3 is a surfactant (anionic, cationic, nonionic, zwitterionic), terpene, anesthetic, amino amide, amino ester, azide-containing compound, or alcohol. In certain embodiments, permeation enhancer P3 is a surfactant (anionic, cationic, nonionic, zwitterionic), terpene, anesthetic, amino amide, amino ester, azide-containing compound, pyrrolidone, sulfoxide, fatty acid, or alcohol. In certain embodiments, permeation enhancer P3 is a surfactant (e.g., sodium dodecyl sulfate, ammonium lauryl sulfate, sodium lauryl sulfate, cetyl trimethylammonium bromide, cetylpyridinium chloride, benzethonium chloride, cocamidopropyl betaine, cetyl alcohol, oleyl alcohol, octyl glucoside, decyl maltoside, sodium octyl sulfate, sodium decyl sulfate, sodium tetradecyl sulfate, sodium heptadecyl sulfate, sodium eicosyl sulfate, nicotine sulfate, sodium taurocholic sulfate, dimethyl sulfoxide, sodium tridecyl phosphate; decyldimethyl ammonio propane sulfonate, chembetaine oleyl, myristyldimethyl ammonio propane sulfonate; benzyl pyridinium chloride, dodecyl pyridinium chloride, cetyl pyridinium chloride, benzyldimethyl dodecyl ammonium chloride, benzyldimethyl dodecyl ammonium chloride, benzyldimethyl myristyl ammonium chloride, benzyldimethyl stearyl ammonium chloride, octyltrimethylammonium bromide, dodecyltrimethylammonium bromide, Polysorbate 20, Polysorbate 40, Polysorbate 60, Polysorbate 80). In certain embodiments, permeation enhancer P3 is a terpene (e.g., limonene, cymene, pinene, camphor, menthol, comphone, phellandrine, sabinene, terpinene, borneol, cineole, geraniol, linalol, pipertone, terpineol, eugenol, eugenol acetate, safrole, benzyl benzoate, humulene, beta-caryophylene, eucakytol, hexanoic acid, octanoic acid, decanoic acid, undecanoic acid, dodecanoic acid, tridecanoic acid, myristic acid, palmitic acid, stearic acid, oleic acid, linoleic acid, linolenic acid, cholic acid; ethyl undecanoate, methyl laurate, methyl myristate, isopropyl myristate, isopropyl palmitate, palmityl palmitate, diethyl sebaccate, glyceryl monolaurate, glyceryl monooleate, ethylpiperazine carboxylate). In certain embodiments, permeation enhancer P3 is a terpene. In certain embodiments, the composition comprises between 0.5-6.0% terpene by weight. In certain embodiments, the composition comprises between 1.5-3.0% terpene by weight. In certain embodiments, the composition comprises between 1.5-2.0% terpene by weight. In certain embodiments, the composition comprises 2.0% terpene by weight. In certain embodiments, the composition comprises between 1.5-3.0% limonene by weight. In certain embodiments, the composition comprises between 1.5-2.0% limonene by weight. In certain embodiments, the composition comprises 2.0% limonene by weight. In certain embodiments, permeation enhancer P3 is an anesthetic (e.g., bupivacaine, tetracaine, procaine, proparacaine, propoxycaine, dimethocaine, cyclomethycaine, chloroprocaine, benzocaine, lidocaine, prilocaine, levobupivicaine, ropivacaine, dibucaine, articaine, carticaine, etidocaine, mepivacaine, piperocaine, trimecaine). In some embodiments, permeation enhancer P3 is bupivacaine. In some embodiments, permeation enhancer P3 is sodium dodecyl sulfate. In some embodiments, permeation enhancer P3 is limonene. In some embodiments, permeation enhancer P3 is a combination of at least two of a surfactant, terpene, and anesthetic. In some embodiments, permeation enhancer P3 is a combination of bupivacaine, sodium dodecyl sulfate, and limonene. In certain embodiments, permeation enhancer P3 is sodium lauroyl sarcosinate, sorbitan monooleate, octoxynol-9, diethyl sebacate, sodium polyacrylate (2500000 MW), or octyldodecanol.

In certain embodiments, the composition is useful in treating a disease. In some embodiments, the composition is useful in treating an infectious disease. In some embodiments, the composition is useful in treating an ear disease (e.g., the barrier is the tympanic membrane). In some embodiments, the composition is useful in treating otitis media.

As described, the gelation temperature (phase transition temperature) of the composition is one factor in determining whether the suitability of the composition (e.g., to allow for sustained delivery to the tympanic membrane). The temperature at which the storage modulus exceeds the loss modulus is considered the gelation temperature. Compositions herein may have a gelation temperature lower or higher than 37° C., but preferably lower than 37° C. to accelerate gelation right after administration upon exposure of the composition, in particular the matrix forming agent, to body heat.

The timing of the sol-gel transition will impact the ease of administration. In general a faster in situ transition is useful for administration to subjects (e.g., children resisting compliance). In certain embodiments, the composition gels within about 5 s, about 10 s, about 20 s, about 30 s, about 1 minute, about 5 minutes, or about 10 minutes of administration (e.g., to the ear canal). In some embodiments, the composition gels in the range of about 1 s to about 20 s after administration.

In certain embodiments, the composition is stored cold (e.g., refrigerated at about 5° C.) prior to administration. Cold storage may be useful for compositions with gelation temperatures below room temperature to prevent gelation prior to administration or during handling.

In one aspect, provided herein are compositions comprising:
(a) a therapeutic agent or a combination of therapeutic agents;
(b) a permeation enhancer or a combination of permeation enhancers, wherein the permeation enhancer or combination of permeation enhancers increases the flux of the therapeutic agent or combination of therapeutic agents across a barrier; and
(c) a matrix forming agent or a combination of matrix forming agents, wherein the matrix forming agent or combination of matrix forming agents comprises a block copolymer containing hydrophobic monomers (e.g., phosphoester monomers);
wherein:
the composition forms a gel at temperatures above a phase transition temperature; and
the phase transition temperature is less than about 37° C.;
and at least one of conditions (i), (ii), and (iii) are met:
(i) the phase transition temperature of the composition is less than the phase transition temperature of a reference composition plus about 5° C.;
(ii) the storage modulus of the composition is greater than about 70% of the storage modulus of the reference composition at a temperature of about 37° C.; and
(iii) the loss modulus of the composition is between about 80% and about 120% of the loss modulus of the reference composition at a temperature of about 37° C.;
wherein the reference composition is the composition in the absence of the permeation enhancer or combination of permeation enhancers.

In one aspect, provided herein are compositions comprising:
(a) a therapeutic agent or a combination of therapeutic agents;
(b) a permeation enhancer or a combination of permeation enhancers, wherein the permeation enhancer or combination of permeation enhancers increases the flux of the therapeutic agent or combination of therapeutic agents across a barrier; and
(c) a matrix forming agent or a combination of matrix forming agents, wherein the matrix forming agent or combination of matrix forming agents comprises a block copolymer containing hydrophobic monomers (e.g., phosphoester monomers);
wherein:
the composition forms a gel at temperatures above a phase transition temperature; and
the phase transition temperature is less than about 37° C.;
and at least one of conditions (i), (ii), and (iii) are met:
(i) the phase transition temperature of the composition is less than the phase transition temperature of a reference composition plus about 5° C.;
(ii) the storage modulus of the composition is greater than about 70% of the storage modulus of the reference composition at a temperature of about 37° C.; and
(iii) the loss modulus of the composition is between about 15% and about 150% of the loss modulus of the reference composition at a temperature of about 37° C.;
wherein the reference composition is the composition in the absence of the permeation enhancer or combination of permeation enhancers.

In another aspect, provided herein are compositions for treating an infectious disease comprising:
(a) a therapeutic agent or a combination of therapeutic agents;

(b) a permeation enhancer or a combination of permeation enhancers, wherein the permeation enhancer or combination of permeation enhancers increases the flux of the therapeutic agent or combination of therapeutic agents across a barrier; and (c) a matrix forming agent or a combination of matrix forming agents, wherein the matrix forming agent or combination of matrix forming agents comprises a copolymer comprising phosphoester monomers.

In another aspect, provided herein are compositions for treating an ear disease comprising:

(a) a therapeutic agent or a combination of therapeutic agents;

(b) a permeation enhancer or a combination of permeation enhancers, wherein the permeation enhancer or combination of permeation enhancers increases the flux of the therapeutic agent or combination of therapeutic agents across the tympanic membrane; and (c) a matrix forming agent or a combination of matrix forming agents, wherein the matrix forming agent or combination of matrix forming agents comprises a copolymer comprising phosphoester monomers.

In another aspect, provided herein are compositions comprising:

(a) a diagnostic agent or a combination of diagnostic agents;

(b) a permeation enhancer or a combination of permeation enhancers, wherein the permeation enhancer or combination of permeation enhancers increases the flux of the therapeutic agent or combination of therapeutic agents across the tympanic membrane; and (c) a matrix forming agent or a combination of matrix forming agents, wherein the matrix forming agent or combination of matrix forming agents comprises a copolymer comprising phosphoester monomers.

In another aspect, provided herein are compositions for treating an infectious disease comprising:

(a) a therapeutic agent or a combination of therapeutic agents;

(b) a permeation enhancer or a combination of permeation enhancers, wherein the permeation enhancer or combination of permeation enhancers increases the flux of the therapeutic agent or combination of therapeutic agents across a barrier; and (c) a matrix forming agent or a combination of matrix forming agents, wherein the matrix forming agent comprises a polysaccharide derivative comprising cross-linkable functional groups.

In another aspect, provided herein are compositions for treating an ear disease comprising:

(a) a therapeutic agent or a combination of therapeutic agents;

(b) a permeation enhancer or a combination of permeation enhancers, wherein the permeation enhancer or combination of permeation enhancers increases the flux of the therapeutic agent or combination of therapeutic agents across the tympanic membrane; and (c) a matrix forming agent or a combination of matrix forming agents, wherein the matrix forming agent comprises a polysaccharide derivative comprising cross-linkable functional groups.

The compositions provided herein typically include a permeation enhancer (e.g., a surfactant, terpene), a therapeutic agent (e.g., an antibiotic), and a matrix forming agent (e.g., a poloxamer derivative, a polyphosphoester containing polymer, a polysaccharide derivative). The permeation enhancer is an agent that alters the stratum corneum of the tympanic membrane to increase the flux of the therapeutic agent across the tympanic membrane. The permeation enhancer facilitates delivery of the therapeutic agent into the middle and/or inner ear. Therapeutic agents include agents that have a therapeutic benefit in the ear. In certain embodiments, the matrix forming agent is a liquid at ambient conditions, which once administered to a subject, gels (e.g., becomes more viscous). In certain embodiments, the matrix forming agents gels upon mixing of two components of the composition. In some embodiments, each component comprises a matrix forming agent (e.g., two polysaccharide derivatives which undergo cross-linking upon mixing). In some embodiments, one component comprises the matrix forming agent, and the second component comprises an activator or catalyst which causes gelation when mixed with the matrix forming agent. In certain embodiments, the pharmaceutical composition does not substantially interfere with the hearing of the subject.

Matrix Forming Agents

The matrix forming agent is a compound or mixture of compounds that forms a gel after administration. In certain embodiments, the matrix forming agent forms a gel after administration into a subject's ear canal. The gel composition acts a reservoir containing the therapeutic agent and permeation enhancer, allowing for sustained release of the therapeutic agent across a barrier (e.g., tympanic membrane). In certain embodiments, the gel maintains contact with the tympanic membrane. In some embodiments, the gel maintains contact for between 0.5 and 1 hours, between 1 and 4 hours, between 1 and 8 hours, between 1 and 16 hours, or between 1 and 24 hours. In some embodiments, the gel maintains contact for between 1 day and 3 days, between 1 and 7 days, or between 1 and 14 days. In some embodiments, the gel allows flux of the therapeutic agent across the tympanic membrane for between 0.5 and 1 hours, between 1 and 4 hours, between 1 and 8 hours, between 1 and 16 hours, or between 1 and 24 hours. In some embodiments, the gel maintains contact for between 1 day and 3 days, between 1 and 7 days, or between 1 and 14 days. Such a reservoir maintains contact with the tympanic membrane increasing the time for the therapeutic agent to cross the tympanic membrane and be delivered to the middle or inner ear. Such a reservoir maximizes exposure of the tympanic membrane to permeation enhancers and the therapeutic agent, and facilitates sustained flux of the therapeutic agent into the middle and inner ear.

In various embodiments, the composition is a sustained release formulation. In various aspects, sustained release of either the permeation enhancer and/or the therapeutic agent can be at a constant rate to deliver an effective amount of either the permeation enhancer or therapeutic agent to the surface of the tympanic membrane, the middle ear, or the inner ear. In various embodiments, the sustained release provides a sufficient flux of therapeutic agent over about 1 day, about 2 days, about 3 days, about 4 days, about 5 days, about 6 days, or about 7 days. In various embodiments, the sustained release provides a sufficient flux of therapeutic agent over a range of about 7 to about 10 days. In various embodiments, the sustained release may be at a constant rate over a range of about 7 days to about 14 days. In various embodiments, the sustained release provides a sufficient flux of therapeutic agent over a range of about 14 to about 21 days. In various embodiments, the sustained release provides a sufficient flux of therapeutic agent over a range of about 21 to about 30 days. As used herein, sufficient flux is the flux necessary for the therapeutic agent to be present in the middle ear in a therapeutically effective amount or prophylactically effective amount. In some embodiments, the sufficient flux is sufficient to provide an antibiotic agent in a concentration equal or greater to the minimum inhibitory concentration of an infectious microorganism. In some embodiments, the infectious microorganism is *H. influenza, S. pneumoniae*, or *M. catarrhalis*.

In various aspects, the sustained release profile is obtained by the addition of a matrix-forming agent to the composition. In various embodiments, the composition may further comprise a matrix forming agent. In various embodiments, the matrix forming agents may undergo a change in viscosity, in situ, based on a phase change, a change in solubility, evaporation of a solvent, or mixing of components comprising the matrix forming agent. Such matrix forming agents gel, in situ after administration into a patient's ear canal to form a reservoir containing the therapeutic agent and permeation enhancer, allowing sustained release of the therapeutic agent. Such a reservoir maintains contact with the tympanic membrane increasing the time for the therapeutic agent to permeate the tympanic membrane, and be delivered to the middle or inner ear. Such a reservoir maximizes exposure of the tympanic membrane to permeation enhancers and the therapeutic agent.

In certain embodiments, the matrix forming agent is a hydrogel, or forms a hydrogel upon administration. Matrix forming agents may include, but are not limited to, polyelectrolyte complexes, thermo-responsive gelling agents, pre-polymers, alginates, un-crosslinked polymers, and monomers, thermo-responsive gelling agents (e.g., poloxamer-polyphosphoester copolymers), and polymers with cross-linkable functional groups. In certain embodiments, the matrix forming agent is separated into a first and second component which form a matrix or gel upon mixing. In some embodiments, a first matrix forming agent component is a first polymer comprising a first type of cross-linkable functional group, and a second matrix forming agent component is a second polymer comprising a second type of cross-linkable functional group, wherein the two types of cross-linkable functional groups form cross-links between the two polymers upon mixing of the first and second component. In some embodiments, a first matrix forming agent component comprises polymers with cross-linkable functional groups, and a second matrix forming agent component comprises an activator, wherein the cross-linkable functional groups form cross-links between the polymers upon mixing of the first and second component. In some embodiments, the activator is an acid, a base, or a catalyst.

Matrix forming agents may further include biocompatible agents. Matrix forming agents may further include biodegradable agents. In certain embodiments the matrix forming agent is degraded and extruded from the body of a patient within 3 days of application, within 7 days of application, with 10 days of application, or within 14 days of application. In various embodiments, the matrix forming agent has little or no effect on hearing threshold when applied into a subject's ear canal. In various aspects, the matrix-forming agents may comprise between about 0 to about 40 percent of the composition. In various embodiments, the matrix-forming agents may comprise between about 0 to about 10 percent of the composition, comprise between about 10 to about 20 percent of the composition, comprise between about 20 to about 30 percent of the composition, comprise between about 30 to about 40 percent of the composition, or comprise between about 40 to about 50 percent of the composition.

The polymer may be a block copolymer. Exemplary polymer types suitable for the block copolymer include, but are not limited to: polyethylene oxide/polypropylene oxide based systems, poloxamers, poloxamer 407, poloxamer 188, poloxamines, methylcellulose, hydroxypropyl methylcellulose, ethyl(hydroxyethyl) cellulose, xyloglucan, cellulose, acetate phthalate, latex, poly(acrylic acid), thermoresponsive polysaccharides (including cellulose derivatives, chitosan, dextran and gellan gum). In some embodiments, the matrix forming agent comprises a polyethylene/polypropylene copolymer or polyethylene/polypropylene block copolymer. In some embodiments, the matrix forming agent comprises a poloxamer. In some embodiments, the matrix forming agent comprises poloxamer 407, poloxamer 188, poloxalene, poloxamer 124, poloxamer 237, or poloxamer 338.

Exemplary poloxamers include, but are not limited to: poloxamer 407, poloxamer 188, poloxalene, poloxamer 124, poloxamer 237, or poloxamer 338, Pluronic® 10R5, Pluronic® 17R2, Pluronic® 17R4, Pluronic® 25R2, Pluronic® 25R4, Pluronic® 31R1, Pluronic® F 108 Cast Solid Surfactant, Pluronic® F 108 NF, Pluronic® F 108 Pastille, Pluronic® F 108NF Prill Poloxamer 338, Pluronic® F 127 NF, Pluronic® F 127 NF 500 BHT Prill, Pluronic® F 127 NF Prill Poloxamer 407, Pluronic® F 38, Pluronic® F 38 Pastille, Pluronic® F 68, Pluronic® F 68 LF Pastille, Pluronic® F 68 NF, Pluronic® F 68 NF Prill Poloxamer 188, Pluronic® F 68 Pastille, Pluronic® F 77, Pluronic® F 77 Micropastille, Pluronic® F 87, Pluronic® F 87 NF, Pluronic® F 87 NF Prill Poloxamer 237, Pluronic® F 88, Pluronic® F 88 Pastille, Pluronic® FT L 61, Pluronic® L 10, Pluronic® L 101, Pluronic® L 121, Pluronic® L 31, Pluronic® L 35, Pluronic® L 43, Pluronic® L 61, Pluronic® L 62, Pluronic® L 62 LF, Pluronic® L 62D, Pluronic® L 64, Pluronic® L 81, Pluronic® L 92, Pluronic® L44 NF INH surfactant Poloxamer 124, Pluronic® N 3, Pluronic® P 103, Pluronic® P 104, Pluronic® P 105, Pluronic® P 123 Surfactant, Pluronic® P 65, Pluronic® P 84, Pluronic® P 85, Synperonic® PE/F 108, Synperonic® PE/P105, Synperonic® PE/P84, Synperonic®, Synperonic® PE/L31, Synperonic® PE/L61, Synperonic® PE/L101, Synperonic® PE/L121, Synperonic® PE/L42, Synperonic® PE/L62, Synperonic® PE/L92, Synperonic® PE/L44, Synperonic® PE/L64, Synperonic® PE/P84, Synperonic® PE/P75, Synperonic® PE/P103, Synperonic® PE/F87, Synperonic® PE/F127, Synperonic® PE/F38, Synperonic® PE/F68, Kolliphor® P 188, Kolliphor® P 407, Kolliphor® P 188 micro, Kolliphor® P 407 micro, Kolliphor® P237, Kolliphor® P 338, Kolliphor® EL, Kolliphor® HS 15, Kolliphor® PS 80, Kolliphor® PS 60, Kolliphor® RH 40, Kolliphor® TPG S, Kolliphor® CS L, Kolliphor® CS A, Kolliphor® CS S, Kolliphor® CS B, Kolliphor® CS 20, and Kolliphor® CS 12. In some embodiments, the matrix forming agent comprises any of the foregoing poloxamers, a derivative thereof, or a block copolymer thereof.

In various embodiments, of the present inventions the polyelectrolyte complex may include, but is not limited to a, chitosan-chondroitin sulfate complex, gelatin, carboxymethylcellulose, glycosaminoglycans and poly (vinyl alcohol). In various aspects, the relative ratios of chitosan to chondroitin sulfate may be between about 1:0.09 to about 1:1.4. In certain embodiments, the polyelectrolyte complex is a chitosan-chondroitin sulfate complex.

In certain embodiments, the percent weight of matrix forming agent in the composition is between about 1% to about 10%, between about 10% to about 20%, between about 20% to about 30%, between about 30% to about 40%, between about 40% to about 50%, or between about 50% to about 90%. In some embodiments, the percent weight of matrix forming agent in the composition is between 1% to about 10%. In some embodiments, the percent weight of matrix forming agent in the composition is between about 10% to about 20%. In some embodiments, the percent weight of matrix forming agent in the composition is between 20% to about 30%.

Polymers Comprising Polyphosphoester Monomers or Blocks

In certain embodiments, the matrix forming comprises a copolymer with phosphoester monomers. The copolymer comprises at least one phosphoester monomer and at least one non-phosphoester monomer. In some embodiments, the copolymer comprises a polyphosphoester block. In some embodiments, the copolymer comprises a polyphosphoester block and a non-polyphosphoester block. In some embodiments, the block copolymer comprises a polyphosphoester block, and another blocks selected from the group consisting of polyethylene oxide, polypropylene oxide, poloxamers, poloxamer 407, poloxamer 188, poloxamines, methylcellulose, hydroxypropyl methylcellulose, ethyl(hydroxyethyl) cellulose, xyloglucan, acetates, phthalates, latex, poly (acrylic acid), N-isopropylacrylamides, cellulose, chitosan, dextran, hyaluronic acid, and derivatives thereof. In some embodiments, the polymer comprises thermoresponsive polysaccharides (e.g., cellulose derivatives, chitosan, dextran and gellan gum). In some embodiments, the block copolymer comprises polyphosphoester blocks, and comprises a polyethylene/polypropylene copolymer or polyethylene/polypropylene block copolymer. In some embodiments, the block copolymer comprises polyphosphoester blocks, and comprises a poloxamer. In some embodiments, the composition has a high degree of hydrophobicity. In some embodiments, the block copolymer has a high degree of hydrophobicity. In some embodiments, the composition is optically transparent. In some embodiments, the block copolymer comprises polyphosphoester blocks, and comprises poloxamer 407. In some embodiments, each block contains between 1 and 200 monomers.

In certain embodiments, the polyphosphoester copolymer or polyphosphoester blocks comprise monomers of Formula (M):

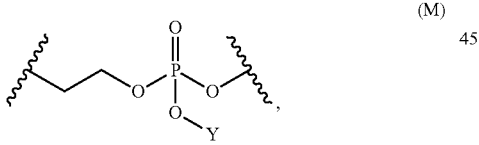

(M)

wherein for each monomer, Y is independently —$R^1$ or -$L^2R^2$, wherein:

each occurrence of $R^1$ is independently hydrogen, optionally substituted alkyl, optionally substituted alkenyl, optionally substituted alkynyl, optionally substituted aryl, or optionally substituted heteroaryl;

each occurrence of $L^2$ is independently a bond, optionally substituted alkylene, optionally substituted alkenylene, optionally substituted alkynylene, optionally substituted heteroalkylene, optionally substituted heteroalkenylene, or optionally substituted heteroalkynylene;

each occurrence of $R^2$ is independently optionally substituted acyl, optionally substituted carbocyclyl, optionally substituted heterocyclyl, optionally substituted aryl, optionally substituted heteroaryl, —$OR^b$, —N($R^b$)$_2$, or an oxygen protecting group; and each occurrence of $R^b$ is independently optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, an oxygen protecting group, or a nitrogen protecting group, or two $R^b$ taken together with the nitrogen to which they are attached form an optionally substituted heterocyclic or optionally substituted heteroaryl ring.

In certain embodiments, the polyphosphoester copolymer or polyphosphoester blocks comprise monomers of Formula (M-i):

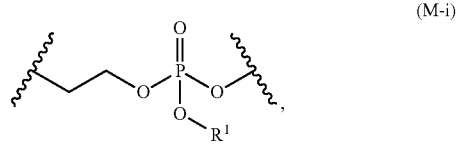

(M-i)

wherein $R^1$ is as defined herein.

In certain embodiments, the polyphosphoester copolymer or polyphosphoester blocks comprise monomers of Formula (M-ii):

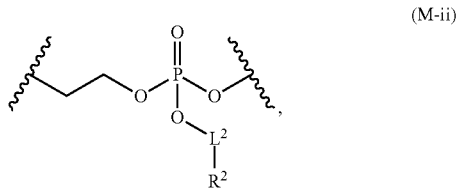

(M-ii)

wherein $L^2$ and $R^2$ are as defined herein.

In certain embodiments, the matrix forming agent comprises polyphosphoester blocks comprising monomers of Formula (M-i), and polyphosphoester blocks comprising monomers of formula (M-ii). In some embodiments, the matrix forming agent comprises polyphosphoester blocks comprising monomers of both Formulae (M-i) and (M-ii)

In certain embodiments, the matrix forming agent is a polymer of Formula (I):

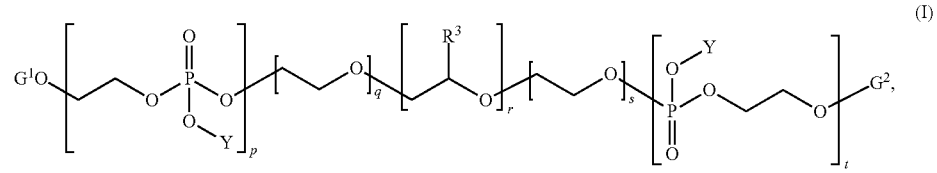

(I)

wherein:
each occurrence of Y is independently —$R^1$ or -$L^2R^2$;
each occurrence of $R^1$ is independently hydrogen, optionally substituted alkyl, optionally substituted alkenyl, optionally substituted alkynyl, optionally substituted aryl, or optionally substituted heteroaryl;
each occurrence of $L^2$ is independently a bond, optionally substituted alkylene, optionally substituted alkenylene, optionally substituted alkynylene, optionally substituted heteroalkylene, optionally substituted heteroalkenylene, or optionally substituted heteroalkynylene;
each occurrence of $R^2$ is independently optionally substituted acyl, optionally substituted carbocyclyl, optionally substituted heterocyclyl, optionally substituted aryl, optionally substituted heteroaryl, —$OR^b$, —N($R^b$)$_2$, or an oxygen protecting group;
each occurrence of $R^3$ is independently optionally substituted alkyl, optionally substituted alkenyl, optionally substituted alkynyl, optionally substituted aryl, optionally substituted heteryaryl, optionally substituted acyl, —$OR^b$, or —N($R^b$)$_2$;
each occurrence of $R^b$ is independently optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, an oxygen protecting group, or a nitrogen protecting group, or two $R^b$ taken together with the nitrogen to which they are attached form an optionally substituted heterocyclic or optionally substituted heteroaryl ring;
each of $G^1$ and $G^2$ is independently hydrogen, optionally substituted alkyl, optionally substituted aryl, or optionally substituted heteroaryl, optionally substituted acyl, optionally substituted phosphate, or an oxygen protecting group; and
each of p, q, r, s, and t is independently an integer between 0 and 200, inclusive, wherein the sum of p and t is at least 1, and the sum of q, r, and s is at least 1.

Phosphoester monomers and polyphosphoester blocks described herein may comprise group Y. In certain embodiments, each Y in a copolymer is the same substituent. In certain embodiments, each Y in a copolymer is one of two specific substituents. In certain embodiments, each Y in a copolymer is one of three specific substituents. In certain embodiments, each Y in a copolymer is one of four specific substituents. In certain embodiments, each Y in a copolymer is one of five specific substituents. In certain embodiments, each Y in a copolymer is one of six specific substituents. In certain embodiments, each Y in a copolymer is one of seven or more specific substituents. In some embodiments, Y is —$R^1$. In some embodiments, Y is -$L^2R^2$.

In certain embodiments, p is 0. In certain embodiments, p is an integer between 1 and 100, inclusive. In some embodiments, p is an integer between 10 and 100, inclusive. In some embodiments, p is an integer between 10 and 50, inclusive. In some embodiments, p is an integer between 10 and 25, inclusive. In some embodiments, p is an integer between 1 and 10, inclusive.

In certain embodiments, t is 0. In certain embodiments, t is an integer between 1 and 100, inclusive. In some embodiments, t is an integer between 10 and 100, inclusive. In some embodiments, t is an integer between 10 and 50, inclusive. In some embodiments, t is an integer between 10 and 25, inclusive. In some embodiments, t is an integer between 1 and 10, inclusive.

In certain embodiments, q is 0. In certain embodiments, q is an integer between 1 and 100, inclusive. In some embodiments, q is an integer between 10 and 100, inclusive. In some embodiments, q is an integer between 10 and 50, inclusive. In some embodiments, q is an integer between 10 and 25, inclusive. In some embodiments, q is an integer between 1 and 10, inclusive.

In certain embodiments, r is 0. In certain embodiments, r is an integer between 1 and 100, inclusive. In some embodiments, r is an integer between 10 and 100, inclusive. In some embodiments, r is an integer between 10 and 50, inclusive. In some embodiments, r is an integer between 10 and 25, inclusive. In some embodiments, r is an integer between 1 and 10, inclusive.

In certain embodiments, s is 0. In certain embodiments, s is an integer between 1 and 100. In some embodiments, s is an integer between 10 and 100, inclusive. In some embodiments, s is an integer between 10 and 50, inclusive. In some embodiments, s is an integer between 10 and 25, inclusive. In some embodiments, s is an integer between 1 and 10, inclusive. In certain embodiments, both q and s are 0. In certain embodiments, exactly one of q and s is 0.

$G^1$ and $G^2$ are terminal groups of the polymer. As generally defined herein $G^1$ and $G^2$ are hydrogen, optionally substituted alkyl, optionally substituted aryl, optionally substituted heteroaryl, optionally substituted acyl, optionally substituted phosphate, or an oxygen protecting group. In some embodiments, $G^1$ and $G^2$ are the same. In some embodiments, $G^1$ and $G^2$ are both hydrogen. In some embodiments, $G^1$ and $G^2$ are different.

In certain embodiments, $G^1$ is hydrogen. In certain embodiments, $G^1$ is optionally substituted alkyl. In certain embodiments, $G^1$ is optionally substituted acyl. In certain embodiments, $G^1$ is optionally substituted optionally substituted phosphate (e.g., —P(=O)(OH)$_2$, —P(=O)(O-alkyl)$_2$, —P(=O)(OH)(O-alkyl), —P(=O)(OH)(O—Y), —P(=O)(O-alkyl)(O—Y)). In certain embodiments, $G^1$ is an oxygen protecting group (e.g., silyl, TBDPS, TBDMS, TIPS, TES, TMS, MOM, THP, t-Bu, Bn, allyl, acetyl, pivaloyl, benzoyl). In certain embodiments, $G^1$ is hydrogen. In certain embodiments, $G^1$ is optionally substituted alkyl. In certain embodiments, $G^1$ is optionally substituted acyl. In certain embodiments, $G^1$ is optionally substituted optionally substituted phosphate (e.g., —P(=O)(OH)$_2$, —P(=O)(O-alkyl)$_2$, —P(=O)(OH)(O-alkyl), —P(=O)(OH)(O—Y), —P(=O)(O-alkyl)(O—Y)). In certain embodiments, $G^1$ is an oxygen protecting group (e.g., silyl, TBDPS, TBDMS, TIPS, TES, TMS, MOM, THP, t-Bu, Bn, allyl, acetyl, pivaloyl, benzoyl). In certain embodiments, $G^1$ is optionally substituted aryl, e.g., optionally substituted phenyl. In certain embodiments, $G^1$ is unsubstituted aryl, e.g., unsubstituted phenyl. In certain embodiments, $G^1$ is optionally substituted heteroaryl, e.g., optionally substituted 5-6 membered heteroaryl, or optionally substituted 9-10 membered bicyclic heteroaryl. In certain embodiments, $G^1$ is unsubstituted heteroaryl, e.g., unsubstituted 5-6 membered heteroaryl, or unsubstituted 9-10 membered bicyclic heteroaryl.

In certain embodiments, $G^2$ is hydrogen. In certain embodiments, $G^2$ is optionally substituted alkyl. In certain embodiments, $G^2$ is optionally substituted acyl. In certain embodiments, $G^2$ is optionally substituted optionally substituted phosphate (e.g., —P(=O)(OH)$_2$, —P(=O)(O-alkyl)$_2$, —P(=O)(OH)(O-alkyl), —P(=O)(OH)(O—Y), —P(=O)(O-alkyl)(O—Y)). In certain embodiments, $G^2$ is an oxygen protecting group (e.g., silyl, TBDPS, TBDMS, TIPS, TES, TMS, MOM, THP, t-Bu, Bn, allyl, acetyl, pivaloyl, benzoyl). In certain embodiments, $G^2$ is hydrogen. In certain embodiments, $G^2$ is optionally substituted alkyl. In certain embodiments, $G^2$ is optionally substituted acyl. In certain embodiments, $G^2$ is optionally substituted optionally substituted phosphate (e.g., —P(=O)(OH)$_2$, —P(=O)(O-alkyl)$_2$, —P(=O)(OH)(O-alkyl), —P(=O)(OH)(O—Y), —P(=O)(O-alkyl)(O—Y)). In certain embodiments, $G^2$ is an oxygen protecting group (e.g., silyl, TBDPS, TBDMS, TIPS, TES, TMS, MOM, THP, t-Bu, Bn, allyl, acetyl, pivaloyl, benzoyl). In certain embodiments, $G^2$ is optionally substituted aryl, e.g., optionally substituted phenyl. In certain embodiments, $G^2$ is unsubstituted aryl, e.g., unsubstituted phenyl. In certain embodiments, $G^2$ is optionally substituted heteroaryl, e.g., optionally substituted 5-6 membered heteroaryl, or optionally substituted 9-10 membered bicyclic heteroaryl. In certain embodiments, $G^2$ is unsubstituted heteroaryl, e.g., unsubstituted 5-6 membered heteroaryl, or unsubstituted 9-10 membered bicyclic heteroaryl.

In general, increasing PPE hydrophobicity decreases the gelation temperature, and accelerates gelation kinetics. Hydrophobicity of the PE monomer may be tuned by selection of pendent group Y (See, e.g., FIG. 7). In certain embodiments, greater numbers of hydrophobic domains will make the polymer more resistant to the effect of the CPEs on micelle formation than P407. The fact that P407-PPE may form gels not only by micelle formation but also by the hydrophobic PPE domains forming a cross-linked network [46] may also have a similar effect, and create an additional means of tuning phase transition behavior. It is noted that excessively hydrophobic PPE blocks may induce polymer aggregation in water, which could be undesirable for administration.

The bioadhesion of P407 can be enhanced by the conjugation of poly(acrylic acid) (PAA), or other reactive groups. In certain embodiments, PE monomers are functionalized with carbonyl and/or with acrylate groups (See, e.g., FIG. 7). In certain embodiments, PE monomers with hydrophobic groups and PE monomers with bioadhesion groups are both incorporated in the matrix forming agent. In some embodiments, the hydrophobic groups and bioadhesion groups are incorporated in the same polymer. In some embodiments, the hydrophobic groups and bioadhesion groups are incorporated in separate polymers.

$R^1$

Phosphoester monomers and polyphosphoester blocks described herein may comprise $R^1$. In certain embodiments, each $R^1$ is the same substituent. In certain embodiments, each $R^1$ in a polymer is one of two specific substituents. In certain embodiments, each $R^1$ in a polymer is one of three specific substituents. In certain embodiments, each $R^1$ in a polymer is one of four specific substituents. In certain embodiments, each $R^1$ in a polymer is one of five specific substituents. In certain embodiments, each $R^1$ in a polymer is one of six specific substituents. In certain embodiments, each $R^1$ in a polymer is one of seven or more specific substituents.

As generally described herein each occurrence of $R^1$ is independently hydrogen, optionally substituted alkyl, optionally substituted alkenyl, or optionally substituted alkynyl. In certain embodiments, each occurrence of $R^1$ is independently hydrogen or optionally substituted alkyl. In certain embodiments, each occurrence of $R^1$ is independently hydrogen or unsubstituted alkyl.

In certain embodiments, $R^1$ is hydrogen. In certain embodiments, $R^{41}$ is a non-hydrogen group.

In certain embodiments, $R^1$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^1$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^1$ is unsubstituted $C_{1-20}$ alkyl. In certain embodiments, $R^1$ is unsubstituted $C_{1-12}$ alkyl. In In certain embodiments, $R^1$ is methyl. In certain embodiments, $R^1$ is ethyl, propyl, or butyl. In certain embodiments, $R^1$ is haloalkyl, e.g., —CHF$_2$, —CHCl$_2$, —CH$_2$CHF$_2$, —CH$_2$CHCl$_2$. In certain embodiments, $R^1$ is perhaloalkyl, e.g., —CF$_3$, —CF$_2$CF$_3$, —CCl$_3$. In certain embodiments, $R^1$ is hydroxyalkyl, e.g., —CH$_2$OH, —CH$_2$CH$_2$OH, —CH$_2$OR$^b$, —CH$_2$CH$_2$OR$^b$. In certain embodiments, $R^1$ is aminoalkyl, e.g., —CH$_2$NH$_2$, —CH$_2$CH$_2$NH$_2$, —CH$_2$NMe$_2$, —CH$_2$CH$_2$NMe$_2$, —CH$_2$N(R$^b$)$_2$, —CH$_2$CH$_2$N(R$^b$)$_2$.

In certain embodiments, $R^1$ is optionally substituted alkenyl, e.g., optionally substituted $C_{2-6}$ alkenyl. In certain embodiments, $R^1$ is unsubstituted alkenyl, e.g., unsubstituted $C_{2-6}$ alkenyl. In certain embodiments, $R^1$ is vinyl, allyl, or prenyl. In certain embodiments, $R^1$ is optionally substituted alkynyl, e.g., optionally substituted $C_{2-6}$ alkynyl. In certain embodiments, $R^1$ is unsubstituted alkynyl, e.g., unsubstituted $C_{2-6}$ alkynyl.

In certain embodiments, $R^1$ is unsubstituted, unbranched $C_{1-20}$ alkyl. In certain embodiments, $R^1$ is unsubstituted, branched $C_{1-20}$ alkyl. In certain embodiments, $R^1$ is of formula:

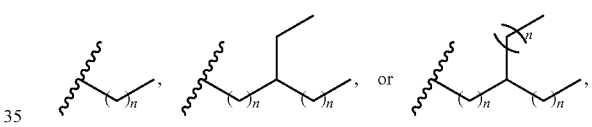

wherein each occurrence of n is independently an integer between 0 and 20, inclusive.

In certain embodiments, $R^1$ is of formula:

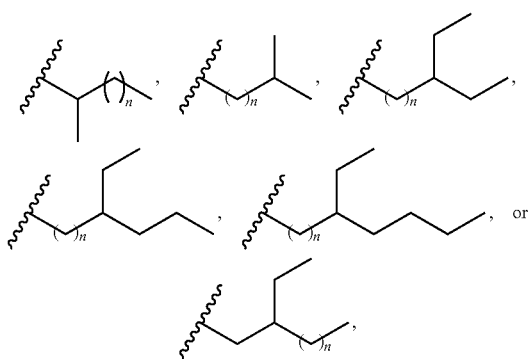

wherein each occurrence of n is independently an integer between 0 and 20, inclusive.

In certain embodiments, $R^1$ is of formula:

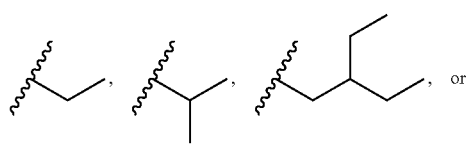

-continued

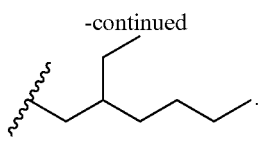

In certain embodiments, $R^1$ is optionally substituted aryl, e.g., optionally substituted phenyl. In certain embodiments, $R^1$ is unsubstituted aryl, e.g., unsubstituted phenyl. In certain embodiments, $R^1$ is optionally substituted heteroaryl, e.g., optionally substituted 5-6 membered heteroaryl, or optionally substituted 9-10 membered bicyclic heteroaryl. In certain embodiments, $R^1$ is unsubstituted heteroaryl, e.g., unsubstituted 5-6 membered heteroaryl, or unsubstituted 9-10 membered bicyclic heteroaryl.

$L^2$ and $R^2$

Phosphoester monomers and polyphosphoester blocks described herein may comprise -$L^2R^2$. In certain embodiments, each -$L^2R^2$ in a copolymer is the same substituent. In certain embodiments, each -$L^2R^2$ in a copolymer is one of two specific substituents. In certain embodiments, each -$L^2R^2$ in a copolymer is one of three specific substituents. In certain embodiments, each -$L^2R^2$ in a copolymer is one of four specific substituents. In certain embodiments, each -$L^2R^2$ in a copolymer is one of five specific substituents. In certain embodiments, each -$L^2R^2$ in a copolymer is one of six specific substituents. In certain embodiments, each -$L^2R^2$ in a copolymer is one of seven or more specific substituents.

As generally described herein, each occurrence of $L^2$ is optionally substituted alkylene, optionally substituted alkenylene, optionally substituted alkynylene, optionally substituted heteroalkylene, optionally substituted heteroalkenylene, or optionally substituted heteroalkynylene. In certain embodiments, each $L^2$ is independently optionally substituted alkylene. In certain embodiments, each $L^2$ is independently optionally substituted alkylene, and each occurrence of $R^2$ is independently optionally substituted acyl. In certain embodiments, each $L^2$ is independently unsubstituted alkylene. In certain embodiments, each $L^2$ is independently unsubstituted alkylene, and each occurrence of $R^2$ is independently optionally substituted acyl.

In certain embodiments, $L^2$ is optionally substituted alkylene, e.g., optionally substituted $C_{1-6}$ alkylene, optionally substituted $C_{1-2}$ alkylene, optionally substituted $C_{2-3}$ alkylene, optionally substituted $C_{3-4}$ alkylene, optionally substituted $C_{4-5}$ alkylene, or optionally substituted $C_{5-6}$ alkylene. In certain embodiments, $L^2$ is unsubstituted alkylene, e.g., unsubstituted $C_{1-6}$ alkylene, unsubstituted $C_{1-2}$ alkylene, unsubstituted $C_{2-3}$ alkylene, unsubstituted $C_{3-4}$ alkylene, unsubstituted $C_{4-5}$ alkylene, or unsubstituted $C_{5-6}$ alkylene. In certain embodiments, $L^2$ is methylene. In certain embodiments, $L^2$ is ethylene, propylene, butylene, pentylene, or hexylene.

In certain embodiments, $L^2$ is optionally substituted alkenylene, e.g., optionally substituted $C_{2-6}$ alkenylene. In certain embodiments, $L^2$ is unsubstituted alkenylene, e.g., unsubstituted $C_{2-6}$ alkenylene. In certain embodiments, $L^2$ is vinylene, allylene, or prenylene. In certain embodiments, $L^2$ is optionally substituted alkynylene, e.g., optionally substituted $C_{2-6}$ alkynylene. In certain embodiments, $L^2$ is unsubstituted alkynylene, e.g., unsubstituted $C_{2-6}$ alkynylene.

In certain embodiments, $L^2$ is optionally substituted heteroalkylene, e.g., optionally substituted $C_{1-6}$ heteroalkylene. In some embodiments, $L^2$ is unsubstituted heteroalkylene, wherein the heteroalkylene contains one oxygen atom. In some embodiments, $L^2$ is unsubstituted heteroalkylene, wherein the heteroalkylene contains one nitrogen atom. In certain embodiments, $L^2$ is optionally substituted heteroalkenylene, e.g., optionally substituted $C_{1-6}$ heteroalkenylene. In some embodiments, $L^2$ is unsubstituted heteroalkenylene, wherein the heteroalkenylene contains one oxygen atom. In some embodiments, $L^2$ is unsubstituted heteroalkenylene, wherein the heteroalkylene contains one nitrogen atom.

As generally described herein each occurrence of $R^2$ is independently optionally substituted acyl, optionally substituted carbocyclyl, optionally substituted heterocyclyl, optionally substituted aryl, optionally substituted heteroaryl, —$OR^b$, —$N(R^b)_2$, or an oxygen protecting group. In certain embodiments, each $R^2$ is independently optionally substituted acyl. In certain embodiments, each $R^2$ is independently optionally substituted acyl, and each occurrence of $L^2$ is independently optionally substituted alkylene.

In certain embodiments, $R^2$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, $R^2$ is unsubstituted carbocyclyl, e.g., unsubstituted $C_{3-6}$ carbocyclyl. In some embodiments, $R^2$ is cyclopropyl, cyclobutyl, cyclopentyl, or cyclohexyl. In certain embodiments, $R^2$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, $R^2$ is unsubstituted heterocyclyl, e.g., unsubstituted 3-6 membered heterocyclyl, unsubstituted 3-4 membered heterocyclyl, unsubstituted 4-5 membered heterocyclyl, or unsubstituted 5-6 membered heterocyclyl.

In certain embodiments, $R^2$ is optionally substituted aryl, e.g., optionally substituted phenyl. In certain embodiments, $R^2$ is unsubstituted aryl, e.g., unsubstituted phenyl. In certain embodiments, $R^2$ is optionally substituted heteroaryl, e.g., optionally substituted 5-6 membered heteroaryl, or optionally substituted 9-10 membered bicyclic heteroaryl. In certain embodiments, $R^2$ is unsubstituted heteroaryl, e.g., unsubstituted 5-6 membered heteroaryl, or unsubstituted 9-10 membered bicyclic heteroaryl.

In certain embodiments, $R^2$ is optionally substituted acyl, e.g., —CHO, —$CO_2H$, or —C(=O)$NH_2$. In certain embodiments, $R^2$ is optionally substituted carbonyl. In certain embodiments, $R^2$ is —C(=O)$R^b$, —C(=O)$OR^b$, —C(=O)NH($R^b$), or —C(=O)N($R^b$)$_2$. In certain embodiments, $R^2$ is —C(=O)$R^b$, and $R^b$ is optionally substituted alkyl, e.g., —C(=O)Me. In certain embodiments, $R^2$ is —C(=O)$R^b$, and $R^b$ is optionally substituted alkenyl. In certain embodiments, $R^2$ is —C(=O)$R^b$, and $R^b$ is optionally substituted carbocyclyl, heterocyclyl, aryl, or heteroaryl. In certain embodiments, $R^2$ is —C(=O)$OR^b$, and $R^b$ is optionally substituted alkyl. In certain embodiments, $R^2$ is —C(=O)$OR^b$, and $R^b$ is optionally substituted alkenyl. In certain embodiments, $R^2$ is —C(=O)$OR^b$, and $R^b$ is optionally substituted carbocyclyl, heterocyclyl, aryl, or heteroaryl. In certain embodiments, $R^2$ is —C(=O)N($R^b$)$_2$, and at least one $R^b$ is optionally substituted alkyl. In certain embodiments, $R^2$ is —C(=O)NH$R^b$, and $R^b$ is optionally substituted alkyl. In certain embodiments, $R^2$ is —C(=O)NH$R^b$, and $R^b$ is optionally substituted alkenyl. In certain embodiments, $R^2$ is —C(=O)NH$R^b$, and $R^b$ is optionally substituted carbocyclyl, heterocyclyl, aryl, or heteroaryl. In certain embodiments, $R^2$ is optionally substituted vinylcarbonyl (e.g., —C(=O)CH=$CH_2$, —C(=O)CMe=$CH_2$). In certain embodiments, $R^2$ is an oxygen protecting group (e.g., silyl, TBDPS, TBDMS, TIPS, TES, TMS, MOM, THP, t-Bu, Bn, allyl, acetyl, pivaloyl, benzoyl)

In certain embodiments, $R^2$ is $-OR^b$, e.g., $-OH$. In certain embodiments, $R^2$ is $-OR^b$, and $R^b$ is optionally substituted alkyl. In certain embodiments, $R^2$ is $-OR^b$, and $R^b$ is unsubstituted $C_{1-6}$ alkyl. In certain embodiments, $R^2$ is $-OR^b$, and $R^b$ is optionally substituted alkenyl. In certain embodiments, $R^2$ is $-OR^b$, and $R^b$ is optionally substituted carbocyclyl, optionally substituted heterocyclyl, optionally substituted aryl optionally substituted heteroaryl. In certain embodiments, $R^2$ is $-OR^b$, and $R^b$ is unsubstituted carbocyclyl, unsubstituted heterocyclyl, unsubstituted aryl unsubstituted heteroaryl. In certain embodiments, $R^2$ is $-OR^b$, and $R^b$ is optionally substituted acyl, e.g., $R^2$ is $-OC(=O)R^b$, $-OC(=O)OR^b$, or $-OC(=O)N(R^b)_2$. In certain embodiments, $R^2$ is $-OR^b$, and $R^b$ is an oxygen protecting group (e.g., silyl, TBDPS, TBDMS, TIPS, TES, TMS, MOM, THP, t-Bu, Bn, allyl, acetyl, pivaloyl, benzoyl).

In certain embodiments, $R^2$ is $-N(R^b)_2$, e.g., $-NH_2$, $-NHR^b$. In certain embodiments, $R^2$ is $-NH(R^b)$, and $R^b$ is optionally substituted alkyl. In certain embodiments, $R^2$ is $-N(R^b)_2$, and at least one $R^b$ is optionally substituted alkyl. In certain embodiments, $R^2$ is $-NH(R^b)$, and $R^b$ is unsubstituted alkyl. In certain embodiments, $R^2$ is $-N(R^b)_2$, and at least one $R^b$ is unsubstituted alkyl. In certain embodiments, $R^2$ is $-NHR^b$, and $R^b$ is optionally substituted carbocyclyl, optionally substituted heterocyclyl, optionally substituted aryl, or optionally substituted heteroaryl. In certain embodiments, $R^2$ is $-NHR^b$, and $R^b$ is unsubstituted carbocyclyl, unsubstituted heterocyclyl, unsubstituted aryl, or unsubstituted heteroaryl. In certain embodiments, $R^2$ is $-NHR^b$, and $R^b$ is optionally substituted acyl, e.g., $R^2$ is $-NHC(=O)R^b$, $-NHC(=O)OR^b$, or $-NHC(=O)NHR^b$. In certain embodiments, $R^2$ is $-N(R^b)_2$, and at least one $R^b$ is a nitrogen protecting group (e.g., Bn, Boc, Cbz, Fmoc, trifluoroacetyl, triphenylmethyl, acetyl, Ts). In certain embodiments, $R^2$ is $-N(R^b)_2$, and both $R^b$ are joined to form an optionally substituted heterocyclic or optionally substituted heteroaryl ring. In certain embodiments, $R^2$ is $-N(R^b)_2$, and both $R^b$ are joined to form an unsubstituted heterocyclic or unsubstituted heteroaryl ring.

In certain embodiments, $-L^2R^2$ is of formula:

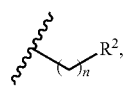

wherein n is an integer between 0 and 20, inclusive.

In certain embodiments, $-L^2R^2$ is of formula:

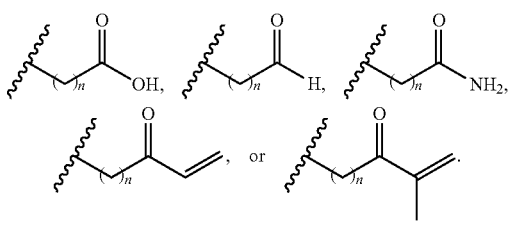

wherein n is an integer between 0 and 20, inclusive.

In certain embodiments, $-L^2R^2$ is of formula:

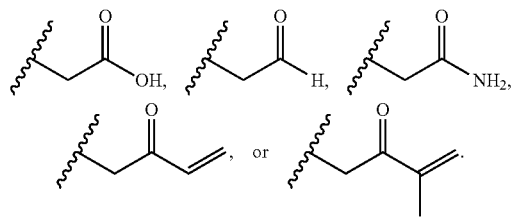

In certain embodiments, $-L^2R^2$ is of formula:

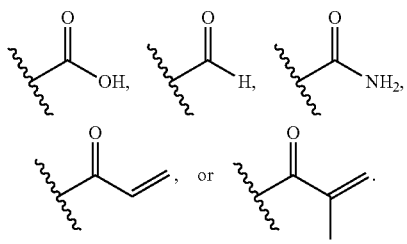

$R^3$

Polymers of Formula (I) comprise $R^3$. In certain embodiments, each $R^3$ is the same substituent. In certain embodiments, each $R^3$ in a polymer is one of two specific substituents. In certain embodiments, each $R^3$ in a polymer is one of three specific substituents. In certain embodiments, each $R^3$ in a polymer is one of four specific substituents. In certain embodiments, each $R^3$ in a polymer is one of five specific substituents. In certain embodiments, each $R^3$ in a polymer is one of six specific substituents. In certain embodiments, each $R^3$ in a polymer is one of seven or more specific substituents.

As generally described herein each occurrence of $R^3$ is independently optionally substituted alkyl, optionally substituted alkenyl, optionally substituted alkynyl, optionally substituted aryl, optionally substituted heteryaryl, optionally substituted acyl, $-OR^b$, or $-N(R^b)_2$. In certain embodiments, each occurrence of $R^3$ is independently unsubstituted alkyl.

In certain embodiments, $R^3$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^3$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^3$ is unsubstituted $C_{1-20}$ alkyl. In certain embodiments, $R^3$ is unsubstituted $C_{1-12}$ alkyl. In certain embodiments, $R^3$ is methyl. In certain embodiments, $R^3$ is ethyl, propyl, or butyl. In certain embodiments, $R^3$ is haloalkyl, e.g., $-CHF_2$, $-CHCl_2$, $-CH_2CHF_2$, $-CH_2CHCl_2$. In certain embodiments, $R^3$ is perhaloalkyl, e.g., $-CF_3$, $-CF_2CF_3$, $-CCl_3$. In certain embodiments, $R^3$ is hydroxyalkyl, e.g., $-CH_2OH$, $-CH_2CH_2OH$, $-CH_2OR^b$, $-CH_2CH_2OR^b$. In certain embodiments, $R^3$ is aminoalkyl, e.g., $-CH_2NH_2$, $-CH_2CH_2NH_2$, $-CH_2NMe_2$, $-CH_2CH_2NMe_2$, $-CH_2N(R^b)_2$, $-CH_2CH_2N(R^b)_2$.

In certain embodiments, $R^3$ is optionally substituted alkenyl, e.g., optionally substituted $C_{2-6}$ alkenyl. In certain embodiments, $R^3$ is unsubstituted alkenyl, e.g., unsubstituted $C_{2-6}$ alkenyl. In certain embodiments, $R^3$ is vinyl, allyl, or prenyl. In certain embodiments, R³ is optionally substituted alkynyl, e.g., optionally substituted $C_{2-6}$ alkynyl. In certain embodiments, R³ is unsubstituted alkynyl, e.g., unsubstituted $C_{2-6}$ alkynyl.

In certain embodiments, R³ is optionally substituted aryl, e.g., optionally substituted phenyl. In certain embodiments, R³ is unsubstituted aryl, e.g., unsubstituted phenyl. In certain embodiments, R³ is optionally substituted heteroaryl, e.g., optionally substituted 5-6 membered heteroaryl, or optionally substituted 9-10 membered bicyclic heteroaryl. In certain embodiments, R³ is unsubstituted heteroaryl, e.g., unsubstituted 5-6 membered heteroaryl, or unsubstituted 9-10 membered bicyclic heteroaryl.

In certain embodiments, R³ is optionally substituted acyl, e.g., —CHO, —CO₂H, or —C(=O)NH₂. In certain embodiments, R³ is optionally substituted carbonyl. In certain embodiments, R³ is —C(=O)R$^b$, —C(=O)OR$^b$, —C(=O)NH(R$^b$), or —C(=O)N(R$^b$)₂. In certain embodiments, R³ is —C(=O)R$^b$, and R$^b$ is optionally substituted alkyl, e.g., —C(=O)Me. In certain embodiments, R³ is —C(=O)R$^b$, and R$^b$ is optionally substituted alkenyl. In certain embodiments, R³ is —C(=O)R$^b$, and R$^b$ is optionally substituted carbocyclyl, heterocyclyl, aryl, or heteroaryl. In certain embodiments, R³ is —C(=O)OR$^b$, and R$^b$ is optionally substituted alkyl. In certain embodiments, R³ is —C(=O)OR$^b$, and R$^b$ is optionally substituted alkenyl. In certain embodiments, R³ is —C(=O)OR$^b$, and R$^b$ is optionally substituted carbocyclyl, heterocyclyl, aryl, or heteroaryl. In certain embodiments, R³ is —C(=O)N(R$^b$)₂, and at least one R$^b$ is optionally substituted alkyl. In certain embodiments, R³ is —C(=O)NHR$^b$, and R$^b$ is optionally substituted alkyl. In certain embodiments, R³ is —C(=O)NHR$^b$, and R$^b$ is optionally substituted alkenyl. In certain embodiments, R³ is —C(=O)NHR$^b$, and R$^b$ is optionally substituted carbocyclyl, heterocyclyl, aryl, or heteroaryl. In certain embodiments, R³ is optionally substituted vinylcarbonyl (e.g., —C(=O)CH=CH₂, —C(=O)CMe=CH₂).

In certain embodiments, R³ is —OR$^b$, e.g., —OH. In certain embodiments, R³ is —OR$^b$, and R$^b$ is optionally substituted alkyl. In certain embodiments, R³ is —OR$^b$, and R$^b$ is unsubstituted $C_{1-6}$ alkyl. In certain embodiments, R³ is —OR$^b$, and R$^b$ is optionally substituted alkenyl. In certain embodiments, R³ is —OR$^b$, and R$^b$ is optionally substituted carbocyclyl, optionally substituted heterocyclyl, optionally substituted aryl optionally substituted heteroaryl. In certain embodiments, R³ is —OR$^b$, and R$^b$ is unsubstituted carbocyclyl, unsubstituted heterocyclyl, unsubstituted aryl unsubstituted heteroaryl. In certain embodiments, R³ is —OR$^b$, and R$^b$ is optionally substituted acyl, e.g., R³ is —OC(=O)R$^b$, —OC(=O)OR$^b$, or —OC(=O)N(R$^b$)₂. In certain embodiments, R³ is —OR$^b$, and R$^b$ is an oxygen protecting group (e.g., silyl, TBDPS, TBDMS, TIPS, TES, TMS, MOM, THP, t-Bu, Bn, allyl, acetyl, pivaloyl, benzoyl).

In certain embodiments, R³ is —N(R$^b$)₂, e.g., —NH₂, —NHR$^b$. In certain embodiments, R³ is —NH(R$^b$), and R$^b$ is optionally substituted alkyl. In certain embodiments, R³ is —N(R$^b$)₂, and at least one R$^b$ is optionally substituted alkyl. In certain embodiments, R³ is —NH(R$^b$), and R$^b$ is unsubstituted alkyl. In certain embodiments, R³ is —N(R$^b$)₂, and at least one R$^b$ is unsubstituted alkyl. In certain embodiments, R³ is —NHR$^b$, and R$^b$ is optionally substituted carbocyclyl, optionally substituted heterocyclyl, optionally substituted aryl, or optionally substituted heteroaryl. In certain embodiments, R³ is —NHR$^b$, and R$^b$ is unsubstituted carbocyclyl, unsubstituted heterocyclyl, unsubstituted aryl, or unsubstituted heteroaryl. In certain embodiments, R³ is —NHR$^b$, and R$^b$ is optionally substituted acyl, e.g., R³ is —NHC(=O)R$^b$, —NHC(=O)OR$^b$, or —NHC(=O)NHR$^b$. In certain embodiments, R³ is —N(R$^b$)₂, and at least one R$^b$ is a nitrogen protecting group (e.g., Bn, Boc, Cbz, Fmoc, trifluoroacetyl, triphenylmethyl, acetyl, Ts). In certain embodiments, R³ is —N(R$^b$)₂, and both R$^b$ are joined to form an optionally substituted heterocyclic or optionally substituted heteroaryl ring. In certain embodiments, R³ is —N(R$^b$)₂, and both R$^b$ are joined to form an unsubstituted heterocyclic or unsubstituted heteroaryl ring.

Synthesis of the Polyphosphoester Block Copolymer

The block copolymers described herein may be prepared by sequential polymerization of monomers corresponding to each block. For example, polymerization of propylene oxide, followed by polymerization of ethylene oxide starting at the terminal groups of the polypropylene oxide, followed by polymerization of phosphoester monomers starting at the terminal groups of the polypropylene oxide-polyethylene oxide polymer. In certain embodiments, a poloxamer comprising polyethylene and polypropylene blocks is treated with a phosphoester monomer precursor. In some embodiments, the precursor is hydroxydioxaphospholane or a dioxaphospholane ester. In certain embodiments, the copolymer of Formula (I):

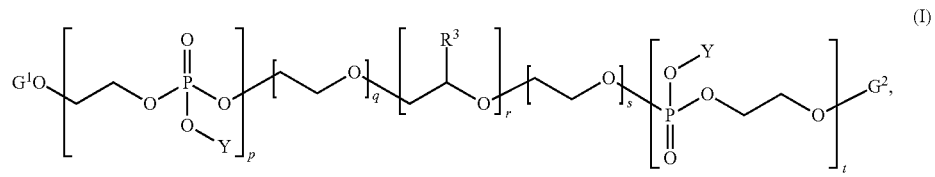

is prepared by contacting a polymer of Formula (P):

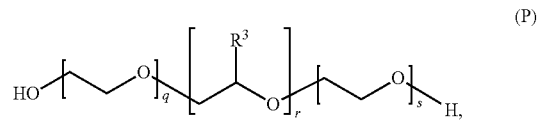

with a compound of Formula (A), or a mixture of compounds of Formula (A):

wherein p, q, r, s, t, G¹, G², and Y are as defined herein.

In certain embodiments, the step of contacting a polymer of Formula (P) with a compound of Formula (A) is performed in the presence of a catalyst. In some embodiments, the catalyst is an organocatalyst. In some embodiments, the catalyst is a base. In some embodiments, the catalyst is an organic base. In some embodiments, the catalyst is a non-nucleophlic base. In some embodiments, the catalyst is N,N-diisopropylethylamine (DIPEA, Hüinig's base), 1,8-diazabicyclo[5.4.0]undec-7-ene (DBU), 2,6-di-tert-butylpyridine, or a phosphazene (e.g., BEMP, t-Bu-P4). In some embodiments, the catalyst is 1,8-diazabicyclo[5.4.0]undec-7-ene (DBU).

In some embodiments, the polymer is treated with a compound of Formula (A-i):

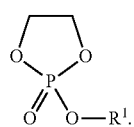

A mixture of compounds of Formula (A-i) may also be used, e.g., with different $R^1$, or a single compound may be used.

In some embodiments, the polymer is treated with a compound Formula (A-ii):

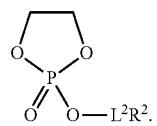

A mixture of compounds of Formula (A-ii) may also be used, e.g., with different $R^1$, or a single compound may be used.

In some embodiments, the polymer is treated with a mixture of compounds of Formula (A-i) and (A-ii).

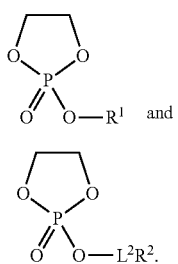

A mixture of compound of Formula (A-i) may also be used, e.g., with different $R^1$, or a single compound may be used. A mixture of compounds of Formula (A-ii) may also be used, e.g., with different $R^1$, or a single compound may be used.

In certain embodiments, a first compound of Formula (A) and a second compound of Formula (A) are contacted with a copolymer of Formula (P) simultaneously. For example, a compound of Formula (A-i) and a compound of Formula (A-ii) are added simultaneously to generate polyphosphoester blocks with a random monomer distribution. In other embodiments, a first compound of Formula (A) is contacted with a copolymer of Formula (P), and subsequently a second compound of Formula (A) is contacted with the product of contacting a compound of Formula (P) with the first compound of Formula (A). For example, a compound of Formula (A-i) is added to generate a first polyphosphoester block with a first monomer (e.g., a monomer of Formula (M-i), and subsequently a compound of Formula (A-ii) is added to generate a second polyphosphoester block with a second monomer (e.g., a monomer of Formula (M-ii).

The number of phosphoester monomers (e.g., variables p and t) in the resulting copolymer will be determined by the reaction conditions, reaction time, and the number of equivalents of compound(s) of Formula (A) vs. equivalents of the compound(s) of Formula (P).

In certain embodiments, the copolymer may be further modified after addition of the polyphosphoester blocks. In some embodiments, one or more group Y is modified after polymerization. In some embodiments, one or more group Y is deprotected after polymerization. In some embodiments, group $G^1$ or $G^2$ is modified after polymerization.

Permeation Enhancers

Permeation enhancer refers to any agent that increases the flux of a therapeutic agent across a barrier (e.g., membrane, layer of cells). In some embodiments, the barrier is skin. In some embodiments, the barrier is the tympanic membrane. Permeation enhancers may include, but are not limited to, surfactants (anionic, cationic, nonionic, zwitterionic), terpenes, amino amides, amino esters, azide-containing compounds, and alcohols. Permeation enhancers may include, but are not limited to, surfactants (anionic, cationic, nonionic, zwitterionic), terpenes, amino amides, amino esters, azide-containing compounds, pyrrolidones, sulfoxides, fatty acids, and alcohols. In certain embodiments, the permeation enhancer is an anionic surfactant. In certain embodiments, the permeation enhancer is a cation surfactant. In certain embodiments, the permeation enhancer is nonionic surfactant. In certain embodiments, the permeation enhancer is a zwitterionic surfactant. In certain embodiments, the permeation enhancer is a terpene. In certain embodiments, the permeation enhancer is an amino amide. In certain embodiments, the permeation enhancer is an amino ester. In certain embodiments, the permeation enhancer is an azide-containing compound. In certain embodiments, the permeation enhancer is a pyrrolidone. In certain embodiments, the permeation enhancer is a sulfoxide. In certain embodiments, the permeation enhancer is a fatty acid. In certain embodiments, the permeation enhancer is an alcohol. In certain embodiments, the permeation enhancer is sodium lauroyl sarcosinate. In certain embodiments, the permeation enhancer is sorbitan monooleate. In certain embodiments, the permeation enhancer is octoxynol-9. In certain embodiments, the permeation enhancer is diethyl sebacate. In certain embodiments, the permeation enhancer is sodium polyacrylate (2500000 molecular weight (MW)). In certain embodiments, the permeation enhancer is octyldodecanol.

Surfactant permeation enhancers may include, but are not limited to, sodium dodecyl sulfate, ammonium lauryl sulfate, sodium laureth sulfate, cetyl trimethlammonium bromide, cetylpyridinium chloride, benzethonium chloride, cocamidopropyl betaine, cetyl alcohol, oleyl alcohol, octyl glucoside, decyl maltoside, sodium octyl sulfate, sodium decyl sulfate, sodium tetradecyl sulfate, sodium heptadecyl sulfate, sodium eicosyl sulfate, nicotine sulfate, sodium taurocholic sulfate, dimethyl sulfoxide, sodium tridecyl phosphate; decyldimethyl ammonio propane sulfonate, chembetaine oleyl, myristyldimethyl ammonio propane sulfonate; benzyl pyridinium chloride, dodecyl pyridinium chloride, cetyl pyridinium chloride, benzyldimethyl dodecyl ammonium chloride, benzyldimethyl dodecyl ammonium chloride, benzyldimethyl myristyl ammonium chloride, benzyldimethyl stearyl ammonium chloride, octyltrimethylammonium bromide, dodecyltrimethylammonium bromide, Polysorbate 20, Polysorbate 40, Polysorbate 60, Polysorbate 80, and benzalkonium chlorides. In some embodiments, the permeation enhancer is sodium dodecyl sulfate, sodium lauryl sulfate, or sodium octyl sulfate. In some embodiments, the permeation enhancer is sodium dodecyl sulfate. In some embodiments, the permeation enhancer is octyltrimethyl-ammonium bromide or dodecyl-trimethyl-ammonium bromide. In some embodiments the permeation enhancer is Polysorbate 20, Polysorbate 40, Polysorbate 60, or Polysorbate 80. In some embodiments the permeation enhancer is a benzalkonium chloride.

In certain embodiments, the permeation enhancer is sodium lauroyl sarcosinate, sorbitan monooleate, octoxynol-9, diethyl sebacate, sodium polyacrylate (2500000 molecular weight (MW)), or octyldodecanol. In certain embodiments, the permeation enhancer is sodium lauroyl sarcosinate. In certain embodiments, the permeation enhancer is sorbitan monooleate. In certain embodiments, the permeation enhancer is octoxynol-9. In certain embodiments, the permeation enhancer is diethyl sebacate. In certain embodiments, the permeation enhancer is sodium polyacrylate (2500000 molecular weight (MW)). In certain embodiments, the permeation enhancer is octyldodecanol.

In various embodiments, the permeation enhancer is an azone-like compound. In certain embodiments, the permeation enhancer is a compound similar to azone (e.g., laurocapram) of the formula:

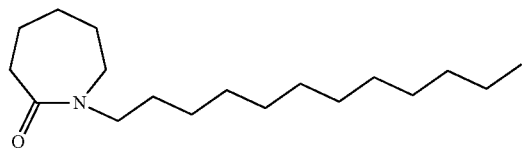

In certain embodiments, the permeation enhancer is 1-benzyl-4-(2-((1,1-biphenyl)-4-yloxy)ethyl)piperazine.

In various embodiments, the permeation enhancer is a lipid. In certain embodiments, the lipid used in the composition is selected from the group consisting of phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid amides; sorbitan trioleate (Span 85) glycocholate; surfactin; a poloxamer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; and phospholipids. In certain embodiments, the lipid used in the composition is selected from the group consisting of phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid amides; sorbitan trioleate (Span 85) glycocholate; surfactin; a poloxamer; a fatty ester (e.g., stearyl methacrylate) a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; and phospholipids. In certain embodiments, the permeation enhancer is a fatty ester. In certain embodiments, the permeation enhancer is stearyl methacrylate. The lipid may be positively charged, negatively charged, or neutral. In certain embodiments, the lipid is a combination of lipids. Phospholipids useful in the inventive compositions include negatively charged phosphatidyl inositol, phosphatidyl serine, phosphatidyl glycerol, phosphatic acid, diphosphatidyl glycerol, poly(ethylene glycol)-phosphatidyl ethanolamine, dimyristoylphosphatidyl glycerol, dioleoylphosphatidyl glycerol, dilauryloylphosphatidyl glycerol, dipalmitotylphosphatidyl glycerol, distearyloylphosphatidyl glycerol, dimyristoyl phosphatic acid, dipalmitoyl phosphatic acid, dimyristoyl phosphitadyl serine, dipalmitoyl phosphatidyl serine, phosphatidyl serine, and mixtures thereof. Useful zwitterionic phospholipids include phosphatidyl choline, phosphatidyl ethanolamine, sphingomyeline, lecithin, lysolecithin, lysophatidylethanolamine, cerebrosides, dimyristoylphosphatidyl choline, dipalmitotylphosphatidyl choline, distearyloylphosphatidyl choline, dielaidoylphosphatidyl choline, dioleoylphosphatidyl choline, dilauryloylphosphatidyl choline, 1-myristoyl-2-palmitoyl phosphatidyl choline, 1-palmitoyl-2-myristoyl phosphatidyl choline, 1-palmitoyl-phosphatidyl choline, 1-stearoyl-2-palmitoyl phosphatidyl choline, dimyristoyl phosphatidyl ethanolamine, dipalmitoyl phosphatidyl ethanolamine, brain sphingomyelin, dipalmitoyl sphingomyelin, distearoyl sphingomyelin, and mixtures thereof. Zwitterionic phospholipids constitute any phospholipid with ionizable groups where the net charge is zero. In certain embodiments, the lipid is phosphatidyl choline.

Exemplary surfactants include, but are not limited to, sodium dioctyl sulfo succinate, sodium dodecyl sulfate, cocoamidopropyl betaine, and sodium laureth sulfate, alkyl and alkyl ether sulfates (e.g., sodium coconut alkyl triethylene glycol ether sulfate; lithium tallow alkyl triethylene glycol ether sulfate; sodium tallow alkyl hexaoxyethylene sulfate), succinamates, sulfosuccinamates (e.g., disodium N-octadecyl-sulfosuccinamate, tetrasodium N-(1,2-dicarboxyethyl)-N-octadecylsulfosuccinamate, diamyl ester of sodium sulfosuccinic acid, dihexyl ester of sodium sulfosuccinic acid, dioctyl esters of sodium sulfosuccinic acid), olefin sulfonates, hydroxy-alkanesulfonates, beta-alkyloxy alkane sulfonates (e.g., potassium-β-methoxydecanesulfonate, sodium 2-methoxytridecanesulfonate, potassium 2-ethoxytetradecylsulfonate, sodium 2-isopropoxyhexadecylsulfonate, lithium 2-t-butoxytetradecylsulfonate, sodium β-methoxyoctadecysulfonate, ammonium β-n-propoxy-dodecylsulfonate), dioctyl esters of sodium sulfosuccinic acid, alkyl ethoxylated sulfates, alkyl sulfates, aliphatic secondary and tertiary amines (e.g., sodium 3-dodecylaminopropionate, N-alkyltaurines, stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O) stearylamine, dihydroxy ethyl stearylamine, and arachidylbehenylamine), alkyl amphoglycinates (e.g., cocoamphoglycinate, lauroamphocarboxyglycinate, cocoamphocarboxyglycinate); alkyl amphopropionates (e.g., isostearoamphopropionate, cocoamphocarboxypropionic acid); alkyl ethoxylated sulfates; alkyl sulfates; aliphatic quaternary ammonium compounds (e.g., tallow propane diammonium dichloride, dialkyldimethylammonium chlorides, ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, and di(coconutalkyl benzyl ammonium chloride); aliphatic phosphonium compounds, aliphatic sulfonium compounds, alkyl amino sulfonates, alkyl betaines (e.g., coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxy methyl betaine, stearyl bis-(2-hydroxypropyl) carboxymethyl betaine, oleyl dimethyl gamma-carboxypropyl betaine, lauryl bis-(2-hydroxypropyl) alpha-carboxyethyl betaine), sulfo betaines (e.g., coco dimethyl sulfopropyl betaine, stearyl dimethyl sulfopropyl betaine, lauryl dimethyl sulfoethyl betaine, lauryl bis(2-hydroxyethyl) sulfopropyl betaine), alkyl amido betaines, 4-[N,N-di(2-hydroxyethyl)-N-octadecylammonio]-butane-1-carboxylate; 5-[S-3-hydroxypropyl-S-hexadecylsulfonio]-3-hydroxy-pentanel-sulfate; 3-[P,P-diethyl-P-3,6,9-trioxatetradexoxylphosphonio]-2-hydroxy-propane-1-phosphate; 3-[N,N-dipropyl-N-3-dodecoxy-2-hydroxypropylammonio]-propane-1-phosphate; 3-(N,N-dimethyl-N-hexadecylammonio)propane-1-sulfonate; 3-(N,N-dimethyl-N-hexadecylammonio)-2-hydroxy-propane-1-sulfonate; 4-[N,N-di-(2-hydroxy-ethyl)-N-(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and 5-[N,N-di(3-hydroxypropyl)-N-hexadecylammonio]-2-hydroxypentane-1-sulfate,
sodium 3-dodecylaminopropane sulfonate; alkyl amphosulfonates; alkyl amphosulfosuccinates; oleoamphopropylsulfonate, and cocoamphopropylsulfonate; polyethylene oxide condensates; long chain tertiary phosphine oxides; long chain dialkyl sulfoxides; Silicone copolyols (e.g., dimethicone copolyols), stearamide diethanolamide (DEA), cocamide monoethanolamide (MEA), glyceryl monoleate, sucrose stearate, Cetheth-2, Poloxamer 181, hydrogenated tallow amide DEA, polyoxyethylene 4 sorbitol beeswax derivative (ATLAS 6-1702), polyoxyethylene 2 cetyl ether (BRIJ 52), polyoxyethylene 2 stearyl ether (BRIJ 72), polyoxyethylene 2 oleyl ether (BRIJ 92), polyoxyethylene 2 oleyl ether (BRIJ 93), sorbitan monopalmitate (SPAN 40), sorbitan monostearate (SPAN 60), sorbitan tristearate (SPAN 65), sorbitan monoleate, NF (SPAN 80) sorbitan trioleate (SPAN 85), fluorinated alkyl quaternary ammonium iodide; mixed mono- and bis-perfluoroalkyl phosphates, ammonium salts; mixed mono- and bis-fluoroalkyl phosphate, ammonium salts, complexed with aliphatic quaternary methosulfates; perfluoroalkyl sulfonic acid, ammonium salts; mixed telomer phosphate diethanolamine salts; amine perfluoroalkyl sulfonates; ammonium perfluoroalkyl sulfonates; potassium perfluoroalkyl sulfonates; potassium fluorinated alkyl carboxylates; ammonium perfluoroalkyl sulfonates; and ammonium perfluoroalkyl carboxylates; sodium dioctyl sulfosuccinate; magnesium dioctyl sulfosuccinate; ammonium dioctyl sulfosuccinate; magnesium dodecyl sulfate; ammonium dodecyl sulfate; cocoamidopropyl betaine sodium dinonyl sulfo succinate; sodium alpha olefin sulfonate; sodium laureth sulfate; magnesium laureth sulfate; ammonium laureth sulfate; cocoamidopropyl betaine; polyethoxylated glycol ether of glyceryl isostewarate; polyethoxylated glycol ether of glyceryl monooleate; PEG-30 glyceryl isostearate; polyoxyethylene glycerol monoleate; polyethylene glycol; PPG-18; PPG-10; 18 dimethicone; 1 dimethicon; cetyl polyethylene glycol; glyceryl monostearate; laureth-23; and PEG 75 lanolin. In certain embodiments, the surfactant is a silicon-containing chemical compound. Exemplary silicon-based detergents, emulsifiers, or surfactants useful in cosmetic compositions include dimethicone, cyclopentasiloxane, cyclohexasiloxane, PEG/dimethicone copolymers, PPG/dimethicone copolymers, phenyltrimethicone, alkyl silicones, amodimethicone, silicone quaternium-18, and dimethiconol.

Terpene permeation enhancers may include, but are not limited to, limonene, cymene, pinene, camphor, menthol, comphone, phellandrine, sabinene, terpinene, borneol, cineole, geraniol, linalol, pipertone, terpineol, eugenol, eugenol acetate, safrole, benzyl benzoate, humulene, beta-caryophyllene, eucakytol, hexanoic acid, octanoic acid, decanoic acid, undecanoic acid, dodecanoic acid, tridecanoic acid, myristic acid, palmitic acid, stearic acid, oleic acid, linoleic acid, linolenic acid, cholic acid; ethyl undecanoate, methyl laurate, methyl myristate, isopropyl myristate, isopropyl palmitate, palmityl palmitate, diethyl sebaccate, glyceryl monolaurate, glyceryl monooleate, and ethylpiperazine carboxylate. Any terpene or terpeniod compound may be used as a permeation enhancer in the inventive compositions. In certain embodiments, the permeation enhancer is limonene.

Alcohol permeation enhancers may include, but are not limited to, methanol, ethanol, propanol, isopropanol, butanol, isobutyl alcohol, and tert-amyl alcohol. In certain embodiments, the permeation enhancer is a compound with more than one hydroxyl group (e.g., glycerol). For example, the permeation enhancer may contain two, three, four, five, or more hydroxyl groups. In certain embodiments, the permeation enhancer is a hydroxyl-containing polymer.

In certain embodiments, an amino amide or amino ester permeation enhancers is an anesthetic agent. Amino amide and amino ester permeation enhancers may include, but are not limited to bupivicaine, tetracaine, procaine, proparacaine, propoxycaine, dimethocaine, cyclomethycaine, chloroprocaine, benzocaine, lidocaine, prilocaine, levobupivicaine, ropivacaine, dibucaine, articaine, carticaine, etidocaine, mepivacaine, piperocaine, and trimecaine. In certain embodiments, the permeation enhancer is bupivacaine.

In certain embodiments, the composition comprises a combination of permeation enhancers. In certain embodiments, the combination comprises permeation enhancers of the same type (e.g., both surfactants, both terpenes). In certain embodiments, the combination comprises permeation enhancers of different types (e.g., a surfactant and a terpene). In certain embodiments, combination comprises a surfactant and a terpene. In certain embodiments, the combination comprises a cationic surfactant and a terpene. In certain embodiments, the combination comprises an anionic surfactant and a terpene. In certain embodiments, the combination comprises a nonionic or zwitterionic surfactant and a terpene.

In certain embodiments, the combination comprises a surfactant and an amino amide or amino ester. In certain embodiments, the combination comprises a cationic surfactant and an amino amide or amino ester. In certain embodiments, the combination comprises an anionic surfactant and an amino amide or amino ester. In certain embodiments, the combination comprises a nonionic or zwitterionic surfactant and an amino amide or amino ester. In certain embodiments, the combination comprises is a terpene and an amino amide or amino ester. In some embodiments, the amino amide or amino ester is an anesthetic agent. In some embodiments, the anesthetic agent is bupivacaine.

In some embodiments, the permeation enhancer is a combination of compounds selected from two or three of groups (i) to (iii):
(i) a surfactant selected from: sodium dodecyl sulfate, ammonium lauryl sulfate, sodium laureth sulfate, cetyl trimethlammonium bromide, cetylpyridinium chloride, benzethonium chloride, cocamidopropyl betaine, cetyl alcohol, oleyl alcohol, octyl glucoside, decyl maltoside, sodium octyl sulfate, sodium decyl sulfate, sodium tetradecyl sulfate, sodium heptadecyl sulfate, sodium eicosyl sulfate, nicotine sulfate, sodium taurocholic sulfate, dimethyl sulfoxide, sodium tridecyl phosphate; decyldimethyl ammonio propane sulfonate, chembetaine oleyl, myristyldimethyl ammonio propane sulfonate; benzyl pyridinium chloride, dodecyl pyridinium chloride, cetyl pyridinium chloride, benzyldimethyl dodecyl ammonium chloride, benzyldimethyl dodecyl ammonium chloride, benzyldimethyl myristyl ammonium chloride, benzyldimethyl stearyl ammonium chloride, octyltrimethylammonium bromide, dodecyltrimethylammonium bromide, Polysorbate 20, Polysorbate 40, Polysorbate 60, Polysorbate 80, and benzalkonium chlorides;
(ii) a terpene selected from: limonene, cymene, pinene, camphor, menthol, comphone, phellandrine, sabinene, terpinene, borneol, cineole, geraniol, linalol, pipertone, terpineol, eugenol, eugenol acetate, safrole, benzyl benzoate, humulene, beta-caryophylene, eucakytol, hexanoic acid, octanoic acid, decanoic acid, undecanoic acid, dodecanoic acid, tridecanoic acid, myristic acid, palmitic acid, stearic acid, oleic acid, linoleic acid, linolenic acid, cholic acid; ethyl undecanoate, methyl laurate, methyl myristate, isopropyl myristate, isopropyl palmitate, palmityl palmitate, diethyl sebaccate, glyceryl monolaurate, glyceryl monooleate, or ethylpiperazine carboxylate;
(iii) and an anesthetic selected from: bupivicaine, tetracaine, procaine, proparacaine, propoxycaine, dimethocaine, cyclomethycaine, chloroprocaine, benzocaine, lidocaine, prilocaine, levobupivicaine, ropivacaine, dibucaine, articaine, carticaine, etidocaine, mepivacaine, piperocaine, and trimecaine.

In some embodiments, permeation enhancer is a combination of compounds from at least two of the groups (i) to (iii), listed above, and includes sodium octyl sulfate, sodium dodecyl sulfate, octyl trimethylammonium bromide, dodecyl trimethylammonium bromide, Polysorbate 20, or Polysorbate 80 as a surfactant. In some embodiments, permeation enhancer is a combination of compounds from at least two of the groups (i) to (iii), listed above, and includes sodium dodecyl sulfate as a surfactant. In some embodiments, permeation enhancer is a combination of compounds from at least two of the groups (i) to (iii) listed above, and includes limonene as a surfactant. In some embodiments, permeation enhancer is a combination of compounds from at least two of the groups (i) to (iii), listed above, and includes bupivacaine as an anesthetic. In some embodiments, permeation enhancer is a combination of compounds from at least two of the groups (i) to (iii), listed above, and includes sodium dodecyl sulfate, octyl trimethylammonium bromide, dodecyl trimethylammonium bromide, Polysorbate 20, or Polysorbate 80 as a surfactant, and limonene as a terpene. In some embodiments, permeation enhancer is a combination of compounds from at least two of the groups (i) to (iii), listed above, and includes sodium dodecyl sulfate as a surfactant, and limonene as a terpene. In some embodiments, permeation enhancer is a combination of compounds from at least two of the groups (i) to (iii), listed above, and includes sodium dodecyl sulfate, octyl trimethylammonium bromide, dodecyl trimethylammonium bromide, Polysorbate 20, or Polysorbate 80 as a surfactant, and bupivacaine as an anesthetic. In some embodiments, permeation enhancer is a combination of compounds from at least two of the groups (i) to (iii), listed above, and includes sodium dodecyl sulfate as a surfactant, and bupivacaine as an anesthetic. In some embodiments, permeation enhancer is a combination of compounds from at least two of the groups (i) to (iii), listed above, and includes limonene as a terpene, and bupivacaine as an anesthetic. In some embodiments, permeation enhancer is a combination of compounds from at least two of the groups (i) to (iii), listed above, and includes sodium dodecyl sulfate, octyl trimethylammonium bromide, dodecyl trimethylammonium bromide, Polysorbate 20, or Polysorbate 80 as a surfactant, limonene as a terpene, and bupivacaine as an anesthetic. In some embodiments, permeation enhancer is a combination of compounds from at least two of the groups (i) to (iii), listed above, and includes sodium dodecyl sulfate as a surfactant, limonene as a terpene, and bupivacaine as an anesthetic.

In certain embodiments, the percent weight of permeation enhancer in the composition is between about 0.1% to about 1%, between about 1% to about 3%, or between about 3% to about 10%. In certain embodiments, the percent weight of permeation enhancer in the composition is between about 0.1% to about 1%. In certain embodiments, the percent weight of permeation enhancer in the composition is between about 1% to about 3%. In certain embodiments, the percent weight of permeation enhancer in the composition is between about 0.1% to about 10%. In certain embodiments, the percent weight of permeation enhancer in the composition is between 0.1% to about 1%, between about 1% to about 2%, between about 2% to about 3%, between about 3% to about 4%, between about 4% to about 5%, between about 5% to about 6%, between about 6% to about 7%, between about 7% to about 8%, between about 8% to about 9%, or between about 9% to about 10%.

In some embodiments, the percent weight of sodium dodecyl sulfate in the composition is between about 0.1% to about 3%. In some embodiments, the percent weight in the composition of sodium dodecyl sulfate is about 1%. In some embodiments, the percent weight of bupivicaine in the composition is between about 0.1 to about 3%. In some embodiments, the percent weight in the composition of bupivicaine is about 0.5%. In some embodiments, the percent weight of limonene in the composition is between about 0.1% to about 3%. In some embodiments, the percent weight in the composition of limonene is about 0.5%.

Therapeutic Agents

A therapeutic agent can be any agent used to treat any ear disease, or symptom of an ear disease. Therapeutic agents may include antimicrobial agents. Therapeutic agents may include, but are not limited to, antimicrobial agents, antibiotics, anesthetics, anti-inflammatories, analgesics, anti-fibrotics, anti-sclerotics, and anticoagulants. Therapeutic agents may include, but are not limited to, antibiotics, anesthetics, anti-inflammatories, analgesics, anti-fibrotics, anti-sclerotics, and anticoagulants. In certain embodiments, the therapeutic agent is an antimicrobial agent. In certain embodiments, the therapeutic agent is an antibiotic agent. In certain embodiments, the therapeutic agent is an anesthetic agent. In certain embodiments, the therapeutic agent is an anti-inflammatory agent. In certain embodiments, the therapeutic agent is an analgesic agent. In certain embodiments, the therapeutic agent is an anti-fibrotic agent. In certain embodiments, the therapeutic agent is an anti-sclerotic agent. In certain embodiments, the therapeutic agent is an anticoagulant agent.

In various aspects, the therapeutic agents may comprise between about 0.01 percent to about 10 percent of the composition. In various embodiments, the therapeutic agents may comprise between about 0.01 percent to about 1 percent of the composition, comprise between about 1 percent to about 2 percent of the composition, comprise between about 2 percent to about 3 percent of the composition, comprise between about 3 percent to about 4 percent of the composition, comprise between about 4 percent to about 5 percent of the composition, comprise between about 5 percent to about 6 percent of the composition, comprise between about 6 percent to about 7 percent of the composition, comprise between about 7 percent to about 8 percent of the composition, comprise between about 8 percent to about 9 percent of the composition, or comprise between about 9 percent to about 10 percent of the composition.

The exact amount required will vary from subject to subject, depending on the species, age, and general condition of the subject, the particular compound, its mode of administration, its mode of activity, condition being treated, and the like. The compositions described herein are preferably formulated in dosage unit form for ease of administration and uniformity of dosage. It will be understood, however, that the total daily usage of the compounds and compositions will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In certain embodiments, the therapeutic agent is an antimicrobial agent. In certain embodiments, the therapeutic agent is an antibiotic. Any antibiotic may be used in the inventive system. In certain embodiments the antibiotic is approved for use in humans or other animals. In certain embodiments the antibiotic is approved for use by the U.S. Food & Drug Administration. In certain embodiments, the antibiotic may be selected from the group consisting of cephalosporins, quinolones, polypeptides, macrolides, penicillins, and sulfonamides. Exemplary antibiotics may include, but are not limited to, ciprofloxacin, cefuroxime, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, enoxacin, gatifloxacin, levofloxacin, lomefloxacin, moxifloxacin, norfloxacin, ofloxacin, trovafloxacin, bacitracin, colistin, polymyxin B, azithromycin, clarithromycin, dirithromycin, erythromycin, roxithromycin, troleandomycin, telithromycin, spectinomycin, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin, mafenide, sulfacetamide, sulfamethizole, sulfasalazine, sulfisoxazole, trimethoprim, and trimethoprim-sulfamethoxazole.

In certain embodiments, the antibiotic is a quinolone. In certain embodiments, the antibiotic is a carbapenem. In certain embodiments, the antibiotic is In certain embodiments, the antibiotic is amoxicillin, azithromicin, cefuroxime, ceftriaxone, trimethoprim, levofloxacin, moxifloxacin, meropenem, or ciprofloxacin. In some embodiments, the antibiotic is ciprofloxacin. In some embodiments, the antibiotic is ciprofloxacin and pharmaceutically acceptable salts thereof. In some embodiments, the antibiotic is ciprofloxacin hydrochloride. In some embodiments, the antibiotic is levofloxacin.

Exemplary antibiotics, include, but are not limited to: Abamectin, Actinomycin (e.g., Actinomycin A, Actinomycin C, Actinomycin D, Aurantin), Alatrofloxacin mesylate, Amikacin sulfate, Aminosalicylic acid, Anthracyclines (e.g., Aclarubicin, Adriamycin, Doxorubicin, Epirubicin, Idarubicin), Antimycin (e.g., Antimycin A), Avermectin, BAL 30072, Bacitracin, Bleomycin, Cephalosporins (e.g., 7-Aminocephalosporanic acid, 7-Aminodeacetoxycephalo sporanic acid, Cefaclor, Cefadroxil, Cefamandole, Cefazolin, Cefepime, Cefixime, Cefmenoxime, Cefmetazole, Cefoperazone, Cefotaxime, Cefotetan, Cefotiam, Cefoxitin, Cefpirome, Cefpodoxime proxetil, Cefsulodin, Cefsulodin sodium, Ceftazidime, Ceftizoxime, Ceftriaxone, Cefuroxime, Cephalexin, Cephaloridine, Cephalosporin C, Cephalothin, Cephalothin sodium, Cephapirin, Cephradine), Ciprofloxacin, Enrofloxacin, Clarithromycin, Clavulanic acid, Clindamycin, Colicin, Cyclosporin (e.g. Cyclosporin A), Dalfopristin/quinupristin, Daunorubicin, Doxorubicin, Epirubicin, GSK 1322322, Geneticin, Gentamicin, Gentamicin sulfate, Gramicidin (e.g. Gramicidin A), Grepafloxacin hydrochloride, Ivermectin, Kanamycin (e.g. Kanamycin A), Lasalocid, Leucomycin, Levofloxacin, Linezolid, Lomefloxacin, Lovastatin, MK 7655, Meropenem, Mevastatin, Mithramycin, Mitomycin, Monomycin, Natamycin, Neocarzinostatin, Neomycin (e.g. Neomycin sulfate), Nystatin, Oligomycin, Olivomycin, Pefloxacin, Penicillin (e.g. 6-Aminopenicillanic acid, Amoxicillin, Amoxicillin-clavulanic acid, Ampicillin, Ampicillin sodium, Azlocillin, Carbenicillin, Cefoxitin, Cephaloridine, Cloxacillin, Dicloxacillin, Mecillinam, Methicillin, Mezlocillin, Nafcillin, Oxacillin, Penicillin G, Penicillin G potassium, Penicillin G procaine, Penicillin G sodium, Penicillin V, Piperacillin, Piperacillin-tazobactam, Sulbactam, Tazobactam, Ticarcillin), Phleomycin, Polymyxin (e.g., Colistin, Polymyxin B), Pyocin (e.g. Pyocin R), RPX 7009, Rapamycin, Ristocetin, Salinomycin, Sparfloxacin, Spectinomycin, Spiramycin, Streptogramin, Streptovaricin, Tedizolid phosphate, Teicoplanin, Telithromycin, Tetracyclines (e.g. Achromycin V, Demeclocycline, Doxycycline, Doxycycline monohydrate, Minocycline, Oxytetracycline, Oxytetracycline hydrochloride Tetracycline, Tetracycline hydrochloride), Trichostatin A, Trovafloxacin, Tunicamycin, Tyrocidine, Valinomycin, (−)-Florfenicol, Acetylsulfisoxazole, Actinonin, Amikacin sulfate, Benzethonium chloride, Cetrimide, Chelerythrine, Chlorhexidine (e.g., Chlorhexidine gluconate), Chlorhexidine acetate, Chlorhexidine gluconate, Chlorothalonil, Co-Trimoxazole, Dichlorophene, Didecyldimethylammonium chloride, Dihydrostreptomycin, Enoxacin, Ethambutol, Fleroxacin, Furazolidone, Methylisothiazolinone, Monolaurin, Oxolinic acid, Povidone-iodine, Spirocheticides (e.g., Arsphenamine, Neoarsphenamine), Sulfaquinoxaline, Thiamphenicol, Tinidazole, Triclosan, Trovafloxacin, Tuberculostatics (e.g., 4-Aminosalicylic acid, AZD 5847, Aminosalicylic acid, Ethionamide), Vidarabine, Zinc pyrithione, and Zirconium phosphate.

In certain embodiments, the therapeutic agent is an Food and Drug Administration (FDA) approved drug for treating infections or infectious diseases. Exemplary FDA approved agents include, but are not limited to: Avycaz (ceftazidime-avibactam), Cresemba (isavuconazonium sulfate), Evotaz (atazanavir and cobicistat, Prezcobix (darunavir and cobicistat), Dalvance (dalbavancin), Harvoni (ledipasvir and sofosbuvir), Impavido (miltefosine), Jublia (efinaconazole), Kerydin (tavaborole), Metronidazole, Orbactiv (oritavancin), Rapivab (peramivir injection), Sivextro (tedizolid phosphate), Triumeq (abacavir, dolutegravir, and lamivudine), Viekira Pak (ombitasvir, paritaprevir, ritonavir and dasabuvir), Xtoro (finafloxacin), Zerbaxa (ceftolozane+tazobactam), Luzu (luliconazole), Olysio (simeprevir), Sitavig (acyclovir), Sovaldi (sofosbuvir), Abthrax (raxibacumab), Afinitor (everolimus), Cystaran (cysteamine hydrochloride), Dymista (azelastine hydrochloride and fluticasone propionate), Fulyzaq (crofelemer), Jetrea (ocriplasmin), Linzess (linaclotide), Qnasl (beclomethasone dipropionate) nasal aerosol, Sirturo (bedaquiline), Sklice (ivermectin), Stribild (elvitegravir, cobicistat, emtricitabine, tenofovir disoproxil fumarate), Tudorza Pressair (aclidinium bromide inhalation powder), Complera (emtricitabine/rilpivirine/tenofovir disoproxil fumarate), Dificid (fidaxomicin), Edurant (rilpivirine), Eylea (aflibercept), Firazyr (icatibant), Gralise (gabapentin), Incivek (telaprevir), Victrelis (boceprevir), Egrifta (tesamorelin), Teflaro (ceftaroline fosamil), Zymaxid (gatifloxacin), Bepreve (bepotastine besilate), Vibativ (telavancin), Aptivus (tipranavir), Astepro (azelastine hydrochloride nasal spray), Intelence (etravirine), Patanase (olopatadine hydrochloride), Viread (tenofovir disoproxil fumarate), Isentress (raltegravir), Selzentry (maraviroc), Veramyst (fluticasone furoate), Xyzal (levocetirizine dihydrochloride), Eraxis (anidulafungin), Noxafil (posaconazole), Prezista (darunavir), Tyzeka (telbivudine), Veregen (kunecatechins), Baraclude (entecavir), Fuzeon (enfuvirtide), Lexiva (fosamprenavir calcium), Reyataz (atazanavir sulfate), Clarinex, Hepsera (adefovir dipivoxil), Pegasys (peginterferon alfa-2a), Sustiva, Vfend (voriconazole), Zelnorm (tegaserod maleate), Avelox (moxifloxacin hydrochloride), Cancidas, Invanz, Peg-Intron (peginterferon alfa-2b), Rebetol (ribavirin), Spectracef, Tavist (clemastine fumarate), Twinrix, Valcyte (valganciclovir HCl), Xigris (drotrecogin alfa), ABREVA (docosanol), Cefazolin, Kaletra, Lamisil (terbinafine hydrochloride), Lotrisone (clotrimazole/betamethasone diproprionate), Lotronex (alosetron HCL), Trizivir (abacavir sulfate, lamivudine, zidovudine AZT), Synercid, Synagis, Viroptic, Aldara (imiquimod), Bactroban, Ceftin (cefuroxime axetil), Combivir, Condylox (pokofilox), Famvir (famciclovir), Floxin, Fortovase, INFERGEN (interferon alfacon-1), Intron A (interferon alfa-2b, recombinant), Mentax (butenafine HCl), Norvir (ritonavir), Omnicef, Rescriptor (delavirdine mesylate), Taxol, Timentin, Trovan, VIRACEPT (nelfinavir mesylate), Zerit (stavudine), AK-Con-A (naphazoline ophthalmic), Allegra (fexofenadine hydrochloride), Astelin nasal spray, Atrovent (ipratropium bromide), Augmentin (amoxicillin/clavulanate), Crixivan (Indinavir sulfate), Elmiron (pentosan polysulfate sodium), Havrix, Leukine (sargramostim), Merrem (meropenem), Nasacort AQ (triamcinolone acetonide), Tavist (clemastine fumarate), Vancenase AQ, Videx (didanosine), Viramune (nevirapine), Zithromax (azithromycin), Cedax (ceftibuten), Clarithromycin (Biaxin), Epivir (lamivudine), Invirase (saquinavir), Valtrex (valacyclovir HCl), Zyrtec (cetirizine HCl), Acyclovir, Penicillin (penicillin g potassium), Cubicin (Daptomycin), Factive (Gemifloxacin), Albenza (albendazole), Alinia (nitazoxanide), Altabax (retapamulin), AzaSite (azithromycin), Besivance (besifloxacin ophthalmic suspension), Biaxin XL (clarithromycin extended-release), Cayston (aztreonam), Cleocin (clindamycin phosphate), Doribax (doripenem), Dynabac, Flagyl ER, Ketek (telithromycin), Moxatag (amoxicillin), Rapamune (sirolimus), Restasis (cyclosporine), Tindamax (tinidazole), Tygacil (tigecycline), and Xifaxan (rifaximin).

In certain embodiments, the therapeutic agent is an anesthetic. Any anesthetic may be used in the inventive system. In certain embodiments the anesthetic is approved for use in humans or other animals. In certain embodiments the anesthetic is approved for use by the U.S. Food & Drug Administration. Exemplary anesthetics may include, but are not limited to bupivicaine, tetracaine, procaine, proparacaine, propoxycaine, dimethocaine, cyclomethycaine, chloroprocaine, benzocaine, lidocaine, prilocain, levobupivicaine, ropivacaine, dibucaine, articaine, carticaine, etidocaine, mepivacaine, piperocaine, and trimecaine. In certain embodiments, the anesthetic is bupivicaine.

In certain embodiments, the therapeutic agent is an anti-inflammatory agent. The anti-inflammatory agent may be a non-steroidal anti-inflammatory agent or a steroidal anti-inflammatory agent. In certain embodiments, the therapeutic agent is a steroidal anti-inflammatory agent. In certain embodiments, the therapeutic agent is a steroid. Exemplary anti-inflammatory agents may include, but are not limited to, acetylsalicylic acid, amoxiprin, benorylate/benorilate, choline magnesium salicylate, diflunisal, ethenzamide, faislamine, methyl salicylate, magnesium salicylate, salicyl salicylate, salicylamide, diclofenac, aceclofenac, acemetacin, alclofenac, bromfenac, etodolac, indometacin, nabumetone, oxametacin, proglumetacin, sulindac, tolmetin, ibuprofen, alminoprofen, benoxaprofen, carprofen, dexibuprofen, dexketoprofen, fenbufen, fenoprofen, flunoxaprofen, flurbiprofen, ibuproxam, indoprofen, ketoprofen, ketorolac, loxoprofen, naproxen, oxaprozin, pirprofen, suprofen, tiaprofenic acid, mefenamic acid, flufenamic acid, meclofenamic acid, tolfenamic acid, phenylbutazone, ampyrone, azapropazone, clofezone, kebuzone, metamizole, mofebutazone, oxyphenbutazone,phenazone, phenylbutazone, sulfinpyrazone, piroxicam, droxicam, lornoxicam, meloxicam, tenoxicam, hydrocortisone, cortisone acetate, prednisone, prednisolone, methylprednisolone, dexamethasone, betamethasone, triamcinolone, beclometasone, fludrocortisone acetate, deoxycorticosterone acetate, and aldosterone.

In various embodiments, combinations of various permeation enhancers and therapeutic agents have been observed to have a synergistic and heightened efficacy. In various aspects, such combinations may include, but are not limited to, ciprofloxacin and limonene. In various aspects, such combinations may include, but are not limited to, ciprofloxacin and sodium dodecyl sulfate. In various aspects such combinations may include, but are not limited to, sodium dodecyl sulfate, limonene, bupivacaine, and ciprofloxacin. In various aspects, such combination may include, but are not limited to, sodium dodecyl sulfate, limonene and ciprofloxacin.

In another aspect, provided herein are pharmaceutical compositions comprising at least one of the compounds as described herein, or a pharmaceutically acceptable derivative thereof. In certain embodiments, the pharmaceutical composition includes a combination of therapeutic agents. In certain embodiments, the composition includes an antibiotic and an additional therapeutic agent. In certain embodiments, the composition includes an antibiotic agent and an anti-inflammatory agent. In other embodiments, the composition includes an antibiotic agent and an anesthetic agent. In certain embodiments, the composition includes more than one antibiotic agent.

In certain embodiments, the additional therapeutic agent is an anti-inflammatory agent (e.g., a steroid). In certain embodiments, the first therapeutic agent is an antibiotic and the additional therapeutic agent is an anti-inflammatory agent. In certain embodiments, the first therapeutic agent is an antibiotic and the additional therapeutic agent is a steroid. Steroids include, but are not limited to, cortisol, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, halometasone, alclometasone dipropionate, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, ciclesonide, and prednicarbate. In some embodiments, the additional anti-inflammatory agent is dexamethasone.

In certain embodiments, the additional therapeutic agent is a β-lactamase inhibitor. In certain embodiments, the first therapeutic agent is an antibiotic (e.g., a β-lactam) and the additional therapeutic agent is a β-lactamase inhibitor. β-Lactamase inhibitors include, but are not limited to, avibactam, clavulanic acid, tazobactam, and sulbactam. The β-lactamase inhibitor may be particularly useful in compositions comprising a β-lactam antibiotic. The β-lactamase inhibitor may increase the efficacy of a β-lactam antibiotic or allow for the β-lactam antibiotic to be present in the composition in a lower concentration than for compositions not containing a β-lactamase inhibitor.

Furthermore, after formulation with an appropriate pharmaceutically acceptable carrier in a desired dosage, the pharmaceutical compositions can be administered to humans and other animals.

Dosage forms include, but are not limited to, pharmaceutically acceptable emulsions, microemulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the compositions can also include adjuvants such as wetting agents, emulsifying and suspending agents, and perfuming agents. In certain embodiments, the composition comprises a solubilizing agents such an Cremophor, alcohols, oils, modified oils, glycols, polysorbates, cyclodextrins, polymers, and combinations thereof.

It will also be appreciated that the compositions described herein can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

In certain embodiments, the composition comprises a diagnostic agent. In some embodiments, the diagnostic agent is a X-ray contrast agent. In some embodiments, the diagnostic agent comprises a radioactive isotope. In some embodiments, the diagnostic agent is a dye.

Other Additives

In certain embodiments, the composition comprises one or more additional additives. For example, an additional additive may be a diluent, binding agent, preservative, buffering agent, lubricating agent, perfuming agent, antiseptic agent, or oil.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent. In certain embodiments, the preservative is benzalkonium chloride.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof.

The composition may comprise water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof.

Formulations suitable for administration (e.g., to the ear canal) include, but are not limited to, liquid and/or semi-liquid preparations such as liniments, lotions, oil-in-water, and/or water-in-oil emulsions such as creams, ointments, and/or pastes, and/or solutions and/or suspensions. Topically administrable formulations may, for example, comprise from about 1% to about 10% (w/w) therapeutic agent, although the concentration of the therapeutic agent can be as high as the solubility limit of the active ingredient in the solvent.

Polysaccharide Matrix Forming Agents

Also provided herein are compositions comprising a polysaccharide based matrix forming agent. The matrix forming agent may form a hydrogel by crosslinking of a first polysaccharide derivative and a second polysaccharide derivative, wherein the first and second polysaccharides are different. For example, the first polysaccharide may be an hyaluronic acid (HA) derivative comprising a first cross-linkable functional group, and the second polysaccharide may be a cellulose derivative comprising a second cross-linkable functional group. To give but another example, the first polysaccharide is an HA derivative comprising a first cross-linkable functional group, and the second polysaccharide is a dextran derivative comprising a second cross-linkable functional group. In certain embodiments, the first and second cross-linkable functional groups are selected from the group consisting of amines, amides, aldehydes, esters, ketones, hydroxyls, hydrazines, hydrazides, maleimides, or sulfhydryls. In some embodiments, the first functional group is an amine, and the second functional group is an aldehyde. In some embodiments, the first functional group is an amine, and the second functional group is a ketone. In some embodiments, the first functional group is an amine, hydroxyl, or sulfhydryl, and the second functional group is an ester. In some embodiments, the first functional group is a maleimide, and the second functional group is a sulfhydryl. In some embodiments, the first functional group is a hydrazine or hydrazide, and the second functional group is an aldehyde or ketone. In some embodiments, the first functional group is a hydrazide, and the second functional group is an aldehyde.

The hydrogels may formed by crosslinking a first polysaccharide derivative and a second polysaccharide derivative, wherein the first and second polysaccharides are the same and wherein the first polysaccharide derivative comprises a first cross-linkable functional group, and the second polysaccharide derivative comprises a second cross-linkable functional group, wherein the first and second cross-linkable functional groups are capable of crosslinking to one another. The polysaccharide may be, e.g., glycosaminoglycan, HA, cellulose, dextran, or a derivative of either.

HA, also referred to as hyaluronan or hyaluronate, is an unbranched polysaccharide containing repeating disaccharide subunits composed of N-acetyl-D glucosamine and D-glucuronic acid. (See Laurent, T. C. (Ed)., *Chemistry, Biology and Medical Applications of Hyaluronan and Its*

*Derivatives*, London: Portland Press, 1998). HA also refers to any of its salts, e.g., sodium hyaluronate, potassium hyaluronate, magnesium hyaluronate, calcium hyaluronate, etc. The term "HA derivative" refers to HA that has been chemically modified from the native form.

Cellulose is a linear polymer of β-D-glucopyranose units joined to one another (Kamide, Cellulose And Cellulose Derivatives: Molecular Characterization and Its Applications, Elsevier, 2005). The term "cellulose derivative" refers to cellulose that has been chemically modified from this native form. In certain embodiments, the polysaccharide is a cellulose derivative such as methylcellulose (MC), carboxymethylcellulose (CMC), hydroxymethylcellulose (HMC), hydroxypropylcellulose (HPC), hydroxyethyl cellulose (HEC), or hydroxypropyl methylcellulose (HPMC), in which one or more of the OH groups is replaced by OR, wherein R represents any of a variety of moieties.

Dextran is a complex, branched polysaccharide. Dextran includes many glucose moieties joined together via α1→6 glycosidic linkages to form straight chains. Branches typically begin from α1→3 linkages, but they may also begin from α1→2 or α1→4 linkages. The term "dextran derivative" refers to dextran that has been chemically modified from this native form. In certain embodiments, the polysaccharide is a dextran derivative, in which one or more of the OH groups is replaced by OR, wherein R represents any of a variety of moieties.

Modifications to the polysaccharides may include the addition or creation of new functional groups (e.g., amine, amide, aldehyde, ester, ketone, hydroxy, hydrazine, hydrazide, maleimide, sulfhydryl, etc.), in which case the polysaccharide is said to be "functionalized." The proportion of sugar subunits that are modified can vary, and the degree of modification can be selected in order to control properties such as gelation time, half-life, stiffness, etc. Certain modifications retain the native sugar backbone structure while other modifications open at least some of the sugar rings. In some embodiments, the polysaccharide derivative is an aldehyde-containing derivative in which polysaccharide has been treated with periodate.

It will be appreciated that in any of the polysaccharide derivatives, only a fraction of the sugar moieties in the polysaccharide are modified. The extent of modification can vary. For example, in certain embodiments, between 5% and 99-100% of the relevant sugar moieties (e.g., glucuronic acid moieties in the case of the HA) are modified. In certain embodiments, between 10% and 75% of the relevant sugar moieties are modified. The extent of modification can be controlled by a variety of methods. For example, the temperature, pH, and time during which the reaction is allowed to proceed can be varied, as can the concentration of the reagents (e.g., carbodiimide, amide, dihydrazide, etc.). To achieve a high degree of modification an excess of the modifying agent(s), e.g., dihydrazide and/or carboiimide, may be used. For example, in one embodiment a 10-100 fold excess of dihydradize is added to a solution comprising HA, and/or a 2-100 fold excess of carbodiimide reagent is then added to the reaction mixture. In certain embodiments, values for these parameters are selected so as to achieve a relatively high degree of modification, e.g., between 50% and 99-100% of the relevant sugar moieties are modified. For example, between 50% and 80% of the relevant sugar moieties may be modified. However, the degree of modification is kept low enough so that the solution will remain in a suitably fluid state rather than becoming too viscous for easy manipulation and syringibility. In certain embodiments, between 10% and 30%, or between 30% and 50% of the relevant sugar moieties are modified.

A variety of polysaccharide derivatives may be used. In certain embodiments, at least one of the polysaccharide derivatives is a derivative of HA. In certain embodiments, both of the polysaccharide derivatives are derivatives of HA. In certain embodiments, the matrix forming agent is separated into a first and second polysaccharide derivative which form a matrix or gel upon mixing. In some embodiments, the first polysaccharide derivative comprises a first type of cross-linkable functional group, and the second polysaccharide derivative comprises a second type of cross-linkable functional group, wherein the two types of cross-linkable functional groups form cross-links between the two polysaccharide derivative upon mixing. The polysaccharide derivatives may be kept separate as two components of the compositions, which are mixed during administration, e.g., during application to the ear canal with a double barrel syringe. In certain embodiments, the polysaccharide is one that is not specifically degraded by an enzyme endogenous to human beings.

In certain embodiments, at least one of the polysaccharide derivatives is a derivative of cellulose. For example, in certain embodiments, the first polysaccharide derivative is a derivative of HA, and the second polysaccharide derivative is a derivative of cellulose.

In certain embodiments, at least one of the polysaccharide derivatives is a derivative of dextran. For example, in certain embodiments, the first polysaccharide derivative is a derivative of HA, and the second polysaccharide derivative is a derivative of dextran.

The first and second polysaccharide derivatives comprise first and second functional groups, respectively, that react with one another to form covalent bonds that join the first and second polysaccharide derivatives to one another. The solutions are thus applied as liquids and are contacted with one another and optionally mixed together either immediately before or at the time of administration or contact one another following administration. Formation of a sufficient number of crosslinks causes a transition from a liquid to a semi-solid or gel-like state.

In certain embodiments, a polysaccharide derivative comprising at least two different cross-linkable functional groups is employed, wherein the cross-linkable functional groups react with one another to form crosslinks under physiological conditions. The cross-linkable functional groups may be selected so that they substantially do not react with one another until exposed to physiological conditions of pH, temperature, and/or salt concentration. Thus it will be appreciated that matrix forming agent does not require two distinguishable HA derivatives but may instead employ a single species that comprises multiple different functional groups capable of becoming crosslinked.

A variety of different polysaccharide derivatives (e.g., HA derivatives) are of use in the composition. In certain embodiments, the first and second cross-linkable functional groups react in sufficient amounts and with sufficient rapidity so as to allow hydrogel formation within a time frame following contact of the solutions with one another. In certain embodiments, the hydrogel forms within between 1-3 seconds and 5 minutes, between 1-3 seconds and 3 minutes, between 1-3 seconds and 60 seconds, between 1-3 seconds and 30 seconds, or between 1-3 seconds and 15 seconds, following contact of the solutions with one another, e.g., following administration. Typically the solutions are mixed together either immediately before or concurrently with their administration to a site within the body (e.g., ear canal). For example, the solutions may be administered using a multiple barrel injection device, e.g., a multiple barrel syringe, wherein each solution is contained in a separate receptacle or barrel prior to administration. The solutions may contact each other during the administration process and/or thereafter. Preferably the derivatives become crosslinked under physiological conditions, e.g., in an aqueous environment at a pH between 6.0 and 8.0.

A variety of cross-linkable polysaccharide derivatives and methods for forming them may be employed. In certain embodiments, the polysaccharide derivatives become crosslinked to one another without needing a separate crosslinking agent, e.g., the first and second derivatives comprise functional groups that react with one another to form a covalent bond. In certain embodiments, the polysaccharide derivatives react with one another to produce a nontoxic, biocompatible product, e.g., water. In certain embodiments, neither of the polysaccharide derivatives is modified by using a crosslinking agent. In certain embodiments, the polysaccharide derivatives become crosslinked without requiring light.

It will be appreciated that in any of the above embodiments, only a fraction of the available functional groups on the first and second polysaccharide derivatives will become crosslinked. The crosslinking density can be controlled, e.g., by appropriately selecting the molecular weights of the polysaccharide derivatives. Exemplary crosslinking densities range from about $1 \times 10^6$ to about $1 \times 10^8$ mol/cm$^3$. In certain embodiments, the crosslinking density ranges from $3$-$50 \times 10^7$ mol/cm$^3$.

Figure 8:
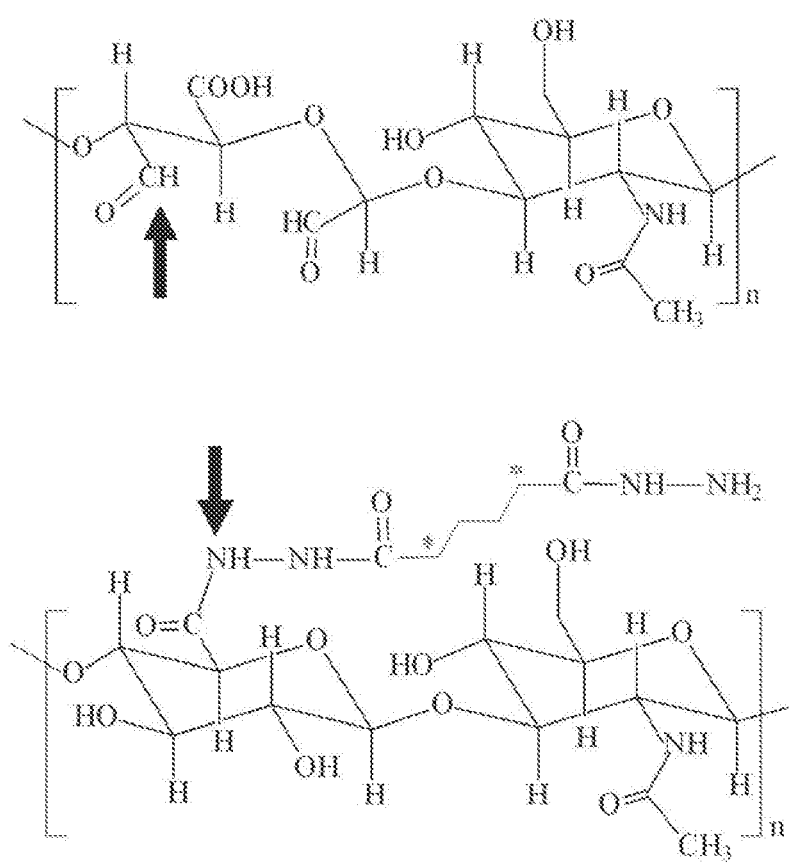
FIG. 8. Cross-linkable hyaluronic acids (HA) derivatives. Top: HA aldehyde derivative. Bottom: HA hydrazide derivative.

Polysaccharide derivatives functionalized as described above can be crosslinked by allowing derivatives comprising different functional groups to react with one another. For example, (i) a first polysaccharide derivative comprising an aldehyde can react with a second polysaccharide derivative comprising an amine; (ii) a first polysaccharide derivative comprising an active ester such as an NHS ester can react with a second polysaccharide derivative comprising an amine; (iv) a first polysaccharide derivative comprising a hydrazide can react with a second HA derivative comprising an aldehyde, etc. In one embodiment of particular interest the first solution contains a polysaccharide derivative functionalized with a dihydrazide, and the second solution contains polysaccharide oxidized to form aldehyde groups (See, e.g., FIG. 8).

In certain embodiments, the composition comprises a matrix forming agent comprising a polysaccharide derivative in solution, wherein the concentration of the polysaccharide derivative is greater than 5 mg/ml, e.g., up to 150 mg/ml. In certain embodiments, the concentration of the polysaccharide derivative is greater than 10 mg/ml. In other embodiments, the concentration of the polysaccharide derivative is greater than 15 mg/ml, greater than 20 mg/ml, or greater than 25 mg/ml. Herein, a polysaccharide derivative greater than 25 mg/ml is referred to as a "high concentration." The solution preferably has a sufficiently low viscosity such that it can be readily manipulated, e.g., so that easy syringibility exists.

In certain embodiments, at least one of the polysaccharide derivatives suitable for in situ crosslinking to form a gel, comprises a portion that comprises a non-polysaccharide polymer, e.g., the polysaccharide derivative comprises a polysaccharide or derivative thereof covalently attached to one or more non-polysaccharide polymers. Non-polysaccharide means that the polymer contains less than 1% sugar monomers by weight, number, or both, e.g., the polymer contains essentially no sugars. In certain embodiments, the non-polysaccharide portion comprises between 1% and 10%-90% of the polymer by weight and/or between 1% and 10%-90% of the monomers are non-sugar monomers. The attachment may occur at any position in the polysaccharide chain, e.g., either of the ends of the chain or at one of the internally located sugar moieties resulting in either a linear or branched structure. The non-polysaccharide polymer can be any of a variety of polymers, e.g., any non-polysaccharide polymer capable of serving as a hydrogel precursor when covalently attached to a polysaccharide derivative.

In certain embodiments, the matrix forming agent comprises first and second crosslinkable hydrogel precursors, wherein one of the hydrogel precursors comprises or consists of a polysaccharide derivative such as an HA, cellulose, or dextran derivative and the other hydrogel precursor comprises or consists of a non-polysaccharide polymer (i.e., less than 1% of the polymer by weight, or less than 1% of the monomers are sugars). Exemplary non-polysaccharide polymers capable of becoming crosslinked to a polysaccharide derivative to form a hydrogel include but are not limited to polyethers such as polyethylene glycol (PEG) or polypropylene glycol (PPG), polyethylene oxides (PEO), polyvinyl alcohol (PVA), polyvinyl pyrrolidone (PVP), polypeptides such as gelatin, chitosan, or poly(-glutamic acid), and derivatives of any of these, or conjugates, blends, or composites comprising any of these.

While polysaccharide derivatives are described in detail, in yet other embodiments, the hydrogel is formed by crosslinking two non-polysaccharide polymers in situ. in a hydrogel that inhibits adhesions. Each of the non-polysaccharide polymers comprises a functional group, wherein the functional groups are capable of reacting with one another to form covalent bonds. Suitable functional groups are those described above for crosslinking of polysaccharide derivatives. Exemplary non-polysaccharide polymers include those described above that contain or may be modified to contain suitable functional groups for crosslinking.

Matrix Forming Agents (and Compositions Thereof)

In one aspect, provided herein are matrix forming agents described herein. In certain embodiments, the matrix forming agent comprises a polymer. In certain embodiments, the matrix forming agent comprises polymers that gel via electrostatic interactions. In certain embodiments, the matrix forming agent comprises polymers that display shear thinning. In certain embodiments, the matrix forming agent comprises rheological blends of polymers. In certain embodiments, rheological polymer blends comprise two different polymers wherein the viscoelastic properties of the rheological polymer blends are more gel-like than those of the constituent polymers measured individually The polymer may be a block copolymer. In certain embodiments, the polymer is not a block copolymer. In certain embodiments, the polymer is a thermosensitive polymer. In certain embodiments, the polymer is poly(N-isopropylacrylamide) (NIPAAm). In certain embodiments, the matrix forming agent or combination of matrix forming agents is not modified by a polyphosphoester. In certain embodiments, the matrix forming agent or combination of matrix forming agents is modified by a polyphosphoester. In certain embodiments, the matrix forming agent or combination of matrix forming agents comprises a polymer of Formula:

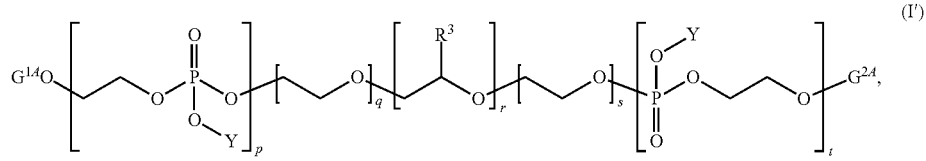

(I')

wherein each occurrence of Y is independently —R¹ or -L²R²;

each occurrence of R¹ is independently hydrogen, optionally substituted alkyl, optionally substituted alkenyl, optionally substituted alkynyl, optionally substituted aryl, or optionally substituted heteroaryl;

each occurrence of L² is independently a bond, optionally substituted alkylene, optionally substituted alkenylene, optionally substituted alkynylene, optionally substituted heteroalkylene, optionally substituted heteroalkenylene, or optionally substituted heteroalkynylene;

each occurrence of R² is independently optionally substituted acyl, optionally substituted carbocyclyl, optionally substituted heterocyclyl, optionally substituted aryl, optionally substituted heteroaryl, —OR$^b$, —N(R$^b$)$_2$, or an oxygen protecting group;

each occurrence of R$^{3A}$ is independently hydrogen, optionally substituted alkyl, optionally substituted alkenyl, optionally substituted alkynyl, optionally substituted aryl, optionally substituted heteryaryl, optionally substituted acyl, —OR$^b$, or —N(R$^b$)$_2$;

each occurrence of R$^b$ is independently optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, an oxygen protecting group, or a nitrogen protecting group, or two R$^b$ taken together with the nitrogen to which they are attached form an optionally substituted heterocyclic or optionally substituted heteroaryl ring;

each of G$^{1A}$ and G$^{2A}$ is independently hydrogen, halogen, optionally substituted amine, optionally substituted alkyl, optionally substituted aryl, or optionally substituted heteroaryl, optionally substituted acyl, optionally substituted phosphate, or an oxygen protecting group; and each of p, q, r, s, and t is independently an integer between 0 and 200, inclusive, wherein the sum of p and t is at least 1, and the sum of q, r, and s is at least 1.

In certain embodiments, the matrix forming agent or combination of matrix forming agents comprises a polymer of Formula:

each of G$^{1A}$ and G$^{2A}$ is independently hydrogen, optionally substituted alkyl, optionally substituted aryl, or optionally substituted heteroaryl, optionally substituted acyl, optionally substituted phosphate, or an oxygen protecting group; and each of p, q, r, s, and t is independently an integer between 0 and 200, wherein the sum of p and t is at least 1, and the sum of q, r, and s is at least 1;

the composition forms a gel at temperatures above a phase transition temperature; and the phase transition temperature is less than about 37° C.;

and at least one of conditions (i), (ii), and (iii) are met:
(i) the phase transition temperature of the composition is less than the phase transition temperature of a reference composition plus about 5° C.;
(ii) the storage modulus of the composition is greater than about 15% of the storage modulus of the reference composition at a temperature of about 37° C.; and
(iii) the loss modulus of the composition is between about 80% and about 120% of the loss modulus of the reference composition at a temperature of about 37° C.;
wherein the reference composition is the composition in the absence of the permeation enhancer or combination of permeation enhancers.

In some embodiments, the matrix forming agent comprises a poloxamer. Exemplary poloxamers include, but are not limited to: poloxamer 407, poloxamer 188, poloxalene, poloxamer 124, poloxamer 237, or poloxamer 338, Pluronic® 10R5, Pluronic® 17R2, Pluronic® 17R4, Pluronic® 25R2, Pluronic® 25R4, Pluronic® 31R1, Pluronic® F 108 Cast Solid Surfactant, Pluronic® F 108 NF, Pluronic® F 108 Pastille, Pluronic® F 108NF Prill Poloxamer 338, Pluronic® F 127 NF, Pluronic® F 127 NF 500 BHT Prill, Pluronic® F 127 NF Prill Poloxamer 407, Pluronic® F 38, Pluronic® F 38 Pastille, Pluronic® F 68, Pluronic® F 68 LF Pastille, Pluronic® F 68 NF, Pluronic® F 68 NF Prill Poloxamer 188, Pluronic® F 68 Pastille, Pluronic® F 77, Pluronic® F 77 Micropastille, Pluronic® F 87, Pluronic® F 87 NF, Pluronic® F 87 NF Prill Poloxamer 237, Pluronic® F 88, Pluronic® F 88 Pastille, Pluronic® FT L 61, Pluronic® L 10, Pluronic® L 101, Pluronic® L 121, Pluronic® L 31, Pluronic® L 35, Pluronic® L 43, Pluronic® L 61, Pluronic® L 62, Pluronic® L 62 LF, Pluronic® L 62D,

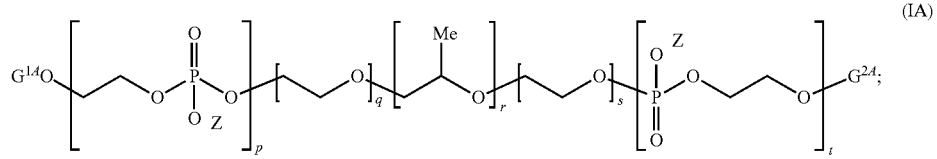

(IA)

wherein:
each occurrence of Z is independently —R⁴;
each occurrence of R⁴ is independently optionally substituted alkyl;

Pluronic® L 64, Pluronic® L 81, Pluronic® L 92, Pluronic® L44 NF INH surfactant Poloxamer 124, Pluronic® N 3, Pluronic® P 103, Pluronic® P 104, Pluronic® P 105, Pluronic® P 123 Surfactant, Pluronic® P 65, Pluronic® P 84, Pluronic® P 85, Synperonic® PE/F 108, Synperonic® PE/P105, Synperonic® PE/P84, Synperonic®, Synperonic® PE/L31, Synperonic® PE/L61, Synperonic® PE/L101, Synperonic® PE/L121, Synperonic® PE/L42, Synperonic® PE/L62, Synperonic® PE/L92, Synperonic® PE/L44, Synperonic® PE/L64, Synperonic® PE/P84, Synperonic® PE/P75, Synperonic® PE/P103, Synperonic® PE/F87, Synperonic® PE/F127, Synperonic® PE/F38, Synperonic® PE/F68, Kolliphor® P 188, Kolliphor® P 407, Kolliphor® P 188 micro, Kolliphor® P 407 micro, Kolliphor® P237, Kolliphor® P 338, Kolliphor® EL, Kolliphor® HS 15, Kolliphor® PS 80, Kolliphor® PS 60, Kolliphor® RH 40, Kolliphor® TPG S, Kolliphor® CS L, Kolliphor® CS A, Kolliphor® CS S, Kolliphor® CS B, Kolliphor® CS 20, and Kolliphor® CS 12. In some embodiments, the matrix forming agent comprises any of the foregoing poloxamers, a derivative thereof, or a block copolymer thereof.

In certain embodiments, the matrix forming agent comprises poloxamer 407, poloxamer 188, poloxalene, poloxamer 124, poloxamer 237, or poloxamer 338. In certain embodiments, the block copolymer comprises poloxamer 407. In certain embodiments, the matrix forming comprises a poloxamer with phosphoester monomers. In certain embodiments, the matrix forming comprises poloxamer 407 with phosphoester monomers. In certain embodiments, the matrix forming agent or combination of matrix forming agents comprises a polymer of Formula:

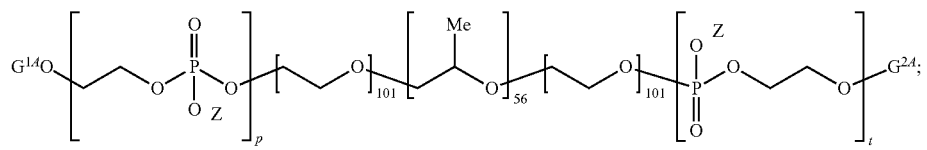

wherein:
each occurrence of Z is independently —$R^4$;
each occurrence of $R^4$ is independently optionally substituted alkyl;
each of $G^{1A}$ and $G^{2A}$ is independently hydrogen, optionally substituted alkyl, optionally substituted aryl, or optionally substituted heteroaryl, optionally substituted acyl, optionally substituted phosphate, or an oxygen protecting group; and
each of p and t is independently an integer between 0 and 200, inclusive, wherein the sum of p and t is at least 1;
the composition forms a gel at temperatures above a phase transition temperature; and the phase transition temperature is less than about 37° C.;
and at least one of conditions (i), (ii), and (iii) are met:
(i) the phase transition temperature of the composition is less than the phase transition temperature of a reference composition plus about 5° C.;
(ii) the storage modulus of the composition is greater than about 15% of the storage modulus of the reference composition at a temperature of about 37° C.; and
(iii) the loss modulus of the composition is between about 80% and about 120% of the loss modulus of the reference composition at a temperature of about 37° C.; wherein the reference composition is the composition in the absence of the permeation enhancer or combination of permeation enhancers.

Polymers of Formula (I') comprise $R^{3A}$. In certain embodiments, each $R^{3A}$ is the same substituent. In certain embodiments, each $R^{3A}$ in a polymer is one of two specific substituents. In certain embodiments, each $R^{3A}$ in a polymer is one of three specific substituents. In certain embodiments, each $R^{3A}$ in a polymer is one of four specific substituents. In certain embodiments, each $R^{3A}$ in a polymer is one of five specific substituents. In certain embodiments, each $R^{3A}$ in a polymer is one of six specific substituents. In certain embodiments, each $R^{3A}$ in a polymer is one of seven or more specific substituents.

As generally described herein each occurrence of $R^{3A}$ is independently optionally hydrogen, substituted alkyl, optionally substituted alkenyl, optionally substituted alkynyl, optionally substituted aryl, optionally substituted heteryaryl, optionally substituted acyl, —$OR^b$, or —$N(R^b)_2$. In certain embodiments, each occurrence of $R^{3A}$ is independently unsubstituted alkyl.

In certain embodiments, $R^{3A}$ is hydrogen. In certain embodiments, $R^{3A}$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^{3A}$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^{3A}$ is unsubstituted $C_{1-20}$ alkyl. In certain embodiments, $R^{3A}$ is unsubstituted $C_{1-12}$ alkyl. In certain embodiments, $R^{3A}$ is methyl. In certain embodiments, $R^{3A}$ is ethyl, propyl, or butyl. In certain embodiments, $R^{3A}$ is haloalkyl, e.g., —$CHF_2$, —$CHCl_2$, —$CH_2CHF_2$, —$CH_2CHCl_2$. In certain embodiments, $R^{3A}$ is perhaloalkyl, e.g., —$CF_3$, —$CF_2CF_3$, —$CCl_3$. In certain embodiments, $R^{3A}$ is hydroxyalkyl, e.g., —$CH_2OH$, —$CH_2CH_2OH$, —$CH_2OR^b$, —$CH_2CH_2OR^b$. In certain embodiments, $R^{3A}$ is aminoalkyl, e.g., —$CH_2NH_2$, —$CH_2CH_2NH_2$, —$CH_2NMe_2$, —$CH_2CH_2NMe_2$, —$CH_2N(R^b)_2$, —$CH_2CH_2N(R^b)_2$.

In certain embodiments, $R^{3A}$ is optionally substituted alkenyl, e.g., optionally substituted $C_{2-6}$ alkenyl. In certain embodiments, $R^{3A}$ is unsubstituted alkenyl, e.g., unsubstituted $C_{2-6}$ alkenyl. In certain embodiments, $R^{3A}$ is vinyl, allyl, or prenyl. In certain embodiments, $R^{3A}$ is optionally substituted alkynyl, e.g., optionally substituted $C_{2-6}$ alkynyl. In certain embodiments, $R^{3A}$ is unsubstituted alkynyl, e.g., unsubstituted $C_{2-6}$ alkynyl.

In certain embodiments, $R^{3A}$ is optionally substituted aryl, e.g., optionally substituted phenyl. In certain embodiments, $R^{3A}$ is unsubstituted aryl, e.g., unsubstituted phenyl. In certain embodiments, $R^{3A}$ is optionally substituted heteroaryl, e.g., optionally substituted 5-6 membered heteroaryl, or optionally substituted 9-10 membered bicyclic heteroaryl. In certain embodiments, $R^{3A}$ is unsubstituted heteroaryl, e.g., unsubstituted 5-6 membered heteroaryl, or unsubstituted 9-10 membered bicyclic heteroaryl.

In certain embodiments, $R^{3A}$ is optionally substituted acyl, e.g., —CHO, —$CO_2H$, or —C(=O)$NH_2$. In certain embodiments, $R^{3A}$ is optionally substituted carbonyl. In certain embodiments, $R^{3A}$ is —C(=O)$R^b$, —C(=O)O$R^b$, —C(=O)NH($R^b$), or —C(=O)N($R^b$)$_2$. In certain embodiments, $R^{3A}$ is —C(=O)$R^b$, and $R^b$ is optionally substituted alkyl, e.g., —C(=O)Me. In certain embodiments, $R^3$ is —C(=O)$R^b$, and $R^b$ is optionally substituted alkenyl. In certain embodiments, $R^{3A}$ is —C(=O)$R^b$, and $R^b$ is optionally substituted carbocyclyl, heterocyclyl, aryl, or heteroaryl. In certain embodiments, $R^{3A}$ is —C(=O)O$R^b$, and $R^b$ is optionally substituted alkyl. In certain embodiments, $R^{3A}$ is —C(=O)O$R^b$, and $R^b$ is optionally substituted alkenyl. In certain embodiments, $R^{3A}$ is —C(=O)O$R^b$, and $R^b$ is optionally substituted carbocyclyl, heterocyclyl, aryl, or heteroaryl. In certain embodiments, $R^{3A}$ is —C(=O)N($R^b$)$_2$, and at least one $R^b$ is optionally substituted alkyl. In certain embodiments, $R^3$ is —C(=O)NH$R^b$, and $R^b$ is optionally substituted alkyl. In certain embodiments, $R^{3A}$ is —C(=O)NH$R^b$, and $R^b$ is optionally substituted alkenyl. In certain embodiments, $R^{3A}$ is —C(=O)NH$R^b$, and $R^b$ is optionally substituted carbocyclyl, heterocyclyl, aryl, or heteroaryl. In certain embodiments, $R^{3A}$ is optionally substituted vinylcarbonyl (e.g., —C(=O)CH=CH$_2$, —C(=O)CMe=CH$_2$).

In certain embodiments, $R^{3A}$ is —O$R^b$, e.g., —OH. In certain embodiments, $R^{3A}$ is —O$R^b$, and $R^b$ is optionally substituted alkyl. In certain embodiments, $R^{3A}$ is —O$R^b$, and $R^b$ is unsubstituted $C_{1-6}$ alkyl. In certain embodiments, $R^{3A}$ is —O$R^b$, and $R^b$ is optionally substituted alkenyl. In certain embodiments, $R^{3A}$ is —O$R^b$, and $R^b$ is optionally substituted carbocyclyl, optionally substituted heterocyclyl, optionally substituted aryl optionally substituted heteroaryl. In certain embodiments, $R^{3A}$ is —O$R^b$, and $R^b$ is unsubstituted carbocyclyl, unsubstituted heterocyclyl, unsubstituted aryl unsubstituted heteroaryl. In certain embodiments, $R^{3A}$ is —O$R^b$, and $R^b$ is optionally substituted acyl, e.g., $R^{3A}$ is —OC(=O)$R^b$, —OC(=O)O$R^b$, or —OC(=O)N($R^b$)$_2$. In certain embodiments, $R^{3A}$ is —O$R^b$, and $R^b$ is an oxygen protecting group (e.g., silyl, TBDPS, TBDMS, TIPS, TES, TMS, MOM, THP, t-Bu, Bn, allyl, acetyl, pivaloyl, benzoyl).

In certain embodiments, $R^{3A}$ is —N($R^b$)$_2$, e.g., —NH$_2$, —NH$R^b$. In certain embodiments, $R^{3A}$ is —NH($R^b$), and $R^b$ is optionally substituted alkyl. In certain embodiments, $R^3$ is —N($R^b$)$_2$, and at least one $R^b$ is optionally substituted alkyl. In certain embodiments, $R^{3A}$ is —NH($R^b$), and $R^b$ is unsubstituted alkyl. In certain embodiments, $R^{3A}$ is —N($R^b$)$_2$, and at least one $R^b$ is unsubstituted alkyl. In certain embodiments, $R^{3A}$ is —NH$R^b$, and $R^b$ is optionally substituted carbocyclyl, optionally substituted heterocyclyl, optionally substituted aryl, or optionally substituted heteroaryl. In certain embodiments, $R^{3A}$ is —NH$R^b$, and $R^b$ is unsubstituted carbocyclyl, unsubstituted heterocyclyl, unsubstituted aryl, or unsubstituted heteroaryl. In certain embodiments, $R^{3A}$ is —NH$R^b$, and $R^b$ is optionally substituted acyl, e.g., $R^{3A}$ is —NHC(=O)$R^b$, —NHC(=O)O$R^b$, or —NHC(=O)NH$R^b$. In certain embodiments, $R^{3A}$ is —N($R^b$)$_2$, and at least one $R^b$ is a nitrogen protecting group (e.g., Bn, Boc, Cbz, Fmoc, trifluoroacetyl, triphenylmethyl, acetyl, Ts). In certain embodiments, $R^{3A}$ is —N($R^b$)$_2$, and both $R^b$ are joined to form an optionally substituted heterocyclic or optionally substituted heteroaryl ring. In certain embodiments, $R^{3A}$ is —N($R^b$)$_2$, and both $R^b$ are joined to form an unsubstituted heterocyclic or unsubstituted heteroaryl ring.

In some embodiments, $G^{1A}$ and $G^{2A}$ are the same. In some embodiments, $G^{1A}$ and $G^{2A}$ are different. In certain embodiments, $G^{1A}$ is hydrogen. In certain embodiments, $G^{1A}$ is optionally substituted alkyl. In certain embodiments, $G^{1A}$ is optionally substituted acyl. In certain embodiments, $G^{1A}$ is optionally substituted optionally substituted phosphate (e.g., —P(=O)(OH)$_2$, —P(=O)(O-alkyl)$_2$, —P(=O)(OH)(O-alkyl), —P(=O)(OH)(O—Y), —P(=O)(O-alkyl)(O—Y)). In certain embodiments, $G^{1A}$ is an oxygen protecting group (e.g., silyl, TBDPS, TBDMS, TIPS, TES, TMS, MOM, THP, t-Bu, Bn, allyl, acetyl, pivaloyl, benzoyl). In certain embodiments, $G^{1A}$ is hydrogen. In certain embodiments, $G^{1A}$ is optionally substituted alkyl. In certain embodiments, $G^{1A}$ is optionally substituted acyl. In certain embodiments, $G^{1A}$ is optionally substituted optionally substituted phosphate (e.g., —P(=O)(OH)$_2$, —P(=O)(O-alkyl)$_2$, —P(=O)(OH)(O-alkyl), —P(=O)(OH)(O—Y), —P(=O)(O-alkyl)(O—Y)). In certain embodiments, $G^{1A}$ is an oxygen protecting group (e.g., silyl, TBDPS, TBDMS, TIPS, TES, TMS, MOM, THP, t-Bu, Bn, allyl, acetyl, pivaloyl, benzoyl). In certain embodiments, $G^{1A}$ is optionally substituted aryl, e.g., optionally substituted phenyl. In certain embodiments, $G^{1A}$ is unsubstituted aryl, e.g., unsubstituted phenyl. In certain embodiments, $G^{1A}$ is optionally substituted heteroaryl, e.g., optionally substituted 5-6 membered heteroaryl, or optionally substituted 9-10 membered bicyclic heteroaryl. In certain embodiments, $G^{1A}$ is unsubstituted heteroaryl, e.g., unsubstituted 5-6 membered heteroaryl, or unsubstituted 9-10 membered bicyclic heteroaryl.

In certain embodiments, $G^{2A}$ is hydrogen. In certain embodiments, $G^{2A}$ is optionally substituted alkyl. In certain embodiments, $G^{2A}$ is optionally substituted acyl. In certain embodiments, $G^{2A}$ is optionally substituted optionally substituted phosphate (e.g., —P(=O)(OH)$_2$, —P(=O)(O-alkyl)$_2$, —P(=O)(OH)(O-alkyl), —P(=O)(OH)(O—Y), —P(=O)(O-alkyl)(O—Y)). In certain embodiments, $G^{2A}$ is an oxygen protecting group (e.g., silyl, TBDPS, TBDMS, TIPS, TES, TMS, MOM, THP, t-Bu, Bn, allyl, acetyl, pivaloyl, benzoyl). In certain embodiments, $G^2$ is hydrogen. In certain embodiments, $G^{2A}$ is optionally substituted alkyl. In certain embodiments, $G^2$ is optionally substituted acyl. In certain embodiments, $G^{2A}$ is optionally substituted optionally substituted phosphate (e.g., —P(=O)(OH)$_2$, —P(=O)(O-alkyl)$_2$, —P(=O)(OH)(O-alkyl), —P(=O)(OH)(O—Y), —P(=O)(O-alkyl)(O—Y)). In certain embodiments, $G^{2A}$ is an oxygen protecting group (e.g., silyl, TBDPS, TBDMS, TIPS, TES, TMS, MOM, THP, t-Bu, Bn, allyl, acetyl, pivaloyl, benzoyl). In certain embodiments, $G^{2A}$ is optionally substituted aryl, e.g., optionally substituted phenyl. In certain embodiments, $G^{2A}$ is unsubstituted aryl, e.g., unsubstituted phenyl. In certain embodiments, $G^{2A}$ is optionally substituted heteroaryl, e.g., optionally substituted 5-6 membered heteroaryl, or optionally substituted 9-10 membered bicyclic heteroaryl. In certain embodiments, $G^{2A}$ is unsubstituted heteroaryl, e.g., unsubstituted 5-6 membered heteroaryl, or unsubstituted 9-10 membered bicyclic heteroaryl. In certain embodiments, $G^{1A}$ and $G^{2A}$ are both hydrogen.

In certain embodiments, each occurrence of Z is independently —$R^4$. As generally described herein each occurrence of $R^4$ is independently optionally substituted alkyl. In certain embodiments, $R^4$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^4$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^4$ is unsubstituted $C_{1-20}$ alkyl. In certain embodiments, $R^4$ is unsubstituted $C_{1-12}$ alkyl. In certain embodiments, $R^4$ is methyl. In certain embodiments, $R^4$ is ethyl, propyl, or butyl. In certain embodiments, $R^4$ is ethyl.

In certain embodiments, $R^4$ is propyl. In certain embodiments, $R^4$ is butyl. In certain embodiments, $R^4$ is n-butyl. In certain embodiments, $R^4$ is s-butyl. In certain embodiments, $R^4$ is of formula:

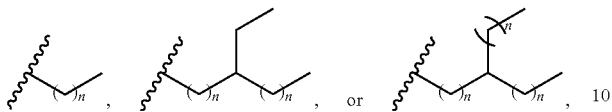

wherein each occurrence of n is independently an integer between 0 and 20, inclusive.

In certain embodiments, $R^4$ is of formula:

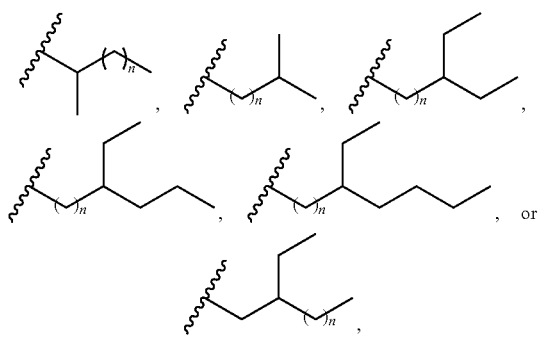

wherein each occurrence of n is independently an integer between 0 and 20, inclusive.

In certain embodiments, $R^4$ is of formula

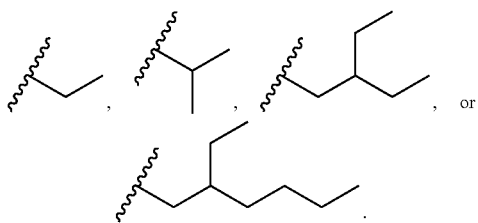

In certain embodiments, $R^4$ is of formula:

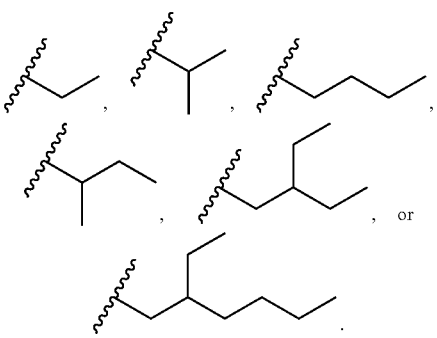

In certain embodiments, $R^4$ is of formula:

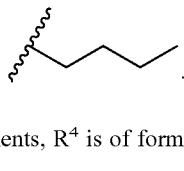

In certain embodiments, $R^4$ is of formula:

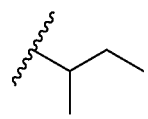

In certain embodiments, p is 0. In certain embodiments, p is an integer between 1 and 100, inclusive. In some embodiments, p is an integer between 10 and 100, inclusive. In some embodiments, p is an integer between 10 and 50, inclusive. In some embodiments, p is an integer between 10 and 25, inclusive. In some embodiments, p is an integer between 1 and 10, inclusive. In certain embodiments, p is 5.

In certain embodiments, t is 0. In certain embodiments, t is an integer between 1 and 100, inclusive. In some embodiments, t is an integer between 10 and 100, inclusive. In some embodiments, t is an integer between 10 and 50, inclusive. In some embodiments, t is an integer between 10 and 25, inclusive. In some embodiments, t is an integer between 1 and 10, inclusive. In certain embodiments, t is 5. In certain embodiments, p is 5 and t is 5.

In certain embodiments, the polymer is of the formula:

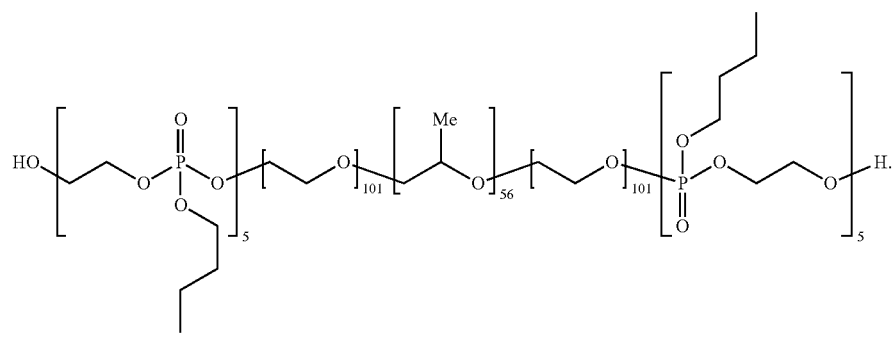

In certain embodiments, the matrix forming agent or combination of matrix forming agents comprises a polymer of Formula (I') is part of a composition. In certain embodiments, the matrix forming agent or combination of matrix forming agents comprises a polymer of Formula (IA) is part of a composition. In certain embodiments, the matrix forming agent or combination of matrix forming agents comprises a polymer of Formula (II) is part of a composition.

Methods of Treatment and Uses

Methods of using the various embodiments of the compositions described herein are generally directed to methods of treating an infectious disease or an ear disease. In certain embodiments, the compositions described herein are used in a method of treating an infectious disease. In certain embodiments, the matrix forming agents described herein are used in a method of treating an infectious disease. In certain embodiments, the compositions described herein are used in a method of treating an ear disease. In certain embodiments, the compositions described herein are used in a method of treating an infectious ear disease. Methods of using the various embodiments of the compositions described herein are generally directed to methods of treating an infectious disease. In various aspects, the compositions may be used to deliver therapeutic or diagnostic agents across the tympanic membrane. Therefore, the compositions are particularly useful in treating diseases of the middle and/or inner ear. In certain embodiments, the compositions described herein are used in a method of treating diseases of the middle ear. In certain embodiments, the compositions described herein are used in a method of treating diseases of the inner ear.

In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate.

In various aspects, compositions described herein can be used to treat ear diseases, including, but not limited to, ear infections, development of fibroids in the middle ear, or otosclerosis. In certain embodiments, the matrix forming agents described herein can be used to treat ear diseases, including, but not limited to, ear infections, development of fibroids in the middle ear, or otosclerosis. In various other aspects, compositions described herein may be used may treat vertigo, Meniere's disease, mastoiditis, cholesteatoma, labyrinthitis, perilymph fistula, superior canal dehiscence syndrome, otorrhea, otalgia, tinnitus, barotrauma, cancers of the ear, autoimmune inner ear disease acoustic neuroma, benign paroxysmal positional vertigo, herpes zoster oticus, purulent labyrinthitis, vestibular neuronitis, eardrum perforation, or myringitis. In various other aspects, compositions described herein may be used may treat vertigo, Meniere's disease, mastoiditis, cholesteatoma, labyrinthitis, perilymph fistula, superior canal dehiscence syndrome, otorrhea, otalgia, tinnitus, barotrauma, cancers of the ear, autoimmune inner ear disease acoustic neuroma, benign paroxysmal positional vertigo, herpes zoster oticus, purulent labyrinthitis, vestibular neuronitis, eardrum perforation, or myringitis. In certain embodiments, the matrix forming agents described herein may be used may treat vertigo, Meniere's disease, mastoiditis, cholesteatoma, labyrinthitis, perilymph fistula, superior canal dehiscence syndrome, otorrhea, otalgia, tinnitus, barotrauma, cancers of the ear, autoimmune inner ear disease acoustic neuroma, benign paroxysmal positional vertigo, herpes zoster oticus, purulent labyrinthitis, vestibular neuronitis, eardrum perforation, or myringitis. In some embodiments, the methods disclosed herein are used for treating otitis media (OM). Different forms of OM, which may be treated by the methods disclosed herein, may be differentiated by the presence of fluid (effusion) and/or by the duration or persistence of inflammation. In certain embodiments, the infectious disease is acute otitis media, chronic otitis media, or secretory otitis media. Effusions, if present, can be of any consistency, from water-like (serous) to viscid and mucous-like (mucoid), to pus-like (purulent); duration is classified as acute, subacute, or chronic. OM with effusion (OME) indicates inflammation with middle ear fluid (MEF), but in the absence of any indications of acute infection. Acute OM (AOM), with or without effusion, is characterized by rapid onset of the signs and symptoms associated with acute infection in the middle ear (e.g., otalgia, fever). In some embodiments, the methods are used for treating otitis media associated with infection by any of a number of pathogenic bacteria, including, for example, *Streptococcus pneumoniae*, *Haemophilus influenzae*, and *Moraxella catarrhalis*.

The infectious disease may be a bacterial infection. In certain embodiments, the bacterial infection is a *Streptococcus*, *Haemophilus*, or *Moraxella* infection. In certain embodiments, the bacterial infection is a *Staphylococcus*, *Escherichia*, or *Bacillus* infection. In certain embodiments, the bacterial infection is an *H. influenzae* infection. In certain embodiments, the bacterial infection is a *S. pneumoniae* infection. In certain embodiments, the bacterial infection is an *M. catarrhalis* infection. In certain embodiments, the infectious disease is an ear infection. In certain embodiments, the infectious disease is otitis media.

In various embodiments, administration of the inventive compositions consists of applying the composition into a subject's ear canal. In certain embodiments, applying the composition into a subject's ear canal comprises spraying the composition into a subject's ear canal. In certain embodiments, administration of the inventive compositions consists of applying the composition into the inner ear of a subject. In certain embodiments, administration of the inventive compositions consists of applying the composition into the middle ear of a subject. In certain embodiments, administration of the inventive compositions consists of applying the composition into the inner ear, sinuses, the eye, vagina, or skin of a subject. In certain embodiments, administration of the inventive compositions consists of applying the composition into the sinuses of a subject. In certain embodiments, administration of the inventive compositions consists of applying the composition into the eye of a subject. In certain embodiments, administration of the inventive compositions consists of applying the composition into the vagina of a subject. In certain embodiments, administration of the inventive compositions consists of applying the composition to the skin of a subject. A subject for treatment can be any mammal in need of treatment. In various aspects, the composition is in direct contact with the tympanic membrane for about 1 day to about 30 days. In various aspects, the composition is in contact with the tympanic membrane from about 1 day to about 3 days, from about 3 days to about 7 days, from about 7 days to about 14 days, from about 14 days to about 21 days, or from about 21 days to about 30 days. In various embodiments, the composition forms a sustained release reservoir, in contact with the tympanic membrane. In various aspects, the composition is applied into the ear canal as a liquid, and the composition gels in situ on the surface of the tympanic membrane. When in contact with the tympanic membrane, the therapeutic agent penetrates the tympanic membrane and is delivered to the middle ear. In various embodiments, the delivery across the tympanic membrane is a sustained release of the therapeutic agent over a number of days. The numbers of days that the composition can be in contact with the tympanic membrane can be, but is not limited to, 5 days, 7 days, 10 days, 14 days, 21 days, or 30 days. The composition may be applied singly, or repeatedly in the course of treatment. In various aspects, the composition may be periodically administered from about every 1 day to about every 7 days, from about every 1 day to about every 14 days, or from about every 1 day to about every 30 days. In various embodiments, the composition is naturally extruded from the subject at the end of treatment via natural processes similar to extrusion of ear wax. In certain embodiments, the composition may naturally break down, and its degradation products may be eliminated by the subject. In various embodiments, administration of the inventive compositions comprises adding the matrix forming agent, the permeation enhancer, and the therapeutic agent to the ear canal; then adding a second therapeutic agent to the ear canal; and mixing the matrix forming agent, the permeation enhancer, and the therapeutic agent on the ear canal. In certain embodiments, the second therapeutic agent is an anesthetic. In certain embodiments, the second therapeutic agent is a local anesthetic.

In various embodiments, administration of the inventive compositions comprises adding the matrix forming agent to the ear canal; adding the permeation enhancer to the ear canal; adding the therapeutic agent to the ear canal; and mixing the matrix forming agent, the permeation enhancer, and the therapeutic agent on the ear canal. In various embodiments, administration of the inventive compositions comprises adding the matrix forming agent to the ear canal; adding the permeation enhancer to the ear canal; adding the therapeutic agent to the ear canal; adding an additional therapeutic agent to the ear canal; and mixing the matrix forming agent, the permeation enhancer, and the therapeutic agents on the ear canal. In certain embodiments, adding the therapeutic agent and adding the permeation enhancer to the ear canal comprises spraying the therapeutic agent and spraying the permeation enhancer into the ear canal.

In various embodiments, administration of the inventive compositions comprises adding the therapeutic agent to the ear canal; adding the permeation enhancer to the ear canal; adding the matrix forming agent to the ear canal; and mixing the matrix forming agent, the permeation enhancer, and the therapeutic agent on the ear canal. In various embodiments, administration of the inventive compositions comprises adding the therapeutic agent to the ear canal; adding an additional therapeutic agent to the ear canal; adding the permeation enhancer to the ear canal; adding the matrix forming agent to the ear canal; and mixing the matrix forming agent, the permeation enhancer, and the therapeutic agents on the ear canal. In certain embodiments, adding the therapeutic agent and adding the permeation enhancer to the ear canal comprises spraying the therapeutic agent and spraying the permeation enhancer into the ear canal. In certain embodiments, the therapeutic agent is an antibiotic or anesthetic agent. In certain embodiments, the therapeutic agent is an antibiotic. In certain embodiments, the therapeutic agent is an anesthetic agent. In certain embodiments, the permeation enhancer is bupivacaine.

In various embodiments, administration of the inventive compositions comprises adding a composition including one or more therapeutic agents, one or more permeation enhancers, and one or more matrix forming agents to the ear canal; and subsequently adding a composition comprising no therapeutic agents or one or more therapeutic agents, no permeation enhancers or one or more permeation enhancers, and no matrix forming agents or one or more matrix forming agents to the ear canal. In certain embodiments, the subsequent addition of the one or more therapeutic agents comprises therapeutic agents that are the same as in the first addition of the one or more therapeutic agents. In certain embodiments, the subsequent addition of the one or more therapeutic agents comprises therapeutic agents that are different from those in the first addition of the one or more therapeutic agents. In certain embodiments, the subsequent addition of permeation enhancers comprises permeation enhancers that are the same as in the first addition of the permeation enhancers. In certain embodiments, the subsequent addition of the permeation enhancers comprises permeation enhancers that are different from those in the first addition of the permeation enhancers. In certain embodiments, the subsequent addition of matrix forming agents comprises matrix forming agents that are the same as in the first addition of the matrix forming agents. In certain embodiments, the subsequent addition of the matrix forming agents comprises matrix forming agents that are different from those in the first addition of the matrix forming agents. In certain embodiments, the time interval between the adding of the first composition and second composition is about one minute. In certain embodiments, the time interval between the adding of the first composition and second composition is less than one minute. In certain embodiments, the time interval between the adding of the first composition and second composition is more than one minute.

A dose is determined based on the minimum inhibitory concentration needed at the site of infection. Without being bound to a particular theory, in various aspects the minimum inhibitory concentration for *H. influenza* or *S. pneumoniae* middle ear infections is about 4 µg/mL for ciprofloxacin. In various aspects, a typical dose will require approximately 12 µg of ciprofloxacin, based on an average middle ear volume of 3 mL. In various embodiments, the compositions will comprise sufficient dose to delivery 12 µg of ciprofloxacin to the middle ear. In various aspects, the administration of the composition comprises a single application. In other aspects, the administration of the composition comprises multiple applications. For example, the composition may be administered two, three, four, or more times. In certain embodiments, the composition is administered repeatedly until the desired clinical outcome is achieved. For example, the infection is resolved. In certain embodiments, the administration of the composition comprises a first administration of the composition, followed by a second administration of the composition after a period of time. In certain embodiments, the period of time between the first first administration of the composition and the second administration of the composition is a week. In certain embodiments, the period of time between the first first administration of the composition and the second administration of the composition is more than one week. In certain embodiments, the period of time between the first first administration of the composition and the second administration of the composition is one month.

In certain embodiments, the period of time between the first first administration of the composition and the second administration of the composition is more than one month. In various embodiments, administration of the inventive compositions comprises a first administration of a composition without a local anesthetic to the ear canal; followed by a second administration of a composition without a local anesthetic to the ear canal. In certain embodiments, administration of the inventive compositions comprises a first administration of a composition with a local anesthetic to the ear canal; followed by a second administration of a composition without a local anesthetic to the ear canal.

In various embodiments, administration of the inventive compositions comprises a first administration of a composition without a local anesthetic to the ear canal; followed by a second administration of a composition without a permeation enhancer other than a local anesthetic to the ear canal. In certain embodiments, administration of the inventive compositions comprises a first administration of a composition with a local anesthetic to the ear canal; followed by a second administration of a composition without a permeation enhancer other than local anesthetic to the ear canal. In certain embodiments, the composition administered first and the composition administered second are the same. In certain embodiments, the composition administered first and the composition administered second are different.

Provided herein are methods of delivering a composition of the disclosure to the surface of tympanic membrane of a subject. In certain embodiments, the subject has an ear disease. In some embodiments, the subject has otitis media. In some embodiments, the subject is a human. In certain embodiments, the subject is a domesticated animal, such as a dog, cat, cow, pig, horse, sheep, or goat.

In certain embodiments, the method of delivering comprises administering the composition into the ear canal via an applicator. In certain embodiments, the method of delivering comprises placing drops of the composition into the ear canal. In some embodiments, the drops are delivered from a dropper (e.g., pipet, eye dropper). In some embodiments, the drops are delivered by a syringe. The syringe may be attached to a needle, rigid catheter, or flexible catheter.

In certain embodiments, the method of delivering comprises placing a dose of the composition into the ear canal using a catheter. In some embodiments the catheter is attached to a syringe. In some embodiments, the catheter is rigid. In some embodiments the catheter is flexible. In certain embodiments, the method of delivering comprises placing a dose of the composition into the ear canal using a needle. In some embodiments, the needle is attached to a syringe. In some embodiments, the needle has a blunt tip.

In certain embodiments, the method of delivering comprises placing a dose of the composition into the ear canal using a double barrel syringe. The double barrel syringe may be used to keep two components of a composition until mixing of the two components occurs during administration (e.g., in situ). In some embodiments, the double barrel syringe is attached to a single catheter or needle. In some embodiments, each barrel of the double barrel syringe is attached to a separate needle or catheter.

In certain embodiments, the method of treating an infectious disease or ear disease comprise instructing a subject to administer, or providing instructions to a subject for self-administration of, the composition.

In another aspect, provided herein are methods of eradicating a biofilm in a subject comprising administering to a subject in need thereof, a composition described herein to a subject in need thereof. In another aspect, provided herein are methods of eradicating a biofilm comprising contacting the biofilm with a composition described herein.

In another aspect, provided herein are methods of inhibiting formation of a biofilm in a subject, comprising administering to a subject in need thereof a composition described herein to a subject in need thereof. In another aspect, provided herein are methods of inhibiting formation of a biofilm comprising contacting a surface with a composition described herein.

Kits

Provided herein are kits comprising any of the compositions described herein, which may additionally comprise the compositions in sterile packaging. Provided herein are kits comprising any of the compositions or matrix-forming agents described herein, which may additionally comprise the compositions or matrix-forming agents in sterile packaging. The kits may comprise two containers for two-part, matrix-forming agents. The therapeutic agent may be included in one or both of the containers of the matrix forming agent, or the therapeutic agent may be packaged separately. The permeation enhancer may be included in one or both of the containers of the matrix forming agent, or the permeation enhancer may be packaged separately. In various aspects the kits may comprise a bottle or bottles, and a dropper or syringe for each bottle.

In certain embodiments, the kit comprises one or more droppers (e.g., pipet, eye dropper). In certain embodiments, the kit comprises one or more syringe. In some embodiments, the syringe is pre-loaded with the composition, or one or more component of the composition. In certain embodiments, the kit comprises one or more needle (e.g., blunt-tipped needle). In certain embodiments, the kit comprises one or more catheter (e.g., flexible catheter).

In certain the kit comprises a double barrel syringe. In some embodiments, the double barrel syringe is pre-loaded with two components of the composition. In some embodiments, the double barrel syringe is attached to a single catheter or needle. In some embodiments, each barrel of the double barrel syringe is attached to a separate needle or catheter.

In certain embodiments, a kit described herein further includes instructions for using the kit, such as instructions for using the kit in a method of the disclosure (e.g., instructions for administering a compound or pharmaceutical composition described herein to a subject). A kit described herein may also include information as required by a regulatory agency such as the U.S. Food and Drug Administration (FDA).

Definitions

Chemistry Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5$^{th}$ Edition, John Wiley & Sons, Inc., New York, 2001; Larock, Comprehensive Organic Transformations, VCH Publishers, Inc., New York, 1989; and Carruthers, Some Modern Methods of Organic Synthesis, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, E. L. Stereochemistry of Carbon Compounds (McGraw-Hill, N Y, 1962); and Wilen, S. H. Tables of Resolving Agents and Optical Resolutions p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of $^{12}$C with $^{13}$C or $^{14}$C are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CHF_2$, —$CH_2F$, —$CF_3$, —$CH_2CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl (C), and the like. Additional examples of alkenyl include heptenyl ($C_7$), octenyl (C), octatrienyl (C), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is not specified (e.g., —CH=CHCH$_3$ or

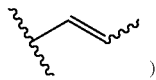
)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl (C), 2-propynyl (C), 1-butynyl ($C_4$), 2-butynyl ($C_4$), and the like. Examples of $C_{2-6}$ alkynyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" is a monocyclic, saturated carbocyclyl group having from 3 to 14 ring carbon atoms ("C$_{3-14}$ cycloalkyl"). In some embodiments, a cycloalkyl group has 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-14}$ cycloalkyl. In certain embodiments, the cycloalkyl group is a substituted C$_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 T electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{1-4}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 T electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$_{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 Rd groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein X$^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$alkenyl, heteroC$_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH) NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S) NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O) SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N (R$^{bb}$)$_2$, —OS(=O)R$^{aa}$, —OSO$_2$R—, —OSi(R$^{aa}$)$_3$, —OP (R$^{cc}$)$_2$, —OP(R$^{cc}$)$_3^+$X$^-$, —OP(OR$^{cc}$)$_2$, —OP(OR$^{cc}$)$_3^+$X$^-$, —OP(=O)(R$^{aa}$)$_2$, —OP(=O)(OR$^{cc}$)$_2$, and —OP(=O)(N(R$^{bb}$))$_2$, wherein X$^-$, R$^{aa}$, R$^{bb}$, and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(N(R$^{bb}$)$_2$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(N(R$^{bb}$)$_2$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3^+$X$^-$, wherein R$^{bb}$ and X$^-$ are as defined herein.

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is $sp^2$ hybridized, and is substituted with an oxygen, nitrogen or sulfur atom, e.g., a group selected from ketones (—$C(=O)R^{aa}$), carboxylic acids (—$CO_2H$), aldehydes (—CHO), esters (—$CO_2R^{aa}$, —$C(=O)SR^{aa}$, —$C(=S)SR^{aa}$), amides (—$C(=O)N(R^{bb})_2$, —$C(=O)NR^{bb}SO_2R^{aa}$, —$C(=S)N(R^{bb})_2$), and imines (—$C(=NR^{bb})R^{aa}$, —$C(=NR^{bb})OR^{aa}$, —$C(=NR^{bb})N(R^{bb})_2$), wherein $R^{aa}$ and $R^{bb}$ are as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{bb})R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, —$P(=O)(OR^{cc})_2$, —$P(=O)(R^{aa})_2$, —$P(=O)(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $X^-$, $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $X^-$, $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $S_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

The term "polysaccharide" refers to a polymer composed of long chains of carbohydrate or monosaccharide units, or derivatives thereof (e.g., monosaccharides modified to comprise cross-linkable functional groups). Exemplary polysaccharides include, but are not limited to, glycans, glucans, starches, glycogens, arabinoxylans, celluloses, hemicelluloses, chitins, pectins, dextrans, pullulans, chrysolaminarins, curdlans, laminarins, lentinans, lichenins, pleurans, zymosans, glycosaminoglycans, dextrans, hyaluronic acids, chitosans, and chondroitins. The monosaccharide monomers of polysaccharides are typically connected by glysolidic linkages.

Polysaccharides may be hydrolyzed to form oligosaccharides, disaccharides, and/or mono saccharides. The term "carbohydrate" or "saccharide" refers to an aldehydic or ketonic derivative of polyhydric alcohols. Monosaccharides are the simplest carbohydrates in that they cannot be hydrolyzed to smaller carbohydrates. Most monosaccharides can be represented by the general formula $C_yH_{2y}O_y$ (e.g., $C_6H_{12}O_6$ (a hexose such as glucose)), wherein y is an integer equal to or greater than 3. Certain polyhydric alcohols not represented by the general formula described above may also be considered monosaccharides. For example, deoxyribose is of the formula $C_5H_{10}O_4$ and is a monosaccharide. Monosaccharides usually consist of five or six carbon atoms and are referred to as pentoses and hexoses, receptively. If the monosaccharide contains an aldehyde it is referred to as an aldose; and if it contains a ketone, it is referred to as a ketose. Monosaccharides may also consist of three, four, or seven carbon atoms in an aldose or ketose form and are referred to as trioses, tetroses, and heptoses, respectively. Glyceraldehyde and dihydroxyacetone are considered to be aldotriose and ketotriose sugars, respectively. Examples of aldotetrose sugars include erythrose and threose; and ketotetrose sugars include erythrulose. Aldopentose sugars include ribose, arabinose, xylose, and lyxose; and ketopentose sugars include ribulose, arabulose, xylulose, and lyxulose. Examples of aldohexose sugars include glucose (for example, dextrose), mannose, galactose, allose, altrose, talose, gulose, and idose; and ketohexose sugars include fructose, psicose, sorbose, and tagatose. Ketoheptose sugars include sedoheptulose. Each carbon atom of a monosaccharide bearing a hydroxyl group (—OH), with the exception of the first and last carbons, is asymmetric, making the carbon atom a stereocenter with two possible configurations (R or S). Because of this asymmetry, a number of isomers may exist for any given monosaccharide formula. The aldohexose D-glucose, for example, has the formula $C_6H_{12}O_6$, of which all but two of its six carbons atoms are stereogenic, making D-glucose one of the 16 (i.e., $2^4$) possible stereoisomers. The assignment of D or L is made according to the orientation of the asymmetric carbon furthest from the carbonyl group: in a standard Fischer projection if the hydroxyl group is on the right the molecule is a D sugar, otherwise it is an L sugar. The aldehyde or ketone group of a straight-chain monosaccharide will react reversibly with a hydroxyl group on a different carbon atom to form a hemiacetal or hemiketal, forming a heterocyclic ring with an oxygen bridge between two carbon atoms. Rings with five and six atoms are called furanose and pyranose forms, respectively, and exist in equilibrium with the straight-chain form. During the conversion from the straight-chain form to the cyclic form, the carbon atom containing the carbonyl oxygen, called the anomeric carbon, becomes a stereogenic center with two possible configurations: the oxygen atom may take a position either above or below the plane of the ring. The resulting possible pair of stereoisomers is called anomers. In an a anomer, the —OH substituent on the anomeric carbon rests on the opposite side (trans) of the ring from the —CH₂OH side branch. The alternative form, in which the —CH₂OH substituent and the anomeric hydroxyl are on the same side (cis) of the plane of the ring, is called a β anomer. The term carbohydrate also includes other natural or synthetic stereoisomers of the carbohydrates described herein.

These and other exemplary substituents are described in more detail in the Detailed Description, Examples, and Claims. The invention is not intended to be limited in any manner by the above exemplary listing of substituents.

Other Definitions

Animal: The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). A non-human animal may be a transgenic animal.

Approximately or About: As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value).

Biocompatible: As used herein, the term "biocompatible" refers to substances that are not toxic to cells. In some embodiments, a substance is considered to be "biocompatible" if its addition to cells in vivo does not induce inflammation and/or other adverse effects in vivo. In some embodiments, a substance is considered to be "biocompatible" if its addition to cells in vitro or in vivo results in less than or equal to about 50%, about 45%, about 40%, about 35%, about 30%, about 25%, about 20%, about 15%, about 10%, about 5%, or less than about 5% cell death.

Biodegradable: As used herein, the term "biodegradable" refers to substances that are degraded under physiological conditions. In some embodiments, a biodegradable substance is a substance that is broken down by cellular machinery. In some embodiments, a biodegradable substance is a substance that is broken down by chemical processes.

Optically transparent: As used herein, the term "optically transparent" refers to substances through which light passes through with little or no light being absorbed or reflected. In some embodiments, optically transparent refers to substances through which light passes through with no light being absorbed or reflected. In some embodiments, optically transparent refers to substances through which light passes through with little light being absorbed or reflected. In some embodiments, an optically transparent substance is substantially clear. In some embodiments, an optically transparent substance is clear.

Effective amount: In general, the "effective amount" of an active agent refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient. The effective amount of a compound used to treat infection is the amount needed to kill or prevent the growth of the organism(s) responsible for the infection.

In vitro: As used herein, the term "in vitro" refers to events that occur in an artificial environment, e.g., in a test tube or reaction vessel, in cell culture, etc., rather than within an organism (e.g. animal, plant, and/or microbe).

In vivo: As used herein, the term "in vivo" refers to events that occur within an organism (e.g. animal, plant, and/or microbe).

Suffering from: An individual who is "suffering from" a disease, disorder, and/or condition has been diagnosed with or displays one or more symptoms of the disease, disorder, and/or condition.

Treating: As used herein, the term "treating" refers to partially or completely alleviating, ameliorating, relieving, delaying onset of, inhibiting progression of, reducing severity of, and/or reducing incidence of one or more symptoms or features of a particular disease, disorder, and/or condition.

For example, "treating" a microbial infection may refer to inhibiting survival, growth, and/or spread of the microbe. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. In some embodiments, treatment comprises delivery of an inventive vaccine nanocarrier to a subject.

Therapeutic agent: Also referred to as a "drug" is used herein to refer to an agent that is administered to a subject to treat a disease, disorder, or other clinically recognized condition that is harmful to the subject, or for prophylactic purposes, and has a clinically significant effect on the body to treat or prevent the disease, disorder, or condition. Therapeutic agents include, without limitation, agents listed in the United States Pharmacopeia (USP), *Goodman and Gilman's The Pharmacological Basis of Therapeutics*, $10^{th}$ Ed., McGraw Hill, 2001; Katzung, B. (ed.) Basic and Clinical Pharmacology, McGraw-Hill/Appleton & Lange; 8th edition (Sep. 21, 2000); Physician's Desk Reference (Thomson Publishing), and/or *The Merck Manual of Diagnosis and Therapy*, $17^{th}$ ed. (1999), or the 18th Ed. (2006) following its publication, Mark H. Beers and Robert Berkow (Eds.), Merck Publishing Group, or, in the case of animals, *The Merck Veterinary Manual*, $9^{th}$ ed., Kahn, C. A. (Ed.), Merck Publishing Group, 2005.

Diagnostic agent: As used herein, the term "diagnostic agent" refers to an agent that is administered to a subject to aid in the diagnosis of a disease, disorder, or condition. In some embodiments, a diagnostic agent is used to define and/or characterize the localization of a pathological process. Diagnostic agents include X-ray contrast agents, radioactive isotopes, and dyes.

Surfactant: As used herein, the term "surfactant" refers to any agent which preferentially absorbs to an interface between two immiscible phases, such as the interface between water and an organic solvent, a water/air interface, or an organic solvent/air interface. Surfactants usually possess a hydrophilic moiety and a hydrophobic moiety. Surfactants may also promote flux of a therapeutic or diagnostic agent across a biological membrane, e.g., a tympanic membrane.

Terpenes: As used herein, the term "terpene" refers to any agent derived, e.g., biosynthetically, or thought to be derived from unit(s) of isoprene (a five carbon unit). For example, isoprene units of terpenes may be linked together to form linear chains or they may be arranged to form rings. Typically, the terpenes disclosed herein promote flux of a therapeutic or diagnostic agent across a biological membrane, e.g., a tympanic membrane. Terpenes may be naturally derived or synthetically prepared.

The terms "composition" and "formulation" are used interchangeably.

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

Materials and Methods

Method and Design: The experiments compared the effect of the polymer matrix and incorporation of CPEs on TM permeability and OM cure rate. For the ex vivo experiments, a sample size of 4 for each formulation was chosen, which would provide 80% power to detect 50% differences in flux based on power analysis using the nonparametric Friedman test (version 7.0, nQuery Advisor, Statistical Solutions, Saugus, Mass.). Sample sizes of 8-10 were used for the in vivo experiments, which were supported by previous publications (Pelton et al., *Antimicrob. Agents Chemother.* 44, 654-657 (2000)). Comparisons between positive and negative efficacy results were assessed using Fisher's exact test. Statistical analysis was conducted using SAS software (version 9.2, SAS Institute, Cary, N.C.). Two-tailed $p<0.05$ with appropriate Bonferroni-Sidak adjustment for multiple comparisons were considered statistically significant in order to control type I error. During ex vivo experiments, data collection was stopped after 48 hours due to microbial growth on harvested TM; whereas during in vivo experiments, data collection was stopped after 7 days because OM would either be cleared or cause the animal severe illness that requires euthanasia. In vivo experiments were blinded. All experiments were randomized.

Materials: 2-chloro-2-oxo-1,3,2-dioxaphospholane (COP), 1,8-diazabicyclo[5.4.0]undec-7-ene (DBU), n-butanol, diethyl ether, acetic acid, anhydrous dichloromethane, anhydrous tetrahydrofuran were used as received from Sigma-Aldrich Company (St. Louis, Mo.). Kolliphor® P 407 microprilled (poloxamer 407), received from BASF (Florham Park, N.J.).

Animal maintenance: Healthy adult male chinchillas weighting 500 to 650 g were purchased from Ryerson Chinchilla Ranch (Plymouth, Ohio) and care for in accordance with protocols approved institutionally and nationally. Experiments were carried out in accordance with the Boston Children's Hospital, Boston University Medical Center, and Massachusetts Eye and Ear Infirmary Animal Use Guidelines and approved by each institution's Animal Care and Use Committee.

Hydrogel formation: P407-PBP hydrogel formulations were made by adding powdered polymers to aqueous solutions. Gels of varying P407-PBP weight percentage (10% to 18%) can be prepared by simple dissolution in a cold room to allow better solubility.

Gelation time: Hydrogel formulation in scintillation vials were immersed in a water bath kept at 37° C. with continuous stirring (200 rpm). The time it took the stir bar to stop rotating after immersion was recorded as the gelation time.

Gelation temperature: Gelation temperature was quantified using linear oscillatory shear rheology measurements (100 rads$^{-1}$, 1% strain, 1° C. min$^{-1}$). Gelation temperature was taken as the temperature at which the storage modulus (G') becomes greater than the loss modulus (G"). The changes of G' and G" over temperatures ranging from 0° C. to above body temperature were recorded to reflect changes in mechanical properties.

In vitro release studies: The release of ciprofloxacin from each formulation was measured using a diffusion system. Transwell® membrane inserts (0.4 µm pore size, 1.1 cm2 area; Costar, Cambridge, Mass.) and 24-well culture plates were employed as the donor and acceptor chambers, respectively. 200 µL of each formulation was pipetted directly onto pre-warmed filter inserts to obtain a solid hydrogel. Filter inserts (donor compartments) with formed gels were suspended in wells (acceptor compartments) filled with pre-warmed phosphate buffered saline (PBS) and the plates then incubated in a 37° C. oven. At each time point (0.5, 1, 2, 6, 12, 24, 48 h), 1 mL aliquots of the PBS receiving media were sampled and inserts sequentially moved into a new well with fresh PBS. Aliquots were suspended in 70:30 acetonitrile/PBS to ensure total drug dissolution. Sample aliquots were chromatographically analyzed with HPLC to determine ciprofloxacin concentrations ($\lambda$=275 nm). More detailed regarding the ciprofloxacin measurement and HPLC conditions can be found in reference (8). Experiments were performed in quadruplicate.

Ex vivo permeation experiment: The cross-TM permeation rate of ciprofloxacin was determined with auditory bullae harvested from healthy chinchillas. All formulations were applied into the bullae kept at 37° C. and deposited onto the TMs. The volume applied was 200 µL, which translates to 2 mg ciprofloxacin. Permeation of ciprofloxacin across TM into the receiving chamber was quantified using HPLC. Detailed information regarding TM harvesting, TM electrical resistance measurement, and configuration of the ex vivo permeation experiment can be found in reference (8).

Cytotoxicity analysis: Cell viabilities were evaluated with an assay of a mitochondrial metabolic activity, the CellTiter 96® Aqueous One Solution Cell Proliferation Assay (Promega Corp.) that uses a tetrazolium compound [3-(4,5-dimethyl-2-yl)-5-(3-carboxymethoxyphenyl)-2-(4-sulfophenyl)-2H-tetrazolium, inner salt; MTS] and an electron coupling reagent (phenazine ethosulfate; PES). On days 1 and 3 of the culture, human dermal fibroblasts (hFB), PC12, and normal adult human primary epidermal keratinocytes (ATCC) were incubated with CellTiter 96® Aqueous One Solution for 120 min at 37° C. The absorbance of the culture medium at 490 nm was immediately recorded with a 96-well plate reader. The quantity of formazan product (converted from tetrazole) as measured by the absorbance at 490 nm is directly proportional to cell metabolic activity in culture. Planar cultures on 24-well plate were used as controls. For each group, n=4. Cell viability was confirmed using a LIVE/DEAD® Viability/Cytotoxicity Kit (Molecular Probes, Invitrogen). Cells were incubated with 1 µM calcein-AM and 2 µM ethidium homodimer-1 (EthD-1) for 30 min at 37° C. to label live and dead cells, respectively. Cell viability was calculated as live/(live+dead)×100.

Histopathology: Formulations were administered to the ear canals of live healthy/OM chinchillas. Seven days later, they were euthanized as described elsewhere (8). Following sacrifice, the TMs were excised and immediately fixed in 10% neutral buffered formalin overnight, then decalcified, embedded in paraffin, sectioned (5 µm thick) and stained with hematoxylin and eosin by the Department of Pathology at Boston Children's Hospital (fee for service), using standard techniques. All stained specimens were evaluated under light microscopy (Olympus FSX-100).

Auditory brainstem response (ABR) measurements: ABR experiments were conducted with a custom-designed stimulus generation and measurement system built around National Instruments (Austin, Tex.) software (Lab View) and hardware. Detailed information regarding ABR can be found in reference (8).

NTHi OM Model and pharmacokinetics: All procedures and manipulations were performed using sedation analgesia with a mixture of ketamine and xylazine given intramuscularly in accordance with approved IACUC protocols at Boston University Medical Center. Baseline plasma samples were obtained through the cephalic sinus 24 hours prior to bacterial inoculation. Isolates of NTHi grown to the mid-log phase were diluted in HBSS, and approximately 25-75 cfu in 100 µL was introduced directly into each middle ear bulla under aseptic conditions. Daily tympanometry and otomicroscopy were performed to determine the presence of fluid in the auditory bullae and signs of infection including bulging tympanic membrane. Erythema and pictures were taken. Once abnormality was identified, the middle ear cavity was accessed 48 to 72 h later as described previously (See Sabharwal et al., Infect. Immun. 77, 1121-1127 (2009)). A direct culture of middle ear was obtained with a calcium alginate swab and immediately streaked onto a blood agar plate. Middle ear fluid was obtained with a 22-gauge angiocatheter connected to an empty tuberculin syringe, 10-20 µL of middle ear fluid was diluted 1:10 in HBSS, and three serial 10-fold dilutions were prepared. One hundred microliters of each dilution was plated onto blood agar. The lower limit of detection of viable organisms in middle ear fluid using this dilution series was 100 cfu $mL^{-1}$. Direct and indirect ear examination was performed every 1 to 2 days until the middle-ear cultures were sterile. Serial plasma samples were obtained during the experiment to determine systemic drug levels.

Statistical Analysis: Data which were Normally Distributed were Described with Means and Standard Deviations and Compared by Unpaired Student t-Tests. Otherwise, Data were Presented as Median±Quartiles. All Data Analyses were Performed Using Origin 8 Software. Methods and Results Isolation of Intact Chinchilla TMs.

The size of the tympanic membrane, middle ear structures, and auditory range of chinchillas closely approximate those of humans. A reproducible ex vivo method for studying flux across the tympanic membrane (TM) has been established. TMs were removed undamaged, with the bony tympanic ring still attached. Their integrity was assessed by measuring their electrical resistance (indicated by RA≥18 kOhm*$cm^2$) in a setup where TMs were placed horizontally in a 12-well plate with donor solution above and recipient solution below. The same set-up was used to measure drug flux, in lieu of a conventional diffusion cell—which would deform or rupture the TM. Skin samples, which had worse reproducibility than TMs, were only used as screening tools, to minimize the use of animals.

Trans-Tympanic Delivery of Antibiotics.

For trans-tympanic delivery of antibiotics ciprofloxacin, a synthetic fluoroquinolone antibiotic, was selected because of its known activity against non-typable Haemophilus influenzae (NTHi) and Streptococcus pneumoniae (SP), its low molecular weight and moderate lipophilicity.

CPEs Enhance Drug Flux Across the Intact TM.

Sodium dodecyl sulfate (SDS; anionic surfactant), and limonene (monocyclic terpene) were selected as chemical permeation enhancers (CPEs) based on their use in transdermal drug delivery and their favorable enhancement/irritation ratio. [28] Bupivacaine, an amino amide local anesthetic, was incorporated in some formulations for its potential clinical benefit to OM-associated otalgia, and because amino-ester anesthetics (e.g. tetracaine) act as CPEs. [15] In the absence of CPEs, ciprofloxacin permeation across the chinchilla TM at 37° C. was undetectable up to 12 hours. At 24 hours, 109 µg (out of 2 mg total ciprofloxacin), or 5.5% of the starting drug load, had permeated the TM; at 48 hours 364 µg (18%) had done so. The addition of limonene accelerated drug permeation; ciprofloxacin was detected in the receiving buffer in as little as 1-2 hours. A two-to-three-fold concentration-dependent increase in ciprofloxacin transfer at 48 hours was also achieved. Ciprofloxacin permeation was further enhanced by the use of all three CPEs together (1% SDS, 0.5% bupivacaine, and 2% limonene; termed 3CPE).

Hydrogels at the TM.

Figure 3:
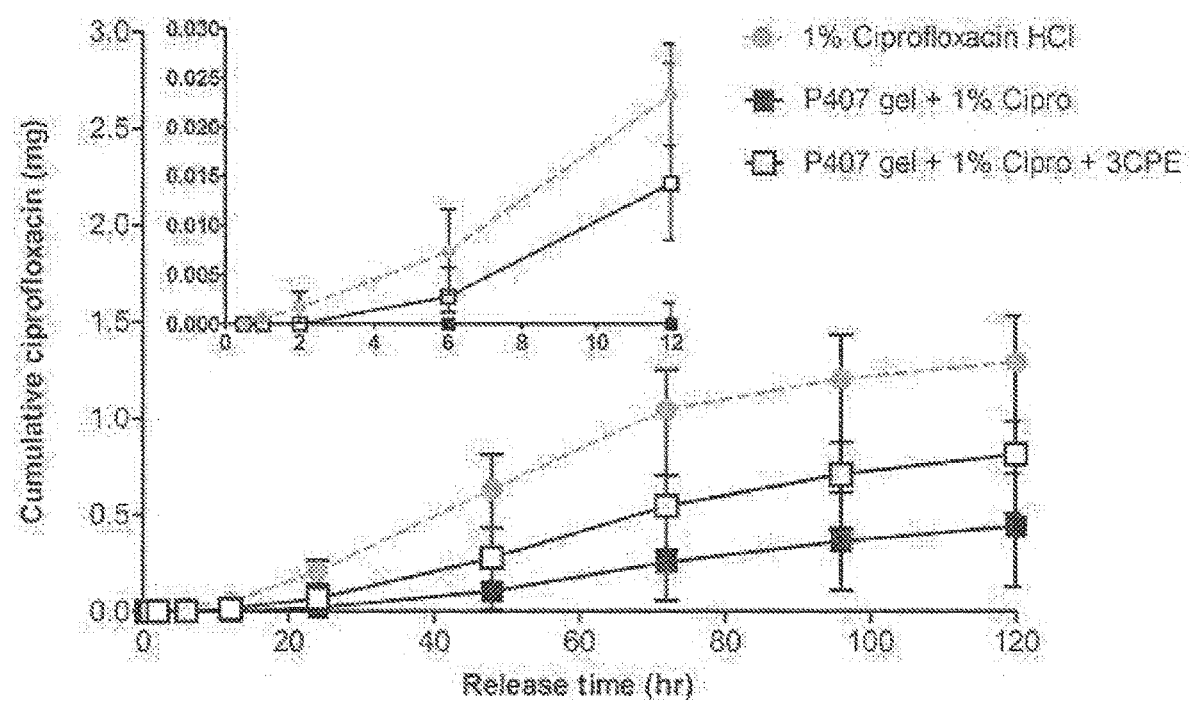
FIG. 3. Graph showing enhanced TM flux from gels containing permeation enhancers. (P407 is poloxamer 407, Cipro=ciprofloxacin, and 3CPE refers to 1% sodium dodecyl sulfate, 0.5% bupivacaine, 2% limonene)

The hydrogel component, Poloxamer 407 (P407) served to hold the drug-CPE combination in place at the TM for the duration of experiment. Drug-loaded 18% P407 formulations formed soft, clear gels when deposited on chinchilla TMs at 37° C. The hydrogel matrix slowed the transtympanic transfer of ciprofloxacin. (FIG. 3). The addition of 3CPE increased flux (but still not to the level of ciprofloxacin+CPE without gel), so that 3 μg of ciprofloxacin crossed the TM after 6 hours and 14 μg crossed after 12 hours (FIG. 3) This increase was seen at all time points, with 3CPE almost doubling the amount of ciprofloxacin crossing the TM in 120 hours (812 μg vs. 441 μg). The formulation of ciprofloxacin in 18% P407 with 3CPE is termed the standard formulation below.

Biocompatibility.

Figures 2A, 2B, 2C, 2D:
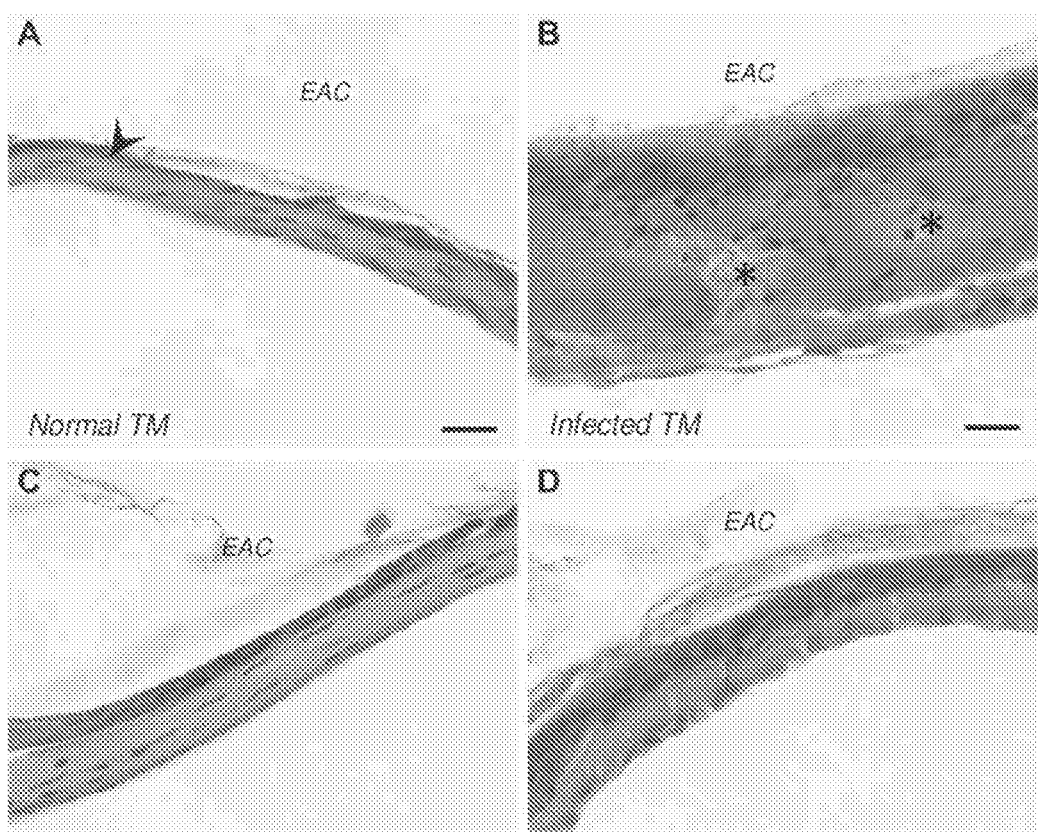
FIGS. 2A-2D. Images of the tympanic membrane (TM) (2A) normal, untreated TM; (2B) TM with otitis media; (2C) TM with gels containing ciprofloxacin; (2D) TM with gels containing ciprofloxacin and permeation enhancers. Space bar=20 μm.

In vivo, TMs exposed to ciprofloxacin-loaded gels without 3CPE for 7 days were mildly edematous but without inflammation (FIG. 2). Slightly more pronounced edema was seen in tissue exposed to ciprofloxacin-loaded gels with 3 CPEs, but again tissue reaction was benign. In contrast, TMs extracted after 7 days of untreated *H. Influenzae* infection were approximately five times thicker and exhibited a prominent neutrophilic inflammatory response.

Measurement of Acoustic Brainstem Response (ABR).

Figure 4:
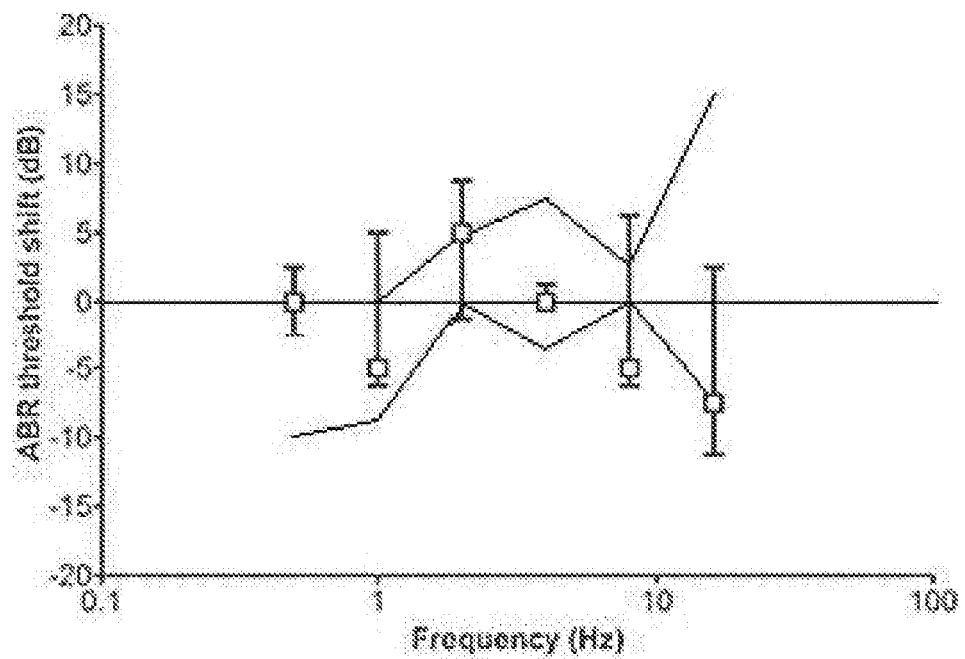
FIG. 4. Graphs showing acoustic brainstem response (ABR) threshold shifts after application of 18% poloxamer 407 (P407) containing chemical permeation enhancers. Horizontal line denotes no change.

Drug-CPE-hydrogels should not affect hearing thresholds or be ototoxic. ABR thresholds after application of the gel-enhancer formulation were similar to pre-application measurements (FIG. 4).

The Chinchilla Model of OM.

The infectious inoculum is placed in the middle ear through the superior bullae, so that there is no open portal for infection through a TM injury, and drug flux across the TM will be unaffected by the inoculation itself. 100% of animals treated in this manner with *S. pneumoniae* (SP) and non-typable *H. influenzae* (NTHi) develop OM. In studies with a single strain of NTHi, OM resolved in approximately 50% of animals treated with the standard formulation (vs. 20% for untreated animals). Ciprofloxacin was undetectable in the blood.

The relatively low cure rate likely reflected inadequate drug flux in vivo, and may be attributable to the following factors. 1) Inadequate drug loading and/or CPE loading. 2) Poor mechanical properties of the gel. At 27° C., the incorporation of CPEs changed the phase transition of P407 solution (FIG. 5) so that the storage modulus did not become greater than the loss modulus, i.e., gelation did not occur. While gelation still occurred at 37° C., these data show that the gelation was not mechanically robust. This view is consistent with a finding on otoscopy that the P407-based gels were spread out in the auditory canal; lack of bioadhesiveness is another possible contributing factor. A separate issue is that gelation took ~20 sec. This may be adequate in anesthetized animals, but not in active toddlers.

Synthesis of a P407-PPE Polymer.

Figure 9:
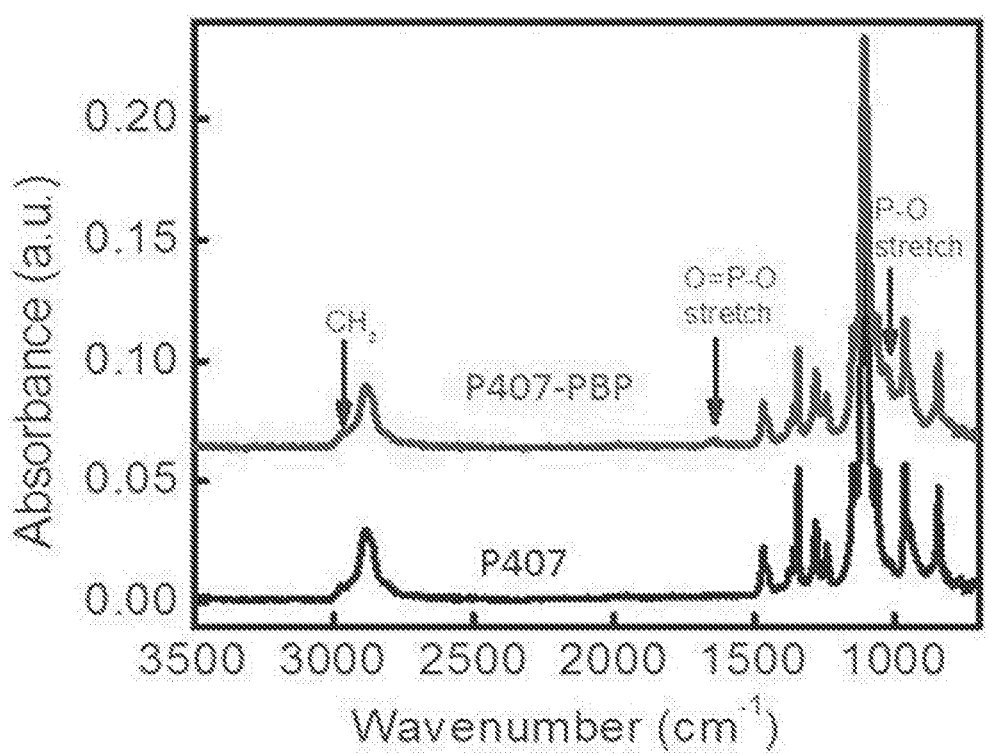
FIG. 9. FTIR for P407-PBP, a poloxamer 407-poly(butoxy)phosphoester, and starting material P407. The additional stretches indicating addition of butoxyphosphoester monomers are indicated.

The hydrophobic monomer, 2-butoxy-2-oxo-1,3,2-dioxaphospholane (BP) was prepared by condensation reaction of 2-chloro-2-oxo-1,3,2-dioxaphospholane (COP) and butanol, then purified by vacuum distillation, and analyzed by proton and phosphorous NMR spectroscopy. Hydrophobic P407-PPE polymer (PBP-P407-PBP) was synthesized by ring opening polymerization (ROP) of BP with P407 in the presence of an organocatalyst, 1,8-diazabicyclo[5.4.0]undec-7-ene (DBU) at −20° C. Upon completion of the reaction (complete monomer consumption confirmed by NMR spectroscopy), excess acetic acid in dichloromethane (DCM) was added to the reaction mixture to quench the reaction. The product was purified by precipitation into ether (3 times) and dried to a white powder under vacuum. Proton and phosphorous NMR spectroscopy, Fourier transform infrared spectroscopy (FTIR), and gel permeation chromatography were used to characterize the polymer and confirm its purity. FTIR spectroscopy of the product, PBP-P407-PBP, and starting material, P407, are compared in FIG. 9. The molecular weight of the copolymer was measured as 30.2 kDa by gel permeation chromatography.

Synthesis of P407-PPE Polymers.

Figure 11A:
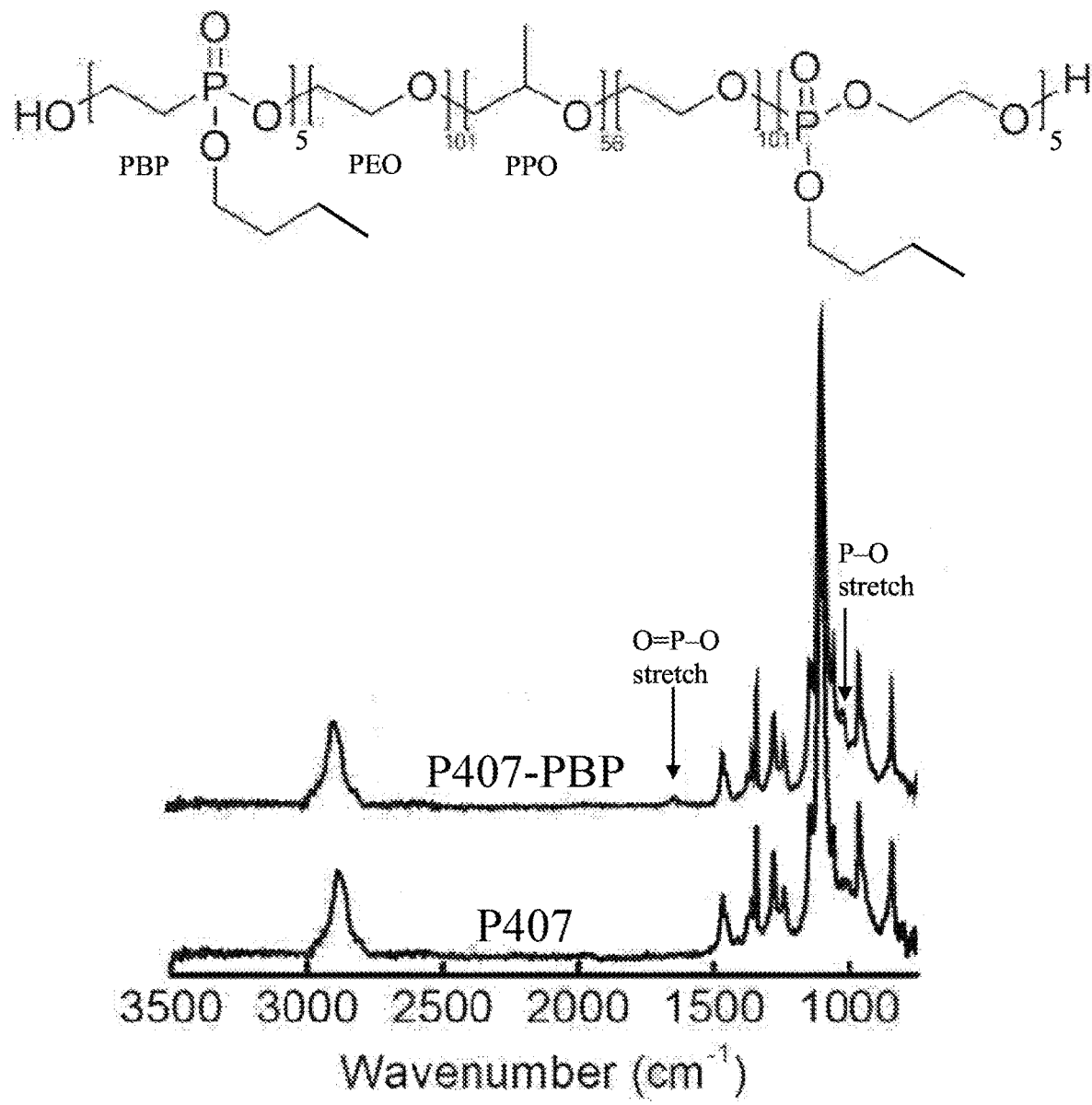
FIG. 11(A) Chemical structure of the P407-polybutylphosphoester with n-butyl side groups; and FTIR spectra of P407 and P407-PBP.
Figure 11B:
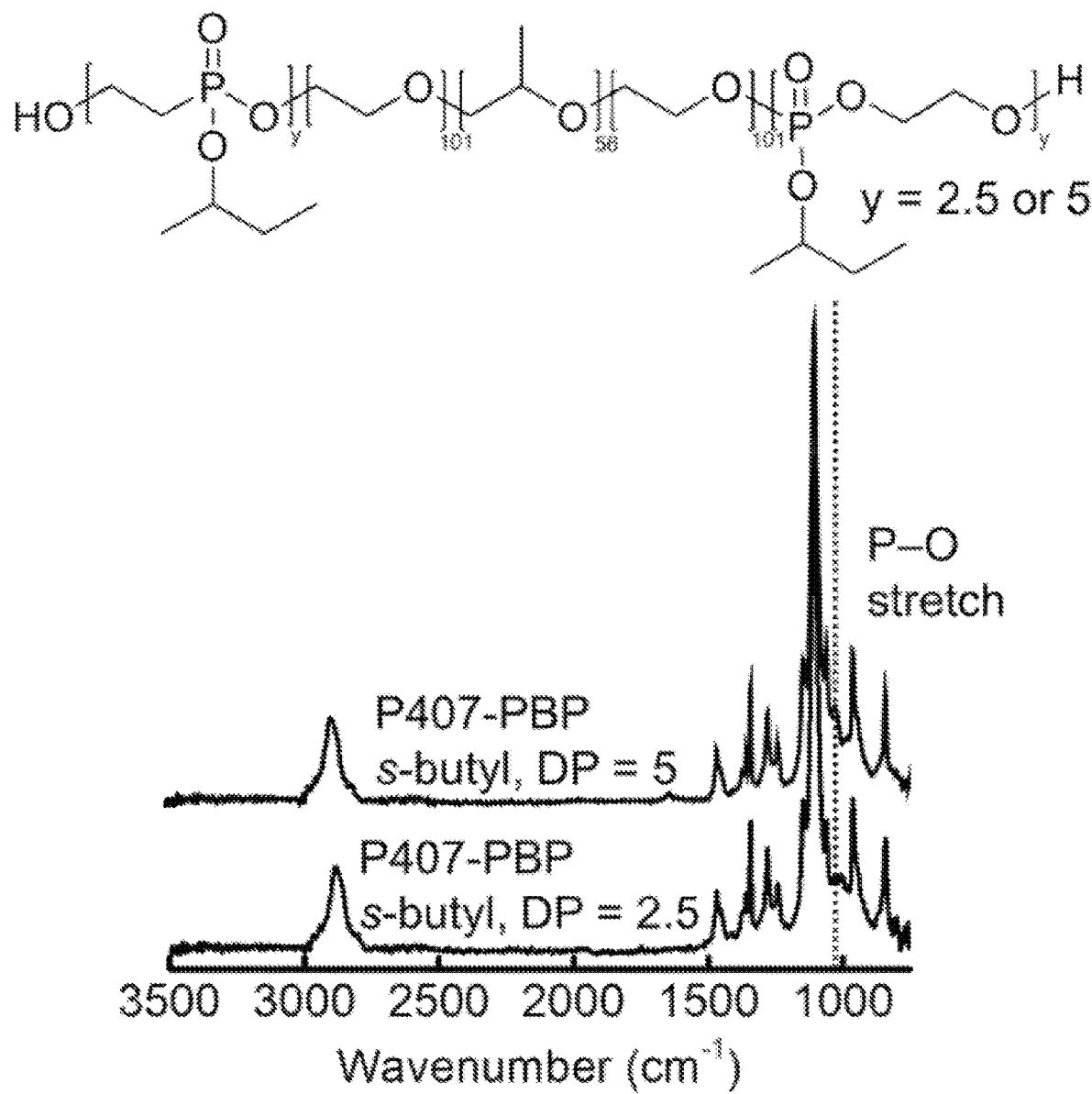
FIG. 11(B) Chemical structure of the P407-polybutylphoester with s-butyl side groups and corresponding FTIR spectra FIG. 12(A). Nuclear magnetic resonance (NMR) of pentablock copolymers P407-PBP.
Figure 12A:
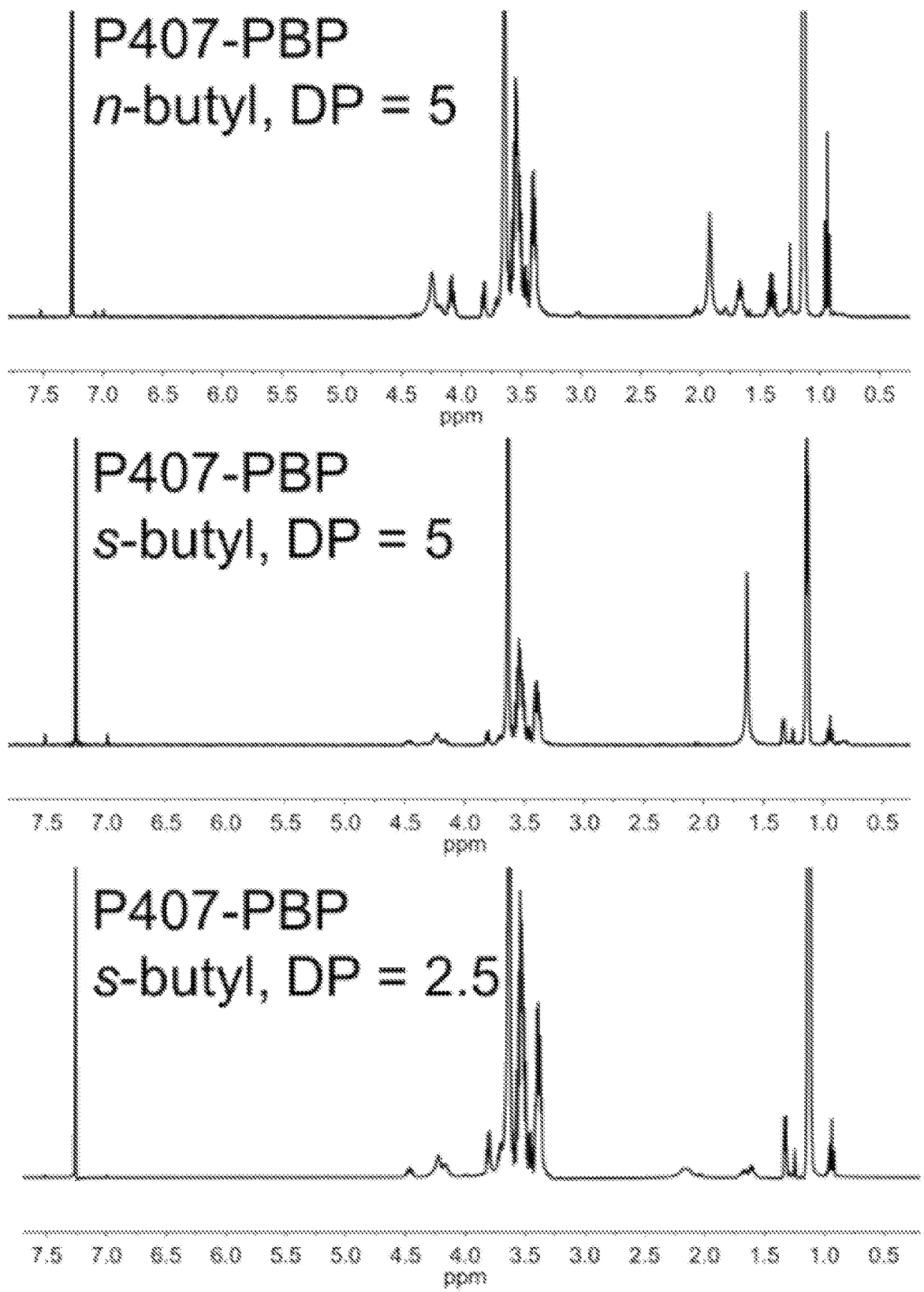
FIG. 12(B). Effect of n- or s-butylphosphoester and degree of polymerization on storage and loss shear moduli of 18% aqueous solutions of P407 derivatives, as a function of temperature. Polymers tested include: P407-PBP, with n- or s-butyl groups, and degree of polymerization (DP) of 2.5 or 5. Data are means±SD, n=4.
Figure 12B:
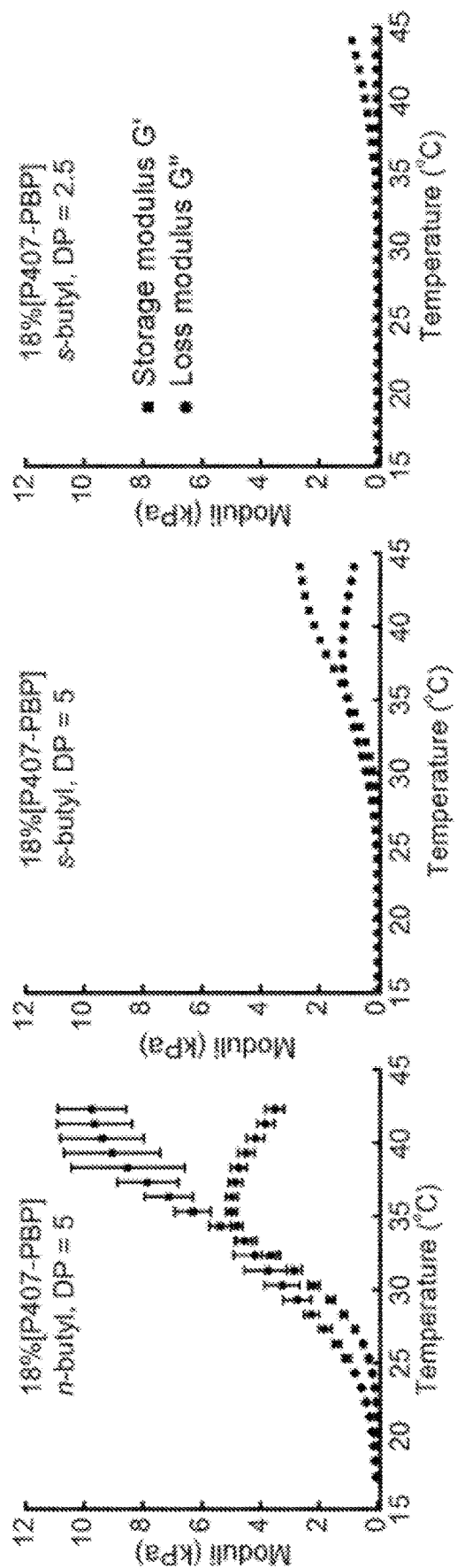

The pentablock copolymer P407-polybutylphosphoester with n-butyl (FIG. 11A) or s-butyl side groups (FIG. 11B) was synthesized via ring-opening polymerization (ROP) in the presence of an organocatalyst, 1,8-diazabicyclo[5.4.0]undec-7-ene (DBU), at −20° C. After purification by precipitation, Fourier transform infrared spectroscopy (FTIR, FIG. 11A-11B) showed peaks near 1650 and 1050 cm-1 which are characteristic of the stretching of O=P—O and P—O respectively in the polybutylphosphoester (PBP) moieties (Lin-Vien et al., *The Handbook of Infrared and Raman Characteristic Frequencies of Organic Molecules* (Academic Press, New York) (1991)). Both were present in the spectrum of the ROP product but not the reactant P407, indicating the successful addition of PPE blocks. Increased molecular weight, demonstrated by gel permeation chromatography (GPC, table S1), indicated that P407 was chemically modified by n-butyl PBP or s-butyl PBP blocks, and not a physical mixture. The number averaged molecular weight ($M_n$) measured by nuclear magnetic resonance (NMR) agreed with that calculated from the chemical formulae (table S1). $M_n$ measured by GPC was ~30% higher than that measured using NMR; that discrepancy is well documented in the literature (Wong et al., *ACS Macro Lett.* 1, 1266-1269 (2012)). In the synthetic scheme, a small degree of polymerization (DP) was targeted to avoid gelation at or below room temperature and to facilitate degradation of the hydrogel. The actual DP of the PPE blocks was determined to be 5 using NMR (FIG. 12A). FIG. 12A depicts the nuclear magnetic resonance (NMR) of pentablock copolymers. DP was calculated using the ratio of peak areas at 0.90 ppm (monomer side chain) and 1.14 ppm (P407 backbone). The chemical shifts (δ, in ppm) for the peaks corresponding to the hydrogens in italics in the following list of polymers is provided below. t/m/broad indicate the shape of a peak (i.e., triplet, multiple, broad). $CDCl_3$ was the solvent. For P407-PBP with n-butyl groups, $^1H$ NMR ($CDCl_3$, ppm): δ 0.90-0.96 (t, 3H, $CH_2CH_2CH_2CH_3$), 1.14 (m, 3H, $CH_2CH(CH_3)O$), 1.36-1.46 (m, 2H, $CH_2CH_2CH_2CH_3$), 1.62-1.72 (m, 2H, $CH_2CH_2CH_2CH_3$), 3.36-3.42 (m, $CH_2CH(CH_3)O$), 3.48-3.58 (m, 2H, $CH_2CH(CH_3)O$), 3.65 (m, 4H, $OCH_2CH_2O$), 4.04-4.14 (m, 2H, $PCH_2CH_2CH_2CH_3$), 4.16-4.30 (broad, 4H, $POCH_2CH_2O$). For P407-PBP with s-butyl groups, $^1H$ NMR ($CDCl_3$, ppm): δ 0.90-0.96 (t, 3H, $CH_3CHCH_2CH_3$), 1.13 (m, 3H, $CH_2CH(CH_3)O$), 1.30-1.34 (b, 3H, $CH_3CHCH_2CH_3$), 1.55-1.73 (m, 2H, $CH_3CHCH_2CH_3$), 3.35-3.42 (m, $CH_2CH(CH_3)O$), 3.48-3.58 (m, 2H, $CH_2CH(CH_3)O$), 3.65 (m, 4H, $OCH_2CH_2O$), 4.11-4.19 (m, 1H, $CH_3CHCH_2CH_3$), 4.19-4.35 (broad, 4H, $POCH_2CH_2O$). Smaller DP, such as DP=2.5, resulted in a high gelation temperature and poor shear strength (FIG. 12B). P407-PBP with an n-butyl group and a DP of 5 was used in subsequent studies because it gelled at a lower temperature and with greater shear moduli than those made with s-butyl groups (FIG. 12B).

TABLE S1

Molecular weight measured by GPC and NMR and polydispersity indices of P407, and pentablock copolymers P407-PBP with n- or s-butyl groups.

| | P407 | P407-PBP n-butyl DP = 5 | P407-PBP s-butyl DP = 5 | P407-PBP s-butyl DP = 2.5 |
|---|---|---|---|---|
| Weight average molecular weight, $M_w$ (kDa) | 18.0 | 23.7 | 23.5 | 21.2 |
| Number average molecular weight, $M_n$ (kDa) | 15.1 | 19.1 | 18.6 | 17.3 |
| $M_n$ calculated using NMR (kDa) | n.a. | 13.9 | 13.9 | 13.4 |
| Polydispersity index, $M_w/M_n$ | 1.2 | 1.2 | 1.3 | 1.2 |

Gel Properties of P407-PPE Polymer

A 18% aqueous solution of commercially available P407 (i.e., 18%[P407]), which demonstrated reverse thermal gelation, was previously the vehicle to deliver the antibiotic ciprofloxacin with CPEs to the TM (8). For 18%[P407], the storage (G') and loss (G") moduli (measured by linear oscillatory shear rheology at 100 rads$^{-1}$, 1% strain, 1° C. min$^{-1}$) were ~1 kPa at room temperature; it behaved as a viscous liquid. G' and G" demonstrated sharp increases at temperatures above 27° C., and plateaued at 6 kPa and 4 kPa respectively (FIG. 13A), demonstrating solid-like behavior. However, when 3CPE was added to the P407 solution at the desired concentrations (which was previously used to enhance permeation across the TM (8)), storage and loss moduli of the formulation were less than 2 kPa over the temperature range of 20-40° C. (FIG. 13B), i.e. the material did not form a gel in the presence of 3CPE.

P407-PBP had faster gelation kinetics than did unmodified P407. The sol-gel transition occurred ~7 seconds after Cip-3CPE-18%[P407-PBP] was submerged into a water bath at 37° C., while a Cip-3CPE-18%[P407] remained as a solution for 48 seconds. The Cip-18%[P407] and Cip-18% [P407-PBP] (in the absence of 3CPE) demonstrated identical gelation kinetics.

Figure 13:
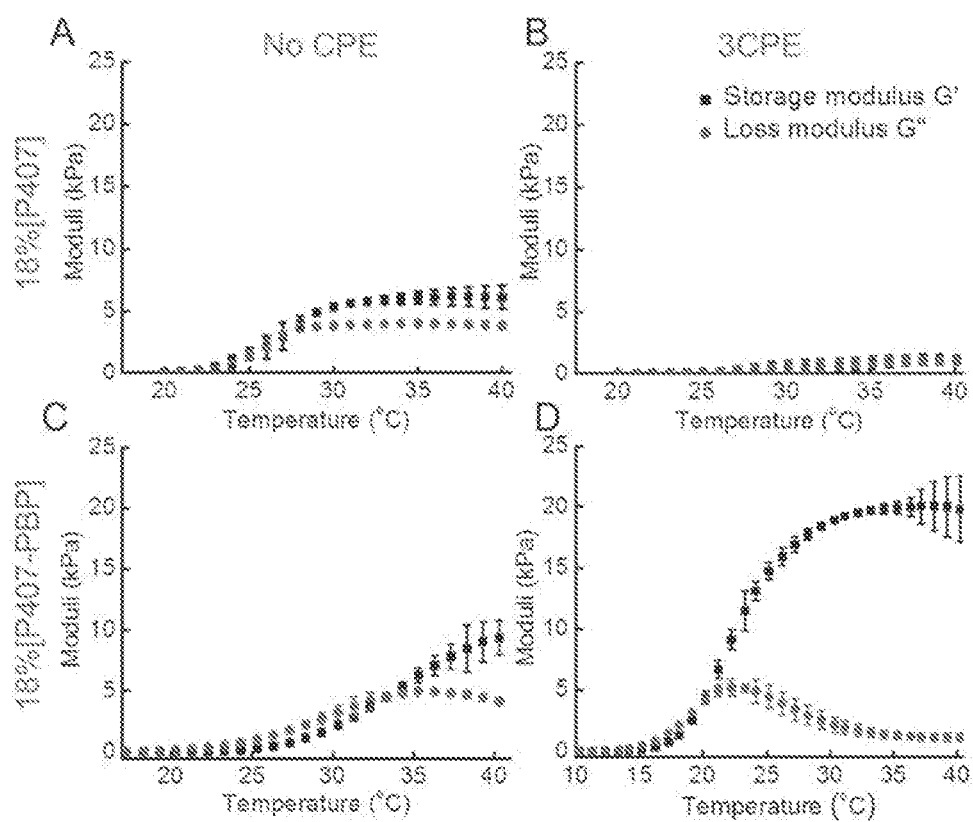
FIG. 13. Gelation of aqueous solutions of 18%[P407].
Figure 14:
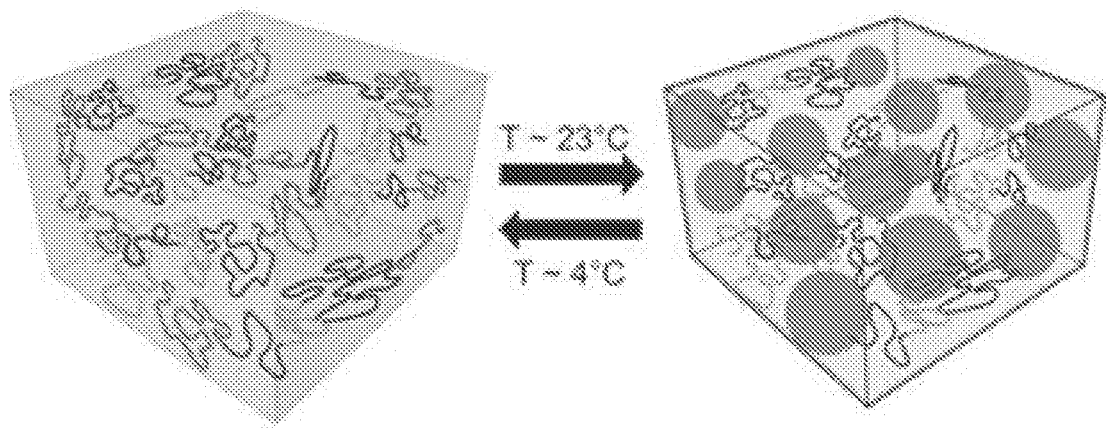
FIG. 14. Schematic of the gelation of P407-PBP aqueous solution, facilitated by hydrophobic interactions of polyphosphoester end groups at elevated temperature (23° C.)

Gelation of P407-PBP was not hindered by the inclusion of 3CPE. Linear oscillatory shear rheology measurements (100 rads$^{-1}$, 1% strain, 1° C. min$^{-1}$) indicated that the storage (G') and loss (G") moduli of Cip-18%[P407-PBP] were 0.3 and 1.0 kPa respectively at room temperature (FIG. 13C). G' and G" both increased gradually in the temperature range 27-38° C. and became 7.8 and 5.0 kPa respectively near body temperature. The sol-gel transition temperature was ~33° C. Introduction of 3CPE to Cip-18%[P407-PBP] increased its storage modulus more than 2.5 fold (FIG. 13D). G' and G" increased from close to zero at room temperature to 20 and 1.3 kPa respectively at 37° C. The polymer solution exhibited a sol-gel transition temperature of 20° C. By TEM, micelles were observed at the low polymer concentrations (1%) required for that imaging modality.

Figure 15:
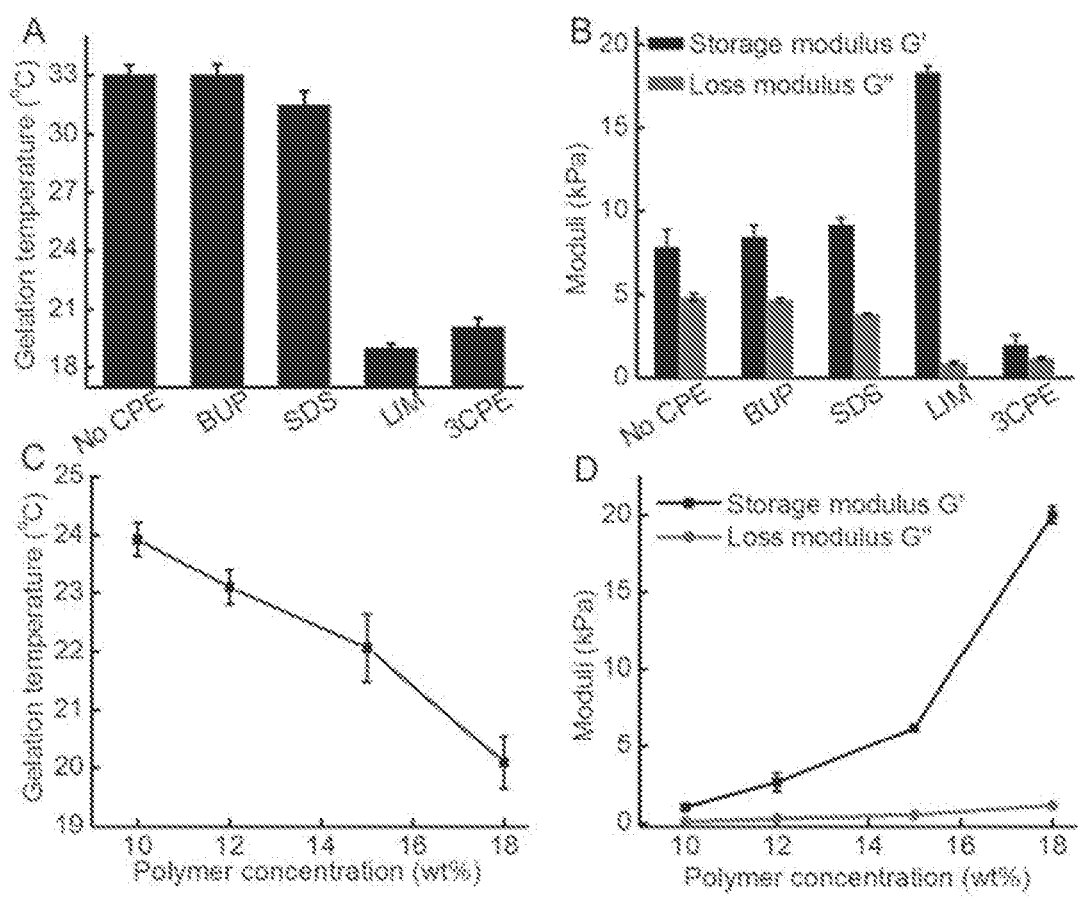
FIG. 15. Effects of individual CPEs and polymer concentrations on formulation rheology.

To evaluate the effect of individual CPEs on temperature-dependent mechanical properties, 1% SDS, 2% limonene or 0.5% bupivacaine were added separately to Cip-18%[P407-PBP] (FIGS. 15A and 15B). Limonene reduced the gelation temperature of Cip-18%[P407-PBP] by 14° C., increased G' by 10.5 kPa and decreased G" by 4.1 kPa, such that they were very similar to those for Cip-3CPE-18%[P407-PBP] (FIGS. 13D and 15B), suggesting that the influences of CPEs are dominated by the effects of limonene. SDS shifted the gelation temperature of Cip-18%[P407-PBP] lower by 1.5° C., but did not affect the plateau values of G' and G". Bupivacaine had minimal effects on the mechanical properties and gelation temperature of Cip-18%[P407-PBP].Syringing of Cip-3CPE-18%[P407-PBP] and Cip-3CPE-15% [P407-PBP] was challenging. For example, Cip-3CPE-15% [P407-PBP] was hard to push through a 20 gauge catheter and extruded as a gel rather than a viscous liquid, which made placement on the TM in vivo difficult. Therefore, for in vivo work, Cip-3CPE-12%[P407-PBP] was selected, because its sol-gel transition was clear (G'>G" at body temperature; FIGS. 15C and 15D), and it did not gel after extrusion through a 20 gauge, 1.8 inch catheter at room temperature.

In Vitro Drug Release and Ex Vivo Drug Flux

Figure 16:
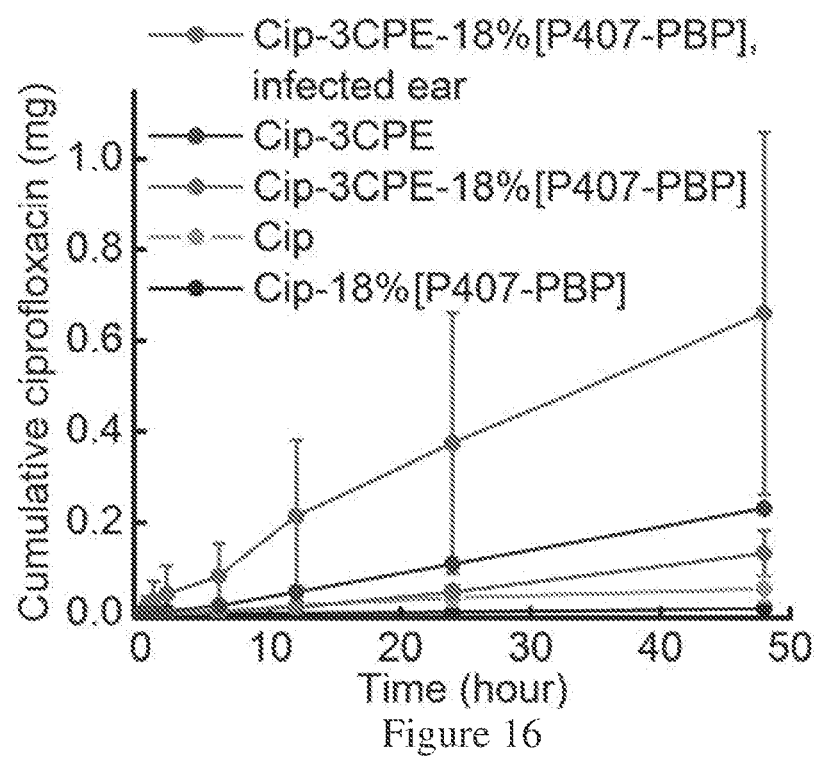
FIG. 16. Ex vivo transfer of ciprofloxacin across the TM into a receiving chamber. The hydrogel formulation Cip-3CPE-18%[P407-PBP] enables high cross-TM drug flux. Data are mean±SD, n=4.
Figure 19:
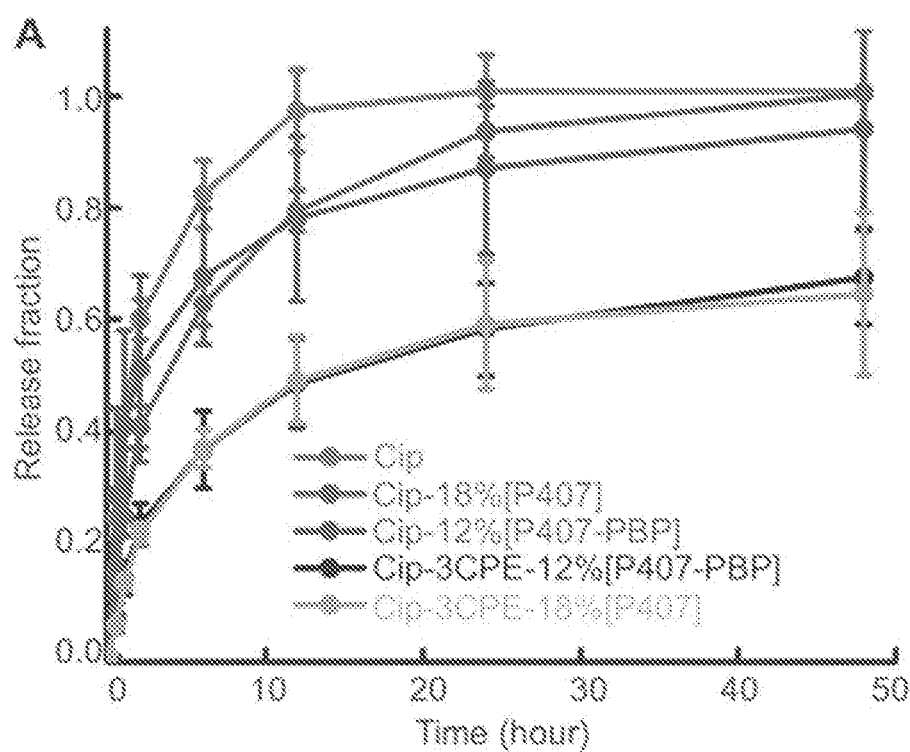
FIG. 19. Cumulative release of ciprofloxacin at 37° C. from Cip and from Cip-18%[P407], Cip-3CPE-18%[P407], Cip-18%[P407-PBP], and Cip-3CPE-18%[P407-PBP] under infinite sink conditions. 2 mg ciprofloxacin were contained in each gel and solution at time zero. Data are means±SD, n=4.

The design of the formulation entailed two components: CPEs that are expected to increase drug flux across the TM (8), and the hydrogel, which is expected to slow flux but will prolong treatment for the duration that is needed for clearance of infection. The effect of the hydrogel and 3CPE on the transport rate of ciprofloxacin were studied by quantifying 1) in vitro diffusion from the bulk hydrogel matrix (albeit in infinite sink conditions, which are unlikely to exist on the TM surface); 2) ex vivo permeation across the TM. In vitro release experiments showed that P407-PBP slowed drug release compared to the free drug solution (FIG. 19). Incorporation of 3CPE caused further slowing of drug release. However, the magnitude of ciprofloxacin release from Cip-3CPE-18%[P407-PBP] was more than 30% greater than from Cip-3CPE-18%[P407]. Drug transport across the TM was studied ex vivo in auditory bullae excised from healthy chinchillas, as described in Methods. Inclusion of 3CPE enhanced the flux across the TM from a 1% ciprofloxacin solution more than 4 fold and from Cip-18% [P407-PBP] more than 10 fold (FIG. 16). Conversely, the presence of a hydrogel tended to decrease flux across the TM; that effect could be overcome by the incorporation of CPEs. The ex vivo model could not be used to demonstrate the principal utility of the hydrogel, which is to prolong the duration of drug flux across the TM by creating a stable depot system, because at 37° C. the TMs degraded after ~48 hours due to microbial growth.

Figure 17:
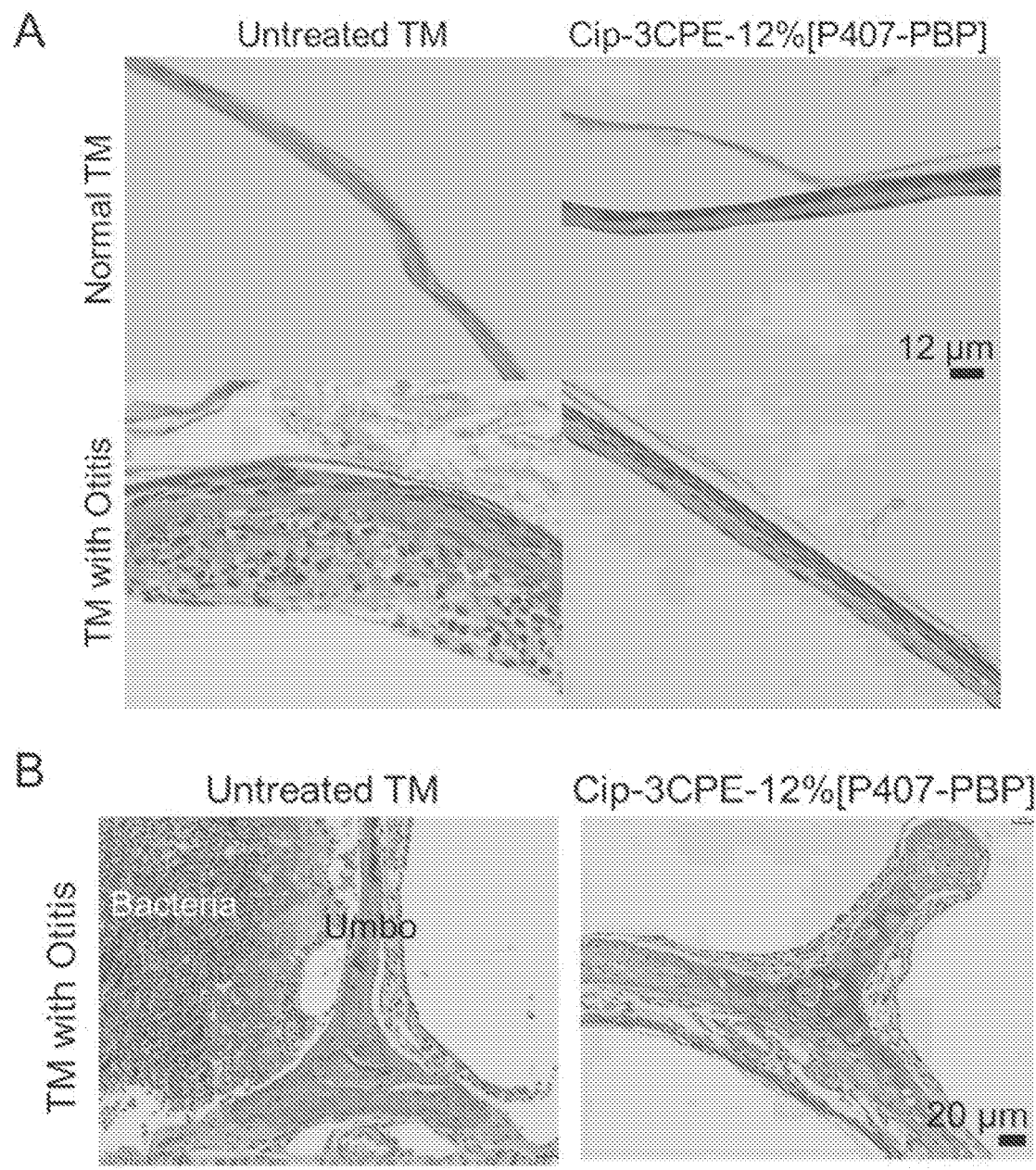
FIG. 17. Representative photomicrographs of Cip-3CPE-12%[P407-PBP] in normal and diseased chinchilla ears.
Figure 20A:
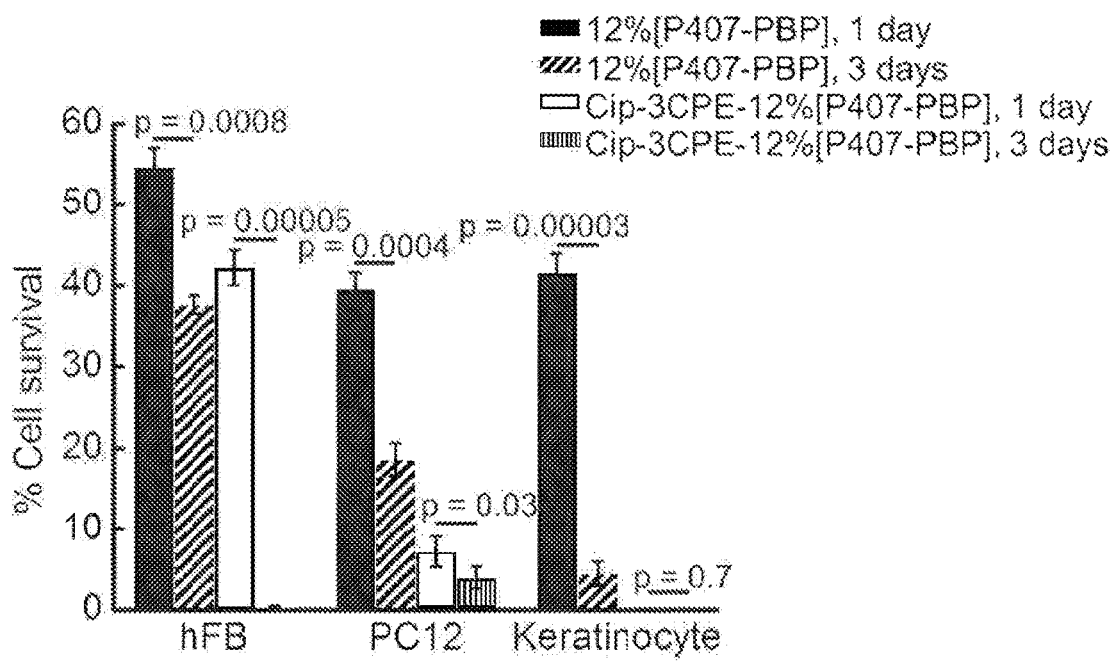
FIG. 20(A) Survival rates (determined by MTS assay) of human fibroblasts (hFB), PC12 cells, and keratinocytes, after incubating with 12%[P407-PBP] and Cip-3CPE-12%[P407-PBP] for 1 or 3 days. Data are means±SD (n=4).
Figure 20B:
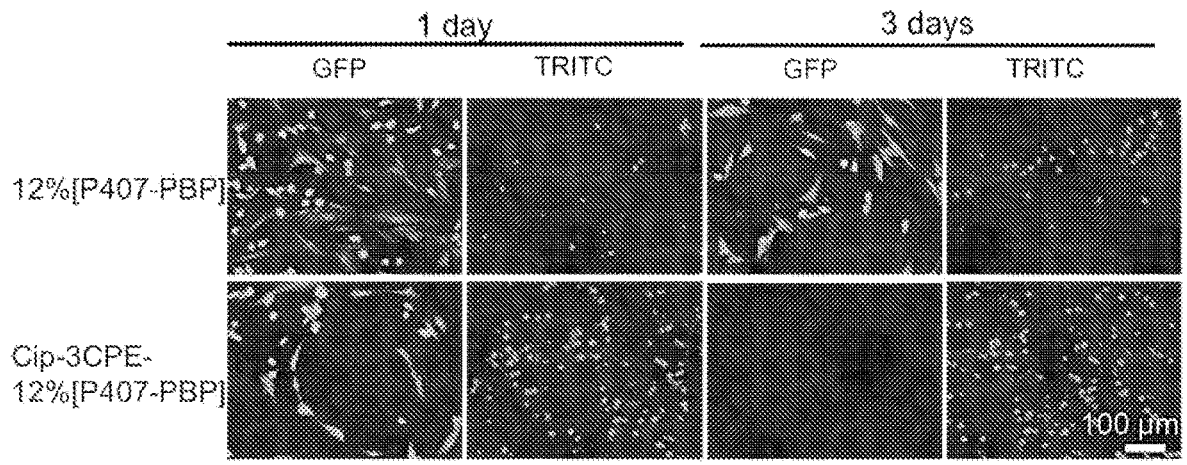
FIG. 20(B) Live/dead assay of hFB, done to confirm the data in (A) by a different assay, after incubation for 1 or 3 days with 12%[P407-PBP] or Cip-3CPE-12%[P407-PBP]. Green (GFP) indicates live cells and red (TRITC) indicates dead cells. (C) hFB cell survival rates were obtained by counting live and dead cells in FIG. 20 (B) and calculating % cell survival=live cells/(live cells+dead cells). Cell counting was done using ImageJ. Data are means±SD (n=4). For all images, pair-sample t-test was applied.
Figure 20C:
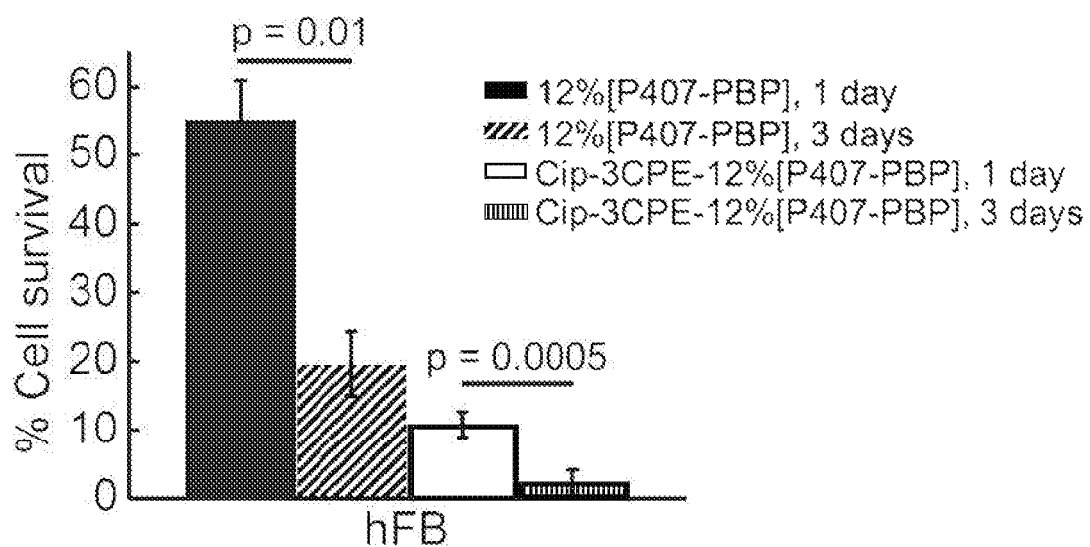
FIG. 20. Cytotoxicity of 12%[P407-PBP] and Cip-3CPE-12%[P407-PBP].
Figure 21:
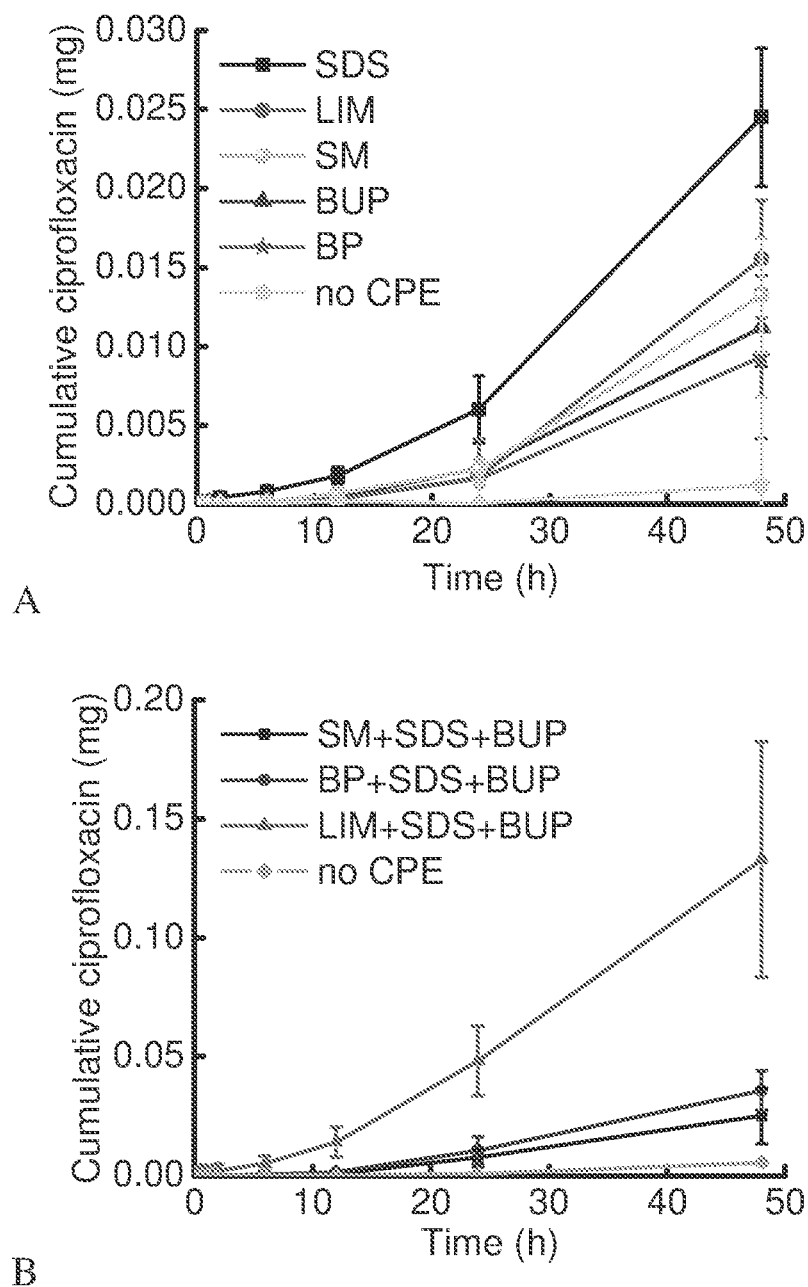
FIG. 21 (B). Permeation enhancement of effect combinations of CPEs. All curves show the cumulative amount of ciprofloxacin permeated across the TM over time. All solutions are made with 12% P407-PBP, 1% Ciprofloxacin. In particular, stearyl methacrylate (SM) and SDS and bupivacaine (BUP)=1.5% SM (solubility limit), 1% SDS, 0.5% BUP; BP and SDS and BUP=1.5% BP (solubility limit), 1% SDS, 0.5% BUP; LIM and SDS and BUP=2% LIM, 1% SDS, 0.5% BUP.
Figure 22:
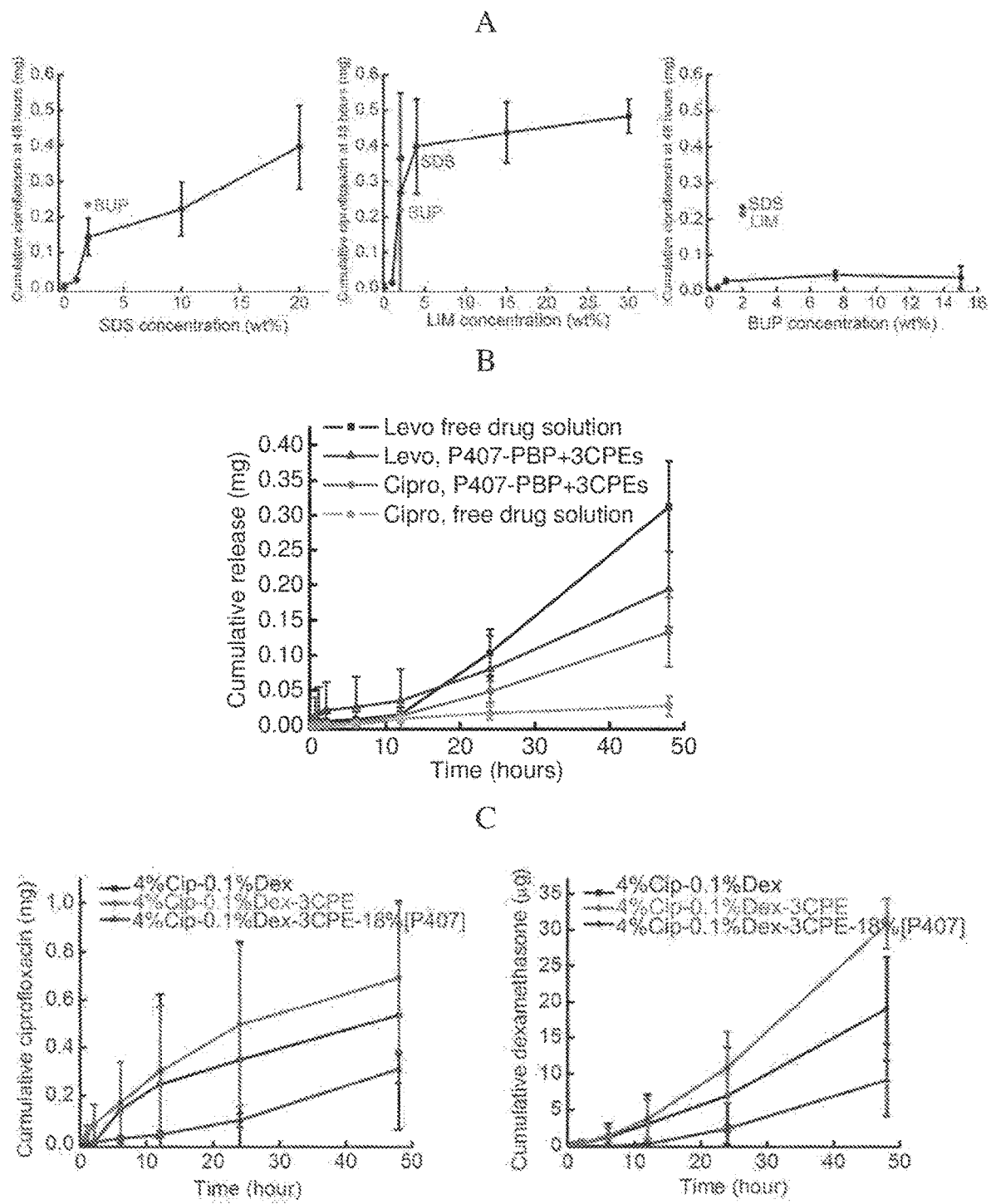
FIG. 22 (B). Trans-tympanic permeation of levofloxacin formulations in comparison with ciprofloxacin formulations. Levofloxacin free drug solution=1.5% Levofloxacin aqueous solution; Levo, P407-PBP+3CPEs=1.5% Levofloxacin, 12% P407-PBP, 1% SDS, 2% LIM, 0.5% BUP; Cipro, P407-PBP+3CPEs=1% Ciprofloxacin, 12% P407-PBP, 1% SDS, 2% LIM, 0.5% BUP; Cipro free drug solution=1% Ciprofloxacin aqueous solution.

Tissue toxicity was a potentially important consideration since CPEs can disrupt the stratum corneum (28). The specific combination of 3CPE were chosen because it effectively enhances permeation and is non-toxic in vivo (See 8; Simons et al., *Chemical penetration enhancers and in situ-forming reservoirs for trans-tympanic drug delivery: progress toward improved treatment of Otitis media*. (Massachusetts Institute of Technology) (2008)). Cytotoxicity of the polymer and 3CPE was evaluated with a 3-(4,5-dimethyl-2-yl)-5-(3-carboxymethoxyphenyl)-2-(4-sulfophenyl)-2H-tetrazolium, inner salt (MTS) assay in three cell lines that are representative of cell types in the auditory system: human dermal fibroblasts (hFB), PC12 cells (a pheochromocytoma cell line frequently used to test neurotoxicity), and normal adult human primary epidermal keratinocytes from abdominal skin (FIG. 20A). A LIVE/DEAD® Viability/Cytotoxicity Kit was used as a confirmatory assay in hFB (FIG. 20B). Test formulations were placed in the upper chamber of a Transwell system with a pore size of 0.4 μm, with cells below. P407-PBP itself showed little toxicity after 1 day, but considerably more on day 3. The presence of 3CPE and ciprofloxacin increased cytotoxicity for all cell types and time points. Nevertheless, biocompatibility was excellent in vivo: TMs treated with 200 μL Cip-3CPE-18%[P407-PBP] were histologically similar to healthy TMs that had not been exposed to any treatment (FIG. 17A). Gels were adherent to the TMs 7 days after application, but had degraded completely within 3 weeks.

Performance in Otitis Media In Vivo

OM due to NTHi was established in chinchillas following direct inoculation into the middle ear, which were then treated with 200 µL of test material deposited through the external canal on the TM. In animals treated with 1% ciprofloxacin alone (n=8), NTHi were detectable in the middle ear fluid of 25% animals on days 1 and 3, but by day 7 only in 62.5% animals had infection had been cleared (FIG. 18A; i.e., zero cfu [colony-forming unit] in middle ear fluid aspirated from the dorsal aspect of the auditory bullae, i.e., not through the TM), an unacceptably low cure rate (31). The clearance rate was similarly low, 60%, in animals with OM treated with Cip-3CPE-18%[P407] (n=5). In contrast, OM was cleared in 10 of 10 animals treated with Cip-3CPE-12% [P407-PBP] (FIG. 18A; p=0.0065 by Fisher's exact test), within 24 hours following application of the formulation.

Figure 18:
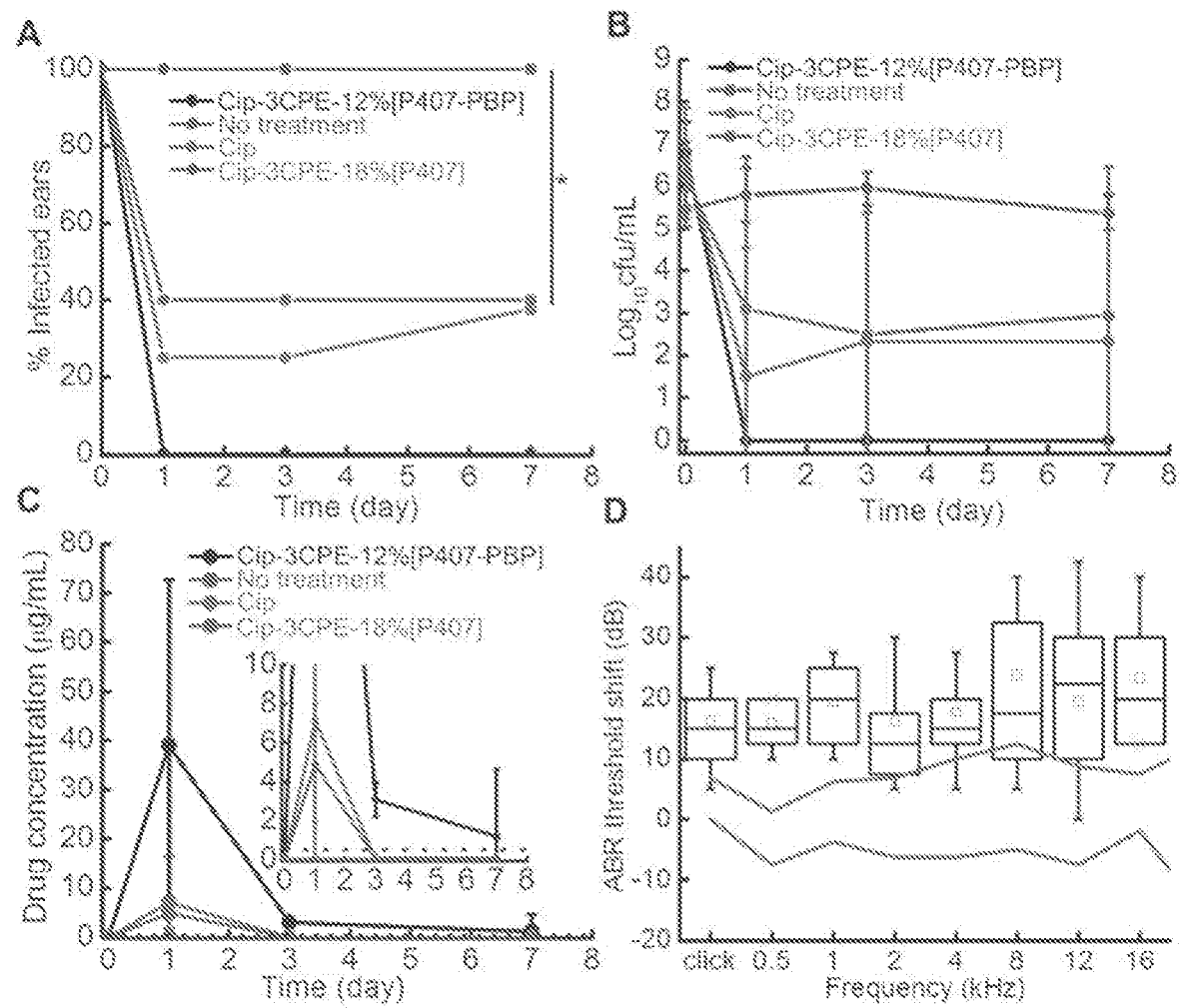

The 100% cure rate in animals treated with Cip-3CPE-12% [P407-PBP] may be explained by the time course of ciprofloxacin levels in the middle ear (FIG. 18B). The concentration of ciprofloxacin peaked at 1 day (39.1 µg mL$^{-1}$ in animals treated with Cip-3CPE-12%[P407-PBP] and 4.2 µg mL$^{-1}$ in those treated with 1% ciprofloxacin solution). Three days after administration of the formulations, ciprofloxacin was still supra-therapeutic (3.06 µg mL$^{-1}$) in the middle ears of animals that received Cip-3CPE-12%[P407-PBP], while the ciprofloxacin concentration dropped to zero in animals treated with 1% ciprofloxacin solution. (The minimum inhibitory concentration (MIC) of NTHi by ciprofloxacin is 0.1-0.5 µg mL$^{-1}$ (See Pérez-Vázquez, et al., *Antimicrob. Agents Chemother.* 47, 3539-3541 (2003); Hirakata et al., *Antimicrob. Agents Chemother.* 53, 4225-4230 (2009)). Seven days after administration, the ciprofloxacin concentration was still 1.2 µg mL$^{-1}$ in the middle ear fluid of animals treated with Cip-3CPE-12% [P407-PBP], i.e. the concentration of antibiotics in the auditory bullae was above MIC throughout a 7-day period in that group. No recurrence of OM was observed.

The fact that ciprofloxacin drops had any effectiveness at all in OM was surprising, given that the TM is relatively impermeable to small molecules (such as $CO_2$ and He) (12, 14, 34) and ototopical antibiotics are only used for middle ear disease in situations where the TM has been breached (e.g. with myringotomy tubes) (Wall et al., *Pediatr. Infect. Dis. J.* 28, 141-144 (2009)). The effect of iprofloxacin drops in OM may be explained by the fact that the TM became 5- to 31-fold more permeable to drug flux in OM (FIG. 16) despite also becoming much thicker (FIG. 17A).

Systemic Distribution of Ciprofloxacin

Ciprofloxacin was undetectable in plasma samples from blood obtained in the transverse sinus (table S2). Given the proximity of that location to the auditory bullae, the absence of ciprofloxacin suggested that no systemic exposure of antibiotics occurred.

Histological Assessment

The single-dose treatment with Cip-3CPE-12%[P407-PBP]was able to reverse the prominent inflammatory response caused by NTHi and to prevent bacterial growth (FIG. 17B).

Seven days after administration of the formulation, the TM was excised intact within the tympanic ring, and processed into hematoxylin and eosin (H&E) stained sections. Normal chinchilla TMs were consistently 10-20 µm thick (FIG. 17A). TMs extracted after 7 days of infection were approximately five times thicker (FIG. 17A) and exhibited an acute inflammatory response with diffuse edema and dense infiltration by inflammatory cells. In comparison, TMs treated with the gel formulation appeared indistinguishable from healthy TMs with a thickness of 10-20 µm (FIG. 17A). No tissue injury, necrosis or inflammatory cells were observed. These results illustrate a benign tissue response to Cip-3CPE-12%[P407-PBP].

Effect of Cip-3CPE-12%[P407-PBP] on Hearing

The effect of Cip-3CPE-12%[P407-PBP] on hearing sensitivity was assessed by auditory brainstem responses (ABR; see Methods; FIG. 18C). Placement of 200 µL of the gel on the TM caused a 16-24 dB positive shift of the ABR threshold (worsening of hearing) to clicks and tone bursts of frequencies from 0.5 Hz to 16 kHz, with an average of 18 dB±8 dB across all frequencies. This mild hearing loss is comparable to the effect of cerumen (See Olusanya, et al., *Ann. Trop. Paediatr.* 23, 121-128 (2003); Akinpelu et al., *Int. J. Pediatr. Otorhi.* 78, 88-90 (2014)).

Gel Properties of a P407-PPE Polymer

Compositions for testing were prepared by mixing 18% wt/vol P407-PBP polymer into an aqueous solution of 1% wt/vol ciprofloxacin. The solutions were stirred overnight and the following CPEs were added: (a) 1% wt/vol sodium dodecylsulfate (SDS); (b) 2% wt/vol limonene (LIM); (c) 0.5% wt/vol bupivacaine (Bup); or (d) 1% wt/vol SDS, 2% wt/vol LIM, and 0.5% wt/vol Bup (3CPE).

Figure 5:
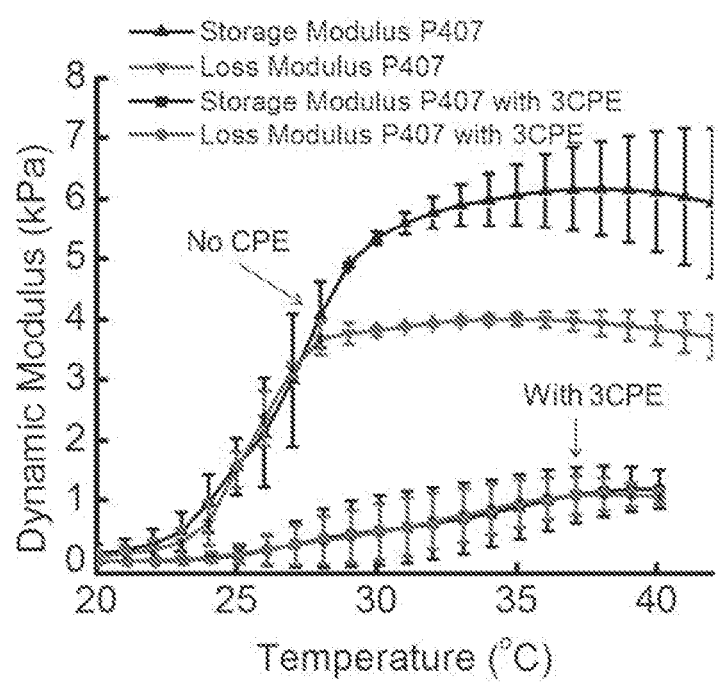
FIG. 5. Linear oscillatory shear rheology measurements (100 rads$^{-1}$, 1% strain, 1° C. min$^{-1}$) for storage and loss modulus of 18% P407 and 18% P407 with 1% sodium dodecylsulfate, 2% limonene, and 0.5% bupivacaine (3CPE).

Changes in mechanical properties during sol-gel transition were quantified using linear oscillatory shear rheology measurements (100 rads$^{-1}$, 1% strain, 1° C. min$^{-1}$). As shown in FIG. 5. The storage (G') and loss (G") moduli of 18% P407 aqueous solution are around 0.1 kPa at room temperature, both demonstrate sharp increases in the temperature range of 25-30° C., and then plateau around 6 kPa and 4 kPa respectively. At temperatures below 27° C., the G' and G" remain close within one standard deviation (as indicated by the error bars) and P407 behaves as a viscous liquid, whereas at temperatures above 28° C., G' becomes significantly larger than G", and P407 demonstrates solid-like behavior. Inclusion of CPEs (3CPE) in the P407 solution diminishes the gelation process and renders the delivery system ineffective. Specifically, Storage and loss moduli of the system remain less than 2 kPa in the entire temperature range of 20-40° C. No cross-over point is observed. The shear rheology results are consistent with our finding on otoscopy that the P407-based gels were spread out in the auditory canal, leading to poor adherence to the TM. The gelation process took ~20 sec.

Figure 10:
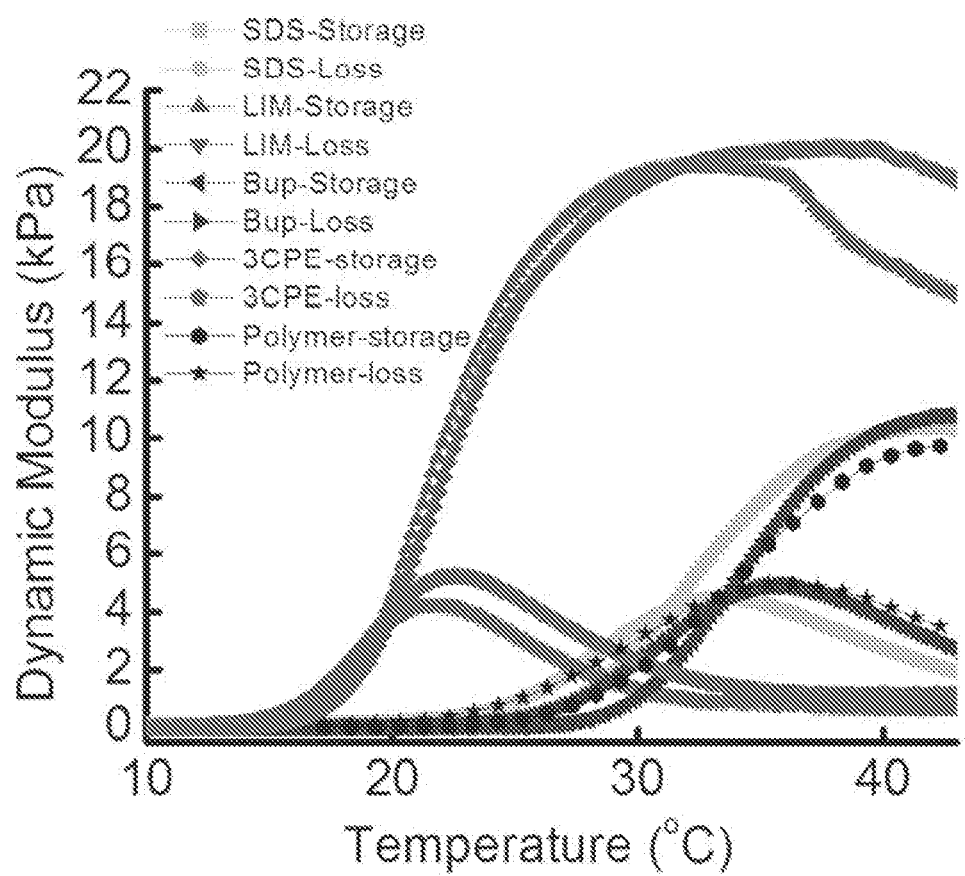
FIG. 10. Linear oscillatory shear rheology measurements (100 rads$^{-1}$, 1% strain, 1° C. min$^{-1}$) for storage and loss modulus of 18% P407-PBP alone (Polymer), with 1% sodium dodecyl sulfate (SDS), with 2% limonene (LIM), with 0.5% bupivacaine (Bup), or with 1% sodium dodecylsulfate, 2% limonene, and 0.5% bupivacaine (3CPE).

Rheology measurements for P407-PBP compositions are shown in FIG. 10. Linear oscillatory shear rheology measurements (100 rads$^{-1}$, 1% straing, 1° C. min$^{-1}$) on 18% P407-PBP indicate that the storage (G') and loss (G") moduli of P407-PBP (containing 10 mg ml$^{-1}$ ciprofloxacin), are around 0.1 and 0.2 kPa respectively under room temperature. G' and G" both increase gradually within the temperature range of 27-38° C. and plateau at 10 and 4 kPa respectively. At temperatures below 33° C., G" is greater than G' and the polymer solution behaves as a viscous liquid, whereas at temperatures above 33° C., G" is smaller than G', indicating solid-like behavior. The cross-over point (33° C.) is thus the sol-gel transition temperature. Introduction of CPEs, with the composition of 1 wt % SDS, 2 wt % limonene and 0.5 wt % bupivacaine, changes the rheology of P407-PBP. Upon increasing temperature, G' and G" increase from close to zero to 10 and 5 kPa respectively at 22° C., and exhibit a cross-over point (i.e., sol-gel transition) at 20° C. G' continues to increase with temperature and plateaus at 20 kPa at body temperature, whereas G" starts to decrease with temperatures higher than 22° C. and plateaus at 1 kPa at body temperature. Additional properties of the P407-PBP compositions with various permeation enhancers are presented in Table E1.

TABLE E1

Rheological properties of exemplary P407-PBP compositions.

| CPE | Phase Transition Temperature (° C.) | Plateau storage modulus (kPa) | Pleateau loss modulus (kPa) |
|---|---|---|---|
| no CPEs | 33 | 9.7 | 4.9 |
| 0.5% bupivacaine | 33 | 10.8 | 4.9 |
| 1% sodium dodecylsulfate | 31 | 10.2 | 4.8 |
| 2% limonene | 20 | 15.1 | 4.4 |
| 3CPE | 20 | 19.1 | 5.3 |

Optimization of Formulations

The standard formulation is defined as ciprofloxacin in 18% P407 with 1% SDS, 0.5% bupivacaine, and 2% limonene. Starting from that formulation, others may be optimized with respect to gelation and mechanical properties, and drug flux across chinchilla TMs.

For example, an optimized formulation should produce a drug flux that results in a concentration in the recipient chamber of at least the minimum inhibitory concentration (MIC; the concentration that inhibits the growth of bacteria by 2 log units) within 12 hours. The MICs of ciprofloxacin are <0.1-0.5 for non-typable $H.$ $influenzae$ (NTHi) and 0.5-4 µg/mL for $S.$ $pneumoniae.$ [31,32] For an optimized formulation, gelation should occur 10 sec after application while being fluid at room temperature, and should provide a drug flux that achieves MIC every day for 10 days. In vivo the optimized formulation should eradicate infection in 100% of animals 5 days after treatment.

For optimization two CPEs (differing in carbon chain length) may be analyzed from each of three principal classes: anionic, cationic, and nonionic (Table 1). Other CPEs that may be included in optimization experiments are: terpenes (e.g. limonene), benzalkonium chloride (an antiseptic and preservative used in eye drops and nasal sprays, also acts as a CPE), and bupivacaine (a potent local anesthetic, also acts as a CPE). Bupivicaine may also serve as an additional therapeutic agent to treat pain from OM.

TABLE E2

Properties of surfactant chemical penetration enhancers (CPEs).

| CPE | Class | M.W. | Length of carbon chains |
|---|---|---|---|
| Sodium octyl sulfate | anionic | 232 | 8 |
| Sodium dodecyl sulfate | anionic | 288 | 12 |
| Octyl-trimethyl-ammonium bromide | cationic | 252 | 8 |
| Dodecyl-trimethyl-ammonium bromide | cationic | 308 | 12 |
| Tween 20 | nonionic | 1228 | 12 |
| Tween 80 | nonionic | 1310 | 17 |

The antibiotic may be selected based on clinical criteria (antimicrobial spectrum, current practice; i.e. translatability), potency, solubility in the delivery vehicle, stability at 37° C. and other physicochemical parameters. The default antibiotic is ciprofloxacin because (a) it is small (331 Da), moderately hydrophobic (log P=0.28), can be dissolved at relatively high concentration in aqueous solution at acidic pH ($pK_a$=6.16), and has a broad antibacterial spectrum, (b) it is currently used clinically to treat acute otorrhea in children with tympanostomy tubes.

To minimize animal experimentation, chinchilla TMs can be used only for CPEs that achieve adequate flux in initial screening with cadaveric human skin (HES). Since flux across TM is likely to be greater than across HES, the screen may also increases the probability that formulations will be successful downstream in in vivo models of OM. The intactness of human cadaveric skin and chinchilla TM samples can be demonstrated by electrical impedance measurements. HES can be tested in Franz diffusion cells; chinchilla TMs in 12-well plates. For each drug, flux is to be measured at the maximum concentration that can be dissolved in the formulation. Flux of drug or CPE can be measured by HPLC with suitable detection.

Single CPEs

For each CPE, ciprofloxacin flux can be measured across HES, measuring flux at a range of concentrations starting with half of the concentration shown to be effective in transdermal applications, [26a] and increasing by the same increment (or a multiple thereof) until adequate concentrations are reached. The results for promising CPEs in HES test can be confirmed in chinchilla TMs prior to additional experiments. The experiments can be repeated with different therapeutic agents other than ciprofloxacin.

Synergistic CPEs.

Figure 6:
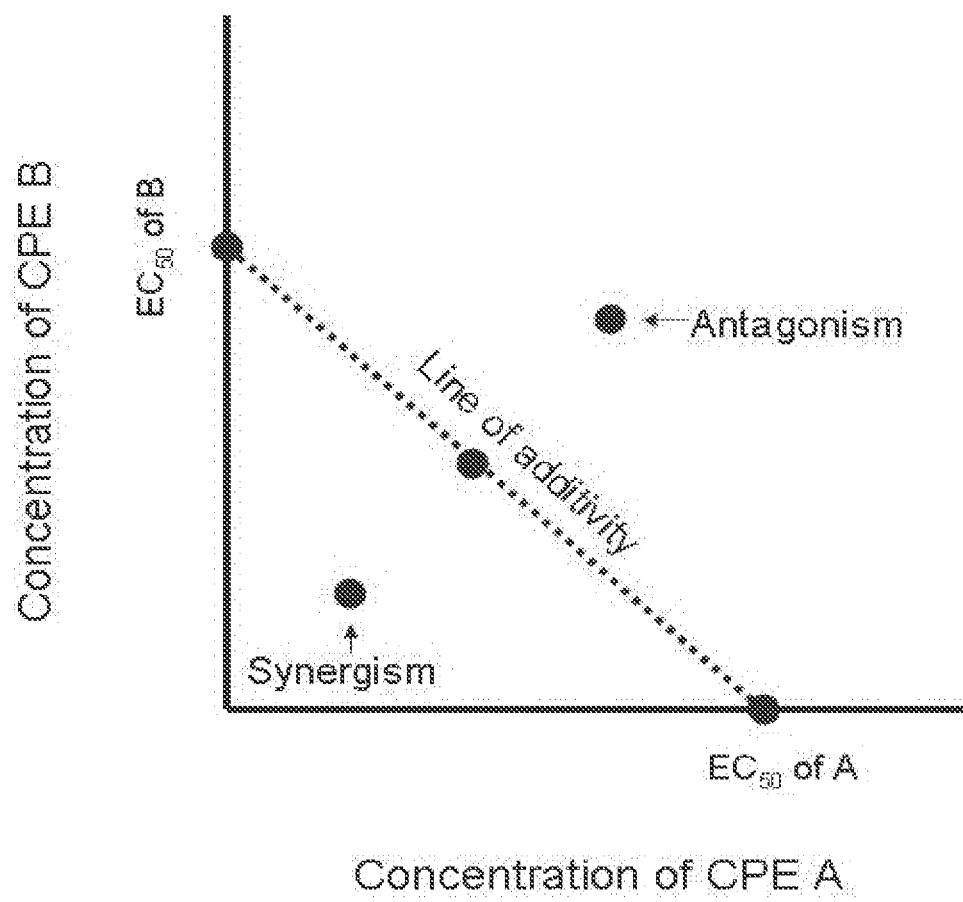
FIG. 6. Isobologram showing concentration of CPE B against concentration of CPE A, and indicating the conditions for synergism and antagonism between CPEs.

Synergism between CPEs may be demonstrated formally by isobolographic analysis (FIG. 6). For the two single enhancers that produce the greatest increase in flux, the concentrations of both that causes 50% of the maximal increase in flux ($EC_{50}$) will be determined. If both are from the same class of enhancer, the next best agent from another class will also be tested, since synergism is often found with processes that act on a common phenomenon by different mechanisms. Synergism (as well as additivity and antagonism) can then be demonstrated by constructing an isobologram (FIG. 6). $EC_{50}$ values can be determined by logit (logistic regression) analysis, using Stata software (Stata Corporation, College Station, Tex.).

Figure 23:
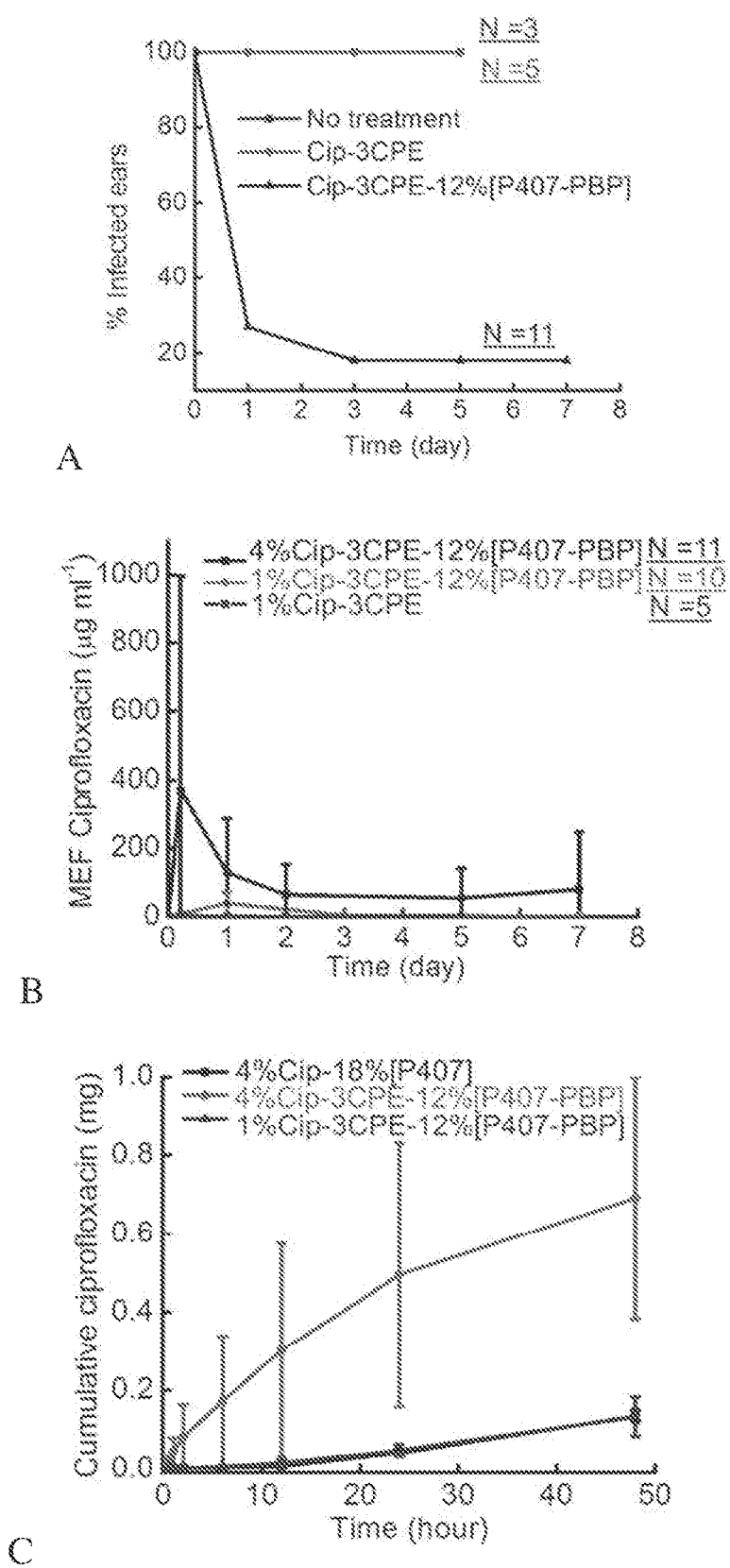
FIG. 23 (C). Ex vivo permeation data for formulation of 18% poloxamer 407 (P407) for various concentrations of Ciproflaxin-3CPE-12%[P407-PBP] and 4% Ciproflaxin-18%[P407].

An anesthetic permeation enhancer can boost the enhancement of drug flux for surfactant and terpene permeation enhancers. For example, bupivacaine can boost the enhancement of drug flux of SDS and Limonene (See FIG. 23).

Antibiotic Flux

In vivo studies with may initially be performed with ciprofloxacin. However, other antibiotics can also be studied to assess trans-tympanic drug diffusion as a function of drug properties. Antibiotics that are commonly used to treat otitis media may be studied, or that could be used to treat OM if systemic distribution and toxicity associated with oral delivery were not an issue. The target organisms include $Streptococcus$ $pneumoniae,$ $Haemophilus$ $influenzae,$ and $Moraxella$ $catarrhalis.$ Criteria to assess for a successful candidate drug include solubility, stability, physicochemical properties, potency, and systemic toxicity. The properties of the TM are also likely to affect which drugs will work best. Candidates after ciprofloxacin include other quinolones with better Gram-positive coverage, greater potency, or less protein binding (e.g., levofloxacin and moxifloxacin) or broad-spectrum agents like the carbapenems (e.g., meropenem). Drugs with pronounced ototoxicity (e.g. vancomycin) will not be studied.

For the antibiotic levoflaxin, the trans-tympanic permeation of levofloxacin formulations (1.5% Levofloxacin aqueous solution and 1.5% Levofloxacin with permeation enhancers and a matrix forming agent) is shown in comparison with ciprofloxacin formulations in FIG. 23(B).

A panel of antibiotics is listed in Table 2, has been selected for a range of physicochemical properties. The flux of additional therapeutic agents (a) dexamethasone, which is used clinically in conjunction with antibiotics, and (b) P-lactamase inhibitors such as clavulanate and tazobactam, can also be investigated in combination with antibiotic candidates.

TABLE E3

Properties of antibiotics for use as therapeutic agents of the composition

| Antibiotic | Class | M.W. | Log P |
|---|---|---|---|
| Amoxicillin | penicillin | 365 | 0.87 |
| Azithromycin | macrolide | 749 | 4.02 |
| Cefuroxime | $2^{nd}$ generation cephalosporin | 424 | −0.16 |
| Ceftriaxone | $3^{rd}$ generation cephalosporin | 555 | −1.47 |
| Trimethoprim | diaminopyrimidine | 290 | 0.91 |
| Ciprofloxacin | quinolone | 331 | 0.28 |

More than one antibiotic used in combination may also be tested if a single antibiotic provides inadequate flux or fails to achieve MIC. Drug combinations which are synergistic may allow increased flux of antibacterial efficacy (peak effect) for a given total drug mass. Synergism can be investigated with the same statistical methodology as for CPEs.

Encapsulation of Bupivacaine

Bupivacaine differs from the other CPEs in that it has a solid (free-base) form. This provides an opportunity to extend the duration of CPE-effect (if needed) by sustained release from the drug delivery composition. Particles releasing bupivacaine can be suspended within formulation. Experiments to verify that bupivacaine levels do not rise to neurotoxic levels in the middle or inner ear may be necessary.

Measurement of Drug Flux Across Human Skin

Heat-stripped epidermis with stratum corneum (HES) can be prepared from fresh frozen, full-thickness, hairless human abdominal skin (National Disease Research Interchange, Philadelphia, Pa.). [38] HES is secured between the orifices of vertical (Franz) diffusion cells (Permegear, Bethlehem, Pa.). At fixed time points, samples are removed from the receiving chamber and analyzed by HPLC.

Ex Vivo Measurement of Flux with Tympanic Membranes

The external auditory meatus and TM within the tympanic ring are separated en bloc from the skull. This bloc (which will act as the donor chamber) is placed into 12-well plates and pre-incubated at 37° C. for 15 minutes. 200 μL of a test solution is added to the donor chamber. At fixed time points, receiving medium are removed. Drug concentrations are quantified by reverse-phase HPLC (1100 series, Agilent Technologies, Palo Alto, Calif.).

Determination of Intactness of HES and TMs

Intactness of skin and TM samples can be assessed with electrical impedance measurements. [39] Skin samples and TMs with initial resistivities (electrical resistance* exposed area) of <35 kOhm*cm$^2$ and <18 kOhm*cm$^2$ respectively are considered damaged.

Hydrogel Formulation

Hydrogels can be prepared by adding polymer powders to aqueous drug-CPE solutions. Gels of varying P407-PPE (co-poloxamer 407/polyphosphoester) weight percentages (5%-20%) are prepared by simple dissolution. In situ covalently cross-linking polymers (1-10 weight %) can be synthesized, [25] dissolved in antibiotic-CPE solution, and delivered in separate barrels of a doubled-barreled syringe.

Example of Synthesis of a P407-PPE Polymer

Phosphate ester precursors (e.g., compound of Formula (A)) can be prepared by condensation reaction of 2-chloro-2-oxo-1,3,2-dioxaphospholane (COP) and an alcohol (e.g., Y—OH, wherein Y is a defined herein), then purified by vacuum distillation, and analyzed by proton and phosphorous NMR spectroscopy. Hydrophobic P407-PPE polymer (PPE-P407-PPE) can be synthesized by ring opening polymerization (ROP) of the phosphate ester with P407 in the presence of an organocatalyst, 1,8-diazabicyclo[5.4.0]undec-7-ene (DBU) at −20° C. Upon completion of the reaction (complete monomer consumption confirmed by NMR spectroscopy), excess acetic acid in dichloromethane (DCM) can be added to the reaction mixture to quench the reaction. The product may be purified by precipitation into ether (3 times) and dried to a white powder under vacuum. Proton and phosphorous NMR spectroscopy, Fourier transform infrared spectroscopy and gel permeation chromatography are used to characterize the polymer and confirm its purity.

Gelation Temperature and Time, Gel Rheology

The storage and loss moduli can be measured every 1° C. during a temperature sweep from 0° C. to 40° C. The temperature at which the storage modulus exceeds the loss modulus is considered the gelation temperature. To measure gelation time, formulations in scintillation vials will be immersed in a 37° C. water bath over a stir plate. The time it takes for the stir bar to stop rotating is noted as the gelation time.

In Vitro Release Kinetics

Release of drug and/or CPE from formulations can be assessed by placing the gels in low molecular-weight cut-off (Transwell) inserts in 12-well plates, with PBS below. At fixed time points (0.5, 1, 2, 6, 24, 48, 120 h), samples of PBS from the receiving chamber are removed and analyzed by HPLC or other analytical technique for drug and/or CPE levels.

Cytotoxicity Testing

Cytotoxicity towards cell types that occur in the tympanic membrane and the surrounding walls of the outer ear can be determined. These cell types include keratinocytes, fibroblasts and PC12 cells (a pheochromocytoma cell line often used to study neurotoxicity).

Cells are exposed to a range of concentrations of drugs, CPEs, and gel components. For the CPEs, the initial upper concentration limit is set by published values for skin toxicity. For the drugs, the upper limit is set by solubility in the formulations to be tested. Cytotoxicity is assessed at 1 to 10 days of exposure to the component(s) being tested, using the MTT assay, which is widely used for cytotoxicity screening. Since it can also reflect cell proliferation, a standard live-dead assay will be used as a confirmatory test. [50]

Biocompatibility Testing

Formulations that show over 80% cell survival will be tested in vivo. Under isoflurane:oxygen anesthesia, 200 μl of test solutions is instilled onto the chinchilla TM. One, four, ten and thirty days later, animals are euthanized for otoscopy and histological analysis of the TM and outer ear, with attention to material residue (and its adherence to the TM), inflammation, thickening of the TM, middle ear effusion, and tissue injury. The time points will allow analysis of how long formulations last in the auditory canal. Dissection will proceed as for removing TM's, but the outer and middle ear will be removed en bloc and demineralized for subsequent sectioning, and processed into hematoxylin-eosin stained sections using standard procedures. Electron microscopy of inner ear structures may also be performed to assess ototoxicity.

Biofilms

An in vitro study of the effects of the formulation components on biofilm formation may be performed as an adjunct to the observations to be obtained in the in vivo model. Formed biofilms can be exposed to concentrations corresponding to dose-response curves of all the diffusible components of the formulations (drug, CPE, hydrogel precursors), alone and in combination, and assessed for changes in morphology and bacterial population. Analogous studies can be done to assess the components' ability to prevent biofilm formation in vitro, and to destroy devitalized biofilms.

Bacterial colonies are suspended in media and the $OD_{490}$ adjusted to 0.65, then diluted 1:6 and incubated at 37° C. with 5% $CO_2$ for approximately 3 hours in order to reach mid-log phase. [30] The suspension is then diluted 1:2500 with media and 200 μL placed into each well of an 8-well chamber slide and incubated at 37° C. with 5% $CO_2$ for approximately 16 hours. The medium is changed every 12 hours, with attention to not disrupt the biofilm, until a desirable biofilm thickness is achieved. Samples are then fixed and stained with a live-dead assay. Biofilm thickness and bacterial survival can be quantitated by confocal microscopy, and further characterized with SEM image and/or immunohistochemical approaches.

In Vivo Chinchilla Testing

To determine the efficacy of the antibacterial hydrogel in vivo, formulations can be applied to the TM's of chinchillas with OM. Prior to bacterial challenge, chinchillas are examined by tympanometry and otomicroscopy to confirm normal middle ear and TM status. Animals will have a test composition placed in the left ear. The right ear is used for controls (no treatment, CPE only, gel only, etc.). In select experiments, middle ear fluid may be sampled to track bactericidal effect and flux of antibiotics and CPEs.

Animals will be challenged by direct inoculation of 25-100 cfu into the middle ear through the superior bullae. After 48-96 hours, infection is confirmed by (a) otoscopy and tympanometry, (b) culture of the middle ear fluid through a 3-5-mm opening in the bulla bone (made under ketamine/xylazine anesthesia); results come back overnight. In our experience, virtually all animals develop disease after direct inoculation. In the event that an animal does not develop disease, it will be excluded from the study. Once the presence of otitis media is confirmed hydrogels will be applied to chinchillas lying on their sides, under ketamine/xylazine anesthesia.

To assess biofilm, the middle ear mucosa will be visualized, [52] and tissue samples from animals analyzed by scanning electron microscopy (SEM) to detect biofilm and live-dead staining to detect viable bacteria within. [21] Immunohistochemistry for bacteria may be used as a confirmatory test. These data will allow for the determination of the effect of the various experimental groups on biofilm formation. The effect of CPEs without antibiotics on biofilm formation in OM can also be studied.

For studies of prophylaxis, a strategy for induction of experimental otitis media designed to mimic the pathogenesis of disease in children may be used, where colonization followed by viral respiratory tract infection leading to negative middle ear pressure is observed. $10^7$-$10^8$ cfu of bacteria is inoculated into the nasopharynx of chinchillas using a small gauge angiocatheter. After 24 hours, nasopharyngeal colonization is confirmed by quantitative culture. [29 g,51] Gel is placed in the left external canal (in contact with the TM). Forty eight hours after gel application barotrauma is introduced by placing a 25 gauge needle in the middle ear (through the superior bullae) and withdrawing of 500 μL of air while anesthetized tympanometry is performed to document the presence of negative middle ear pressure within the middle ear cavity. This creates negative pressure that remains for several hours and induces bacterial otopathogens to ascend the Eustachian tube into the middle ear. Animals are observed daily for the development of OM and if changes in TM are observed, culture is performed. (If no changes are observed culture will be performed 3-4 days after barotrauma to confirm the absence of culture positive disease).

In both paradigms, 0.2 mL of test composition (hydrogel with drug and CPE) is applied onto the TM through a syringe with an attached angiocatheter, under otoscopic observation. The entire surface of the TM is coated. Clinical examinations take place as above and/or 1, 3, 5, and 7 days after drug administration to monitor disease. Otoscopy will be used to follow contact of the hydrogel with the TM. Every other day, middle ear fluid, if present, is collected via an angiocatheter inserted through the incision made during initial culture confirmation under aseptic conditions. In the absence of middle ear fluid, lavage will be performed with 500 μL of Hanks solution and aspiration through an angiocatheter. Quantitative middle ear fluid cultures are performed by 10 fold dilution of the middle ear fluid and incubation at 37° C. for 16 hours.

Drug levels in the middle ear can be determined by (a) addition of methanol to middle ear fluid until all protein is precipitated, (b) centrifugation to remove any precipitated protein and cellular debris, and (c) analysis by HPLC.

Less than 2 mL of blood can be collected by superior sagittal sinus puncture at specified intervals after initiating treatment to measure systemic (plasma) drug concentrations. Blood (<2 mL) will be drawn from animals that have had formulations deposited in their ears for biocompatibility testing or the OM models, by superior sagittal sinus puncture, placed on ice immediately, and plasma separated by centrifugation. Samples will be stored at −20° C. and antibiotic and/or CPE concentrations subsequently measured. The levels after days one, four, and ten provide useful survey of values over the course of treatment.

Acoustic Brain Response

Impairment of hearing could be caused by a conductive effect of the gels, or by direct toxicity to the middle or inner ear. It is difficult a priori to predict the thickness of the formulation that will be applied in an eventual therapeutic system in humans. A range of thicknesses from 100 m to 500 m will be applied, which fills the auditory canal of the chinchilla completely, prior to measurement of the acoustic brain response (ABR). To identify possible ototoxic effects, testing will be repeated after removing the gels (by rinsing and/or curettage, depending on the consistency).

ABR experiments will be conducted with a custom-designed system built around National Instruments (Austin, Tex.) software (Lab View) and hardware including a GPIB controller and an ADC board. The custom LabView program computes the stimuli, and downloads them to a programmable stimulus generator (Hewlett Packard 33120A). The stimulus is then filtered by an antialiasing filter (KrohnHite 3901) and attenuated (Tucker-Davis Technologies). Simultaneously with stimulus output, the 2 ADC channels sample the amplified ABR signal and the output of a microphone sealed in the ear canal of the animal.

The acoustic stimuli will be pairs of 20-ms tone bursts of opposite polarity. The frequency of the bursts will increase from 500 Hz to 16 kHz in octave steps. Each burst will be sine windowed, with 40 ms between two bursts. ABR responses to 250 pairs of stimuli will be averaged at each stimulus level. The ABR response will be computed from the sum of the averaged response to the two different polarities. Stimulus level will be varied in 10 dB steps. A visual judgment of threshold at each stimulus frequency will be determined post-measurement in a blinded fashion.

The attenuated stimulus will be played through a hearing-aid earphone placed within the intact ear canal of adult male chinchillas (400-600 g) anesthetized by IP administration of ketamine and pentobarbital (50 mg/kg). The earphone coupler includes a microphone that monitors the sound stimulus level. ABRs, obtained in a sound-attenuating booth, will be measured with a differential amplifier with a gain of 10,000 and a measurement bandwidth of 100 Hz to 3 kHz. The measurements will be obtained from the positive electrode in the muscle behind the measured ear; the negative electrode will be at the cranial vertex, and the ground electrode behind the contralateral ear.

REFERENCES 1. (a) Berman, S., Otitis media in children. N Engl J Med 1995, 332, 1560-5; (b) Fried, V. M.; Makuc, D. M.; Rooks, R. N. Ambulatory health care visits by children: principal diagnosis and place of visit.; 137; Washington, D.C.: Government Printing Office, 1998.: 1998.
2. Teele, D. W.; Klein, J. O.; Rosner, B., Epidemiology of otitis media during the first seven years of life in children in greater Boston: a prospective, cohort study. The Journal of infectious diseases 1989, 160 (1), 83-94.
3. Casselbrant, M. L.; Mandel, E. M., Epidemiology. In Evidence-based otitis media, Rosenfeld, R. M.; Bluestone, C. D., Eds. Decker, Inc.: Hamilton, British Columbia, 1999; pp 117-137.
4. Faden, H.; Duffy, L.; Boeve, M., Otitis media: back to basics. The Pediatric infectious disease journal 1998, 17 (12), 1105-12; quiz 1112-3.
5. Lanphear, B. P.; Byrd, R. S.; Auinger, P.; Hall, C. B., Increasing prevalence of recurrent otitis media among children in the United States. Pediatrics 1997, 99 (3), E1.
6. Acuin, J. Otitis Media: Burden of Illness and Management Options; World Health Organization: Geneva, Switzerland, 2004.
7. (a) Bluestone, C. D.; Klein, J. O., Otitis media in infants and children. 4th ed.; BC Decker: Hamilton, Ontario, Canada, 2006; (b) Bluestone, C. D.; Klein, J. O., Otitis media in infants and children. BC Decker: Hamilton, O N, 2007.
8. Khoo, X.; Simons, E.; Chiang, H.; Hickey, J.; Sabharwal, V.; Pelton, S.; Rosowski, J.; Langer, R.; Kohane, D., Formulations for trans-tympanic antibiotic delivery. Biomaterials 2013, 34, 1281-8.
9. Paradise, J. L., Short-course antimicrobial treatment for acute otitis media: not best for infants and young children. Jama 1997, 278 (20), 1640-2.
10. Antibiotic/Antimicrobial Resistance. www.cdc.gov/drugresistance/.
11. Doyle, W. J.; Alper, C. M.; Seroky, J. T.; Karnavas, W. J., Exchange rates of gases across the tympanic membrane in rhesus monkeys. Acta oto-laryngologica 1998, 118 (4), 567-73.
12. Suzuki, K.; Baba, S., Antimicrobial ear drop medication therapy. Acta Otolaryngol Suppl 1996, 525, 68-72.
13. Middleton, J. D., Mechanism of action of surfactants on water binding properties of isolated stratum corneum. J Soc Cosmet Chem 1969, 20, 399-403.
14. Kushla, G. P.; Zatz, J. L.; Mills, O. H., Jr.; Berger, R. S., Noninvasive assessment of anesthetic activity of topical lidocaine formulations. J Pharm Sci 1993, 82 (11), 1118-22.
15. Walker, R. B.; Smith, E. W., The role of percutaneous penetration enhancers. Adv Drug Deliv Rev 1996, 18, 295-301.
16. (a) Jia, X.; Colombo, G.; Padera, R.; Langer, R.; Kohane, D. S., Prolongation of sciatic nerve blockade by in situ cross-linked hyaluronic acid. Biomaterials 2004, 25 (19), 4797-804; (b) Yeo, Y.; Bellas, E.; Highley, C. B.; Langer, R.; Kohane, D. S., Peritoneal adhesion prevention with an in situ cross-linkable hyaluronan gel containing tissue-type plasminogen activator in a rabbit repeated-injury model. Biomaterials 2007, 28, 3704-13; (c) Hoare, T.; Kohane, D. S., Hydrogels in drug delivery: progress and challenges. Polymer 2008, 49, 1993-2007.
17. Yeo, Y.; Kohane, D. S., Polymers in the prevention of peritoneal adhesions. Eur J Pharm Biopharm 2008, 68, 57-66.
18. (a) Hall-Stoodley, L.; Hu, F. Z.; Gieseke, A.; Nistico, L.; Nguyen, D.; Hayes, J.; Forbes, M.; Greenberg, D. P.; Dice, B.; Burrows, A.; Wackym, P. A.; Stoodley, P.; Post, J. C.; Ehrlich, G. D.; Kerschner, J. E., Direct detection of bacterial biofilms on the middle-ear mucosa of children with chronic otitis media. Jama 2006, 296 (2), 202-11; (b) Post, J. C.; Hiller, N. L.; Nistico, L.; Stoodley, P.; Ehrlich, G. D., The role of biofilms in otolaryngologic infections: update 2007. Curr Opin Otolaryngol Head Neck Surg 2007, 15 (5), 347-51; (c) Liu, Y. C.; Post, J. C., Biofilms in pediatric respiratory and related infections. Curr Allergy Asthma Rep 2009, 9 (6), 449-55.
19. Nistico, L.; Kreft, R.; Gieseke, A.; Coticchia, J. M.; Burrows, A.; Khampang, P.; Liu, Y.; Kerschner, J. E.; Post, J. C.; Lonergan, S.; Sampath, R.; Hu, F. Z.; Ehrlich, G. D.; Stoodley, P.; Hall-Stoodley, L., Adenoid reservoir for pathogenic biofilm bacteria. J Clin Microbiol 2011, 49 (4), 1411-20.
20. Hoa, M.; Syamal, M.; Sachdeva, L.; Berk, R.; Coticchia, J., Demonstration of nasopharyngeal and middle ear mucosal biofilms in an animal model of acute otitis media. Ann Otol Rhinol Laryngol 2009, 118 (4), 292-8.
21. (a) Hoa, M.; Tomovic, S.; Nistico, L.; Hall-Stoodley, L.; Stoodley, P.; Sachdeva, L.; Berk, R.; Coticchia, J. M., Identification of adenoid biofilms with middle ear pathogens in otitis-prone children utilizing SEM and FISH. Int J Pediatr Otorhinolaryngol 2009, 73 (9), 1242-8; (b) Lee, M. R.; Pawlowski, K. S.; Luong, A.; Furze, A. D.; Roland, P. S., Biofilm presence in humans with chronic suppurative otitis media. Otolaryngol Head Neck Surg 2009, 141 (5), 567-71; (c) Hoa, M.; Syamal, M.; Schaeffer, M. A.; Sachdeva, L.; Berk, R.; Coticchia, J., Biofilms and chronic otitis media: an initial exploration into the role of biofilms in the pathogenesis of chronic otitis media. Am J Otolaryngol 2010, 31 (4), 241-5.
22. Tapiainen, T.; Kujala, T.; Kaijalainen, T.; Ikaheimo, I.; Saukkoriipi, A.; Renko, M.; Salo, J.; Leinonen, M.; Uhari, M., Biofilm formation by *Streptococcus pneumoniae* isolates from paediatric patients. Apmis 2010, 118 (4), 255-60.
23. (a) Kohane, D. S.; Yieh, J.; Lu, N. T.; Langer, R.; Strichartz, G. R.; Berde, C. B., A re-examination of tetrodotoxin for prolonged duration local anesthesia. Anesthesiology 1998, 89 (1), 119-31; (b) Kohane, D. S.; Sankar, W. N.; Shubina, M.; Hu, D.; Rifai, N.; Berde, C. B., Sciatic nerve blockade in infant, adolescent, and adult rats: a comparison of ropivacaine with bupivacaine. Anesthesiology 1998, 89 (5), 1199-208; (c) Kohane, D. S.; Lu, N. T.; Gokgol-Kline, A. C.; Shubina, M.; Kuang, Y.; Hall, S.; Strichartz, G. R.; Berde, C. B., The local anesthetic properties and toxicity of saxitonin homologues for rat sciatic nerve block in vivo. Reg Anesth Pain Med 2000, 25 (1), 52-9; (d) Kohane, D. S.; Lu, N. T.; Crosa, G. A.; Kuang, Y.; Berde, C. B., High concentrations of adrenergic antagonists prolong sciatic nerve blockade by tetrodotoxin. Acta Anaesthesiol Scand 2001, 45 (7), 899-905; (e) Kohane, D. S.; Lu, N. T.; Cairns, B. E.; Berde, C. B., Effects of adrenergic agonists and antagonists on tetrodotoxin-induced nerve block. Reg Anesth Pain Med 2001, 26 (3), 239-45; (f) Padera, R.; Bellas, E.; Tse, J. Y.; Hao, D. D.; Kohane, D. S., Local myotoxicity from sustained release of bupivacaine from microparticles. Anesthesiology 2008, 108, 921-8.

24. Kohane, D. S.; Kuang, Y.; Lu, N. T.; Langer, R.; Strichartz, G. R.; Berde, C. B., Vanilloid receptor agonists potentiate the in vivo local anesthetic activity of percutaneously injected site 1 sodium channel blockers. Anesthesiology 1999, 90, 524-534.

25. (a) Ito, T.; Fraser, I. P.; Yeo, Y.; Highley, C. B.; Bellas, E.; Kohane, D. S., Anti-inflammatory function of an in-situ cross-linkable conjugate hydrogel of hyaluronic acid and dexamethasone. Biomaterials 2007, 28 (10), 1778-1786; (b) Hudson, S. P.; Langer, R.; Fink, G. R.; Kohane, D. S., Injectable in situ cross-linking hydrogels for local antifungal therapy. Biomaterials 2010, 31, 1444-52; (c) Yeo, Y.; Adil, M.; Bellas, E.; Astashkhina, A.; Chaudary, N.; Kohane, D. S., Prevention of peritoneal adhesions with an in situ cross-linkable hyaluronan hydrogel delivering budesonide. J Control Release 2007, 120, 178-85; (d) Hoare, T.; Bellas, E.; Zurakowski, D.; Kohane, D. S., Rheological blends for drug delivery. II: Prolongation of nerve blockade, biocompatibility, and in vitro-in vivo correlations. J Biomed Mater Res A 2010, 92, 586-95; (e) Hoare, T.; Zurakowski, D.; Langer, R.; Kohane, D. S., Rheological blends for drug delivery. I: Characterization in vitro. J Biomed Mater Res A 2010, 92, 575-85; (f) Chen, P. C.; Kohane, D. S.; Park, Y. J.; Bartlett, R. H.; Langer, R.; Yang, V. C., Injectable microparticle-gel system for prolonged and localized lidocaine release. II. In vivo anesthetic effects. J Biomed Mater Res A 2004, 70 (3), 459-66; (g) Chen, P. C.; Park, Y. J.; Chang, L. C.; Kohane, D. S.; Bartlett, R. H.; Langer, R.; Yang, V. C., Injectable microparticle-gel system for prolonged and localized lidocaine release. I. In vitro characterization. J Biomed Mater Res A 2004, 70 (3), 412-9; (h) Yeo, Y.; Bellas, E.; Firestone, W.; Langer, R.; Kohane, D. S., Complex coacervates for thermally sensitive controlled release of flavor compounds. J Agric Food Chem 2005, 53 (19), 7518-25; (i) Yeo, Y.; Burdick, J. A.; Highley, C. B.; Marini, R.; Langer, R.; Kohane, D. S., Peritoneal application of chitosan and UV-cross-linkable chitosan. J Biomed Mater Res A 2006, 78 (4), 668-75; (j) Yeo, Y.; Highley, C. B.; Bellas, E.; Ito, T.; Marini, R.; Langer, R.; Kohane, D. S., In situ cross-linkable hyaluronic acid hydrogels prevent post-operative abdominal adhesions in a rabbit model. Biomaterials 2006, 27, 4698-4705; (k) Yeo, Y.; Ito, T.; Bellas, E.; Highley, C. B.; Marini, R.; Kohane, D. S., In situ cross-linkable hyaluronan hydrogels containing polymeric nanoparticles for preventing post-surgical adhesions. Ann Surg 2007, 245, 819-824; (l) Ito, T.; Yeo, Y.; Highley, C. B.; Bellas, E.; Benitez, C. A.; Kohane, D. S., The prevention of peritoneal adhesions by in-situ cross-linking hydrogels of hyaluronic acid and cellulose derivatives. Biomaterials 2007, 28 (6), 975-83; (m) Ito, T.; Yeo, Y.; Highley, C. B.; Bellas, E.; Kohane, D. S., Dextran-based in situ cross-linked injectable hydrogels to prevent peritoneal adhesions. Biomaterials 2007, 28, 3428-26; (n) Hoare, T.; Yeo, Y.; Bellas, E.; Bruggeman, J. P.; Kohane, D. S., Prevention of peritoneal adhesions using hyaluronic acid-hydroxypropylmethyl cellulose rheological blends Acta biomaterialia 2014, 10, 1187-93.

26. (a) Simons, E. J.; Bellas, E.; Lawlor, M. W.; Kohane, D. S., Effect of chemical permeation enhancers on nerve blockade. Mol Pharmaceutics 2009, 6, 265-273; (b) Sagie, I.; Kohane, D. S., Prolonged sensory-selective nerve blockade. Proc Natl Acad Sci USA 2010, 107, 3740-5.

27. (a) Zumbuehl, A.; Ferreira, L.; Kuhn, D.; Asthashkina, A.; Long, L.; Yeo, Y.; Iaconis, T.; Ghannoum, M.; Fink, G. R.; Langer, R.; Kohane, D. S., Antifungal hydrogels. Proc Natl Acad Sci USA 2007, 104, 12994-8; (b) Tsifansky, M. D.; Yeo, Y.; Evgenov, O. V.; Bellas, E.; Benjamin, J.; Kohane, D. S., Microparticles for inhalational delivery of antipseudomonal antibiotics. AAPS Journal 2008, 10, 254-60; (c) Ciolino, J. B.; Hoare, T. R.; Iwata, N. G.; Behlau, I.; Dohlman, C. H.; Langer, R.; Kohane, D. S., A drug-eluting contact lens. Invest Ophthalmol Vis Sci 2009, 50, 3346-42; (d) Ciolino, J. B.; Hudson, S. P.; Mobbs, A. N.; Hoare, T. R.; Iwata, N.; Fink, G. R.; Kohane, D. S., A prototype antifungal contact lens. Invest Ophthalmol Vis Sci 2011, 52 (9), 6286-91; (e) Malavia, N.; Zurakowski, D.; Schroeder, A.; Princiotto, A.; Laury, A.; Epstein-Barash, H.; Sodroski, J.; Langer, R.; Madani, N.; Kohane, D. S., Liposomes for HIV prophylaxis. Biomaterials 2011, 32 (33), 8663-8.

28. Karande, P.; Jain, A.; Ergun, K.; Kispersky, V.; Mitragotri, S., Design principles of chemical penetration enhancers for transdermal drug delivery. Proc Natl Acad Sci USA 2005, 102 (13), 4688-93.

29. (a) Karasic, R. B.; Trumpp, C. E.; Gnehm, H. E.; Rice, P. A.; Pelton, S. I., Modification of otitis media in chinchillas rechallenged with nontypable *Haemophilus influenzae* and serological response to outer membrane antigens. The Journal of infectious diseases 1985, 151 (2), 273-9; (b) Pelton, S. I.; Figueira, M.; Albut, R.; Stalker, D., Efficacy of linezolid in experimental otitis media. Antimicrob Agents Chemother 2000, 44 (3), 654-7; (c) Babl, F. E.; Pelton, S. I.; Li, Z., Experimental acute otitis media due to nontypeable *Haemophilus influenzae*: comparison of high and low azithromycin doses with placebo. Antimicrob Agents Chemother 2002, 46 (7), 2194-9; (d) Bouchet, V.; Hood, D. W.; Li, J.; Brisson, J. R.; Randle, G. A.; Martin, A.; Li, Z.; Goldstein, R.; Schweda, E. K.; Pelton, S. I.; Richards, J. C.; Moxon, E. R., Host-derived sialic acid is incorporated into *Haemophilus influenzae* lipopolysaccharide and is a major virulence factor in experimental otitis media. Proc Natl Acad Sci USA 2003, 100 (15), 8898-903; (e) Sabharwal, V.; Figueira, M.; Pelton, S. I.; Pettigrew, M. M., Virulence of *Streptococcus pneumoniae* serotype 6C in experimental otitis media. Microbes Infect 2012, 14 (9), 712-8; (f) Sabharwal, V.; Stevenson, A.; Figueira, M.; Orthopoulos, G.; Trzcinski, K.; Pelton, S. I., Capsular switching as a strategy to increase pneumococcal virulence in experimental otitis media model. Microbes Infect 2014, 16 (4), 292-9; (g) Figueira, M.; Moschioni, M.; De Angelis, G.; Barocchi, M.; Sabharwal, V.; Masignani, V.; Pelton, S. I., Variation of pneumococcal Pilus-1 expression results in vaccine escape during Experimental Otitis Media [EOM]. PLoS One 2014, 9 (1), e83798.

30. Jurcisek, J. A.; Dickson, A. C.; Bruggeman, M. E.; Bakaletz, L. O., In vitro biofilm formation in an 8-well chamber slide. J Vis Exp 2011, (47).

31. (a) Perez-Vazquez, M.; Roman, F.; Aracil, B.; Canton, R.; Campos, J., In vitro activities of garenoxacin (BMS-284756) against *Haemophilus influenzae* isolates with different fluoroquinolone susceptibilities. Antimicrob Agents Chemother 2003, 47 (11), 3539-41; (b) Hirakata, Y.; Ohmori, K.; Mikuriya, M.; Saika, T.; Matsuzaki, K.; Hasegawa, M.; Hatta, M.; Yamamoto, N.; Kunishima, H.; Yano, H.; Kitagawa, M.; Arai, K.; Kawakami, K.; Kobayashi, I.; Jones, R. N.; Kohno, S.; Yamaguchi, K.; Kaku, M., Antimicrobial activities of piperacillin-tazobactam against *Haemophilus influenzae* isolates, including beta-lactamase-negative ampicillin-resistant and beta-lactamase-positive amoxicillin-clavulanate-resistant isolates, and mutations in their quinolone resistance-determining regions. Antimicrob Agents Chemother 2009, 53 (10), 4225-30.

32. (a) Kayser, F. H.; Novak, J., In vitro activity of ciprofloxacin against gram-positive bacteria. An overview. Am J Med 1987, 82 (4A), 33-9; (b) Patel, S. N.; McGeer, A.; Melano, R.; Tyrrell, G. J.; Green, K.; Pillai, D. R.; Low, D. E., Susceptibility of *Streptococcus pneumoniae* to fluoroquinolones in Canada. Antimicrob Agents Chemother 2011, 55 (8), 3703-8.

33. Jacobs, M. R., How can we predict bacterial eradication? Int J Infect Dis 2003, 7 Suppl 1, S13-20.

34. Barnet, C. S.; Tse, J. Y.; Kohane, D. S., Site 1 sodium channel blockers prolong the duration of sciatic nerve blockade from tricyclic antidepressants. Pain 2004, 110 (1-2), 432-8.

35. Christodoulou, P.; Doxas, P. G.; Papadakis, C. E.; Prassopoulos, P.; *Maris*, T.; Helidonis, E. S., Transtympanic iontophoresis of gadopentetate dimeglumine: Preliminary results.
Otolaryngol Head Neck Surg 2003, 129 (4), 408-13.

36. Bernards, C. M.; Hill, H. F., Physical and chemical properties of drug molecules governing their diffusion through the spinal meninges. Anesthesiology 1992, 77, 750-756.

37. (a) Kohane, D. S.; Lipp, M.; Kinney, R. C.; Anthony, D. C.; Louis, D. N.; Lotan, N.; Langer, R., Biocompatibility of lipid-protein-sugar particles containing bupivacaine in the epineurium. J Biomed Mater Res 2002, 59 (3), 450-9; (b) Kohane, D. S.; Lipp, M.; Kinney, R. C.; Lotan, N.; Langer, R., Sciatic nerve blockade with lipid-protein-sugar particles containing bupivacaine. Pharm Res 2000, 17 (10), 1243-9; (c) Kohane, D. S.; Smith, S. E.; Louis, D. N.; Colombo, G.; Ghoroghchian, P.; Hunfeld, N. G.; Berde, C. B.; Langer, R., Prolonged duration local anesthesia from tetrodotoxin-enhanced local anesthetic microspheres. Pain 2003, 104 (1-2), 415-21; (d) Colombo, G.; Langer, R.; Kohane, D. S., Effect of excipient composition on the biocompatibility of bupivacaine-containing microparticles at the sciatic nerve. J Biomed Mater Res A 2004, 68 (4), 651-9; (e) Colombo, G.; Padera, R.; Langer, R.; Kohane, D. S., Prolonged duration local anesthesia with lipid-protein-sugar particles containing bupivacaine and dexamethasone. J Biomed Mater Res A 2005, 75A (2), 458-464.

38. Pliquett, U.; Prausnitz, M., Electrical Impedance Spectroscopy for Rapid and Noninvasive Analysis of Skin Electroporation. In Electrochemotherapy, Electrogenetherapy, and Transdermal Drug Delivery, Jaroszeski, M.; Heller, R.; Gilbert, R., Eds. Humana Press: 2000; Vol. 37, pp 377-406.

39. Tang, H.; Mitragotri, S.; Blankschtein, D.; Langer, R., Theoretical description of transdermal transport of hydrophilic permeants: application to low-frequency sonophoresis. J Pharm Sci 2001, 90 (5), 545-68.

40. Kushner, J.; Blankschtein, D.; Langer, R., Experimental demonstration of the existence of highly permeable localized transport regions in low-frequency sonophoresis. J Pharm Sci 2004, 93 (11), 2733-45.

41. Hecht, E.; Mortensen, K.; Gradzielski, M.; Hoffmann, H., Interaction of ABA block copolymers with ionic surfactants: influence on micellization and gelation. The Journal of Physical Chemistry 1995, 99 (13), 4866-4874.

42. (a) Wetton, R. E.; Allen, G., The dynamic mechanical properties of some polyethers. Polymer 1966, 7 (7), 331-365; (b) Jones, D. S.; Bruschi, M. L.; de Freitas, O.; Gremiao, M. P. D.; Lara, E. H. G.; Andrews, G. P., Rheological, mechanical and mucoadhesive properties of thermoresponsive, bioadhesive binary mixtures composed of poloxamer 407 and carbopol 974P designed as platforms for implantable drug delivery systems for use in the oral cavity. International Journal of Pharmaceutics 2009, 372 (1-2), 49-58.

43. Wan, A. C. A.; Mao, H.-Q.; Wang, S.; Phua, S. H.; Lee, G. P.; Pan, J.; Lu, S.; Wang, J.; Leong, K. W., Poly (phosphoester) ionomers as tissue-engineering scaffolds. Journal of Biomedical Materials Research Part B: Applied Biomaterials 2004, 70B (1), 91-102.

44. Iwasaki, Y.; Wachiralarpphaithoon, C.; Akiyoshi, K., Novel Thermoresponsive Polymers Having Biodegradable Phosphoester Backbones. Macromolecules 2007, 40 (23), 8136-8138.

45. (a) Wen, J.; Mao, H.-Q.; Li, W.; Lin, K. Y.; Leong, K. W., Biodegradable polyphosphoester micelles for gene delivery. Journal of Pharmaceutical Sciences 2004, 93 (8), 2142-2157; (b) Li, Q.; Wang, J.; Shahani, S.; Sun, D. D. N.; Sharma, B.; Elisseeff, J. H.; Leong, K. W., Biodegradable and photocrosslinkable polyphosphoester hydrogel. Biomaterials 2006, 27 (7), 1027-1034; (c) Zhao, Z.; Wang, J.; Mao, H.-Q.; Leong, K. W., Polyphosphoesters in drug and gene delivery. Advanced Drug Delivery Reviews 2003, 55 (4), 483-499.

46. McCormick, C. L.; Sumerlin, B. S.; Lokitz, B. S.; Stempka, J. E., RAFT-synthesized diblock and triblock copolymers: thermally-induced supramolecular assembly in aqueous media. Soft Matter 2008, 4 (9), 1760-1773.

47. Bromberg, L., Properties of Aqueous Solutions and Gels of Poly(ethylene oxide)-b-poly(propylene oxide)-b-poly (ethylene oxide)-g-poly(acrylic acid). The Journal of Physical Chemistry B 1998, 102 (52), 10736-10744.

48. (a) Dumortier, G.; Grossiord, J. L.; Agnely, F.; Chaumeil, J. C., A review of poloxamer 407 pharmaceutical and pharmacological characteristics. Pharm Res 2006, 23 (12), 2709-28; (b) Barreiro-Iglesias, R.; Bromberg, L.; Temchenko, M.; Hatton, T. A.; Alvarez-Lorenzo, C.; Concheiro, A., Pluronic-g-poly(acrylic acid) copolymers as novel excipients for site specific, sustained release tablets. European Journal of Pharmaceutical Sciences 2005, 26 (5), 374-385; (c) Cole, M. L.; Whateley, T. L., Interaction of Nonionic Block Copolymeric (Poloxamer) Surfactants with Poly (Acrylic Acid), Studied by Photon Correlation Spectroscopy. Journal of Colloid and Interface Science 1996, 180 (2), 421-427.

49. Kohane, D. S.; Plesnila, N.; Thomas, S. S.; Le, D.; Langer, R.; Moskowitz, M. A., Lipid-sugar particles for intracranial drug delivery: safety and biocompatibility. Brain Res 2002, 946 (2), 206-13.
50. Gabriel, D.; Monteiro, I. P.; Huang, D.; Langer, R.; Kohane, D. S., A photo-triggered layered surface coating producing reactive oxygen species. Biomaterials 2013, 34, 9763-9769.
51. Sabharwal, V.; Ram, S.; Figueira, M.; Park, I. H.; Pelton, S. I., Role of complement in host defense against pneumococcal otitis media. *Infect Immun* 2009, 77 (3), 1121-7.
52. Novotny, L. A.; Clements, J. D.; Bakaletz, L. O., Kinetic analysis and evaluation of the mechanisms involved in the resolution of experimental nontypeable *Haemophilus influenzae*-induced otitis media after transcutaneous immunization. Vaccine 2013, 31 (34), 3417-26.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:
1. A composition comprising:
  (a) an antibiotic or a combination of antibiotics, wherein each antibiotic is a β-lactamase inhibitor or has a molecular weight of about 290 g/mol to about 749 g/mol;
  (b) a permeation enhancer or a combination of permeation enhancers selected from the group consisting of limonene, cymene, pinene, camphor, menthol, comphone, phellandrine, sabinene, terpinene, borneol, cineole, geraniol, linalol, pipertone, terpineol, eugenol, eugenol acetate, safrole, benzyl benzoate, humulene, beta-caryophylene, eucakytol, hexanoic acid, octanoic acid, decanoic acid, undecanoic acid, dodecanoic acid, tridecanoic acid, myristic acid, palmitic acid, stearic acid, oleic acid, linoleic acid, linolenic acid, cholic acid; ethyl undecanoate, methyl laurate, methyl myristate, isopropyl myristate, isopropyl palmitate, palmityl palmitate, diethyl sebaccate, glyceryl monolaurate, glyceryl monooleate, and ethylpiperazine carboxylate; and a permeation enhancer with a molecular weight of about 232 g/mol to about 1310 g/mol; wherein the permeation enhancer or combination of permeation enhancers increases the flux of the therapeutic agent or combination of therapeutic agents across a barrier; and
  (c) a matrix forming agent or a combination of matrix forming agents, wherein the matrix forming agent or combination of matrix forming agents comprises a polymer;
wherein:
  the composition forms a gel at temperatures above a phase transition temperature; and
  the phase transition temperature is less than about 37° C.;
and at least one of conditions (i), (ii), and (iii) are met:
  (i) the phase transition temperature of the composition is less than the phase transition temperature of a reference composition plus about 5° C.;
  (ii) the storage modulus of the composition is greater than about 15% of the storage modulus of the reference composition or greater than about 500 Pa, whichever is smaller, at a temperature of about 37° C.; and
  (iii) the loss modulus of the composition is between about 15% and about 150% of the loss modulus of the reference composition at a temperature of about 37° C.;
wherein the reference composition is the composition in the absence of the permeation enhancer or combination of permeation enhancers;

wherein the polymer comprises a polymer of Formula (I'):

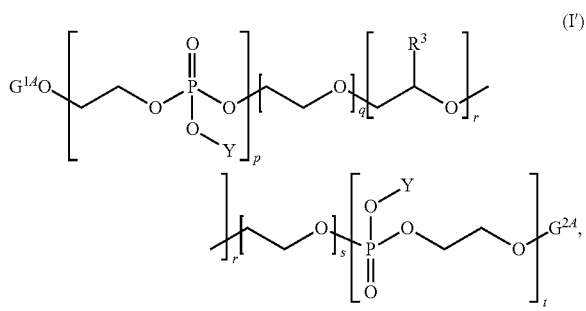

wherein:
  each occurrence of Y is independently —$R^1$ or -$L^2R^2$;
  each occurrence of R is independently hydrogen, optionally substituted alkyl, optionally substituted alkenyl, optionally substituted alkynyl, optionally substituted aryl, or optionally substituted heteroaryl;
  each occurrence of $L^2$ is independently a bond, optionally substituted alkylene, optionally substituted alkenylene, optionally substituted alkynylene, optionally substituted heteroalkylene, optionally substituted heteroalkenylene, or optionally substituted heteroalkynylene;
  each occurrence of $R^2$ is independently optionally substituted acyl, optionally substituted carbocyclyl, optionally substituted heterocyclyl, optionally substituted aryl, optionally substituted heteroaryl, —$OR^b$, —$N(R^b)_2$, or an oxygen protecting group;
  each occurrence of $R^3$ is independently hydrogen, optionally substituted alkyl, optionally substituted alkenyl, optionally substituted alkynyl, optionally substituted aryl, optionally substituted heteryaryl, optionally substituted acyl, —$OR^b$, or —$N(R)_2$;
  each occurrence of $R^b$ is independently optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, an oxygen protecting group, or a nitrogen protecting group, or two $R^b$ taken together with the nitrogen to which they are attached form an optionally substituted heterocyclic ring or optionally substituted heteroaryl ring;
  each of $G^{1A}$ and $G^{2A}$ is independently hydrogen, halogen, optionally substituted amine, optionally substituted alkyl, optionally substituted aryl, or optionally substituted heteroaryl, optionally substituted acyl, optionally substituted phosphate, or an oxygen protecting group; and
  each of p, q, r, s, and t is independently an integer between 1 and 200, inclusive, wherein the sum of p and t is at least 1, and the sum of q, r, and s is at least 1.

2. A composition comprising:
  (a) an antibiotic or a combination of antibiotics, wherein each antibiotic is a β-lactamase inhibitor or has a molecular weight of about 290 g/mol to about 749 g/mol;
  (b) a permeation enhancer or a combination of permeation enhancers selected from the group consisting of limonene, cymene, pinene, camphor, menthol, comphone, phellandrine, sabinene, terpinene, borneol, cineole, geraniol, linalol, pipertone, terpineol, eugenol, eugenol acetate, safrole, benzyl benzoate, humulene, beta-caryophylene, eucakytol, hexanoic acid, octanoic acid, decanoic acid, undecanoic acid, dodecanoic acid, tridecanoic acid, myristic acid, palmitic acid, stearic acid, oleic acid, linoleic acid, linolenic acid, cholic acid; ethyl undecanoate, methyl laurate, methyl myristate, isopropyl myristate, isopropyl palmitate, palmityl palmitate, diethyl sebaccate, glyceryl monolaurate, glyceryl monooleate, and ethylpiperazine carboxylate; and a permeation enhancer with a molecular weight of about 232 g/mol to about 1310 g/mol; and
  (c) a matrix forming agent or a combination of matrix forming agents, wherein the matrix forming agent or combination of matrix forming agents comprises a polymer;
wherein:
  the composition forms a gel at temperatures above a phase transition temperature; and
  the phase transition temperature is less than about 37° C.;
and at least one of conditions (i), (ii), and (iii) are met:
  (i) the phase transition temperature of the composition is less than the phase transition temperature of a reference composition plus about 5° C.;
  (ii) the storage modulus of the composition is greater than about 15% of the storage modulus of the reference composition at a temperature of about 37° C.; and
  (iii) the loss modulus of the composition is between about 80% and about 120% of the loss modulus of the reference composition at a temperature of about 37° C.;
wherein the reference composition is the composition in the absence of the permeation enhancer or combination of permeation enhancers;
wherein the polymer comprises a polymer of Formula (I'):

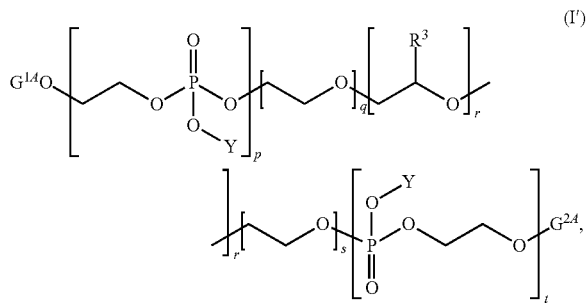

wherein:
  each occurrence of Y is independently —$R^1$ or -$L^2R^2$;
  each occurrence of R is independently hydrogen, optionally substituted alkyl, optionally substituted alkenyl, optionally substituted alkynyl, optionally substituted aryl, or optionally substituted heteroaryl;
  each occurrence of $L^2$ is independently a bond, optionally substituted alkylene, optionally substituted alkenylene, optionally substituted alkynylene, optionally substituted heteroalkylene, optionally substituted heteroalkenylene, or optionally substituted heteroalkynylene;
  each occurrence of $R^2$ is independently optionally substituted acyl, optionally substituted carbocyclyl, optionally substituted heterocyclyl, optionally substituted aryl, optionally substituted heteroaryl, —$OR^b$, —$N(R^b)_2$, or an oxygen protecting group;
  each occurrence of $R^3$ is independently hydrogen, optionally substituted alkyl, optionally substituted alkenyl, optionally substituted alkynyl, optionally substituted aryl, optionally substituted heteryaryl, optionally substituted acyl, —OR$^b$, or —N(R)$_2$;
each occurrence of R$^b$ is independently optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, an oxygen protecting group, or a nitrogen protecting group, or two R$^b$ taken together with the nitrogen to which they are attached form an optionally substituted heterocyclic ring or optionally substituted heteroaryl ring;
each of G$^{1A}$ and G$^{2A}$ is independently hydrogen, halogen, optionally substituted amine, optionally substituted alkyl, optionally substituted aryl, or optionally substituted heteroaryl, optionally substituted acyl, optionally substituted phosphate, or an oxygen protecting group; and
each of p, q, r, s, and t is independently an integer between 1 and 200, inclusive, wherein the sum of p and t is at least 1, and the sum of q, r, and s is at least 1.

3. A matrix forming agent or a combination of matrix forming agents, wherein the matrix forming agent or combination of matrix forming agents comprises a polymer of Formula (I'):

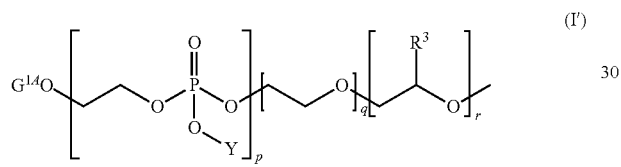

-continued

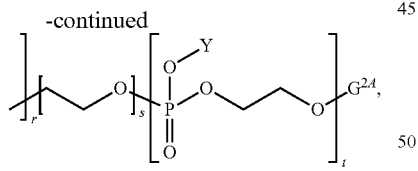

wherein:
each occurrence of Y is independently —R$^1$ or -L$^2$R$^2$;
each occurrence of R$^1$ is independently hydrogen, optionally substituted alkyl, optionally substituted alkenyl, optionally substituted alkynyl, optionally substituted aryl, or optionally substituted heteroaryl;
each occurrence of L$^2$ is independently a bond, optionally substituted alkylene, optionally substituted alkenylene, optionally substituted alkynylene, optionally substituted heteroalkylene, optionally substituted heteroalkenylene, or optionally substituted heteroalkynylene;
each occurrence of R$^2$ is independently optionally substituted acyl, optionally substituted carbocyclyl, optionally substituted heterocyclyl, optionally substituted aryl, optionally substituted heteroaryl, —OR$^b$, —N(R$^b$)$_2$, or an oxygen protecting group;
each occurrence of R$^3$ is independently hydrogen, optionally substituted alkyl, optionally substituted alkenyl, optionally substituted alkynyl, optionally substituted aryl, optionally substituted heteryaryl, optionally substituted acyl, —OR$^b$, or —N(R)$_2$;
each occurrence of R$^b$ is independently optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, an oxygen protecting group, or a nitrogen protecting group, or two R$^b$ taken together with the nitrogen to which they are attached form an optionally substituted heterocyclic ring or optionally substituted heteroaryl ring;
each of G$^{1A}$ and G$^{2A}$ is independently hydrogen, halogen, optionally substituted amine, optionally substituted alkyl, optionally substituted aryl, or optionally substituted heteroaryl, optionally substituted acyl, optionally substituted phosphate, or an oxygen protecting group; and
each of p, q, r, s, and t is independently an integer between 1 and 200, inclusive, wherein the sum of p and t is at least 1, and the sum of q, r, and s is at least 1.

4. The polymer of claim 3, wherein the matrix forming agent or combination of matrix forming agents comprises a polymer of Formula:

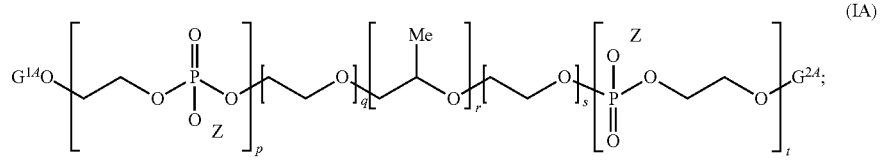

wherein:
each occurrence of Z is independently —R$^4$;
each occurrence of R$^4$ is independently optionally substituted alkyl;
each of G$^{1A}$ and G$^{2A}$ is independently hydrogen, optionally substituted alkyl, optionally substituted aryl, or optionally substituted heteroaryl, optionally substituted acyl, optionally substituted phosphate, or an oxygen protecting group; and
each of p, q, r, s, and t is an integer between 1 and 200, wherein the sum of p and t is at least 1, and the sum of q, r, and s is at least 1;
the composition forms a gel at temperatures above a phase transition temperature; and
the phase transition temperature is less than about 37° C.;
and at least one of conditions (i), (ii), and (iii) are met:
(i) the phase transition temperature of the composition is less than the phase transition temperature of a reference composition plus about 5° C.;
(ii) the storage modulus of the composition is greater than about 15% of the storage modulus of the reference composition at a temperature of about 37° C.; and (iii) the loss modulus of the composition is between about 80% and about 120% of the loss modulus of the reference composition at a temperature of about 37° C.;
wherein the reference composition is the composition in the absence of the permeation enhancer or combination of permeation enhancers.

5. The polymer of claim 3, wherein the polymer is of the formula:

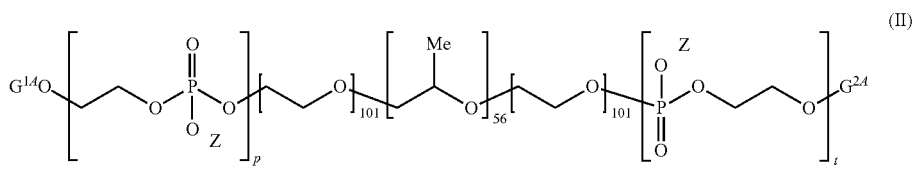

(II)

6. The polymer of claim 3, wherein the polymer is of the formula:

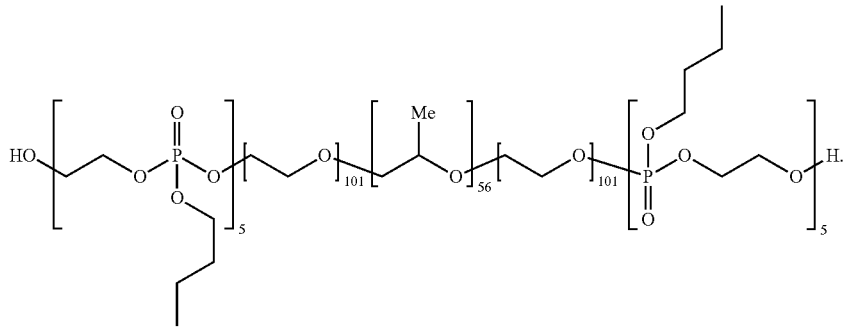

7. The polymer of claim 3, further comprising an antibiotic that is a β-lactamase inhibitor or has a molecular weight of about 290 g/mol to about 749 g/mol.

8. The composition of claim 3, wherein the polymer further comprises blocks selected from the group consisting polyethylene oxide, polypropylene oxide, poloxamers, poloxamer 407, poloxamer 188, poloxamines, methylcellulose, hydroxypropyl methylcellulose, ethyl(hydroxyethyl)cellulose, xyloglucan, acetates, phthalates, latex, poly(acrylic acid), N-isopropylacrylamides, cellulose, chitosan, dextran, and hyaluronic acid, and derivatives thereof.

9. The composition of claim 3, wherein the polymer comprises phosphoester monomers of Formula (M):

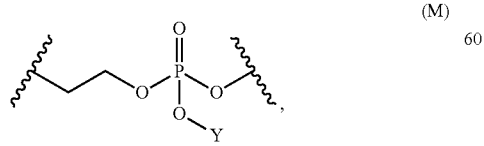

(M)

wherein for each monomer Y is independently —$R^1$ or -$L^2R^2$, wherein:

each occurrence of $R^1$ is independently optionally substituted alkyl, optionally substituted alkenyl, or optionally substituted alkynyl;

each occurrence of $L^2$ is independently optionally substituted alkylene, optionally substituted alkenylene, optionally substituted alkynylene, optionally substituted heteroalkylene, optionally substituted heteroalkenylene, or optionally substituted heteroalkynylene;

each occurrence of $R^2$ is independently optionally substituted acyl, optionally substituted carbocyclyl, optionally substituted heterocyclyl, optionally substituted aryl, optionally substituted heteroaryl, —$OR^b$, —$N(R^b)_2$; and each occurrence of $R^b$ is independently optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, an oxygen protecting group, or a nitrogen protecting group, or two $R^b$ taken together with the nitrogen to which they are attached form an optionally substituted heterocyclic or optionally substituted heteroaryl ring.

10. The composition of claim 1, wherein the polymer is of formula:

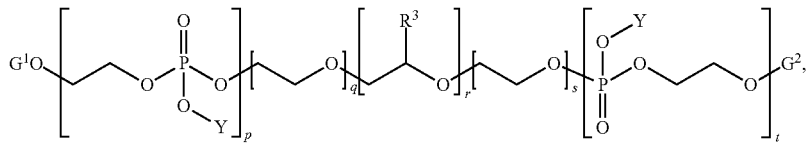

wherein:
each occurrence of R¹ is independently hydrogen, optionally substituted alkyl, optionally substituted alkenyl, or optionally substituted alkynyl;
each occurrence of R³ is independently optionally substituted alkyl, optionally substituted alkenyl, optionally substituted alkynyl, optionally substituted aryl, optionally substituted heteryaryl, optionally substituted acyl, —OR$^b$, or —N(R$^b$)$_2$; and
each of G$^{1A}$ and G$^{2A}$ is independently hydrogen, optionally substituted alkyl, optionally substituted acyl, optionally substituted phosphate, or an oxygen protecting group.

11. The composition of claim 10, wherein each R¹ is unsubstituted $C_{1-20}$ alkyl.

12. The composition of claim 1, wherein each L² is a bond or unsubstituted $C_{1-6}$ alkylene.

13. The composition of claim 12, wherein each L² is a bond.

14. The composition of claim 12, wherein each L² is unsubstituted $C_{1-6}$ alkylene.

15. A kit for treating an ear disease comprising a container, a composition of claim 1, and instructions for administering the composition to a subject in need thereof.

16. The composition of claim 1, wherein each instance of Y is R¹.

17. The composition of claim 16, wherein R¹ is optionally substituted alkyl.

18. The composition of claim 17, wherein R¹ is optionally substituted $C_{1-6}$ alkyl.

19. The composition of claim 1, wherein each of p and t is an integer between 1 and 100, inclusive.

20. The composition of claim 17, wherein each of p and t is an integer between 1 and 10, inclusive.

21. The composition of claim 19, wherein r is an integer between 10 and 100, inclusive.

22. The polymer of claim 3, wherein the polymer is of the formula:

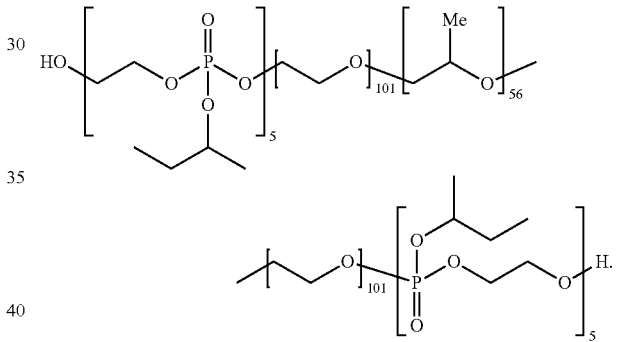

23. The composition of claim 1, wherein the polymer is of the formula:

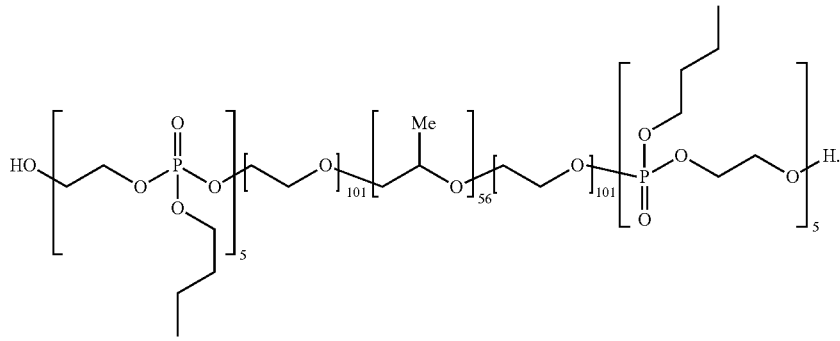

24. The composition of claim 1, wherein the polymer is of the formula:
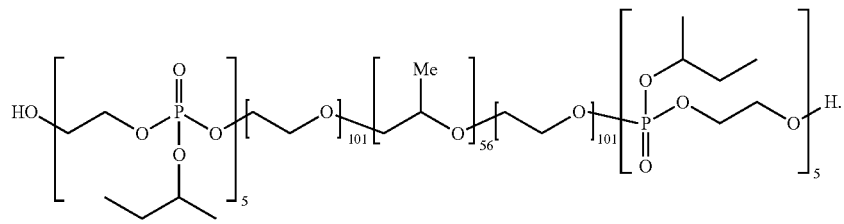
25. The composition of claim 2, wherein the polymer is of the formula:
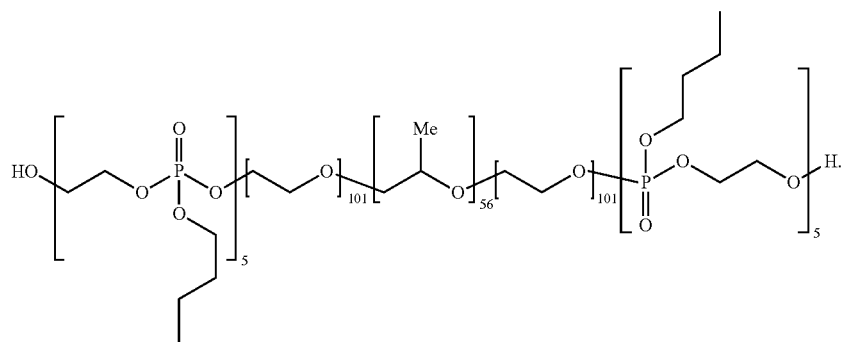
26. The composition of claim 2, wherein the polymer is of the formula:
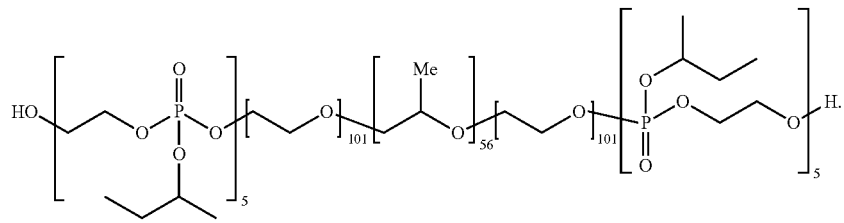
* * * * *